US007951432B2

(12) United States Patent
Tanaka

(10) Patent No.: US 7,951,432 B2
(45) Date of Patent: May 31, 2011

(54) FIVE-RING LIQUID CRYSTAL COMPOUND HAVING CYCLOHEXANE RING, LIQUID CRYSTAL COMPOSITION, AND LIQUID CRYSTAL DISPLAY DEVICE

(75) Inventor: Hiroyuki Tanaka, Chiba (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 0 days.

(21) Appl. No.: 12/478,112

(22) Filed: Jun. 4, 2009

(65) Prior Publication Data

US 2009/0302273 A1 Dec. 10, 2009

(30) Foreign Application Priority Data

Jun. 9, 2008 (JP) ................................ 2008-150973

(51) Int. Cl.

| | |
|---|---|
| ***C09K 19/34*** | (2006.01) |
| ***C09K 19/30*** | (2006.01) |
| ***C09K 19/12*** | (2006.01) |
| ***C07D 319/06*** | (2006.01) |
| ***C07C 19/08*** | (2006.01) |
| ***C07C 25/13*** | (2006.01) |
| ***C07C 43/225*** | (2006.01) |

(52) U.S. Cl. ............... 428/1.1; 252/299.61; 252/299.63; 252/299.66; 549/369; 549/373; 549/374; 568/631; 568/642; 568/645; 568/647; 570/127; 570/129; 570/131

(58) Field of Classification Search .................. 428/1.1; 252/299.61, 299.62, 299.63, 299.66, 299.67, 252/299.5; 560/127, 128, 129, 130; 549/369, 549/373, 374; 568/631, 642, 645, 647; 570/127, 570/129, 131

See application file for complete search history.

(56) References Cited

U.S. PATENT DOCUMENTS

| | | | | |
|---|---|---|---|---|
| 5,262,085 | A | 11/1993 | Bartmann et al. | |
| 5,728,319 | A * | 3/1998 | Matsui et al. | 252/299.63 |
| 7,419,706 | B2 | 9/2008 | Heckmeier et al. | |
| 7,531,106 | B2 | 5/2009 | Kirsch et al. | |
| 7,722,783 | B2 * | 5/2010 | Haseba et al. | 252/299.01 |
| 2005/0017216 | A1 | 1/2005 | Poetsch et al. | |
| 2005/0279968 | A1 | 12/2005 | Manabe et al. | |
| 2006/0061699 | A1 | 3/2006 | Kirsch et al. | |
| 2008/0193682 | A1 | 8/2008 | Lietzau et al. | |
| 2010/0127211 | A1 * | 5/2010 | Tanaka | 252/299.61 |

FOREIGN PATENT DOCUMENTS

| | | |
|---|---|---|
| EP | 0786445 | 7/1997 |
| EP | 0844229 | 5/1998 |
| GB | 2229438 | 9/1990 |
| JP | H10-251186 | 9/1998 |
| JP | 2006241040 A * | 9/2006 |
| WO | 2006/125530 | 11/2006 |
| WO | WO 2008105286 A1 * | 9/2008 |

OTHER PUBLICATIONS

English translation by computer for JP 2006-241040, http://www4.ipdl.inpit.go.jp/Tokujitu/PAJdetail.ipdl?N0000=60&N0120=01&N2001=2&N3001=2006-241040.*

* cited by examiner

*Primary Examiner* — Shean C Wu

(74) *Attorney, Agent, or Firm* — J.C. Patents

(57) ABSTRACT

A liquid crystal compound represented by formula (1), a liquid crystal composition comprising the compound, and a liquid crystal display device comprising the composition:

(1)

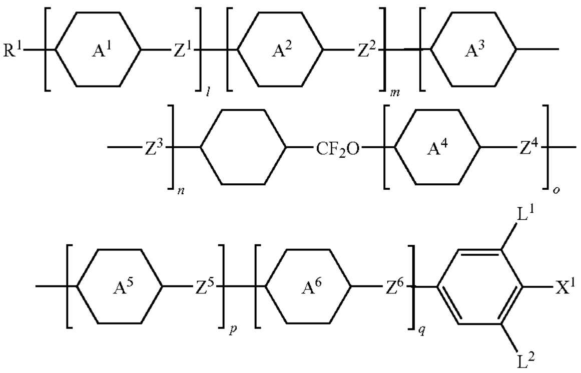

For example, $R^1$ is alkyl having 1 to 20; ring $A^1$, ring $A^2$, ring $A^3$, ring $A^4$, ring $A^5$, and ring $A^6$ are 1,4-cyclohexylene or 1,4-phenylene; $Z^1$, $Z^2$, $Z^3$, $Z^4$, $Z^5$, and $Z^6$ is a single bond; $X^1$ is hydrogen or halogen; l, m, n, o, p, and q are 0 or 1, and l+m+n+o+p+q is 3.

17 Claims, No Drawings

FIVE-RING LIQUID CRYSTAL COMPOUND HAVING CYCLOHEXANE RING, LIQUID CRYSTAL COMPOSITION, AND LIQUID CRYSTAL DISPLAY DEVICE

BACKGROUND OF THE INVENTION

1. Field of the Invention

The invention relates to a new liquid crystal compound, a liquid crystal composition and a liquid crystal display device. The invention relates in particular to a five-ring liquid crystal compound having a wide temperature range of liquid crystal phases, a high clearing point, a good compatibility with other liquid crystal compounds, an appropriate optical anisotropy, and an appropriate dielectric anisotropy, and a composition comprising the compound, and a liquid crystal display device using the composition.

2. Related Art

Liquid crystal display devices using liquid crystal compounds have been widely applied to displays for watches, calculators, personal computers and so forth. In these display devices, the optical anisotropy, the dielectric anisotropy, and so forth of the liquid crystal compounds have been utilized.

In the liquid crystal display devices, a classification based on the operation mode of liquid crystals includes phase change (PC), twisted nematic (TN), super twisted nematic (STN), bistable twisted nematic (BTN), electrically controlled birefringence (ECB), optically compensated bend (OCB), in-plane switching (IPS), vertical alignment (VA), polymer sustained alignment (PSA) and so forth. A classification based on a driving mode includes a passive matrix (PM) and an active matrix (AM). The PM is further classified into static, multiplex, and so forth, and the AM is classified into a thin film transistor (TFT), metal insulator metal (MIM) and so forth.

A liquid crystal display device comprises a liquid crystal composition having suitable properties. The composition desirably has suitable properties for improving the characteristics of the device. General physical properties necessary for a liquid crystal compound which is a component of the composition are listed as follows.

(1) being chemically stable and physically stable,
(2) having a high clearing point (the phase transition temperature of a liquid crystal phase to an isotropic phase),
(3) being low in the minimum temperature of liquid crystal phases (a nematic phase, a smectic phase, and so forth), especially of the nematic phase,
(4) having an excellent compatibility with other liquid crystal compounds,
(5) having an appropriate optical anisotropy, and
(6) having an appropriate dielectric anisotropy.

A voltage holding ratio can be increased by using a composition containing a chemically and physically stable liquid crystal compound as described in item (1). The temperature range of a nematic phase is wide in a composition containing a liquid crystal compound having a high clearing point or a low minimum temperature of liquid crystal phases as described in items (2) and (3), and thus the device is usable in a wide temperature range.

The liquid crystal compound is generally used as a composition prepared by being mixed with many other liquid crystal compounds to obtain characteristics that cannot be attained with a single compound. Thus, it is desirable that the liquid crystal compound used for a display device has a good compatibility with other liquid crystal compounds and so forth, as described in item (4).

Recently, a liquid crystal display device has been required to have high quality in display performance such as contrast, display capacity, and response time. For example, a liquid crystal compound capable of decreasing the threshold voltage of its composition is required for decreasing the driving voltage of this device. It is desirable that the product (Δn×d) of the optical anisotropy (Δn) of the liquid crystal composition and the cell gap (d) of the liquid crystal display device is constant in order to attain a good liquid crystal display. Refer to E. Jakeman, et al., Phys. Lett., 39A, 69 (1972). Therefore, the liquid crystal compound is required to have the value of the optical anisotropy corresponding to the cell gap of the liquid crystal display device. Thus, the liquid crystal compound having an appropriate optical anisotropy as described in item (5) has been demanded.

Threshold voltage ($V_{th}$), as is well known, is represented by the following equation. Refer to H. J. Deuling, et al., Mol. Cryst. Liq. Cryst., 27 (1975) 81.

$$V_{th}=\pi(K/\epsilon_0\Delta\epsilon)^{1/2}$$

In the equation above, K is an elastic constant and $\epsilon_0$ is a dielectric constant in vacuum. As is shown by the equation, two methods are possible to decrease the threshold voltage $V_{th}$, either by increasing the value of the dielectric anisotropy ($\Delta\epsilon$) or by decreasing the value of the elastic constant (K). However, the elastic constant (K) is not easily controlled by the present technology, and a compound having a large dielectric anisotropy ($\Delta\epsilon$) is most commonly used to respond to the present demand. Under these circumstances, liquid crystal compounds having an appropriate dielectric anisotropy as described in item (6), and liquid crystal compounds having a large dielectric anisotropy have been developed actively.

Until now, liquid crystal compounds have been developed to attain an appropriate optical anisotropy corresponding to the cell gap of the liquid crystal display device and an appropriate dielectric anisotropy. However, only a few examples are reported concerning liquid crystal compounds having a relatively small optical anisotropy, a high clearing point, a good compatibility with other compounds, and an appropriate dielectric anisotropy.

A variety of liquid crystal compounds having a high clearing point and a large dielectric anisotropy have been synthesized until now and some of them are used practically. For example, four-ring-containing compounds having a $CF_2O$-bonding group are disclosed in patent literatures Nos. 1 to 6. However, these compounds do not have a sufficiently high clearing point, so that the usable temperature range of their compositions are not sufficiently wide for the use of display devices.

Furthermore, five-ring-containing compounds (S-1) to (S-3) having a tetrahydropyran ring and the $CF_2O$-bonding group are disclosed in patent literatures Nos. 7 to 12. These compounds do not have a sufficiently high clearing point. The compounds (S-4) and (S-5) having tetrahydropyran and dioxane rings are also disclosed in patent literature No. 11. However, the temperature range of liquid crystal phases is not sufficiently wide and the clearing points are not sufficiently high in these compounds.

(S-1)

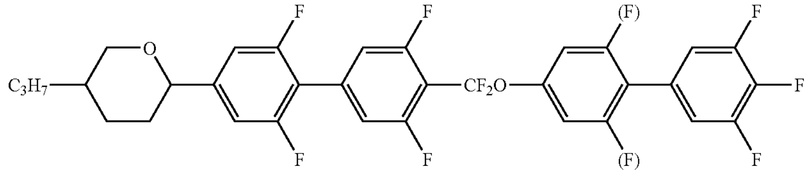

(S-2)

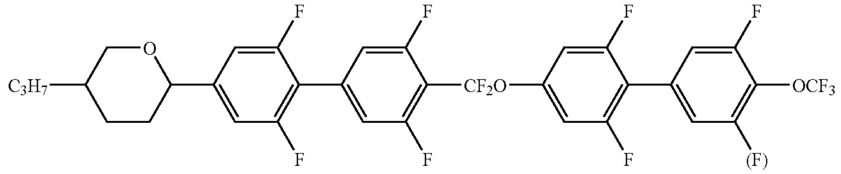

(S-3)

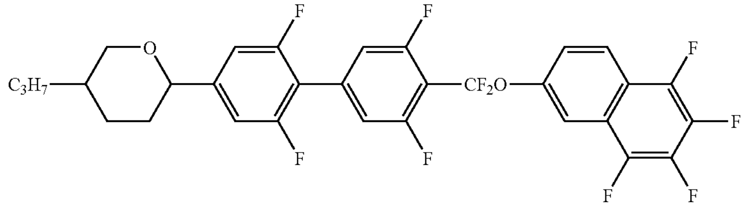

(S-4)

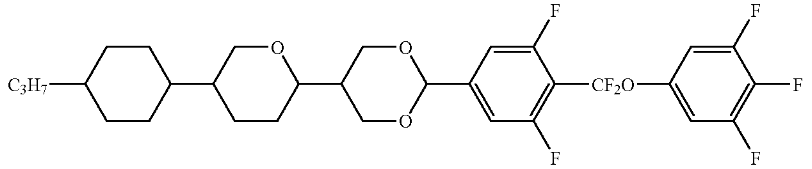

(S-5)

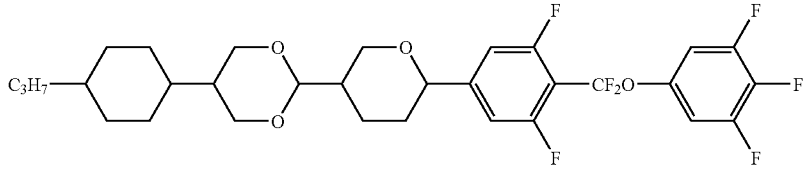

The patent literatures cited are No. 1: WO 1996/11897 A, No. 2: JP H10-204016 A/1998, No. 3: GB 2229438 C, No. 4: DE 4023106 A; No. 5: JP H10-251186 A/1998, No. 6: WO 2004/035710 A, No. 7: WO2004/048501 A, No. 8: JP 2004-352721 A; No. 9: WO 2005/019378 A, No. 10: WO 2005/019381 A, No. 11: WO 2006/125511 A, and No. 12: WO2006/125530 A.

SUMMARY OF THE INVENTION

The invention concerns a compound represented by formula (1):

(1)

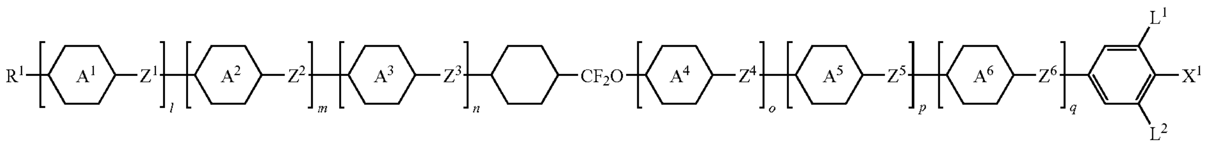

wherein $R^1$ is alkyl having 1 to 20 carbons, and in the alkyl having 2 to 20 carbons, arbitrary $—CH_2—$ may be replaced by —O—, —S— or —CH═CH—; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by halogen; $Z^1$, $Z^2$, $Z^3$, $Z^4$, $Z^5$, and $Z^6$ are each independently a single bond, $—CH_2CH_2—$, —CH═CH—, —C≡C—, —COO—, —OCO—, $—CF_2O—$, $—OCF_2—$, $—CH_2O—$, $—OCH_2—$, —CF═CF—, $—(CH_2)_4—$, $—(CH_2)_2CF_2O—$, $—(CH_2)_2OCF_2—$, $—CF_2O(CH_2)_2—$, $—OCF_2(CH_2)_2—$, $—CH═CH—(CH_2)_2—$, or $—(CH_2)_2—CH═CH—$; $L^1$ and $L^2$ are each independently hydrogen or halogen; $X^1$ is hydrogen, halogen, —C≡N, —N═C═S, $—SF_5$, or alkyl having 1 to 10 carbons, and in the alkyl having 2 to 10 carbons, arbitrary $—CH_2—$ may be replaced by —O—, —S— or —CH═CH—, and arbitrary hydrogen may be replaced by halogen; and l, m, n, o, p, and q are each independently 0 or 1, and l+m+n+o+p+q is 3.

The invention also concerns a liquid crystal composition comprising a first component and a second component, wherein the first component is at least the compound.

The invention also concerns a liquid crystal display device comprising the liquid crystal composition, and so forth.

DETAILED DESCRIPTION OF THE INVENTION

The first advantage of the invention is to provide a liquid crystal compound having general physical properties required for compounds, stability to heat, light and so forth, a wide temperature range of liquid crystal phases, a high clearing point, a good compatibility with other liquid crystal compounds, an appropriate optical anisotropy, and an appropriate dielectric anisotropy. The second advantage is to provide a liquid crystal composition comprising this compound and having a wide temperature range of liquid crystal phases, a small viscosity, an appropriate optical anisotropy, and a low threshold voltage. The third advantage is to provide a liquid crystal display device containing this composition and having a wide temperature range usable, a short response time, a small electric power consumption, a large contrast, and a low driving voltage.

The invention provides a liquid crystal compound, a liquid crystal composition, a liquid crystal display device containing the liquid crystal composition and so forth as described below. Furthermore, desirable examples regarding terminal groups, rings, bonding groups and so forth in the compound represented by formula (1) will be described below.

1. A compound represented by formula (1):

$-OCO-$, $-CF_2O-$, $-OCF_2-$, $-CH_2O-$, $-OCH_2-$, $-CF{=}CF-$, $-(CH_2)_4-$, $-(CH_2)2CF_2O-$, $-(CH_2)_2OCF_2-$, $-CF_2O(CH_2)_2-$, $-OCF_2(CH_2)_2-$, $-CH{=}CH-(CH_2)_2-$, or $-(CH_2)_2-CH{=}CH-$; $L^1$ and $L^2$ are each independently hydrogen or halogen; $X^1$ is hydrogen, halogen, $-C{\equiv}N$, $-N{=}C{=}S$, $-SF_5$, or alkyl having 1 to 10 carbons, and in the alkyl having 2 to 10 carbons, arbitrary $-CH_2-$ may be replaced by $-O-$, $-S-$ or $-CH{=}CH-$, and arbitrary hydrogen may be replaced by halogen; and l, m, n, o, p, and q are each independently 0 or 1, and l+m+n+o+p+q is 3.

2. The compound according to item 1, wherein in formula (1) $R^1$ is alkyl having 1 to 20 carbons, alkenyl having 2 to 21 carbons, alkoxy having 1 to 19 carbons, alkenyloxy having 2 to 20 carbons, or alkylthio having 1 to 19 carbons; and $X^1$ is hydrogen, halogen, $-C{\equiv}N$, $-N{=}C{=}S$, $-SF_5$, alkyl having 1 to 10 carbons, alkenyl having 2 to 11 carbons, alkoxy having 1 to 9 carbons, alkenyloxy having 2 to 10 carbons, thioalkyl having 1 to 9 carbons, $-CH_2F$, $-CHF_2$, $-CF_3$, $-(CH_2)_2-F$, $-CF_2CH_2F$, $-CF_2CHF_2$, $-CH_2CF_3$, $-CF_2CF_3$, $-(CH_2)_3-F$, $-(CF_2)_3-F$, $-CF_2CHFCF_3$, $-CHFCF_2CF_3$, $-(CH_2)_4-F$, $-(CF_2)_4-F$, $-(CH_2)_5-F$, $-(CF_2)_5-F$, $-OCH_2F$, $-OCHF_2$, $-OCF_3$, $-O-(CH_2)_2-F$, $-OCF_2CH_2F$, $-OCF_2CHF_2$, $-OCH_2CF_3$, $-O-(CH_2)_3-F$, $-O-(CF_2)_3-F$, $-OCF_2CHFCF_3$, $-OCHFCF_2CF_3$, $-O(CH_2)_4-F$, $-O-(CF_2)_4-F$, $-O-(CH_2)_5-F$, $-O-(CF_2)_5-F$, $-CH{=}CHF$, $-CH{=}CF_2$, $-CF{=}CHF$, $-CH{=}CHCH_2F$, $-CH{=}CHCF_3$, (1)

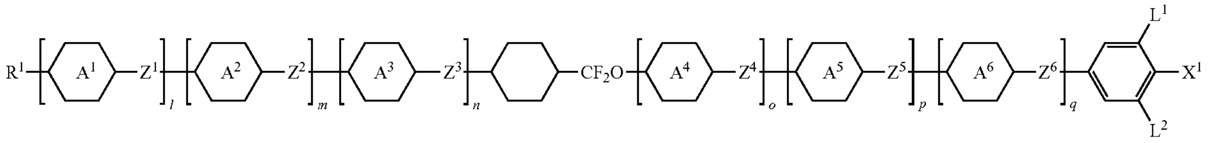

wherein $R^1$ is alkyl having 1 to 20 carbons, and in the alkyl having 2 to 20 carbons, arbitrary $-CH_2-$ may be replaced by $-O-$, $-S-$ or $-CH{=}CH-$; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by halogen; $Z^1$, $Z^2$, $Z^3$, $Z^4$, $Z^5$, and $Z^6$ are each independently a single bond, $-CH_2CH_2-$, $-CH{=}CH-$, $-C{\equiv}C-$, $-COO-$, $-(CH_2)_2-CH{=}CF_2$, $-CH_2CH{=}CHCF_3$, or $-CH{=}CHCF_2CF_3$.

3. The compound according to item 1 or 2, wherein in formula (1) $Z^1$, $Z^2$, $Z^3$, $Z^4$, $Z^5$, and $Z^6$ are each independently a single bond, $-CH_2CH_2-$, $-CH{=}CH-$, $-C{\equiv}C-$, $-COO-$, $-CF_2O-$, $-CH_2O-$, or $-OCH_2-$.

4. The compound according to item 1, which is represented by any one of formulas (1-1) to (1-4):

(1-1)

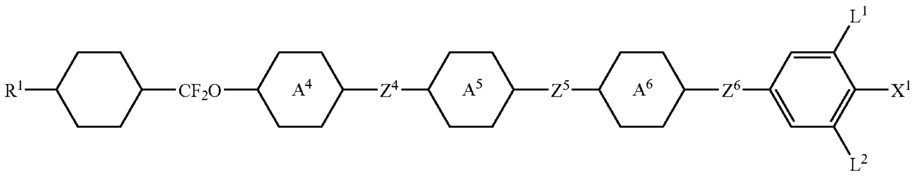

(1-2)

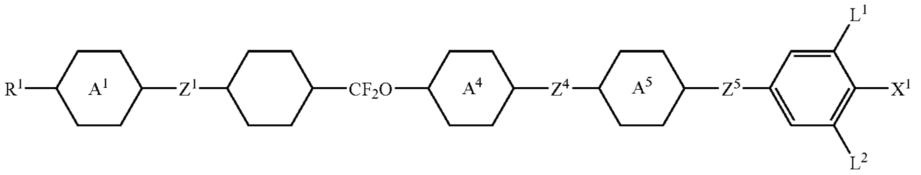

-continued (1-3)

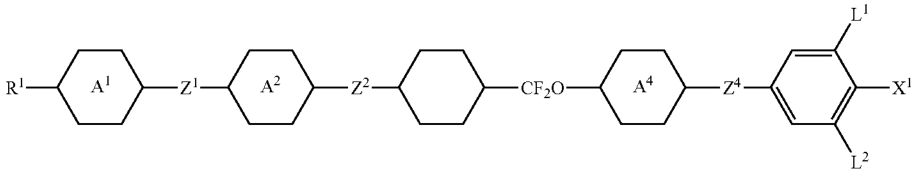

(1-4)

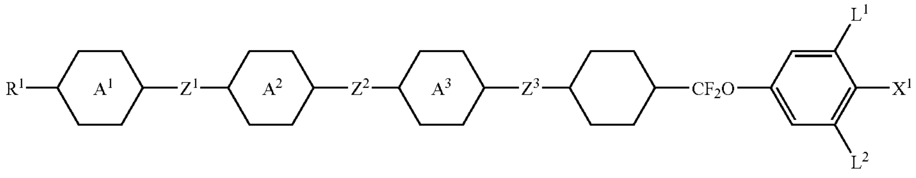

wherein $R^1$ is alkyl having 1 to 15 carbons, alkenyl having 2 to 15 carbons, alkoxy having 1 to 15 carbons, or alkenyloxy having 2 to 15 carbons; ring $A^1$, ring $A^2$, ring $A^3$, ring $A^4$, ring $A^5$, and ring $A^6$ are each independently 1,4-cyclohexylene, rine, —C≡N, $—CF_3$, $—CHF_2$, $—CH_2F$, $—OCF_3$, $—OCHF_2$, or $—OCH_2F$.

5. The compound according to item 1, which is represented by any one of formulas (1-5) to (1-8):

(1-5)

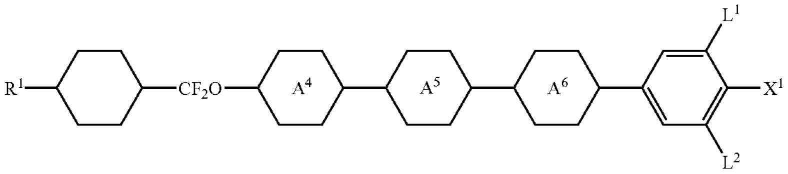

(1-6)

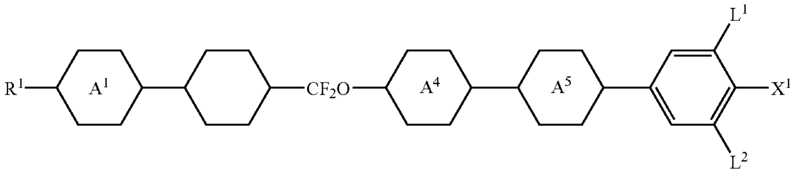

(1-7)

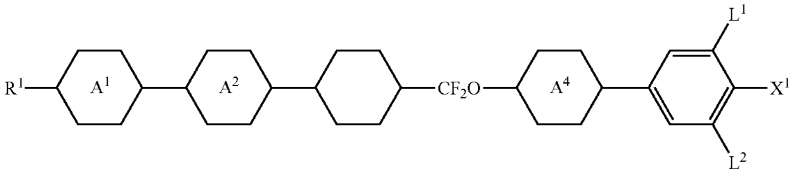

(1-8)

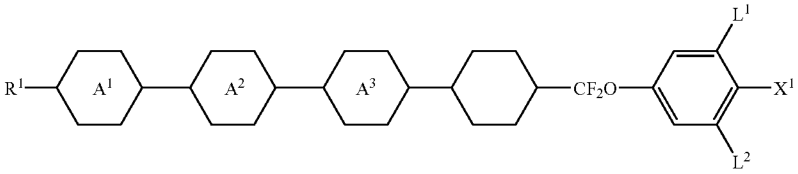

1,3-dioxane-2,5-diyl, 1,4-phenylene, or 1,4-phenylene in which arbitrary hydrogen is replaced by fluorine; $Z^1$, $Z^2$, $Z^3$, $Z^4$, $Z^5$, and $Z^6$ are each independently a single bond, $—CH_2CH_2—$, —CH═CH—, —C≡C—, —COO—, $—CF_2O—$, $—CH_2O—$, or $—OCH_2—$; $L^1$ and $L^2$ are each independently hydrogen or fluorine; and $X^1$ is fluorine, chlowherein $R^1$ is alkyl having 1 to 15 carbons or alkenyl having 2 to 15 carbons; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by fluorine; $L^1$ and $L^2$ are each independently hydrogen or fluorine; and $X^1$ is fluorine, chlorine, —C≡N, $—CF_3$, $—CHF_2$, $—CH_2F$, $—OCF_3$, $—OCHF_2$, or $—OCH_2F$.

6. The compound according to item 1, which is represented by any one of formulas (1-9) to (1-19):
(1-9)
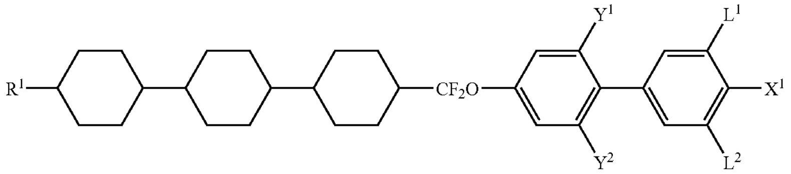
(1-10)
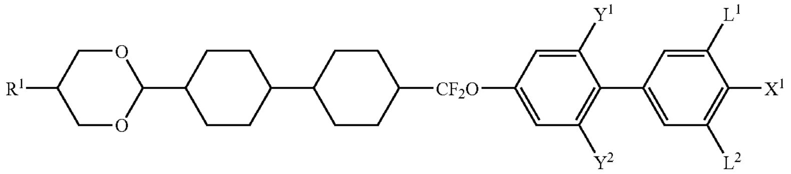
(1-11)
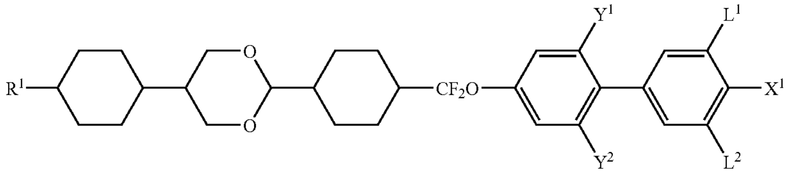
(1-12)
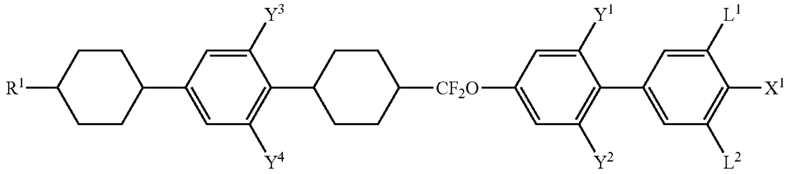
(1-13)
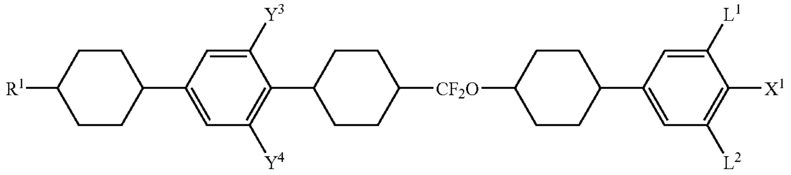
(1-14)
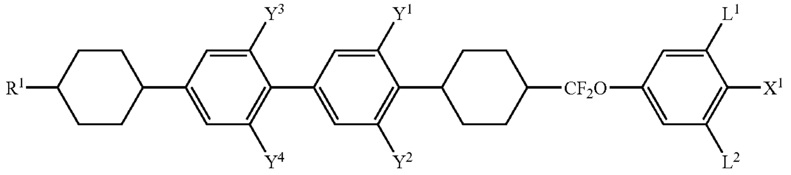
(1-15)
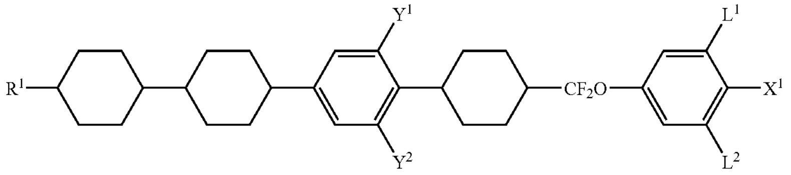
(1-16)
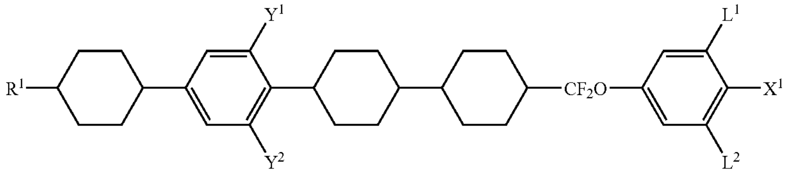

-continued
(1-17)
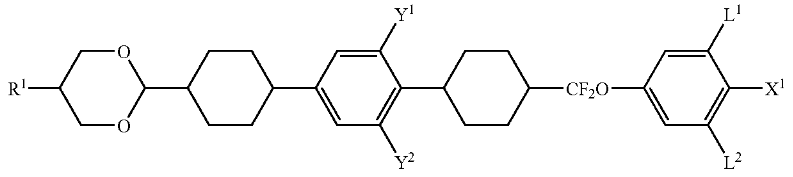
(1-18)
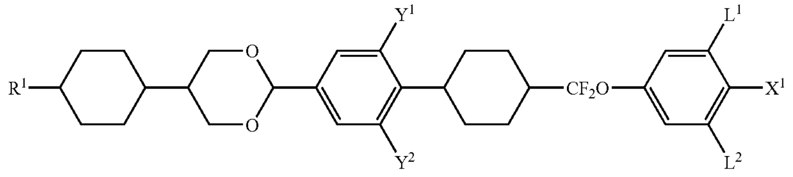
(1-19)
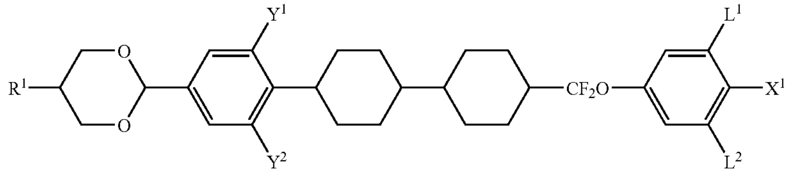
wherein $R^1$ is alkyl having 1 to 15 carbons; $L^1$, $L^2$, $Y^1$, $Y^2$, $Y^3$, and $Y^4$ are each independently hydrogen or fluorine; and $X^1$ is fluorine or $—OCF_3$.
7. The compound according to item 1, which is represented by any one of formulas (1-20) to (1-41):
(1-20)
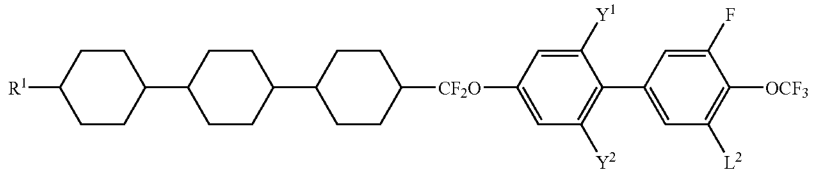
(1-21)
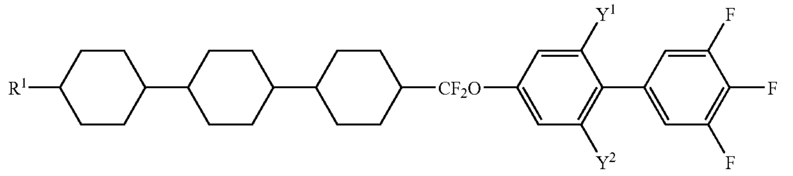
(1-22)
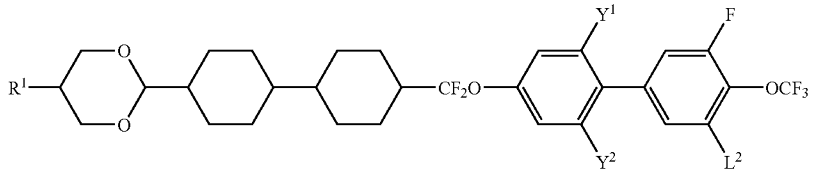
(1-23)
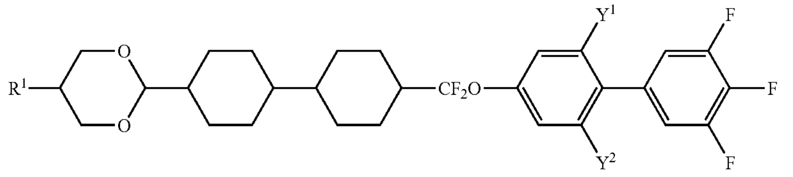

-continued
(1-24)
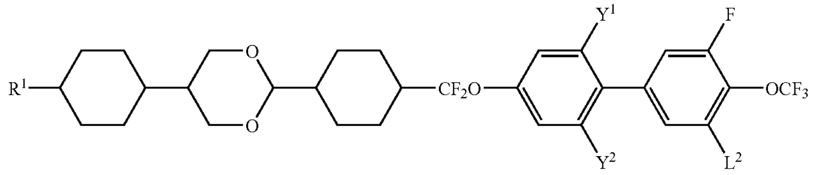
(1-25)
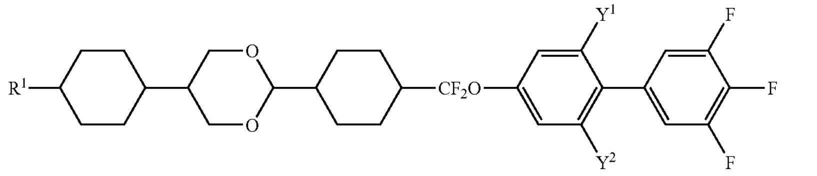
(1-26)
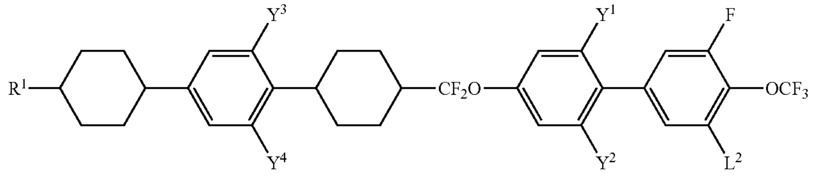
(1-27)
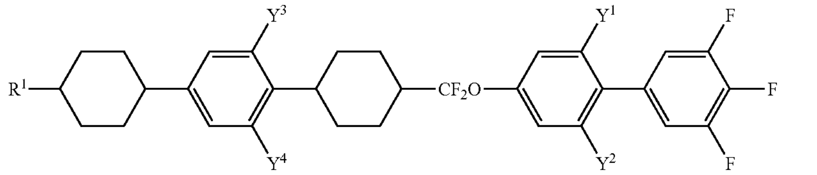
(1-28)
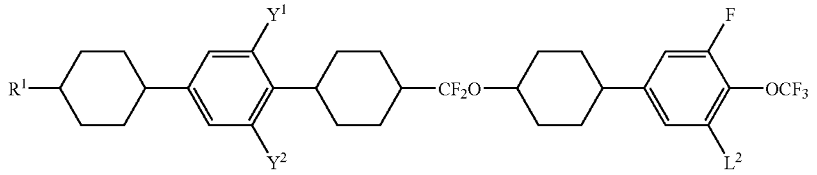
(1-29)
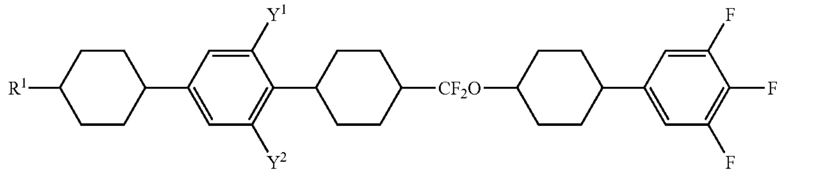
(1-30)
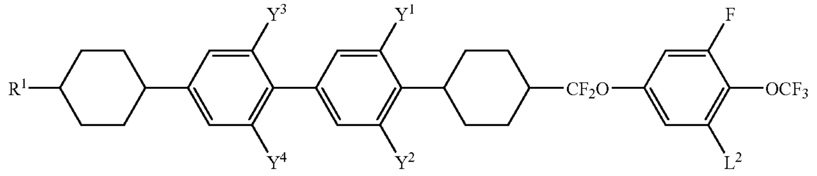
(1-31)
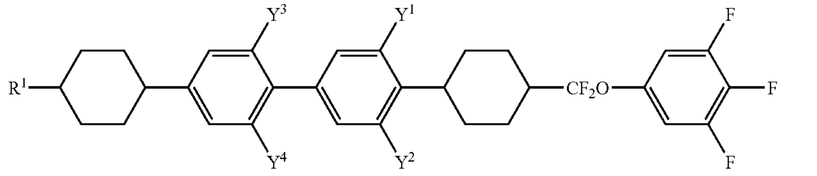
(1-32)
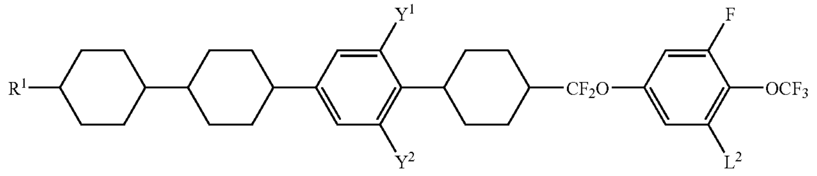

-continued
(1-33)
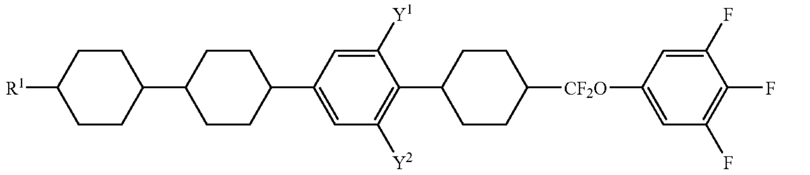
(1-34)
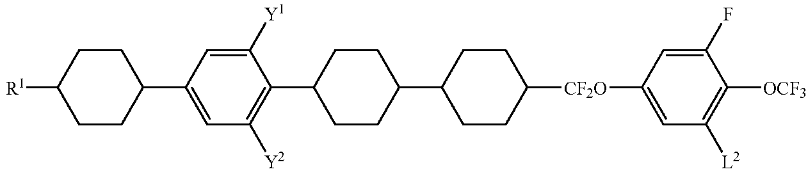
(1-35)
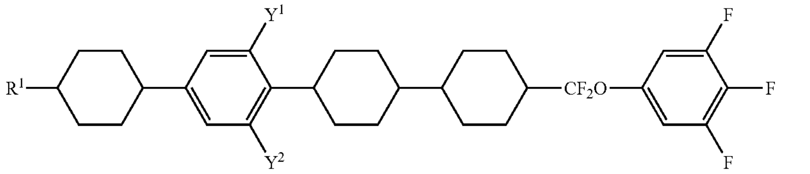
(1-36)
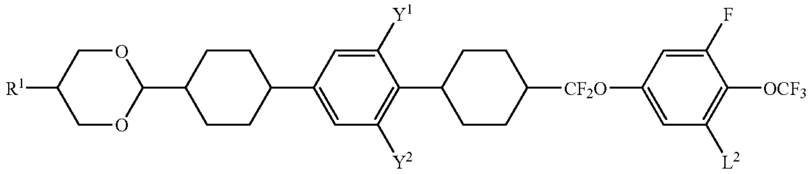
(1-37)
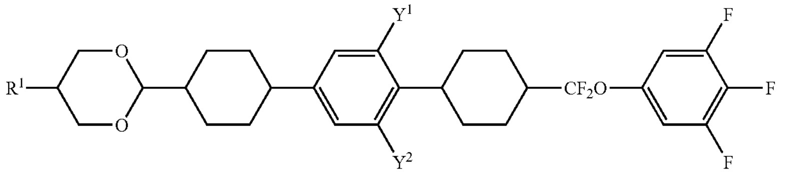
(1-38)
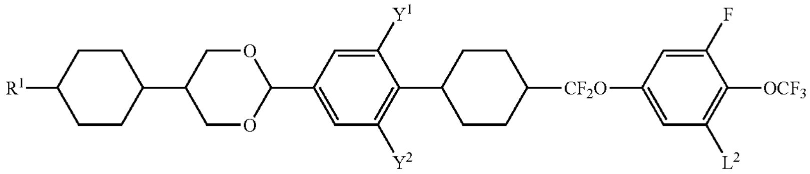
(1-39)
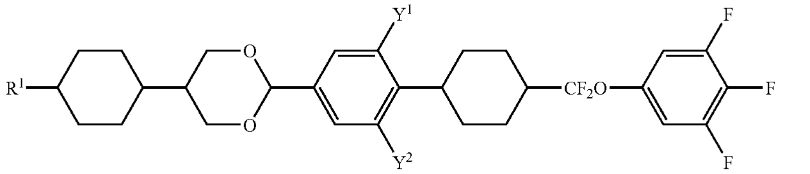
(1-40)
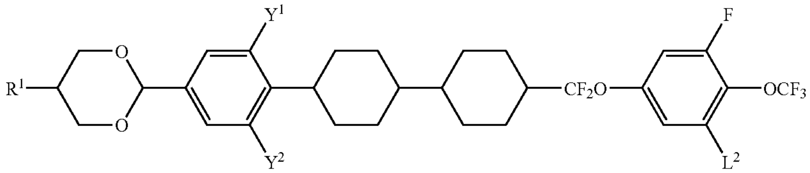

-continued (1-41)

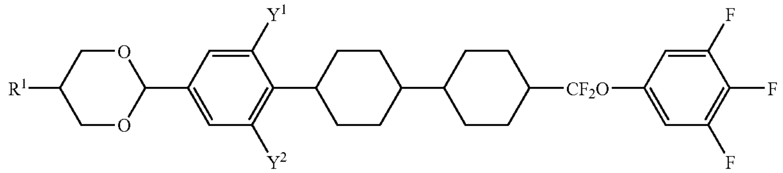

wherein $R^1$ is alkyl having 1 to 15 carbons; $L^2$, $Y^1$, $Y^2$, $Y^3$, and $Y^4$ are each independently hydrogen or fluorine.

8. A liquid crystal composition comprising a first component and a second component, wherein the first component is at least one compound according to any one of items 1 to 7.

9. The liquid crystal composition according to item 8, comprising at least one compound selected from the group consisting of compounds represented by formulas (2), (3), and (4) as the second component:

(2)

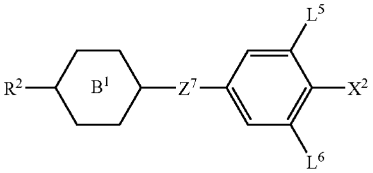

(3)

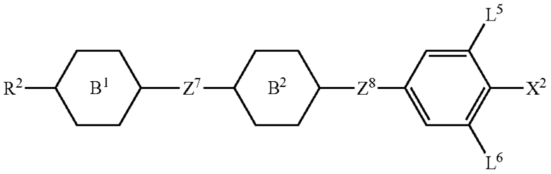

(4)

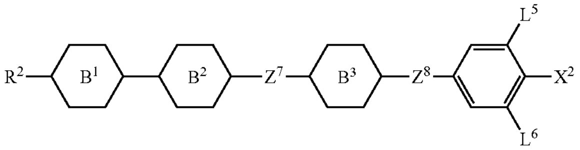

wherein $R^2$ is alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; $X^2$ is fluorine, chlorine, $—OCF_3$, $—OCHF_2$, $—CF_3$, $—CHF_2$, $—CH_2F$, $—OCF_2CHF_2$, or $—OCF_2CHFCF_3$; ring $B^1$, ring $B^2$, and ring $B^3$ are each independently 1,4-cyclohexylene, 1,3-dioxane-2,5-diyl, pyrimidine-2,5-diyl, tetrahydropyrane-2,5-diyl, 1,4-phenylene, or 1,4-phenylene in which arbitrary hydrogen is replaced by fluorine; $Z^7$ and $Z^8$ are each independently $—(CH_2)_2—$, $—(CH_2)_4—$, —COO—, $—CF_2O—$, $—OCF_2—$, —CH═CH—, —C≡C—, $—CH_2O—$, or a single bond; and $L^5$ and $L^6$ are each independently hydrogen or fluorine.

10. The liquid crystal composition according to item 8, comprising at least one compound selected from the group of compounds represented by formula (5) as the second component:

(5)

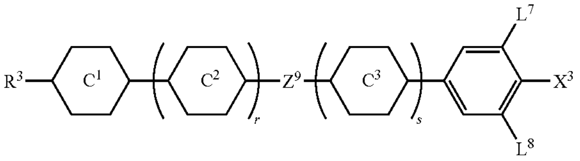

wherein $R^3$ is alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; $X^3$ is —C≡N or —C≡C—C≡N; ring $C^1$, ring $C^2$, and ring $C^3$ are each independently 1,4-cyclohexylene, 1,4-phenylene, 1,4-phenylene in which arbitrary hydrogen is replaced by fluorine, 1,3-dioxane-2,5-diyl, tetrahydropyrane-2,5-diyl, or pyrimidine-2,5-diyl; $Z^9$ is $—(CH_2)_2—$, —COO—, $—CF_2O—$, $—OCF_2—$, —C≡C—, $—CH_2O—$, or a single bond; $L^7$ and $L^8$ are each independently hydrogen or fluorine; and r and s are each independently 0 or 1.

11. The liquid crystal composition according to item 8, comprising at least one compound selected from the group of compounds represented by formulas (6), (7), (8), (9), and (10) as the second component:

(6)

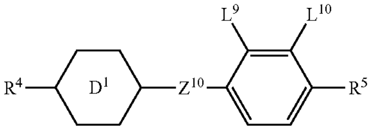

(7)

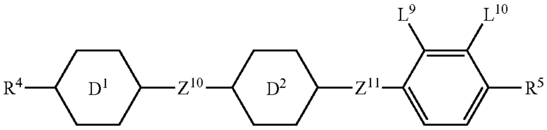

(8)

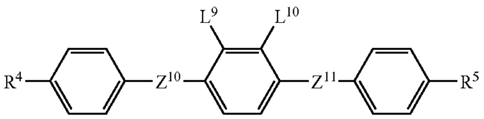

(9)

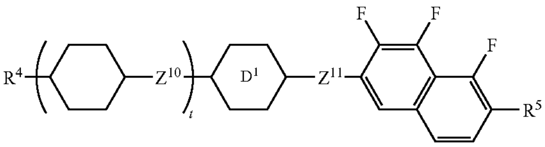

-continued (10)

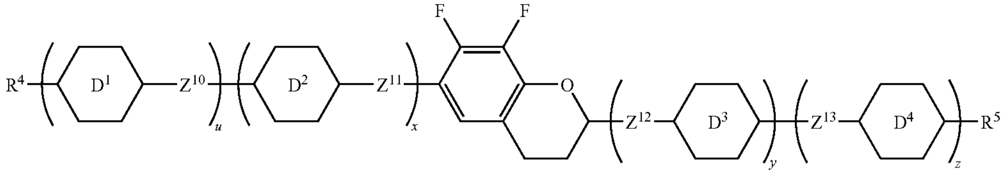

wherein $R^4$ and $R^5$ are each independently alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; ring $D^1$, ring $D^2$, ring $D^3$, and ring $D^4$ are each independently 1,4-cyclohexylene, 1,4-cyclohexenylene, 1,4-phenylene, 1,4-phenylene in which arbitrary hydrogen is replaced by fluorine, tetrahydropyrane-2,5-diyl, or decahydronaphthalene-2,6-diyl; $Z^{10}$, $Z^{11}$, $Z^{12}$, and $Z^{13}$ are each independently $—(CH_2)_2—$, —COO—, $—CH_2O—$, $—OCF_2—$, $—OCF_2(CH_2)_2—$, or a single bond; $L^9$ and $L^{10}$ are each independently fluorine or chlorine; and t, u, x, y, and z are each independently 0 or 1, and u+x+y+z is 1 or 2.

12. The liquid crystal composition according to item 8, comprising at least one compound selected from the group of compounds represented by formulas (11), (12), and (13) as the second component:

(11)

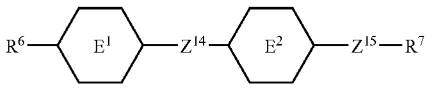

(12)

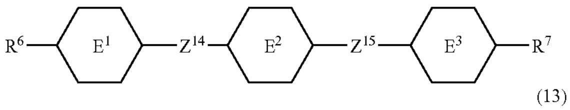

(13)

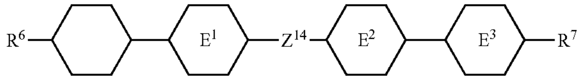

wherein, $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, or 2,5-difluoro-1,4-phenylene; and $Z^{14}$ and $Z^{15}$ are each independently —C≡C—, —COO—, $—(CH_2)_2—$, —CH═CH—, or a single bond.

13. The liquid crystal composition according to item 9, further comprising at least one compound selected from the group of compounds represented by formula (5) according to item 10.

14. The liquid crystal composition according to item 9, further comprising at least one compound selected from the group of compounds represented by formulas (11), (12), and (13) according to item 12.

15. The liquid crystal composition according to item 10, further comprising at least one compound selected from the group of compounds represented by formulas (11), (12), and (13) according to item 12.

16. The liquid crystal composition according to item 11, further comprising at least one compound selected from the group of compounds represented by formulas (11), (12), and (13) according to item 12.

17. The liquid crystal composition according to any one of items 8 to 16, further comprising at least one optically active compound.

18. The liquid crystal composition according to any one of items 8 to 17, further comprising at least one antioxidant and/or ultraviolet radiation absorbent.

19. A liquid crystal display device comprising the liquid crystal composition according to any one of items 8 to 18.

Terms are used in this specification as follows. A liquid crystal compound is a generic name for a compound having liquid crystal phases such as a nematic phase and a smectic phase, and a compound having no liquid crystal phases but useful as a component for a liquid crystal composition. The terms of a liquid crystal compound, a liquid crystal composition and a liquid crystal display device may be abbreviated to a compound, a composition and a device, respectively. A liquid crystal display device is a generic name for a liquid crystal display panel and a liquid crystal display module. A maximum temperature of a nematic phase means a phase transition temperature of a nematic phase-isotropic phase and may simply be abbreviated to a clearing point or a maximum temperature. A minimum temperature of a nematic phase may simply be abbreviated to a minimum temperature. The compound represented by formula (1) may be abbreviated to the compound (1). This abbreviation may also apply to the compound represented by formula (2) and so forth. In formulas (1) to (13), the symbols $A^1$, $B^1$, $C^1$, and so forth surrounded by a hexagonal shape correspond to ring $A^1$, ring $B^1$, ring $C^1$, and so forth, respectively. The symbols $A^1$, $B^1$, $C^1$, and so forth are described in different formulas and the meanings of the symbols are defined in each formula. The amount of a compound expressed by a percentage means a weight percentage (% by weight) based on the total weight of its composition.

The expression of "arbitrary A may be replaced by B, C or D" includes a case in which arbitrary A is replaced by B, a case in which arbitrary A is replaced by C, a case in which arbitrary A is replaced by D, and a case in which at least two A are replaced by at least two of B to D. For example, alkyl in which arbitrary $—CH_2—$ may be replaced by —O— or —CH═CH— includes alkyl, alkenyl, alkoxy, alkoxyalkyl, alkoxyalkenyl, alkenyloxyalkyl and so forth. It is undesirable that two successive $—CH_2—$ are replaced by two —O— affording —O—O—. It is also undesirable that $—CH_2—$ of terminal $CH_3$ in alkyl and so forth is replaced by —O— affording —O—H. The invention will be further explained as follows.

The compounds of the invention have general physical properties required for a compound, stability to heat, light and so forth, a wide temperature range of liquid crystal phases, a high clearing point, a good compatibility with other liquid crystal compounds, an appropriate optical anisotropy, and an appropriate dielectric anisotropy. The liquid crystal composition of the invention comprises at least one of the compounds and has a high maximum temperature of a nematic phase, a low minimum temperature of a nematic phase, a small viscosity, an appropriate optical anisotropy, and a low threshold voltage. The liquid crystal display device of the invention comprises the composition and has a wide temperature range usable, a short response time, a small electric power consumption, a large contrast ratio, and a low driving voltage.

1-1. Compounds of the Invention

The first aspect of the invention concerns compounds represented by formula (1):

(1)

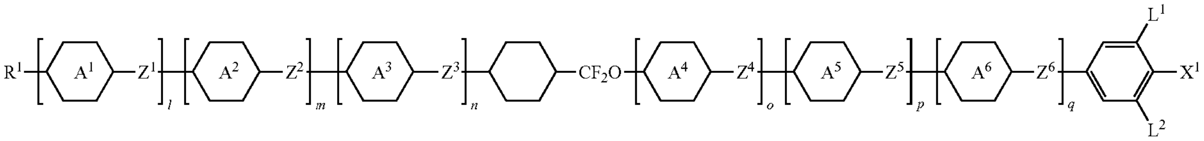

In formula (1), $R^1$ is alkyl having 1 to 20 carbons, and in the alkyl having 2 to 20 carbons, arbitrary $—CH_2—$ may be replaced by —O—, —S— or —CH═CH—. Examples of groups in which arbitrary $—CH_2—$ in $CH_3—(CH_2)_3—$ is replaced by —O—, —S—, or —CH═CH— are $CH_3—(CH_2)_2—O—$, $CH_3O—(CH_2)_2—$, $CH_3OCH_2O—$, $CH_3—(CH_2)_2—S—$, $CH_3S—(CH_2)_2—$, $CH_3SCH_2S—$, $CH_2═CH—(CH_2)_3—$, $CH_3CH═CH—(CH_2)_2—$, $CH_3CH═CHCH_2O—$, and so forth.

Examples of such $R^1$ are alkyl, alkoxy, alkoxyalkyl, alkoxyalkoxy, thioalkyl, thioalkylalkoxy, alkenyl, alkenyloxy, alkenyloxyalkyl, alkoxyalkenyl, and so forth. These groups may be a straight chain or a branched chain, but the straight chain is more desirable. When $R^1$ is optically active, even the branched chain is desirable. A desirable configuration of —CH═CH— in the alkenyl depends on the position of a double bond. A trans configuration is desirable in the alkenyl having a double bond at an odd number-position such as $—CH═CHCH_3$, $—CH═CHC_2H_5$, $—CH═CHC_3H_7$, $—CH═CHC_4H_9$, $—C_2H_4CH═CHCH_3$, and $—C_2H_4CH═CHC_2H_5$. A cis configuration is desirable in the alkenyl having a double bond at an even number-position such as $—CH_2CH═CHCH_3$, $—CH_2CH═CHC_2H_5$, and $—CH_2CH═CHC_3H_7$. An alkenyl compound having a desirable configuration has a high maximum temperature or a wide temperature range of liquid crystal phases. The details are explained in Mol. Cryst. Liq. Cryst., 1985, 131, 109 and Mol. Cryst. Liq. Cryst., 1985, 131, 327.

Specific examples of the alkyl are $—CH_3$, $—C_2H_5$, $—C_3H_7$, $—C_4H_9$, $—C_5H_{11}$, $—C_6H_{13}$, $—C_7H_{15}$, $—C_8H_{17}$, $—C_9H_{19}$, $—C_{10}H_{21}$, $—C_{11}H_{23}$, $—C_{12}H_{25}$, $—C_{13}H_{27}$, $—C_{14}H_{29}$, and $—C_{15}H_{31}$.

Specific examples of the alkoxy are $—OCH_3$, $—OC_2H_5$, $—OC_3H_7$, $—OC_4H_9$, $—OC_5H_{11}$, $—OC_6H_{13}$, $—OC_7H_{15}$, $—OC_8H_{17}$, $—OC_9H_{19}$, $—OC_{10}H_{21}$, $—OC_{11}H_{23}$, $—OC_{12}H_{25}$, $—OC_{13}H_{27}$, and $—OC_{14}H_{29}$.

Specific examples of the alkoxyalkyl are $—CH_2OCH_3$, $—CH_2OC_2H_5$, $—CH_2OC_3H_7$, $—(CH_2)_2—OCH_3$, $—(CH_2)_2—OC_2H_5$, $—(CH_2)_2—OC_3H_7$, $—(CH_2)_3—OCH_3$, $—(CH_2)_4—OCH_3$, and $—(CH_2)_5—OCH_3$.

Specific examples of the alkenyl are $—CH═CH_2$, $—CH═CHCH_3$, $—CH_2CH═CH_2$, $—CH═CHC_2H_5$, $—CH_2CH═CHCH_3$, $—(CH_2)_2—CH═CH_2$, $—CH═CHC_3H_7$, $—CH_2CH═CHC_2H_5$, $—(CH_2)_2—CH═CHCH_3$, and $—(CH_2)_3—CH═CH_2$.

Specific examples of the alkenyloxy are $—OCH_2CH═CH_2$, $—OCH_2CH═CHCH_3$, and $—OCH_2CH═CHC_2H_5$.

Examples of desirable $R^1$ are alkyl having 1 to 15 carbons and alkenyl having 2 to 15 carbons. More desirable examples of $R^1$ are $—CH_3$, $—C_2H_5$, $—C_3H_7$, $—C_4H_9$, $—C_5H_{11}$, $—C_6H_{13}$, $—C_7H_{15}$, $—C_8H_{17}$, $—C_9H_{19}$, $—C_{10}H_{21}$ $—C_{11}H_{23}$, $—C_{12}H_{25}$, $—C_{13}H_{27}$, $—C_{14}H_{29}$, $—C_{15}H_{31}$, $—CH═CH_2$, $—CH═CHCH_3$, $—CH_2CH═CH_2$, $—CH═CHC_2H_5$, $—CH_2CH═CHCH_3$, $—(CH_2)_2—CH═CH_2$, $—CH═CHC_3H_7$, $—CH_2CH═CHC_2H_5$, $—(CH_2)_2—CH═CHCH_3$, and $—(CH_2)_3—CH═CH_2$.

In formula (1), ring $A^1$, ring $A^2$, ring $A^3$, ring $A^4$, ring $A^5$, and ring $A^6$ are each independently, 1,4-cyclohexylene (14-1), 1,3-dioxane-2,5-diyl (14-2), 1,4-phenylene (14-3), or 1,4-phenylene in which arbitrary hydrogen is replaced by halogen. Examples of 1,4-phenylene in which arbitrary hydrogen is replaced by halogen are formulas (14-4) to (14-20). Desirable examples are groups represented by formulas (14-4) to (14-9).

(14-1)

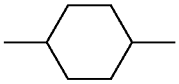

(14-2)

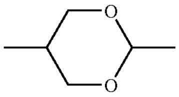

(14-3)

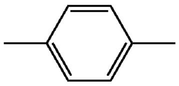

(14-4)

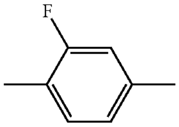

(14-5)

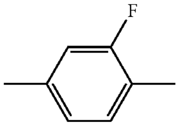

(14-6)

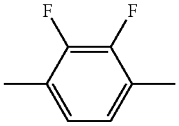

-continued (14-7)

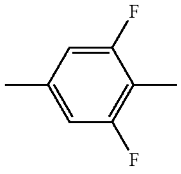

(14-8)

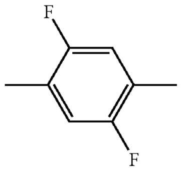

(14-9)

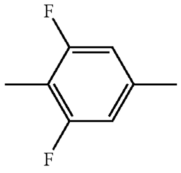

(14-10)

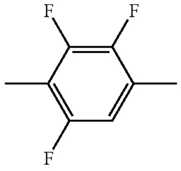

(14-11)

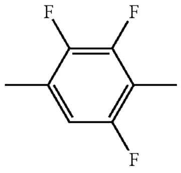

(14-12)

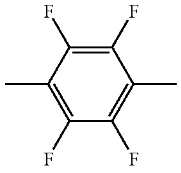

(14-13)

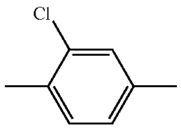

(14-14)

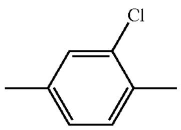

(14-15)

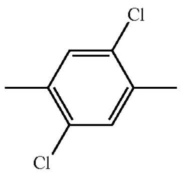

-continued (14-16)

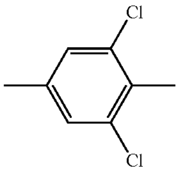

(14-17)

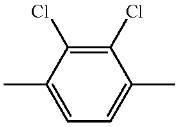

(14-18)

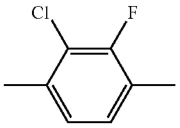

(14-19)

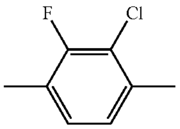

(14-20)

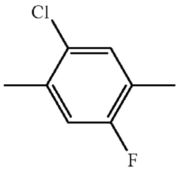

Desirable examples of ring $A^1$, ring $A^2$, ring $A^3$, ring $A^4$, ring $A^5$, and ring $A^6$ are 1,4-cyclohexylene (14-1), 1,3-dioxane-2,5-diyl (14-2), 1,4-phenylene (14-3), 2-fluoro-1,4-phenylene (14-4) and (14-5), 2,3-difluoro-1,4-phenylene (14-6), 2,5-difluoro-1,4-phenylene (14-8), and 2,6-difluoro-1,4-phenylene (14-7) and (14-9).

More desirable examples of ring $A^1$, ring $A^2$, ring $A^3$, ring $A^4$, ring $A^5$, and ring $A^6$ are 1,4-cyclohexylene, 1,3-dioxane-2,5-diyl, 1,4-phenylene, 2-fluoro-1,4-phenylene, and 2,6-difluoro-1,4-phenylene.

In formula (1), $Z^1$, $Z^2$, $Z^3$, $Z^4$, $Z^5$, and $Z^6$ are each independently, a single bond, $-CH_2CH_2-$, $-CH{=}CH-$, $-C{\equiv}C-$, $-COO-$, $-OCO-$, $-CF_2O-$, $-OCF_2-$, $-CH_2O-$, $-OCH_2-$, $-CF{=}CF-$, $-(CH_2)_4-$, $-(CH_2)_2-CF_2O-$, $-(CH_2)_2-OCF_2-$, $-CF_2O-(CH_2)_2-$, $-OCF_2-(CH_2)_2-$, $-CH{=}CH-(CH_2)_2-$, or $-(CH_2)_2-CH{=}CH-$.

In these bonding groups, trans is preferable to cis in the configuration with regard to a double bond of bonding groups such as $-CH{=}CH-$, $-CF{=}CF-$, $-CH{=}CH-(CH_2)_2-$, and $-(CH_2)_2-CH{=}CH-$. Desirable examples of $Z^1$, $Z^2$, $Z^3$, $Z^4$, $Z^5$, and $Z^6$ are each independently a single bond, $-CH_2CH_2-$, $-CH{=}CH-$, $-C{\equiv}C-$, $-COO-$, $-CF_2O-$, $-CH_2O-$, or $-OCH_2-$. A more desirable example of $Z^1$, $Z^2$, $Z^3$, $Z^4$, $Z^5$, and $Z^6$ is a single bond.

In formula (1), $L^1$ and $L^2$ are each independently hydrogen or halogen. Desirable examples of $L^1$ and $L^2$ are each independently hydrogen or fluorine.

In formula (1), $X^1$ is hydrogen, halogen, $-C{\equiv}N$, $-N{=}C{=}S$, $-SF_5$, or alkyl having 1 to 10 carbons, and in the alkyl having 2 to carbons, arbitrary $-CH_2-$ may be replaced by $-O-$, $-S-$ or $-CH{=}CH-$ and arbitrary hydrogen may be replaced by halogen.

Specific examples of alkyl in which arbitrary hydrogen is replaced by halogen are $—CH_2F$, $—CHF_2$, $—CF_3$, $—(CH_2)_2—F$, $—CF_2CH_2F$, $—CF_2CHF_2$, $—CH_2CF_3$, $—CF_2CF_3$, $—(CH_2)_3—F$, $—(CF_2)_3—F$, $—CF_2CHFCF_3$, $—CHFCF_2CF_3$, $—(CH_2)_4—F$, $—(CF_2)_4—F$, $—(CH_2)_5—F$, and $—(CF_2)_5—F$.

Specific examples of alkoxy in which arbitrary hydrogen is replaced by halogen are $—OCH_2F$, $—OCHF_2$, $—OCF_3$, $—O—(CH_2)_2—F$, $—OCF_2CH_2F$, $—OCF_2CHF_2$, $—OCH_2CF_3$, $—O—(CH_2)_3—F$, $—O—(CF_2)_3—F$, $—OCF_2CHFCF_3$, $—OCHFCF_2CF_3$, $—O—(CH_2)_4—F$, $—O—(CF_2)_4—F$, $—O—(CH_2)_5—F$, and $—O—(CF_2)_5—F$.

Specific examples of alkenyl in which arbitrary hydrogen is replaced by halogen are $—CH{=}CHF$, $—CH{=}CF_2$, $—CF{=}CHF$, $—CH{=}CHCH_2F$, $—CH{=}CHCF_3$, $—(CH_2)_2—CH{=}CF_2$, $—CH_2CH{=}CHCF_3$, and $—CH{=}CHCF_2CF_3$.

Specific examples of $X^1$ are hydrogen, fluorine, chlorine, $—C{\equiv}N$, $—N{=}C{=}S$, $—SF_5$, $—CH_3$, $—C_2H_5$, $—C_3H_7$, $—C_4H_9$, $—C_5H_{11}$, $—C_6H_{13}$, $—C_7H_{15}$, $—C_8H_{17}$, $—C_9H_{19}$, $—C_{10}H_{21}$, $—CH_2F$, $—CHF_2$, $—CF_3$, $—(CH_2)_2—F$, $—CF_2CH_2F$, $—CF_2CHF_2$, $—CH_2CF_3$, $—CF_2CF_3$, $—(CH_2)_3—F$, $—(CF_2)_3—F$, $—CF_2CHFCF_3$, $—CHFCF_2CF_3$, $—(CH_2)_4—F$, $—(CF_2)_4—F$, $—(CH_2)_5—F$, $—(CF_2)_5—F$, $—OCH_3$, $—OC_2H_5$, $—OC_3H_7$, $—OC_4H_9$, $—OC_5H_{11}$, $—OCH_2F$, $—OCHF_2$, $—OCF_3$, $—O—(CH_2)_2—F$, $—OCF_2CH_2F$, $—OCF_2CHF_2$, $—OCH_2CF_3$, $—O—(CH_2)_3—F$, $—O—(CF_2)_3—F$, $—OCF_2CHFCF_3$, $—OCHFCF_2CF_3$, $—O—(CH_2)_4—F$, $—O—(CF_2)_4—F$, $—O—(CH_2)_5—F$, $—O—(CF_2)_5—F$, $—CH{=}CH_2$, $—CH{=}CHCH_3$, $—CH_2CH{=}CH_2$, $—CH{=}CHC_2H_5$, $—CH_2CH{=}CHCH_3$, $—(CH_2)_2—CH{=}CH_2$, $—CH{=}CHC_3H_7$, $—CH_2CH{=}CHC_2H_5$, $—(CH_2)_2—CH{=}CHCH_3$, $—(CH_2)_3—CH{=}CH_2$, $—CH{=}CHF$, $—CH{=}CF_2$, $—CF{=}CHF$, $—CH{=}CHCH_2F$, $—CH{=}CHCF_3$, $—(CH_2)_2—CH{=}CF_2$, $—CH_2CH{=}CHCF_3$, and $—CH{=}CHCF_2CF_3$.

Desirable examples of $X^1$ are fluorine, chlorine, $—C{\equiv}N$, $—CF_3$, $—CHF_2$, $—CH_2F$, $—OCF_3$, $—OCHF_2$, and $—OCH_2F$. More desirable examples of $X^1$ are fluorine and $—OCF_3$.

In formula (1), l, m, n, o, p, and q are each independently 0 or 1, and l+m+n+o+p+q is 3. Desirable examples of subscripts l, m, n, o, p, and q are combinations (l=m=o=1 and n=p=q=0) and (l=m=n=1 and o=p=q=0).

1-2. Physical Properties of Compound (1)

The physical properties of compound (1) are further explained in detail. The compound (1) is a five-ring-containing liquid crystal compound having a cyclohexane ring. The compound is highly stable physically and chemically under the condition that a device is usually used, and has a good compatibility with other liquid crystal compounds. The composition comprising the compound is stable under the condition that the device is usually used. The compound does not deposit as crystals (or a smectic phase) when the composition is kept at a low temperature. The compound has a wide range of liquid crystal phases and a high clearing point because of the five-ring compound. Accordingly, the compound can expand the temperature range of a nematic phase in its composition and can be used as a display device in a wide temperature range. The compound has an appropriate optical anisotropy. The compound having optical anisotropy corresponding to the thickness of a cell in a device is suitable for making a device exhibiting a high display capability. Furthermore, the compound is useful as a component for reducing the threshold voltage of the composition, because of the appropriate dielectric anisotropy.

Physical properties such as a clearing point, optical anisotropy and dielectric anisotropy can be arbitrarily adjusted by appropriately selecting a combination of the subscripts l, m, n, o, p, and q, and kind of rings $A^1$ to $A^6$, left-side terminal group $R^1$, right-terminal group $X^1$, bonding groups $Z^1$ to $Z^6$, and lateral groups $L^1$ and $L^2$ of the compound (1). The effect of the combination and the kind on the physical properties of the compound (1) will be explained in detail below.

When subscripts l, m, n, o, p, and q are the combination (l=m=n=1 and o=p=q=0), the temperature range of liquid crystal phases is wide, the clearing point is high, and the compatibility with other compounds is large. When the subscripts are the combination (l=m=o=1 and n=p=q=0), the dielectric anisotropy is large.

When ring $A^1$ and ring $A^2$ are 1,4-cyclohexylene, ring $A^3$ is 1,4-phenylene or 1,4-phenylene in which arbitrary hydrogen is replaced by halogen, and the subscripts are the combination (l=m=n=1 and o=p=q=0), the clearing point is high, the compatibility with other compounds is large, and the optical anisotropy is relatively small. When ring $A^1$ is 1,3-dioxane-2,5-diyl, ring $A^2$ is 1,4-cyclohexylene, ring $A^3$ is 1,4-phenylene or 1,4-phenylene in which arbitrary hydrogen is replaced by halogen, and the subscripts are the combination (l=m=n=1 and o=p=q=0), the clearing point is high, the compatibility with other compounds is large, the optical anisotropy is relatively small, and the dielectric anisotropy is large. When ring $A^1$ and ring $A^2$ are 1,4-cyclohexylene or 1,3-dioxane-2,5-diyl, ring $A^4$ is 1,4-phenylene or 1,4-phenylene in which arbitrary hydrogen is replaced by halogen, and the subscripts are the combination (l=m=o=1 and n=p=q=0), the optical anisotropy is relatively small and the dielectric anisotropy is large. When ring $A^1$, ring $A^2$, and ring $A^3$ are 1,4-cyclohexylene or 1,3-dioxane-2,5-diyl, and the subscripts are the combination (l=m=n=1 and o=p=q=0), the clearing point is quite high and the optical anisotropy is small.

When $R^1$ is a straight chain, the temperature range of liquid crystal phases is wide and the viscosity is small. When $R^1$ is a branched chain, the compatibility with other liquid crystal compounds is good. A compound in which $R^1$ is an optically active group is useful as a chiral dopant. A reverse twisted domain which may occur in a device can be prevented by adding the compound to the composition. A compound in which $R^1$ is not optically active is useful as a component of the composition. When $R^1$ is alkenyl, a desirable configuration depends on the position of a double bond. An alkenyl compound having a desirable configuration has a high maximum temperature or a wide temperature range of liquid crystal phases.

When bonding groups $Z^1$, $Z^2$, $Z^3$, $Z^4$, $Z^5$, and $Z^6$ are a single bond, $—CH_2CH_2—$, $—CH{=}CH—$, $—CF_2O—$, $—OCF_2—$, $—CH_2O—$, $—OCH_2—$, $—CF{=}CF—$, $—(CH_2)_3—O—$, $—O—(CH_2)_3—$, $—(CH_2)_2—CF_2O—$, $—OCF_2—(CH_2)_2—$, or $—(CH_2)_4—$, the viscosity is small. When the bonding group is a single bond, $—(CH_2)_2—$, $—CF_2O—$, $—OCF_2—$, or $—CH{=}CH—$, the viscosity is smaller. When the bonding group is $—CH{=}CH—$, the temperature range of liquid crystal phases is wide and an elastic constant ratio, $K_{33}/K_{11}$ is large, wherein $K_{33}$ stands for a bend elastic constant and $K_{11}$ stands for a splay elastic constant. When the bonding group is $—C{\equiv}C—$, the optical anisotropy is large. When $Z^1$, $Z^2$, $Z^3$, $Z^4$, $Z^5$, and $Z^6$ are a single bond, $—(CH_2)_2—$, $—CH_2O—$, $—CF_2O—$, $—OCF_2—$, or $—(CH_2)_4—$, the compound is relatively stable chemically and is relatively hard to be deteriorated.

When right-terminal group $X^1$ is fluorine, chlorine, $—C{\equiv}N$, $—N{=}C{=}S$, $—SF_5$, $—CF_3$, $—CHF_2$, $—CH_2F$, $—OCF_3$, $—OCHF_2$, or $—OCH_2F$, the dielectric anisotropy is large. When $X^1$ is —C≡N, —N═C═S or alkenyl, the optical anisotropy is large. When $X^1$ is fluorine, $—OCF_3$ or alkyl, the compound (1) is chemically stable.

When both of lateral groups $L^1$ and $L^2$ are fluorine and $X^1$ is fluorine, chlorine, —C≡N, —N═C═S, $—SF_5$, $—CF_3$, $—CHF_2$, $—CH_2F$, $—OCF_3$, $—OCHF_2$, or $—OCH_2F$, the dielectric anisotropy is large. When $L^1$ is fluorine and $X^1$ is $—OCF_3$, or when both of $L^1$ and $L^2$ are fluorine and $X^1$ is $—OCF_3$, or when all of $L^1$, $L^2$ and $X^1$ are fluorine, the dielectric anisotropy is large, the temperature range of liquid crystal phases is wide, and the compound is chemically stable and hard to be deteriorated.

As described above, the compound having intended physical properties can be obtained by suitably selecting the kind of rings, terminal groups, bonding groups and so forth. Therefore, the compound (1) is useful as a component of a composition applied to devices such as PC, TN, STN, ECB, OCB, IPS, and VA.

1-3. Specific Examples of Compound (1)

Desirable examples of the compound (1) are the compounds (1-5) to (1-8). More desirable examples are the compounds (1-9) to (1-19). Further desirable examples are the compounds (1-20) to (1-41).

(1-5)

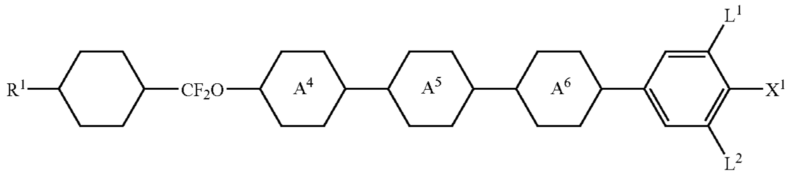

(1-6)

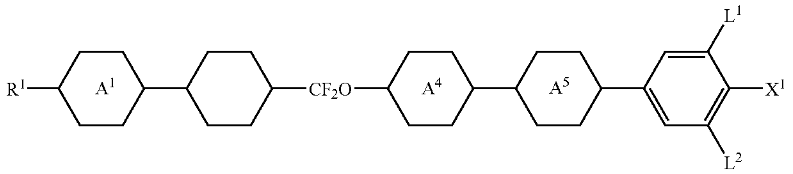

(1-7)

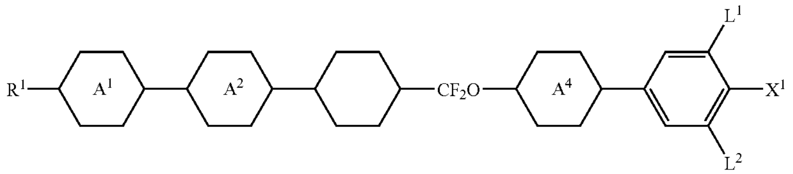

(1-8)

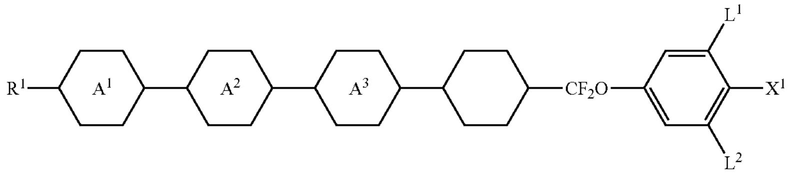

In these formulas, $R^1$ is alkyl having 1 to 15 carbons or alkenyl having 2 to 15 carbons; ring $A^1$, ring $A^2$, ring $A^3$, ring $A^4$, ring $A^5$, and ring $A^6$ are each independently, 1,4-cyclohexylene, 1,3-dioxane-2,5-diyl, 1,4-phenylene, or 1,4-phenylene in which arbitrary hydrogen is replaced by fluorine; $L^1$ and $L^2$ are each independently hydrogen or fluorine; $X^1$ is fluorine, chlorine, —C≡N, $—CF_3$, $—CHF_2$, $—CH_2F$, $—OCF_3$, $—OCHF_2$, or $—OCH_2F$.

(1-9)

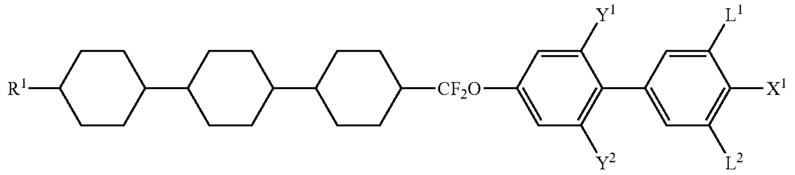

-continued
(1-10)
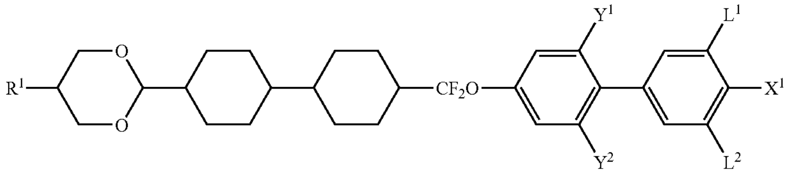
(1-11)
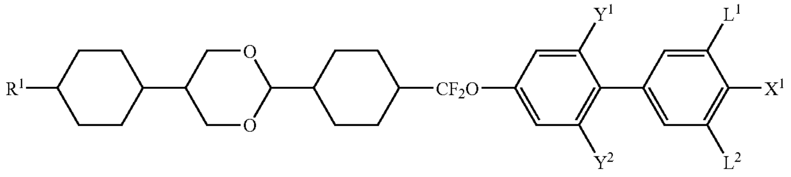
(1-12)
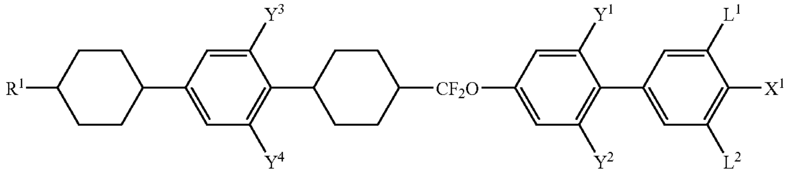
(1-13)
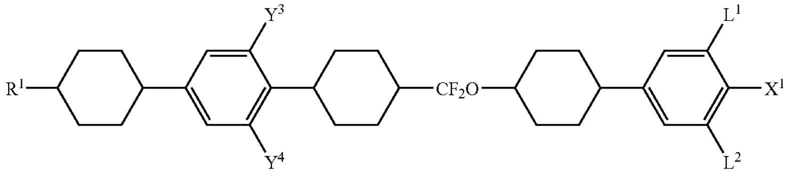
(1-14)
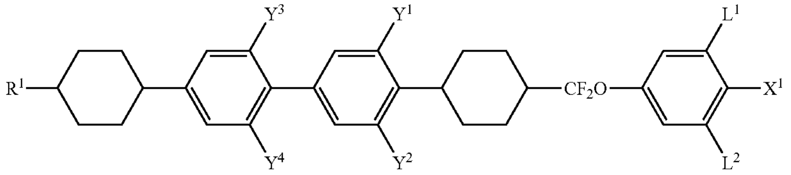
(1-15)
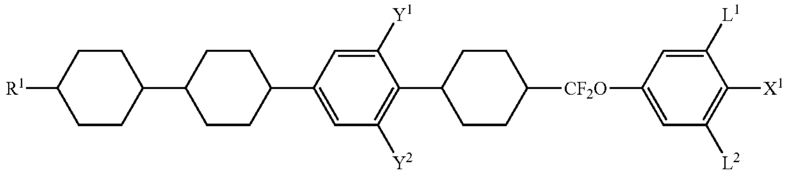
(1-16)
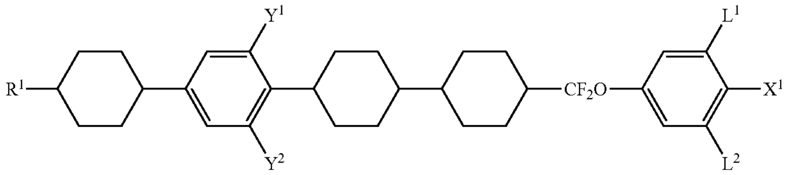
(1-17)
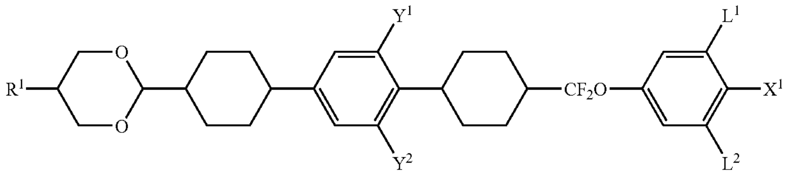
(1-18)
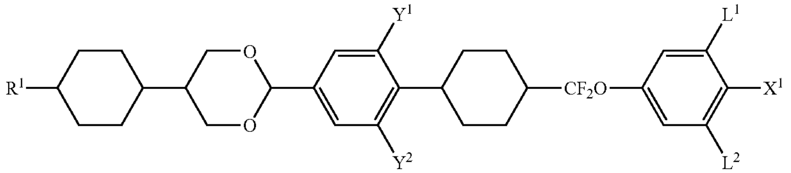

-continued
(1-19)
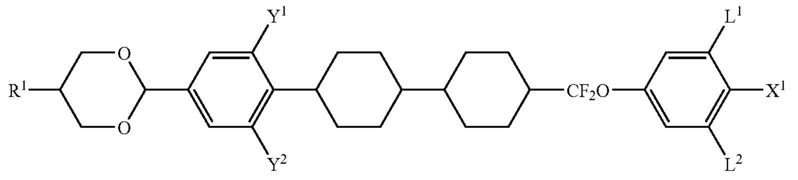
In these formulas, $R^1$ is alkyl having 1 to 15 carbons; $L^1$, $L^2$, $Y^1$, $Y^2$, $Y^3$, and $Y^4$ are each independently hydrogen or fluorine; and $X^1$ is fluorine or $-OCF_3$.
(1-20)
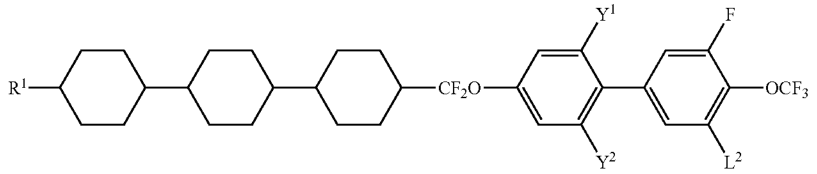
(1-21)
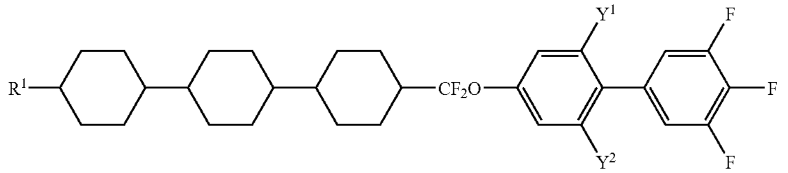
(1-22)
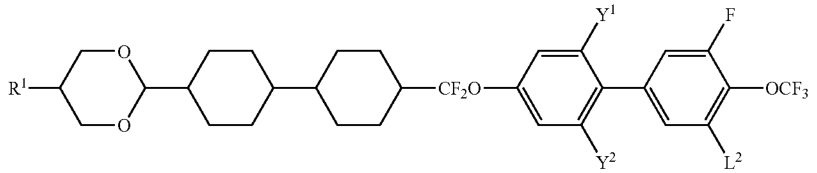
(1-23)
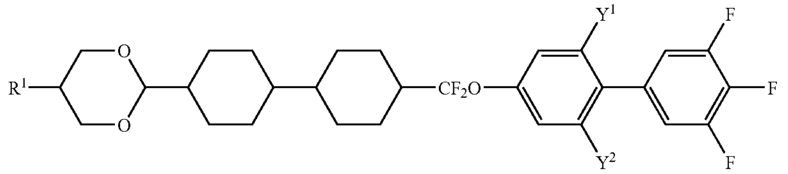
(1-24)
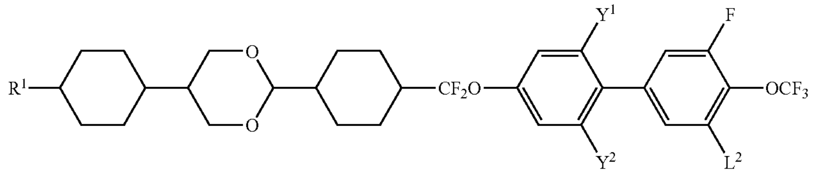
(1-25)
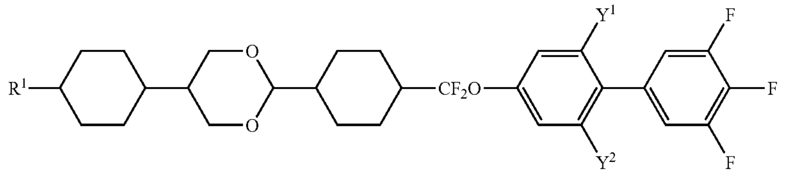
(1-26)
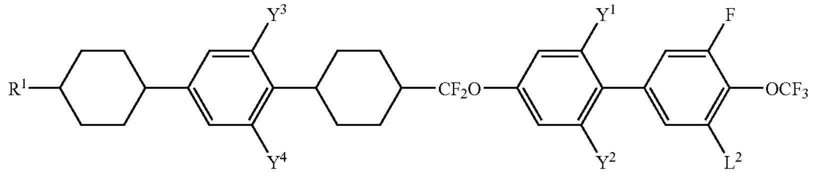

-continued
(1-27)
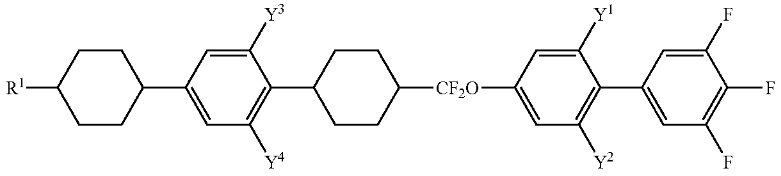
(1-28)
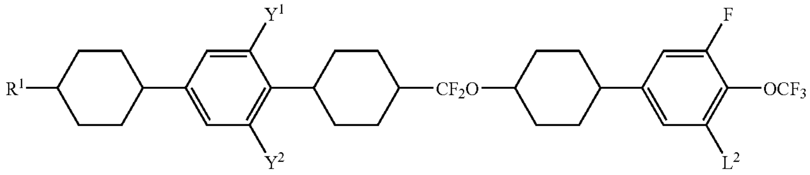
(1-29)
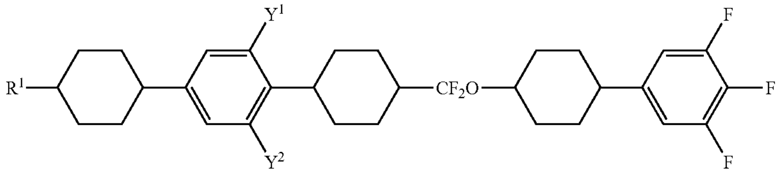
(1-30)
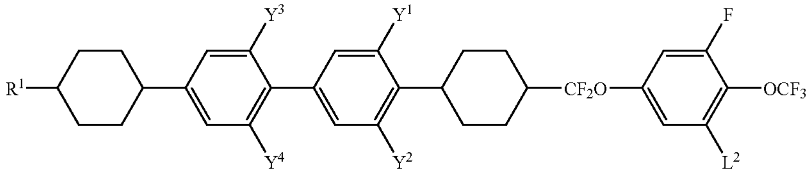
(1-31)
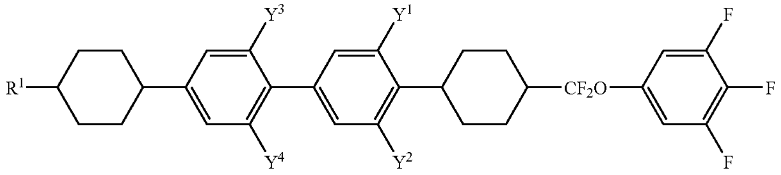
(1-32)
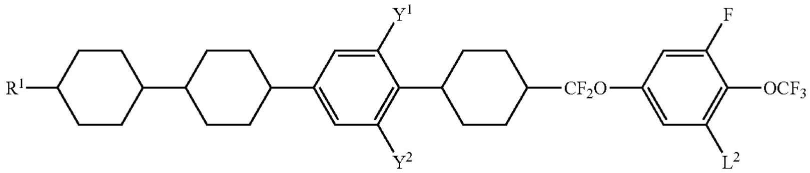
(1-33)
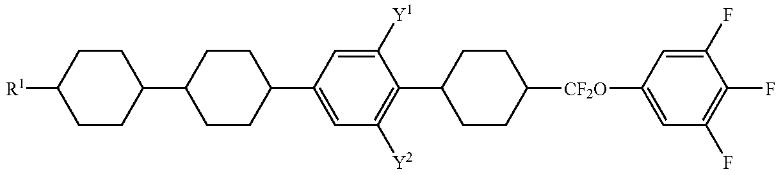
(1-34)
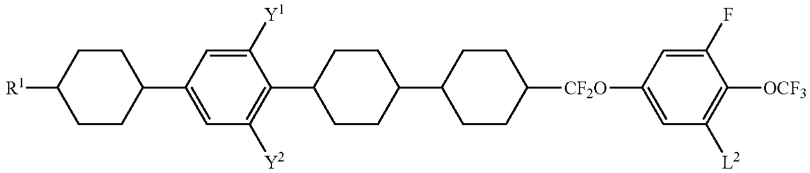
(1-35)
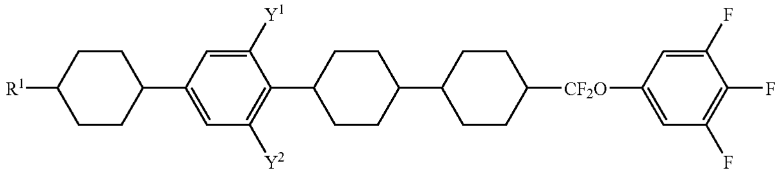

-continued (1-36)

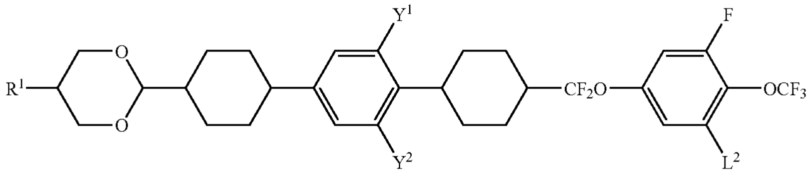

(1-37)

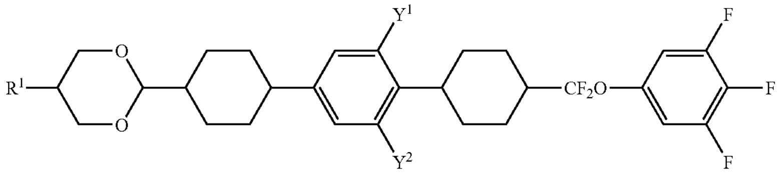

(1-38)

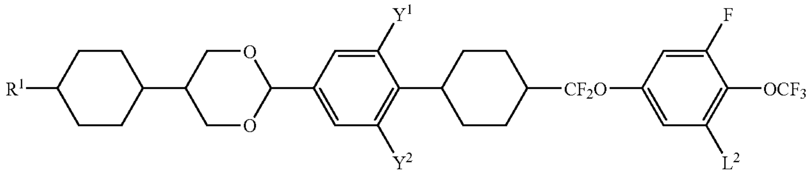

(1-39)

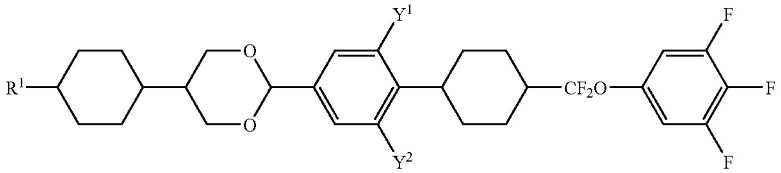

(1-40)

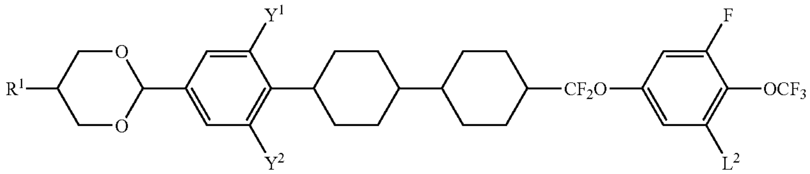

(1-41)

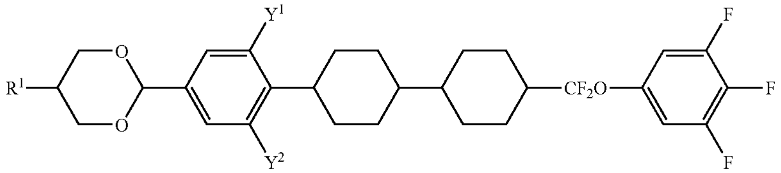

In these formulas, $R^1$ is alkyl having 1 to 15 carbons; $L^2$, $Y^1$, $Y^2$, $Y^3$, and $Y^4$ are each independently hydrogen or fluorine.

1-4. Synthesis of Compound (1)

Next, methods for synthesizing the compound (1) will be explained. The compound (1) can be synthesized based on suitable combinations of techniques inorganic synthetic chemistry. Methods for introducing objective terminal groups, rings, and bonding groups to starting materials are described in Organic Syntheses, John Wiley & Sons, Inc; Organic Reactions, John Wiley & Sons, Inc; Comprehensive Organic Synthesis, Pergamon Press; New Experimental Chemistry Courses (Shin Jikken Kagaku Kouza, in Japanese), Maruzen Co. Ltd.; and so forth.

1-4-1. Method for Forming Bonding Groups $Z^1$ to $Z^6$

One example of forming bonding groups $Z^1$ to $Z^6$ of the compound (1) is shown in the following scheme. In the scheme, $MSG^1$ or $MSG^2$ is a monovalent organic group having at least one ring. A plurality of $MSG^1$ (or $MSG^2$) used in the scheme may be the same or different from each other. The compounds (1A) to (1J) correspond to the compound (1).

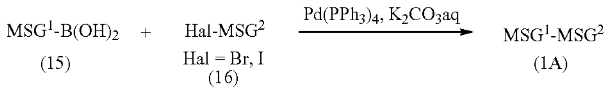

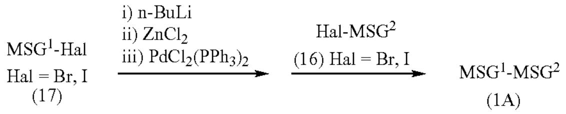

-continued
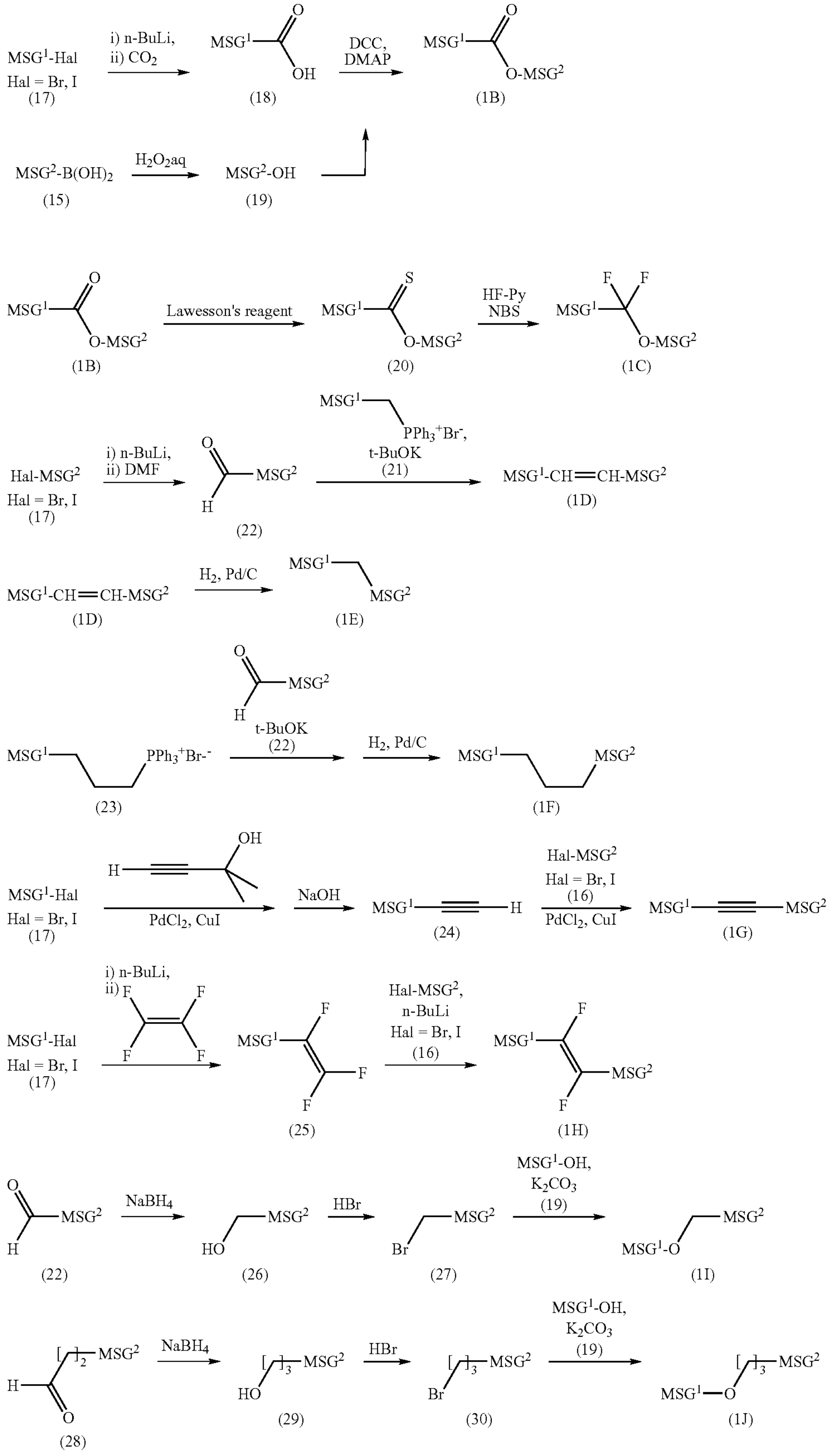

Next, as for bonding groups $Z^1$ to $Z^6$ of the compound (1), methods for forming each bonding group will be explained in the following items (I) to (XI).

(I) Formation of Single Bond

The compound (1A) is synthesized by reacting the aryl boric acid (15) with the compound (16) synthesized according to a known method, in the presence of an aqueous carbonate solution and a catalyst such as tetrakis(triphenylphosphine)palladium. The compound (1A) is also synthesized by reacting the compound (17) synthesized according to a known method with n-butyl lithium, and then with zinc chloride, and finally with the compound (16) in the presence of a catalyst such as dichlorobis(triphenylphosphine)palladium.

(II) Formation of —COO— and —OCO—

The compound (17) is reacted with n-butyl lithium, and then with carbon dioxide, to give the carboxylic acid (18). The compound (1B) having —COO— is synthesized by dehydrating the compound (18) and the phenol (19) synthesized according to a known method, in the presence of DCC (1,3-dicyclohexylcarbodiimide) and DMAP (4-dimethylamino pyridine). The compound having —OCO— is also synthesized according to this method.

(III) Formation of $—CF_2O—$ and $—OCF_2—$

The compound (20) is obtained by treating the compound (1B) with a thionating agent such as Lawesson's reagent. The compound (20) is fluorinated with a hydrogen fluoride-pyridine complex and NBS (N-bromosuccinimide) to synthesize the compound (1C) having $—CF_2O—$. Refer to M. Kuroboshi et al., Chem. Lett., 1992, 827. The compound (1C) is also synthesized by fluorinating the compound (20) with (diethylamino)sulfur trifluoride (DAST). Refer to W. H. Bunnelle et al., J. Org. Chem. 1990, 55, 768. The compound having $—OCF_2—$ is also synthesized according to this method. These bonding groups can also be synthesized according to the method described in Peer. Kirsch et al., Angew. Chem. Int. Ed. 2001, 40, 1480.

(IV) Formation of —CH═CH—

The compound (17) is treated with n-butyl lithium and then reacted with a formamide such as N,N-dimethylformamide (DMF) to give the aldehyde (22). The compound (1D) is synthesized by reacting the aldehyde (22) with phosphorus ylide generated by treating the phosphonium salt (21), which is synthesized according to a known method, with a base such as potassium tert-butoxide. Since a cis isomer may be formed depending on reaction conditions, the cis isomer is isomerized to a trans isomer according to a known method as required.

(V) Formation of $—(CH_2)_2—$

The compound (1E) is synthesized by hydrogenating the compound (1D) in the presence of a catalyst such as palladium carbon.

(VI) Formation of $—(CH_2)_4—$

The compound having $—(CH_2)_2—CH═CH—$ is obtained according to the method described in item (IV) using the phosphonium salt (23) instead of the phosphonium salt (21). The compound is hydrogenated catalytically to synthesize the compound (1F).

(VII) Formation of —C≡C—

The compound (24) is obtained by reacting the compound (17) with 2-methyl-3-butyne-2-ol in the presence of dichloropalladium and copper halide, and then deprotected under a basic condition. The compound (1G) is synthesized by reacting the compound (24) with the compound (16) in the presence of a catalyst of dichlorobis(triphenylphosphine)palladium and copper halide.

(VIII) Formation of —CF═CF—

The compound (17) is treated with n-butyl lithium, and then reacted with tetrafluoroethylene to give the compound (25). The compound (1H) is synthesized by treating the compound (16) with n-butyllithium and then by reacting with the compound (25).

(IX) Formation of $—CH_2O—$ or $—OCH_2—$

The compound (26) is obtained by reducing the compound (22) with a reducing agent such as sodium borohydride. The product is halogenated with hydrobromic acid or the like to give the compound (27). The compound (1I) is synthesized by reacting the compound (27) with the compound (19) in the presence of potassium carbonate or the like.

(X) Formation of $—(CH_2)_3O—$ or $—O(CH_2)_3—$

The compound (1J) is synthesized according to a method similar to that described in the preceding item (IX), using the compound (28) instead of the compound (22).

1-4-2. Methods for Forming Rings $A^1$ to $A^6$

Starting materials are commercially available or synthetic methods therefor are well known for the rings of 1,4-cyclohexylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5,6-tetrafluoro-1,4-phenylene and so forth.

1-4-3. Method for Forming $—CF_2O—$ Bonding Group

There are a plurality of methods for synthesizing the compound (1) and examples thereof are shown here. After the ester derivative (33) are derived by the dehydration condensation of the carboxylic acid derivative (31) and the alcohol derivative (32) in the presence of DCC, DMAP and so forth, it is converted into the thion-O-ester derivative (34) by treatment with a thionating agent such as Lawesson's reagent. The compound (1) can be derived by fluorination of the derivative (34) with a hydrogen fluoride-pyridine complex and NBS.

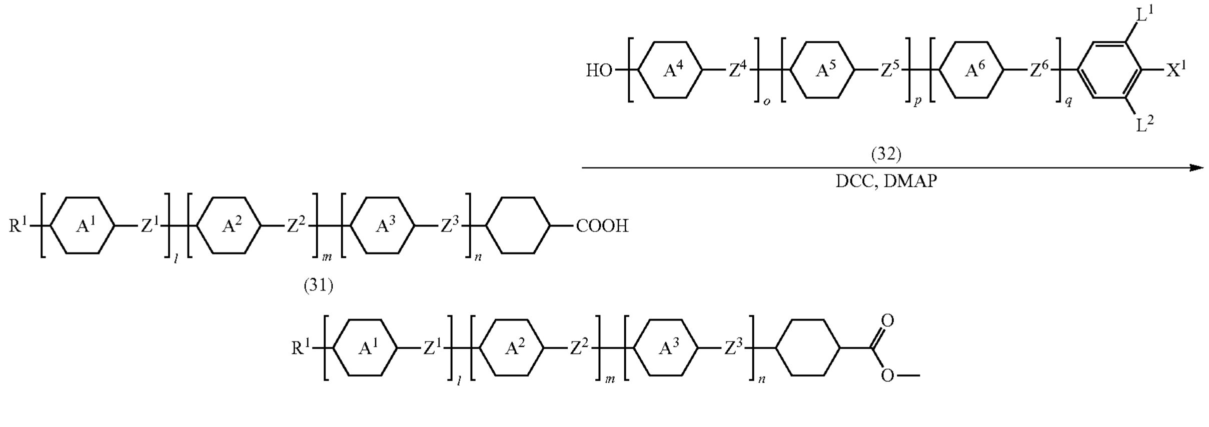

(32)

(31)

-continued

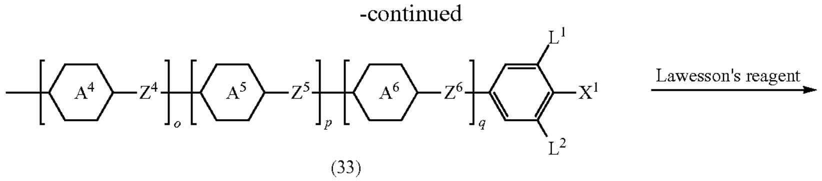

(33)

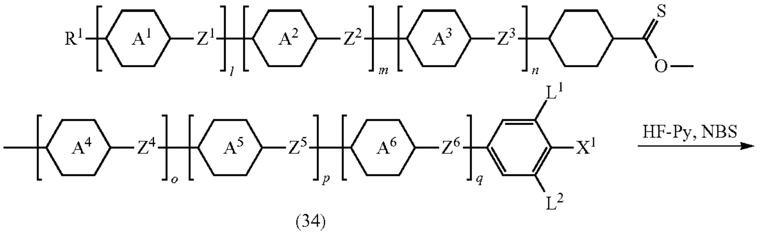

(34)

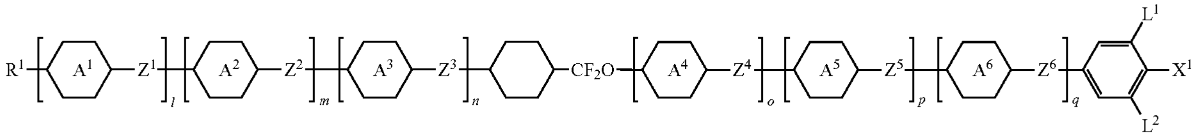

(1)

In these formulas, rings $A^1$ to $A^6$, $Z^1$ to $Z^6$, $L^1$, $L^2$, $R^1$, $X^1$, l, m, n, o, p, and q have the meanings identical to those described in item [1].

In the compound (1), when the subscripts are the combination (l=m=n=1 and o=p=q=0), or when o=1 and ring $A^4$ is 1,4-phenylene or 1, 4-phenylene in which arbitrary hydrogen is replaced by fluorine, such compounds can also be synthesized according to the following two methods.

After the difluorometylenecyclohexane derivative (36) is derived by the reaction of dibromodifluoromethane and diethylaminophosphine on the cyclohexanone derivative (35), it is converted into the bromodifluoromethane derivative (37) by the reaction of bromine. After the cyclohexene derivative (39) is derived by reacting the phenol derivative (38) with the derivative (37) in the presence of a base such as potassium carbonate, the compound (1) can be synthesized by catalytic hydrogenation.

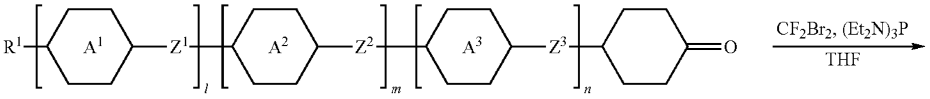

(35)

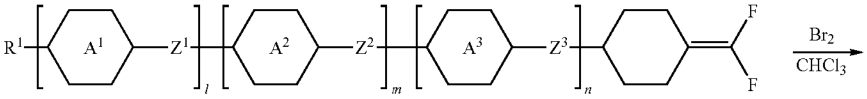

(36)

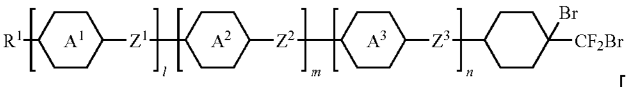

(37)

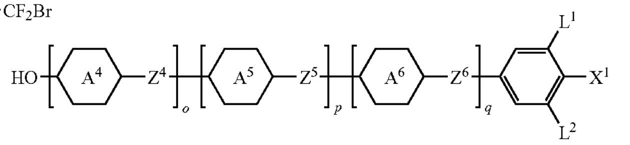

(38)

$K_2CO_3$, DMF

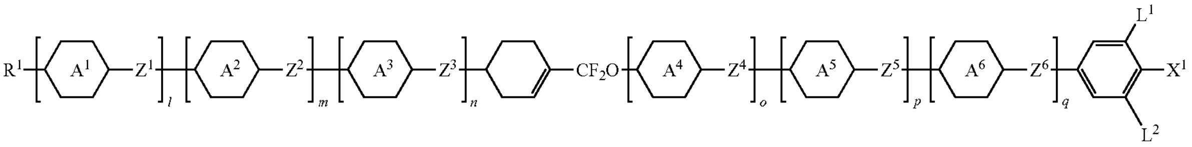

(39)

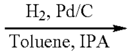

-continued

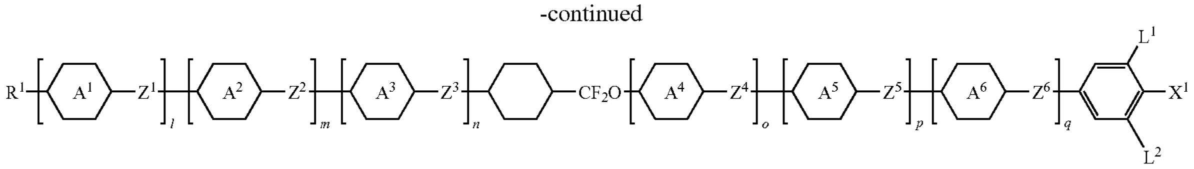

(1)

In these formulas, ring $A^4$ is 1,4-phenylene or 1,4-phenylene in which arbitrary hydrogen is replaced by fluorine. Ring $A^1$, ring $A^2$, ring $A^3$, ring $A^5$, ring $A^6$, $Z^1$ to $Z^6$, $L^1$, $L^2$, $R^1$, $X^1$, l, m, n, o, p, and q have the meanings identical to those described in item [1].

The dithianilium salt (40) is obtained by reacting the carboxylic acid derivative (31) with alkanedithiol and trifluoromethanesulfonic acid according to the method described in P. Kirsch et al., Angew. Chem. Int. Ed., 2001, 40, 1480. The compound (1) can be obtained by reacting the phenol derivative (38) with the dithianilium salt (40), and then by reacting with $Et_3N.3HF$, and finally by treating the reaction product with bromine.

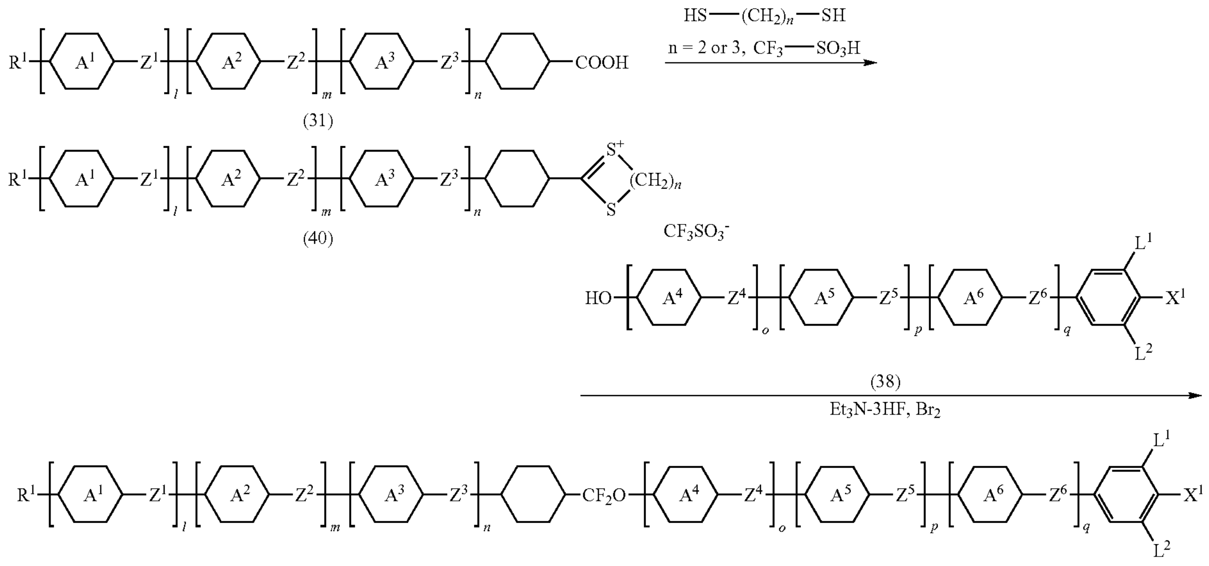

(1)

In these formulas, ring $A^4$ is 1,4-phenylene or 1,4-phenylene in which arbitrary hydrogen is replaced by fluorine. Ring $A^1$, ring $A^2$, ring $A^3$, ring $A^5$, ring $A^6$, $Z^1$ to $Z^6$, $L^1$, $L^2$, $R^1$, $X^1$, l, m, n, o, p, and q have the meanings identical to those described in item [1].

1-4-4. Method for preparing compound (1) having 1,3-dioxane-2,5-diyl ring.

The compound (1) having a 1,3-dioxane-2,5-diyl ring is synthesized, for example, according to the following method. The intermediate (43) having a dioxane ring is synthesized by the action of the aldehyde derivative (42) on the propanediol derivative (41) in the presence of an acid catalyst such as p-toluenesulfonic acid. The objective can be derived by using the intermediate (43) instead of the compound (35) according to the method for preparing the compound (1) described above.

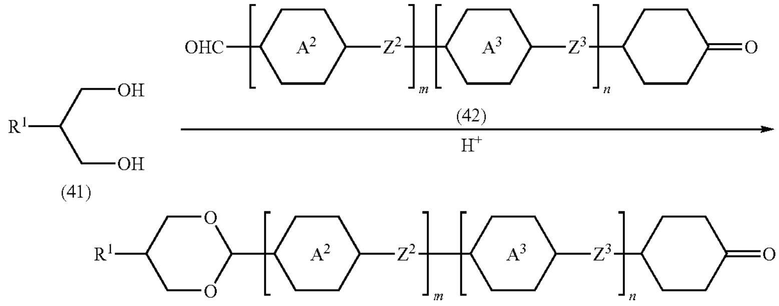

(43)

In these formulas, ring $A^2$, ring $A^3$, $Z^2$, $Z^3$, $R^1$, m, and n have the meanings identical to those described in item [1].

In the compound (1), when ring $A^2$ or ring $A^3$ is 1,3-dioxane-2,5-diyl, such a compound is synthesized according to the following method. The diethyl malonate derivative (45) is synthesized by reacting the bromide (44) with diethyl malonate in the presence of sodium ethoxide, and then converted into the propanediol derivative (46) by reduction. The intermediate (49) having a dioxane ring can be derived by the action of formic acid on the intermediate (48) obtained by reacting the derivative (46) with the aldehyde derivative (47).

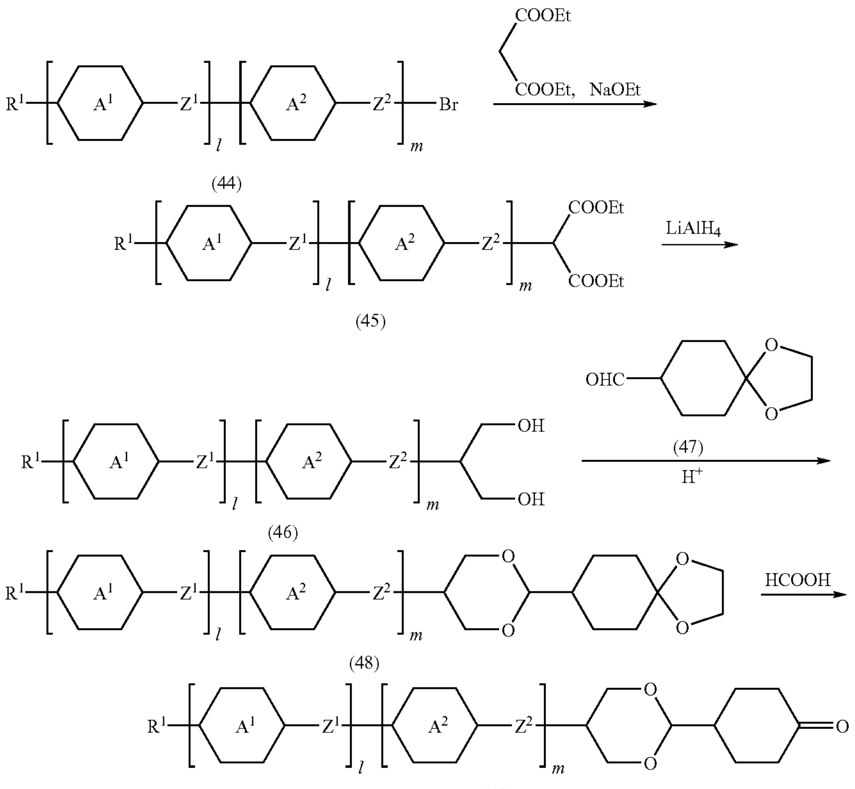

(44)

(45)

(46)

(48)

(49)

In these formulas, ring $A^1$, ring $A^2$, $Z^1$, $Z^2$, $R^1$, l, and m have the meanings identical to those described in item [1].

1-4-5. Method for Preparing Phenol Derivative (38)

The phenol derivative (38) which is a starting material of the compound (1) is synthesized, for example, according to the following method. When o=p=q=0 in formula (38), the objective phenol derivative (38-1) is easily synthesized by peracetic acid-oxidation of a boronic acid ester derivative obtained by reacting the Grignard reagent prepared from the bromobenzene derivative (50) with trialkylborate (refer to R. L. Kidwell et. al., Organic Syntheses, Vol. 5, P918, 1973), or peracetic acid-oxidation of the boronic acid derivative (51) obtained easily by acid hydrolysis of a boronic acid ester.

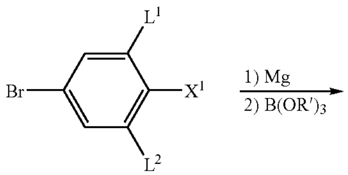

(50)

-continued

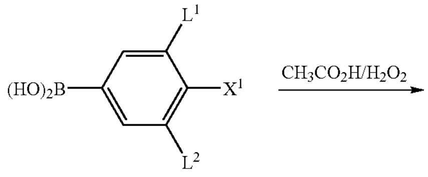

(51)

-continued

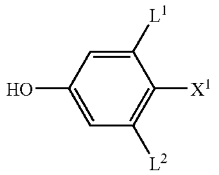

(38-1)

In these formulas, $L^1$, $L^2$, and $X^1$ have the meanings identical to those described in item [1].

In formula (38), when $Z^4$, $Z^5$ and $Z^6$ are a single bond, o=1, and p=q=0, or when o=p=1 and q=0, or when o=p=q=1, the compound (53) is obtained, for example, by the coupling reaction of the anisole derivative (52) with the boronic acid derivative (51) in the presence of a base and tetrakis(triphenylphosphine)palladium(0) as a catalyst. Refer to Akira Suzuki, et al., Journal of Synthetic Organic Chemistry, Japan, Vol. 46, No. 9, 848 (1988). The objective phenol derivative (38-2) can be synthesized by demethylation of the compound (53) with the action of boron tribromide thereon.

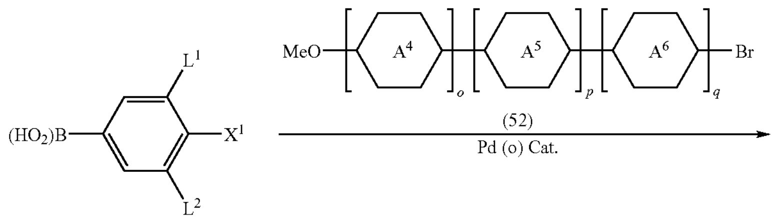

(51)

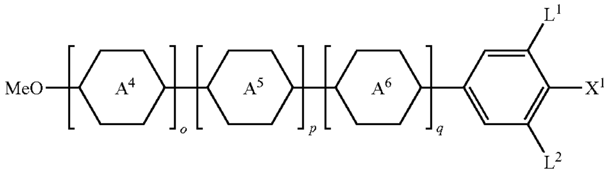

(53)

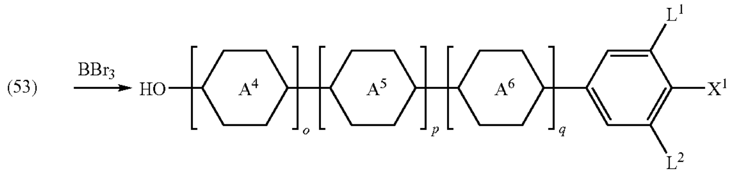

(38-2)

In these formulas, ring $A^4$ to ring $A^6$, $L^1$, $L^2$, o, p, q, and $X^1$ have the meanings identical to those described in item [1].

When o=p=q=0 in formula (38), such compounds are also synthesized according to the following method. The benzylether derivative (54) is treated with n- or sec-butyl lithium at −70° C. or lower in THF, and then reacted with trialkylborate to give the boric acid ester derivative. This derivative or its hydrolysis product is oxidized with peracetic acid to give the phenol derivative (55). After the derivative (55) is converted to its phenolate with sodium hydride, the phenolate is etherified by the reaction of fluoroalkyl bromide and then deprotected by catalytic dehydrogenation, and thus the objective phenol derivative (38-3) can be synthesized.

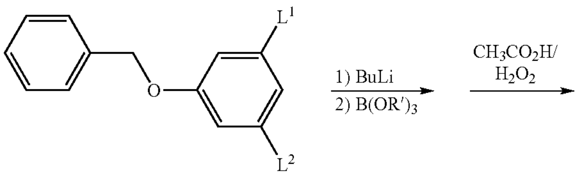

(54)

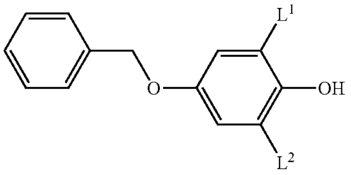

(55)

-continued

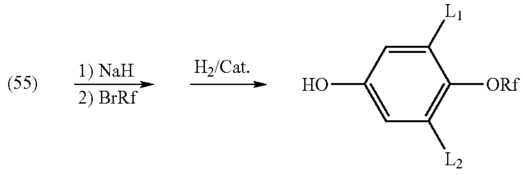

(38-3)

In these formulas, $L^1$ and $L^2$ have the meanings identical to those described in item [1] and Rf is a fluoroalkyl group excluding a trifluoromethyl group.

In the compound (1), a derivative having a biphenyl structure in the right side of the $CF_2O$ bonding group, for example, the derivative in which l=m=o=1, n=p=q=0 and $Z^4$ is a single bond, and a derivative having a terphenyl structure, for example, the derivative in which l=o=p=1, and both of $Z^4$ and $Z^5$ is a single bond, and a derivative having a quaterphenyl structure, for example, the derivative (1-42) in which o=p=q=1 and all of $Z^4$, $Z^5$ and $Z^6$ are a single bond, can be synthesized according to the method especially shown below. That is, the compound (56) is obtained from the compound (35) described above and the phenol derivative (38-1) or (38-2) according to a method similar to that of the synthesis of the compound (1). The compound (56) is lithiated by the action of n- or sec-butyl lithium, and then converted to an organometallic compound by the addition of zinc chloride, which is further reacted with the bromobenzene derivative (50) described above or the bromobenzene derivative (58) in the presence of a catalyst such as tetrakis(triphenylphosphine)palladium (0) to give the derivative (1-42). The bromobenzene derivative (58) is obtained by reacting the compound (57) with fluoroalkyl bromide.

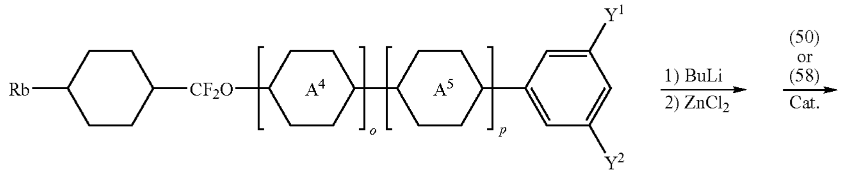

(56)

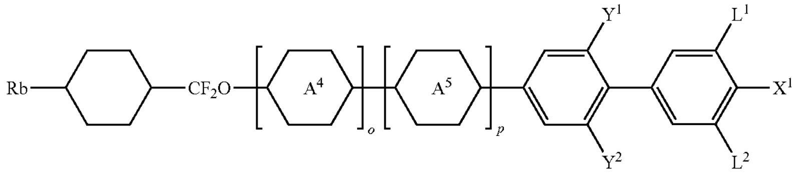

(1-42)

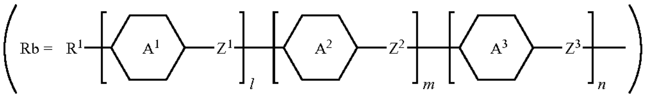

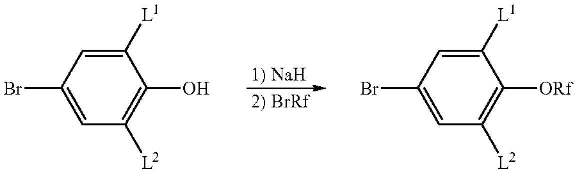

(57) (58)

In these formulas, ring $A^1$ to ring $A^5$, $Z^1$ to $Z^3$, $L^1$, $L^2$, $R^1$, and $X^1$ have the meanings identical to those described in item [1], $Y^1$ and $Y^2$ are hydrogen or fluorine, and Rf is fluoroalkyl excluding trifluoromethyl.

2. Composition of the Invention

The second aspect of the invention is a composition comprising the compound (1), preferably a liquid crystal composition which can be used for a liquid crystal display device. The liquid crystal composition of the invention is required to include the compound (1) as a component A. The composition may contain the component A and a liquid crystal compound that is not described in this specification. The composition may contain the component A and a component B, C, D, or E described below. It is desirable that the content of the component A is in the range of approximately 0.1% to approximately 99% by weight in order to exhibit excellent characteristics, preferably approximately 0.1% to approximately 90% by weight and more preferably approximately 0.1% to approximately 60% by weight based on the total weight of the composition.

The component B is at least one compound selected from the group consisting of the compounds (2), (3) and (4). The component C is at least one compound selected from the group consisting of the compound (5). The component D is at least one compound selected from the group consisting of the compounds (6), (7), (8), (9), and (10). The composition E is at least one compound selected from the group consisting of the compounds (11), (12) and (13). The component E is effective in adjusting the threshold voltage, temperature range of liquid crystal phases, optical anisotropy, dielectric anisotropy, viscosity and so forth of the composition.

A compound which is a component of a composition may be a compound having isotope-rich elements instead of natural elements. For example, even analogues in which hydrogen is replaced by deuterium have no major difference in their physical characteristics.

In the component B, suitable examples of the compound (2) are the compounds (2-1) to (2-16), suitable examples of the compound (3) are the compounds (3-1) to (3-112), and suitable examples of the compound (4) are the compounds (4-1) to (4-52).

(2-1)

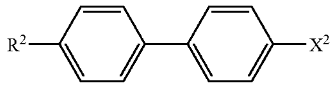

(2-2)

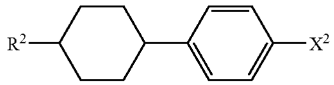

(2-3)

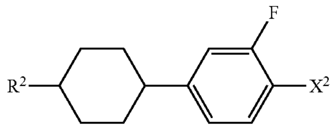

(2-4)

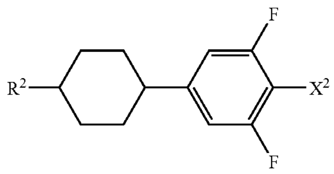

(2-5)

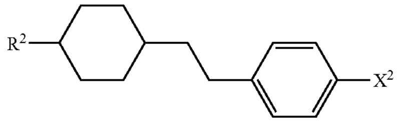

-continued
(2-6)
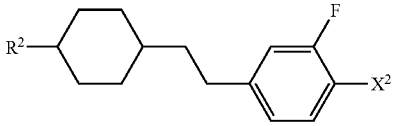
(2-7)
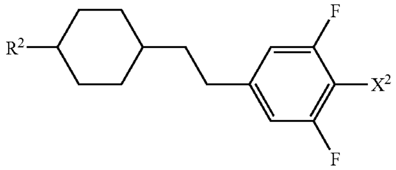
(2-8)
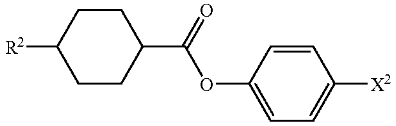
(2-9)
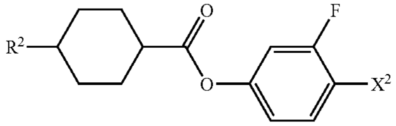
(2-10)
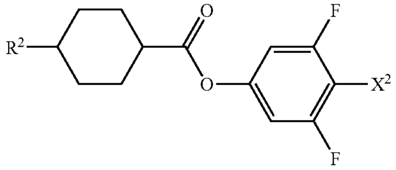
(2-11)
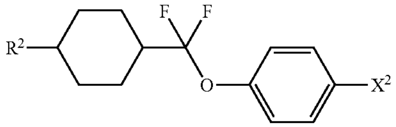
(2-12)
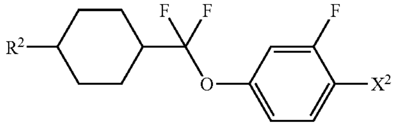
(2-13)
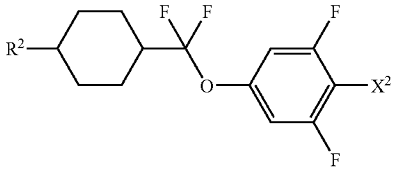
(2-14)
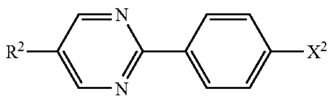
(2-15)
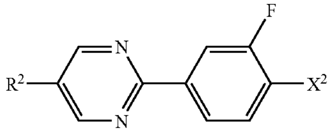
-continued
(2-16)
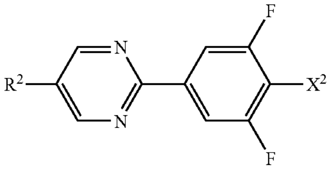
(3-1)
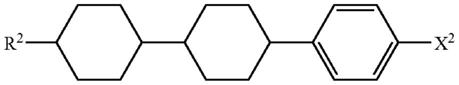
(3-2)
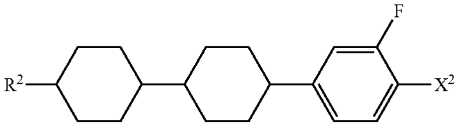
(3-3)
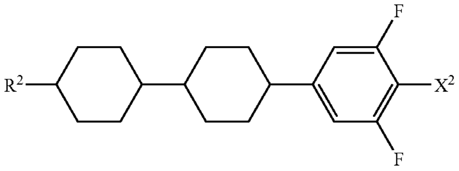
(3-4)
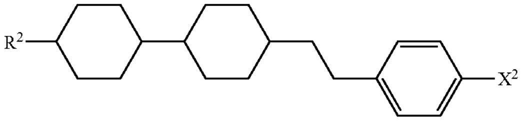
(3-5)
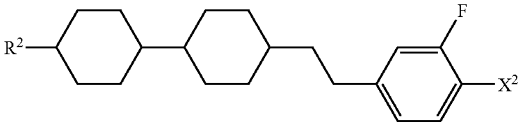
(3-6)
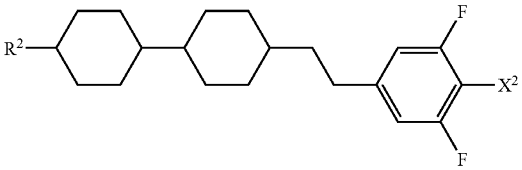
(3-7)
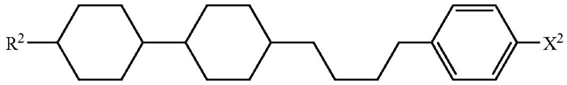
(3-8)
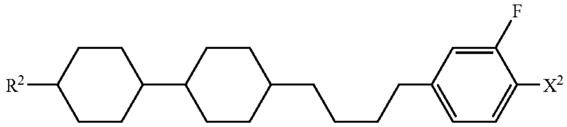
(3-9)
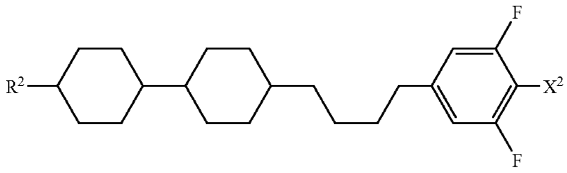

-continued
(3-10)
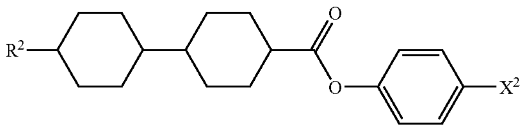
(3-11)
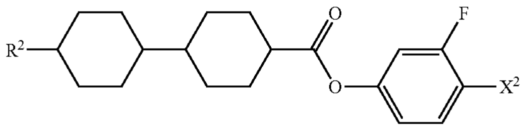
(3-12)
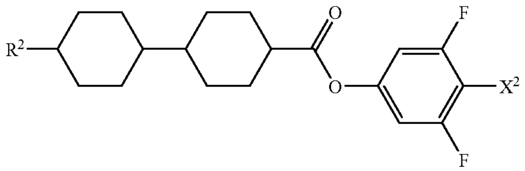
(3-13)
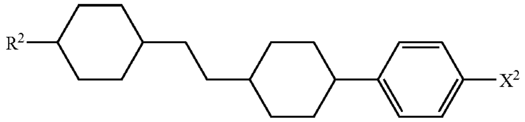
(3-14)
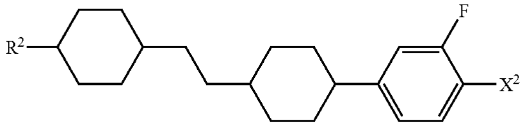
(3-15)
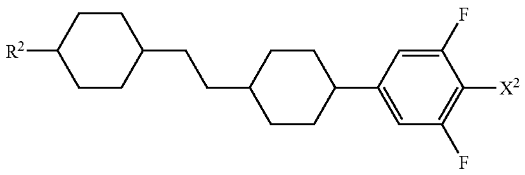
(3-16)
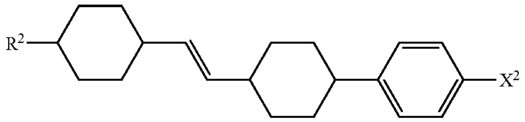
(3-17)
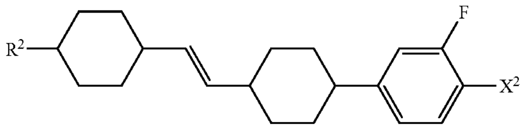
(3-18)
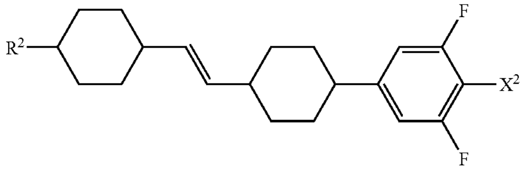
(3-19)
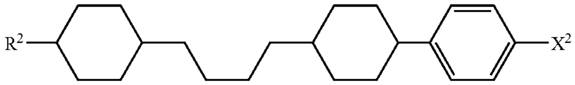
-continued
(3-20)
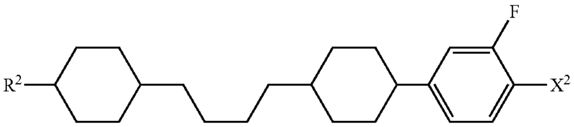
(3-21)
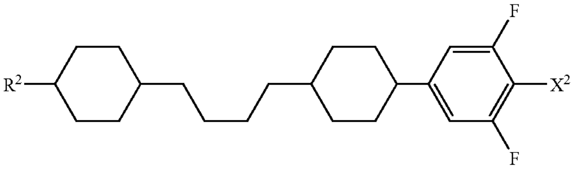
(3-22)
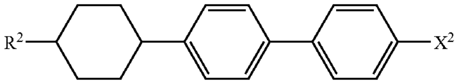
(3-23)
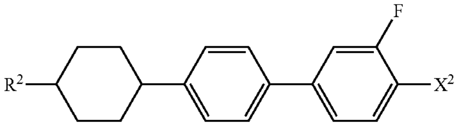
(3-24)
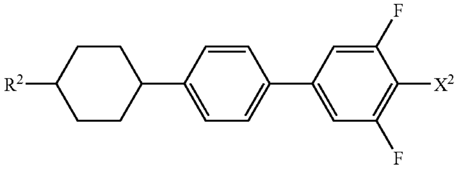
(3-25)
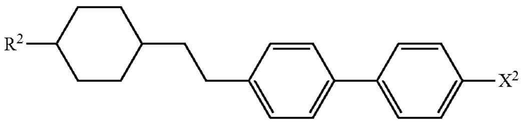
(3-26)
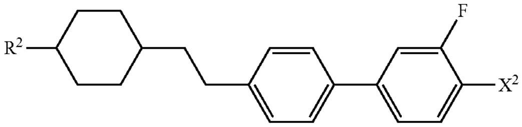
(3-27)
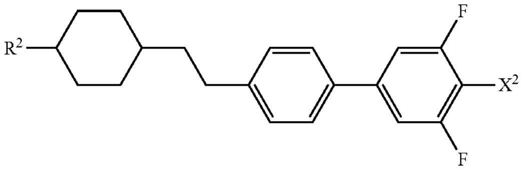
(3-28)
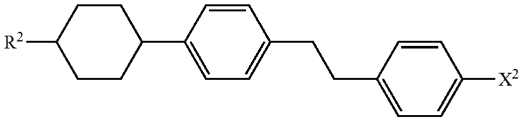
(3-29)
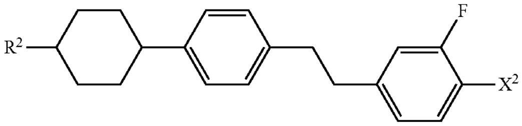

-continued
(3-30)
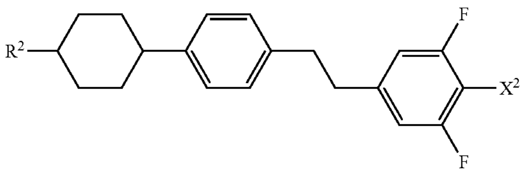
(3-31)
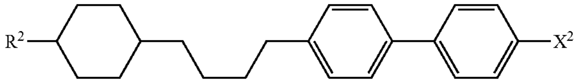
(3-32)
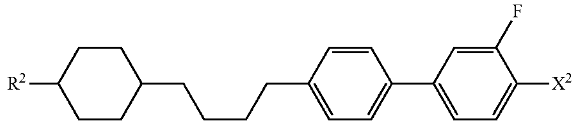
(3-33)
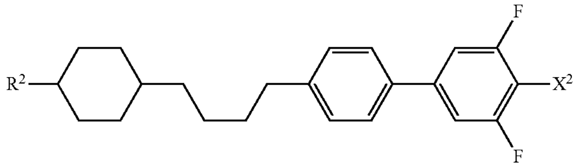
(3-34)
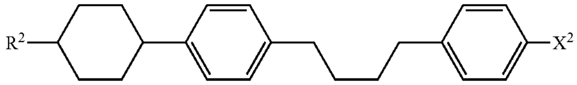
(3-35)
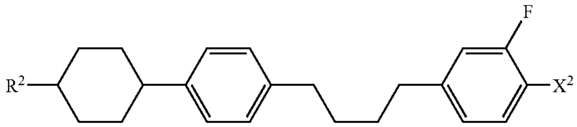
(3-36)
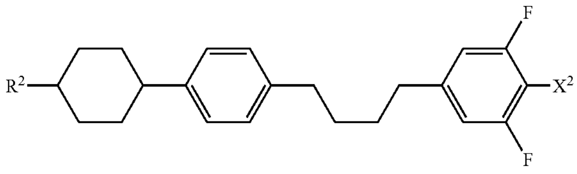
(3-37)
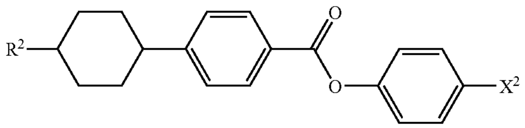
(3-38)
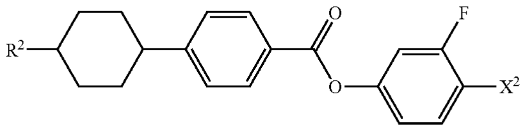
-continued
(3-39)
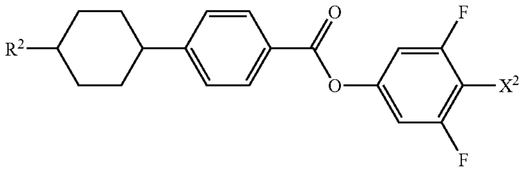
(3-40)
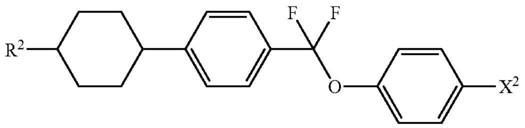
(3-41)
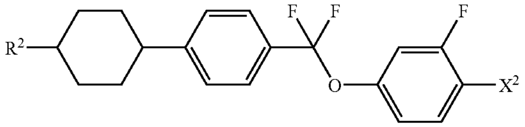
(3-42)
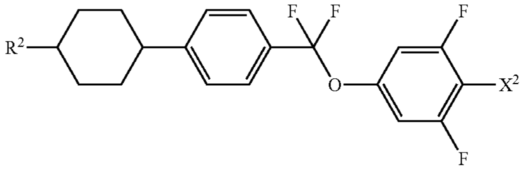
(3-43)
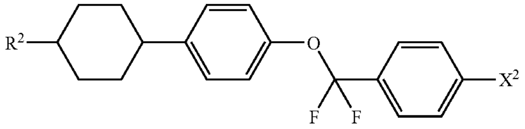
(3-44)
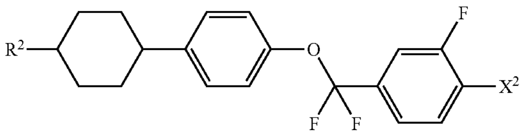
(3-45)
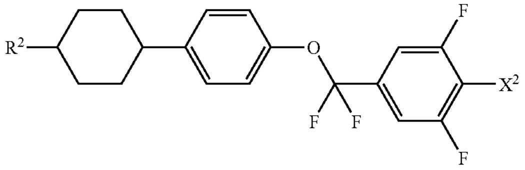
(3-46)
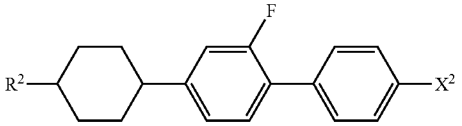
(3-47)
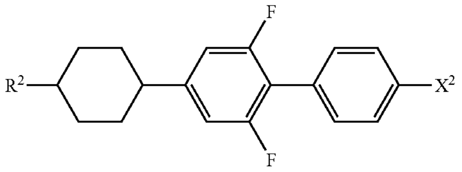

-continued
(3-48)
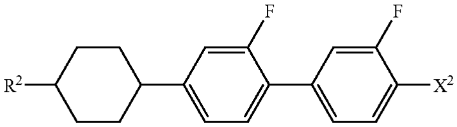
(3-49)
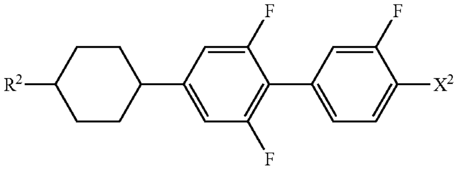
(3-50)
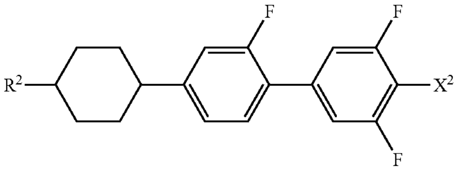
(3-51)
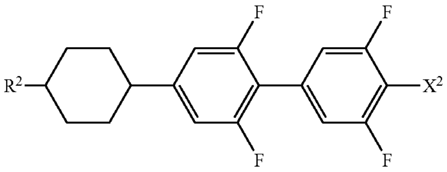
(3-52)
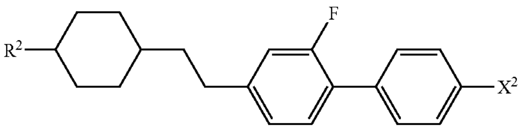
(3-53)
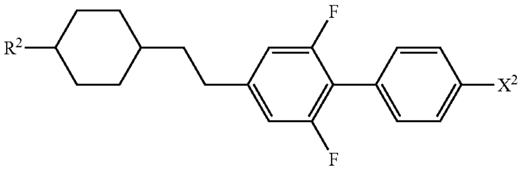
(3-54)
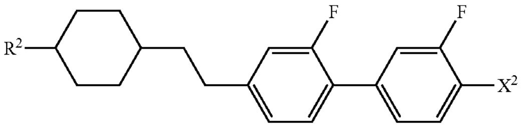
(3-55)
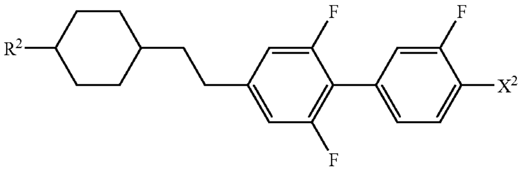
(3-56)
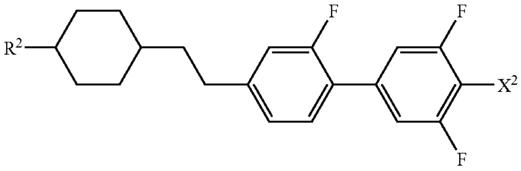
-continued
(3-57)
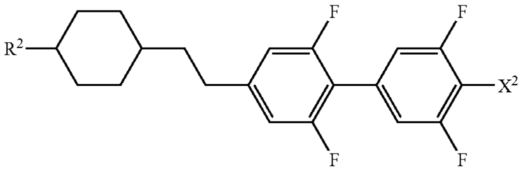
(3-58)
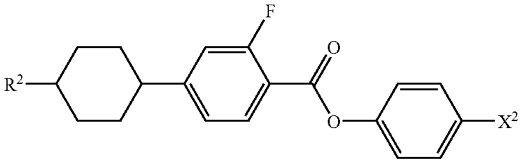
(3-59)
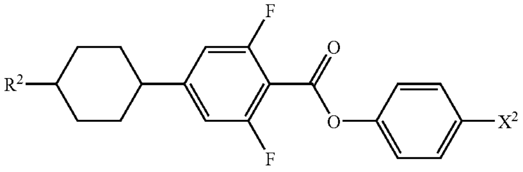
(3-60)
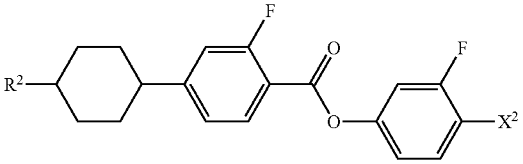
(3-61)
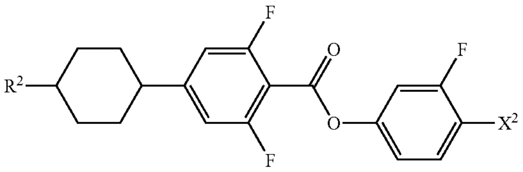
(3-62)
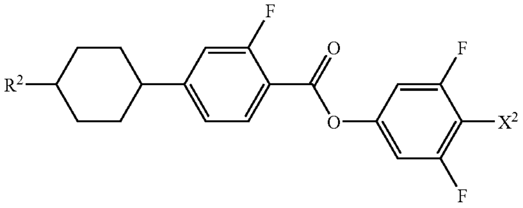
(3-63)
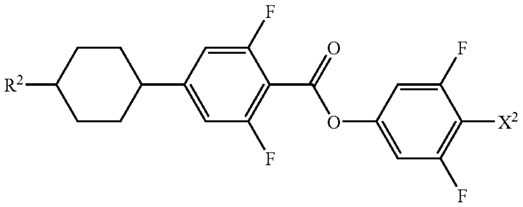
(3-64)
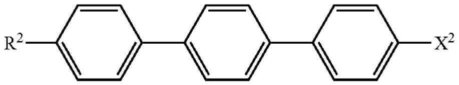

-continued
(3-65)
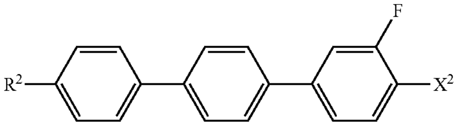
(3-66)
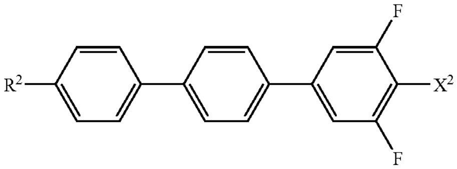
(3-67)
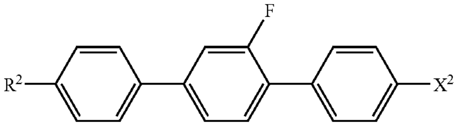
(3-68)
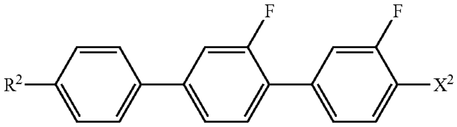
(3-69)
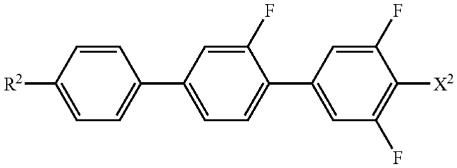
(3-70)
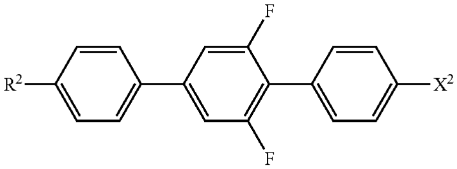
(3-71)
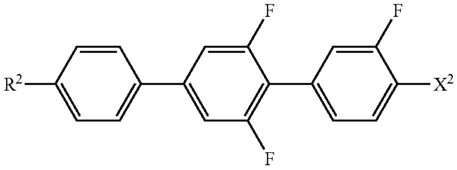
(3-72)
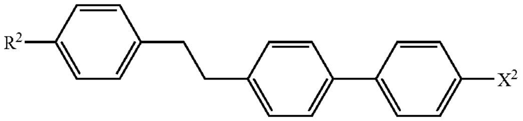
(3-73)
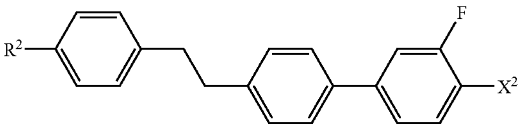
(3-74)
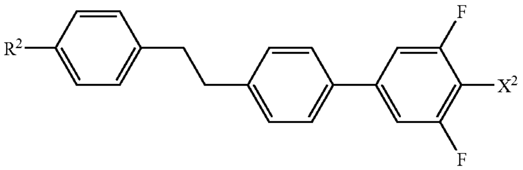
-continued
(3-75)
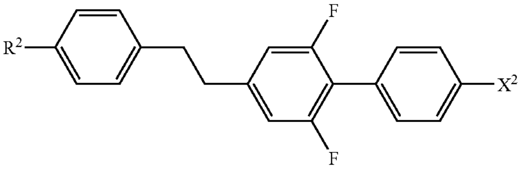
(3-76)
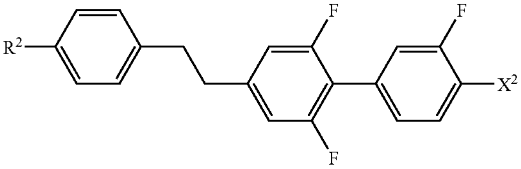
(3-77)
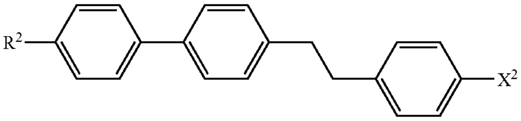
(3-78)
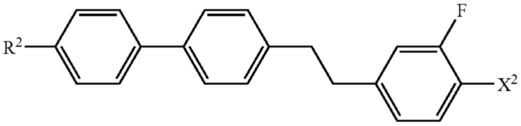
(3-79)
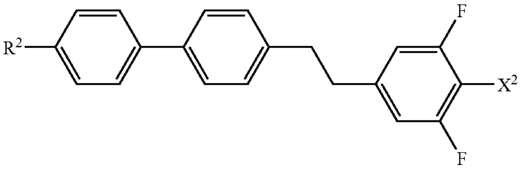
(3-80)
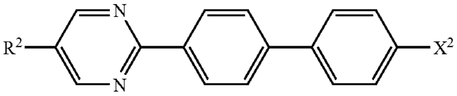
(3-81)
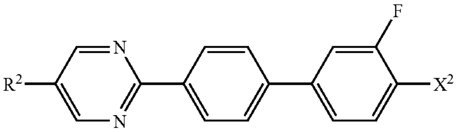
(3-82)
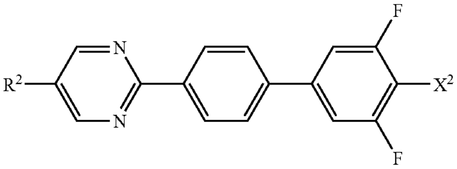
(3-83)
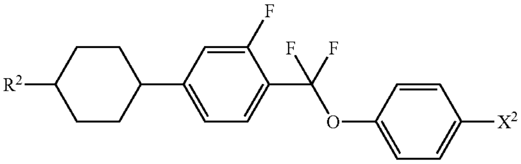

-continued
(3-84)
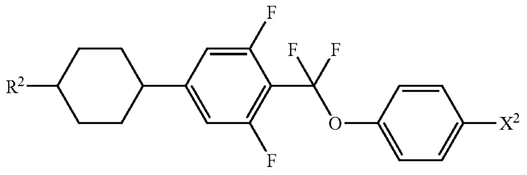
(3-85)
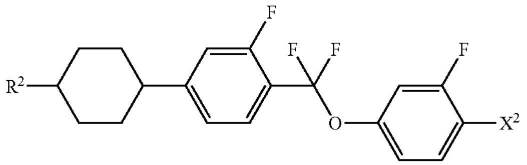
(3-86)
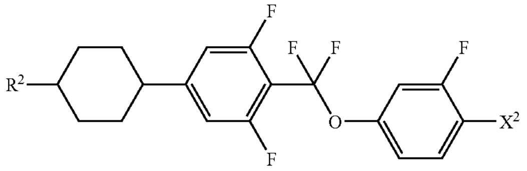
(3-87)
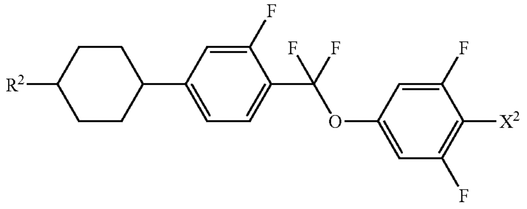
(3-88)
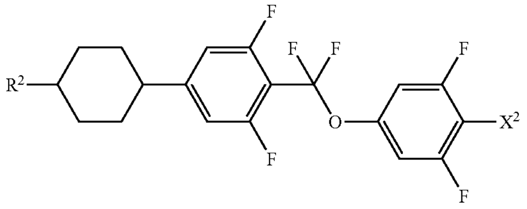
(3-89)
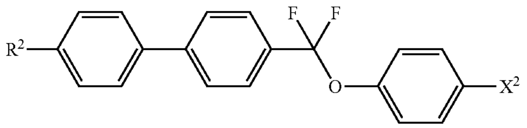
(3-90)
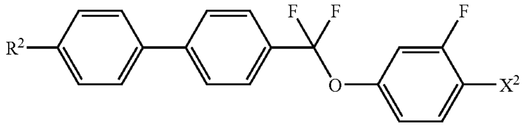
(3-91)
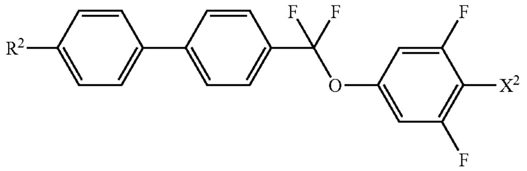
-continued
(3-92)
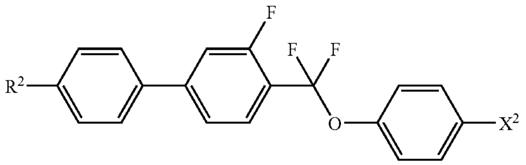
(3-93)
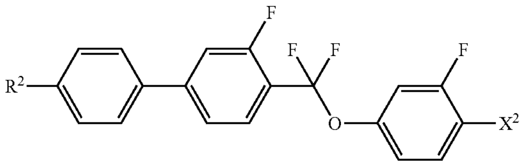
(3-94)
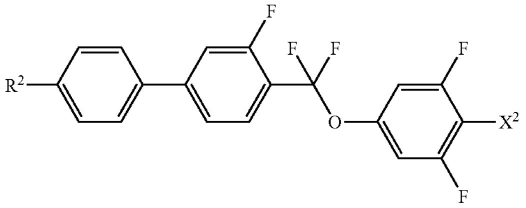
(3-95)
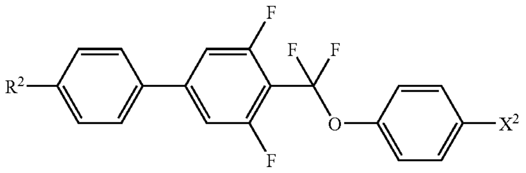
(3-96)
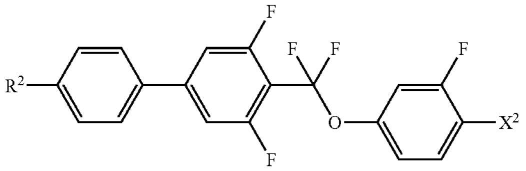
(3-97)
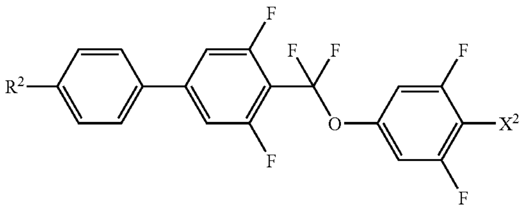
(3-98)
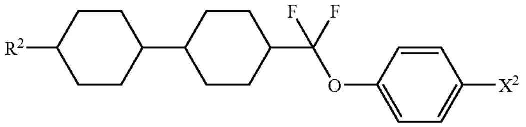
(3-99)
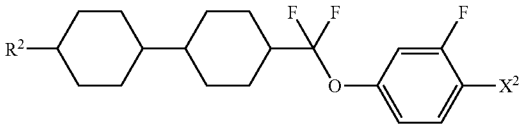

-continued
(3-100)
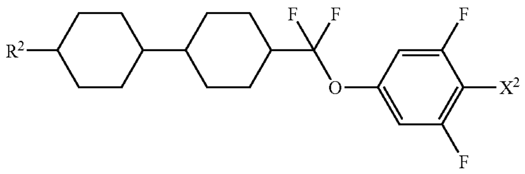
(3-101)
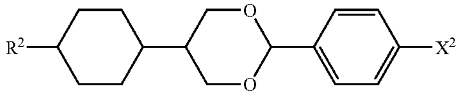
(3-102)
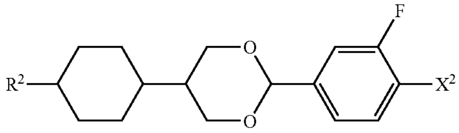
(3-103)
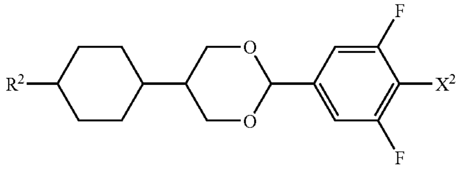
(3-104)
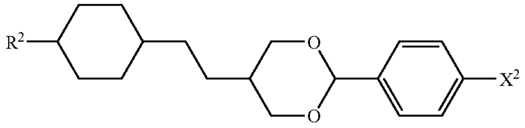
(3-105)
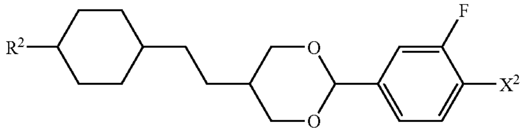
(3-106)
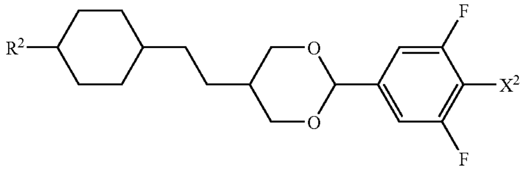
(3-107)
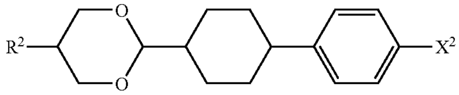
(3-108)
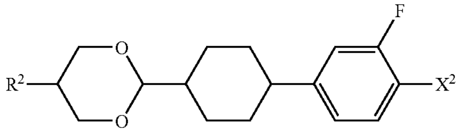
(3-109)
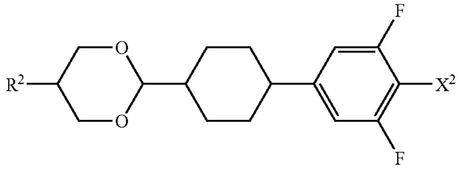
-continued
(3-110)
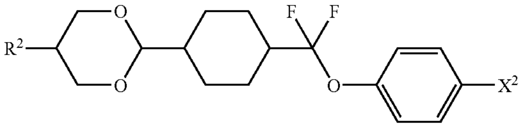
(3-111)
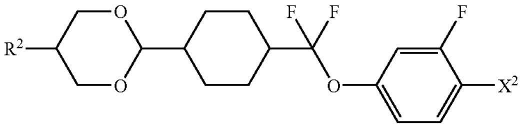
(3-112)
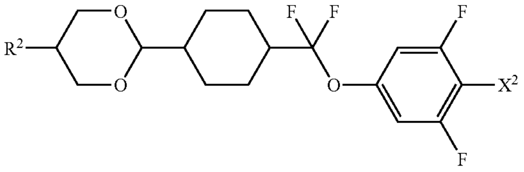
(4-1)
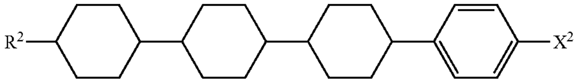
(4-2)
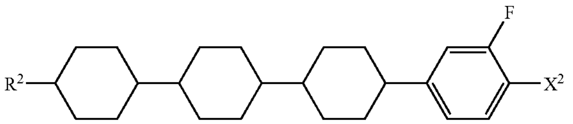
(4-3)
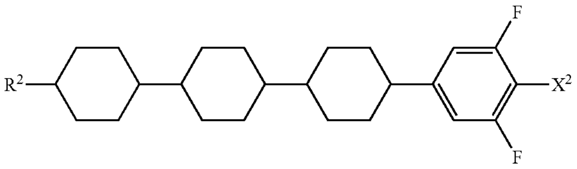
(4-4)
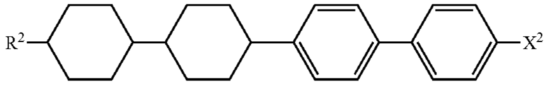
(4-5)
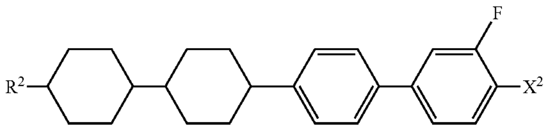
(4-6)
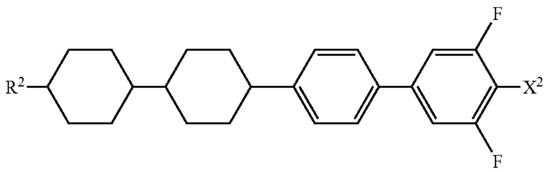
(4-7)
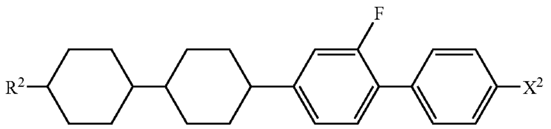

-continued
(4-8)
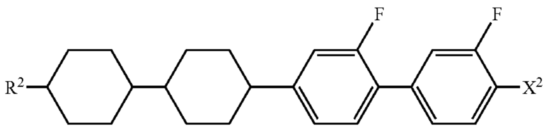
(4-9)
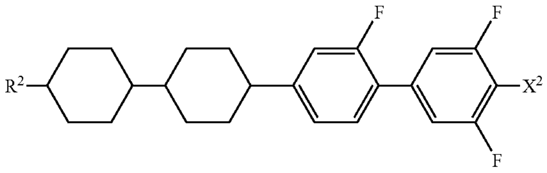
(4-10)
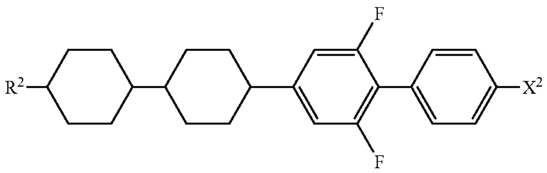
(4-11)
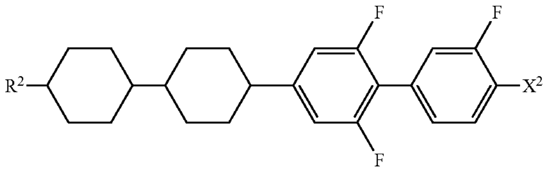
(4-12)
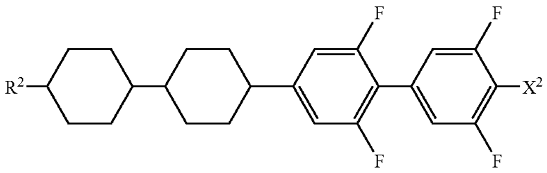
(4-13)
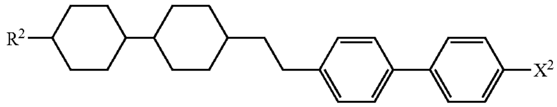
(4-14)
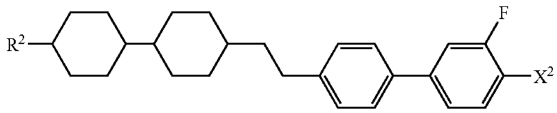
(4-15)
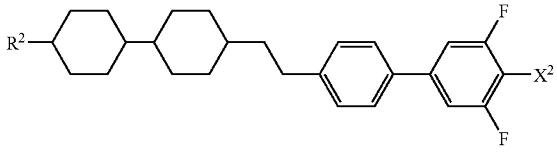
(4-16)
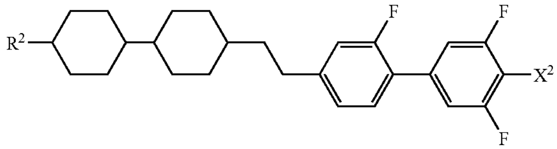
-continued
(4-17)
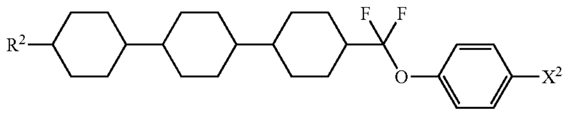
(4-18)
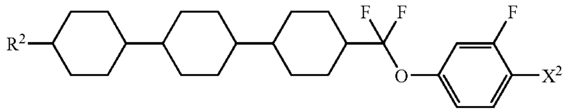
(4-19)
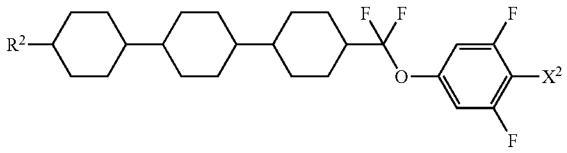
(4-20)
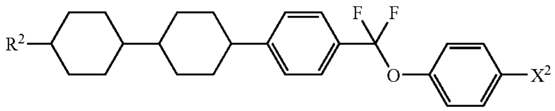
(4-21)
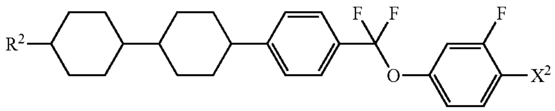
(4-22)
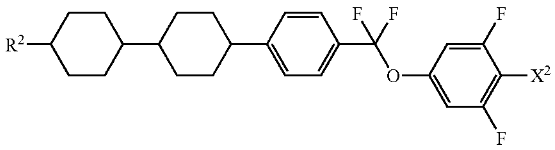
(4-23)
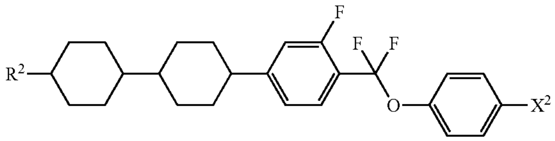
(4-24)
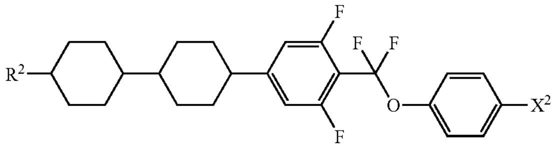
(4-25)
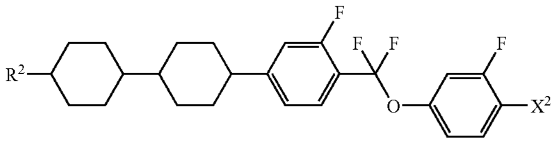
(4-26)
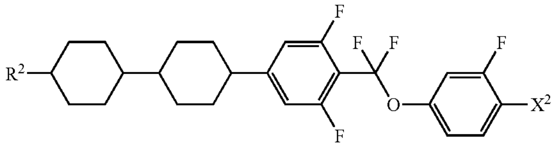

-continued
(4-27)
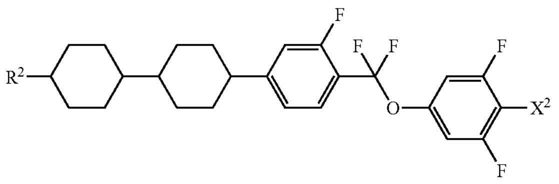
(4-28)
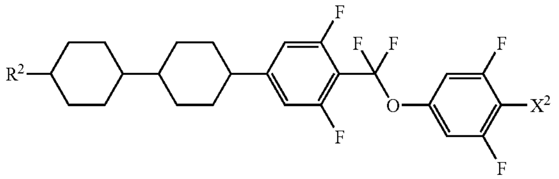
(4-29)
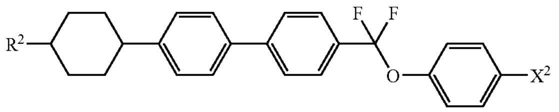
(4-30)
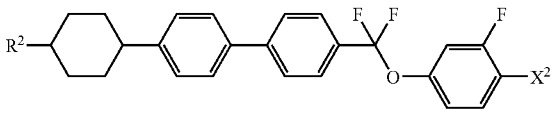
(4-31)
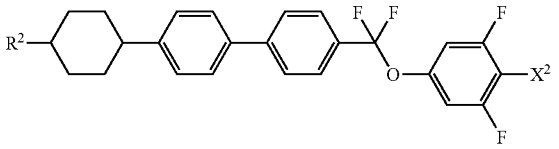
(4-32)
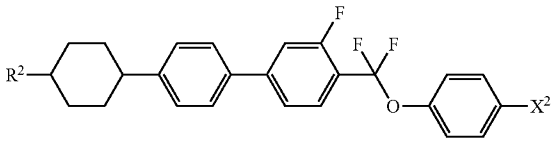
(4-33)
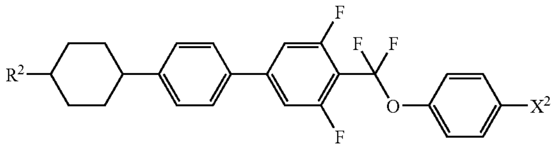
(4-34)
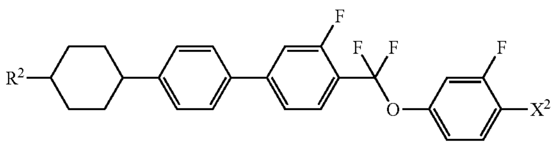
(4-35)
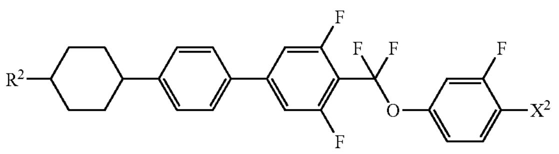
-continued
(4-36)
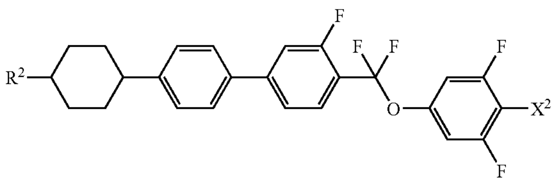
(4-37)
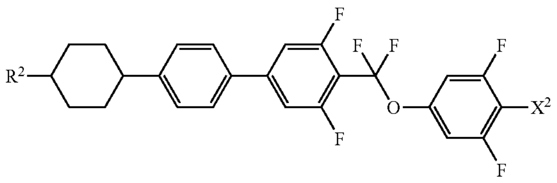
(4-38)
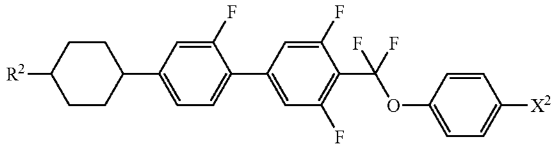
(4-39)
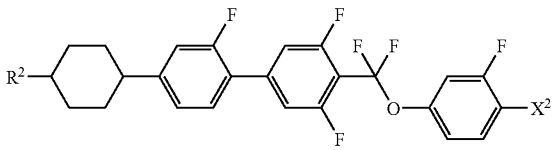
(4-40)
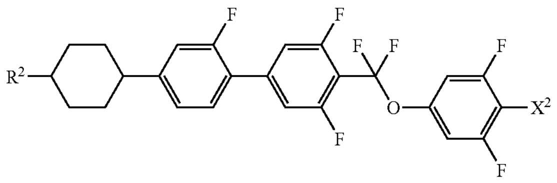
(4-41)
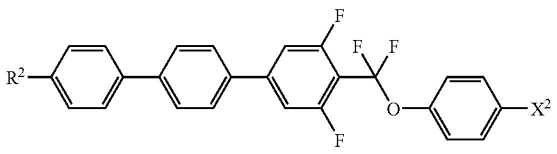
(4-42)
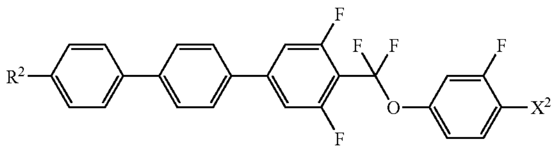
(4-43)
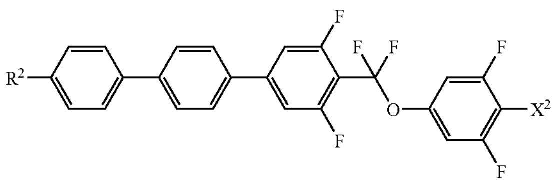

-continued (4-44)

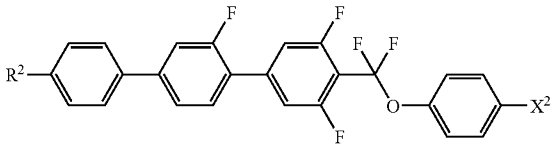

(4-45)

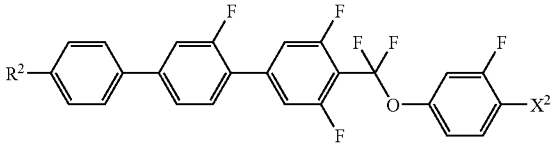

(4-46)

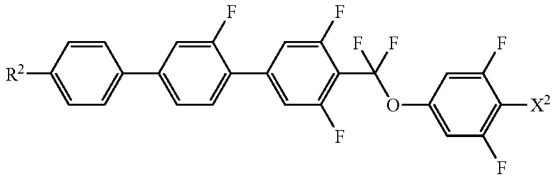

(4-47)

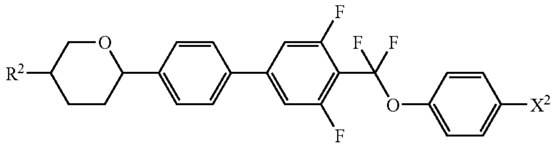

(4-48)

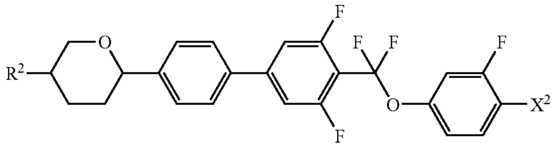

(4-49)

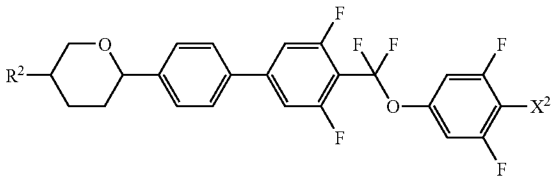

(4-50)

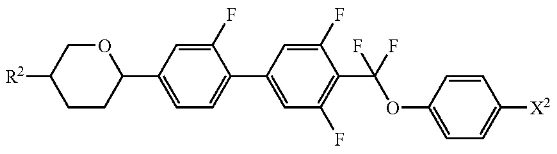

(4-51)

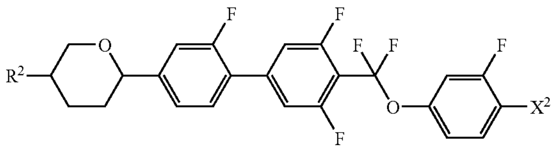

-continued (4-52)

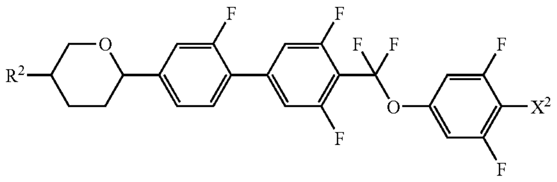

In these formulas, $R^2$ and $X^2$ have the meanings identical to those described above.

The component B is used to prepare a composition for TFT because dielectric anisotropy is positive, and thermal stability and chemical stability are quite excellent. The component E is desirably added to adjust the viscosity of the composition. A suitable content of the component B is in the range of approximately 1% to approximately 99% by weight based on the total weight of the composition, preferably approximately 10% to approximately 97% by weight, more preferably approximately 40% to approximately 95% by weight. Examples of desirable compound (5) are the compounds (5-1) to (5-62).

(5-1)

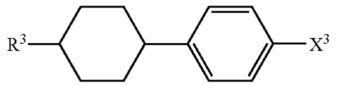

(5-2)

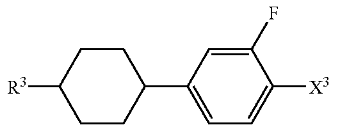

(5-3)

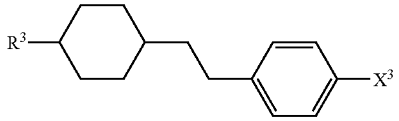

(5-4)

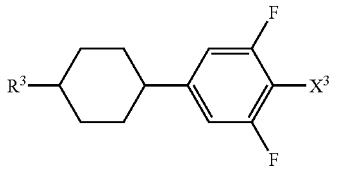

(5-5)

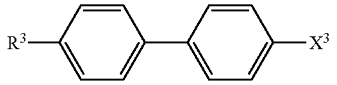

(5-6)

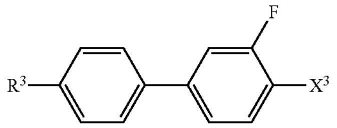

(5-7)

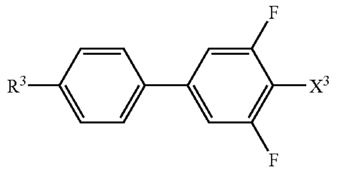

-continued
(5-8)
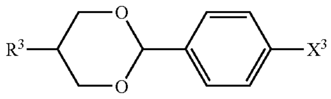
(5-9)
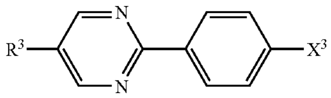
(5-10)
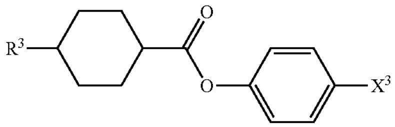
(5-11)
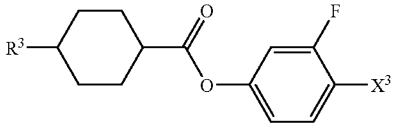
(5-12)
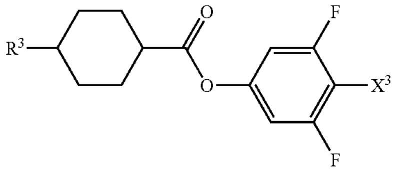
(5-13)
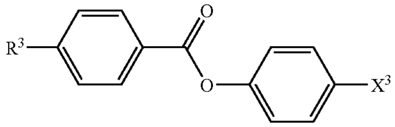
(5-14)
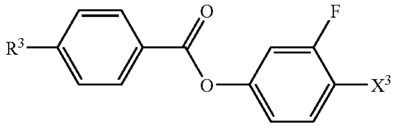
(5-15)
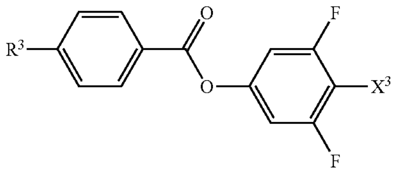
(5-16)
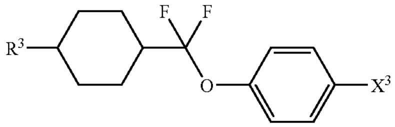
(5-17)
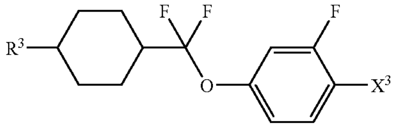
(5-18)
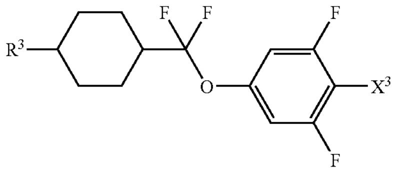
-continued
(5-19)
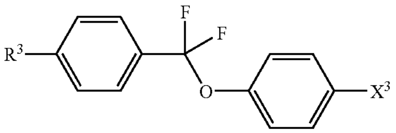
(5-20)
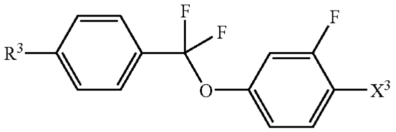
(5-21)
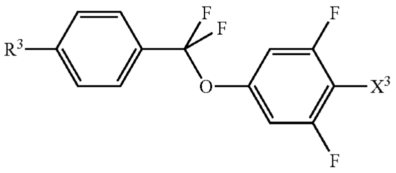
(5-22)
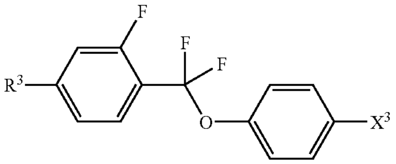
(5-23)
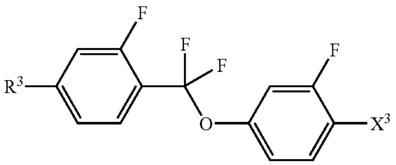
(5-24)
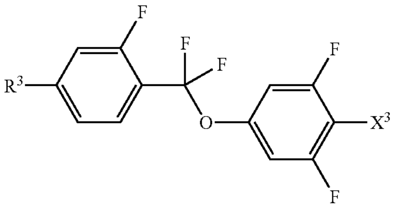
(5-25)
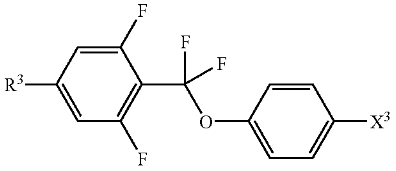
(5-26)
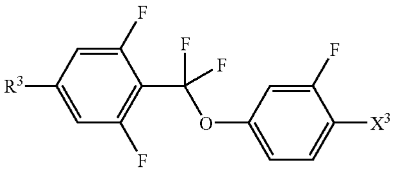
(5-27)
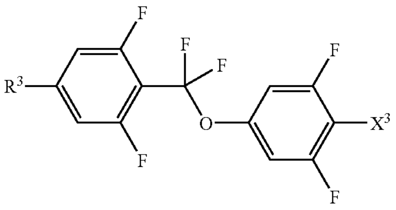

-continued
(5-28)
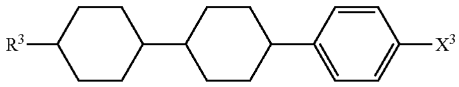
(5-29)
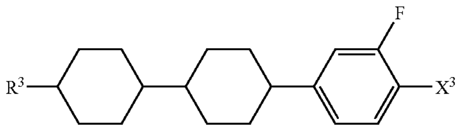
(5-30)
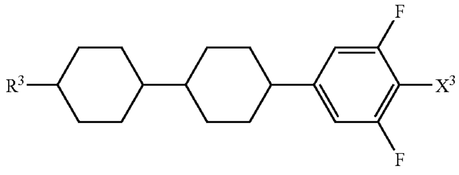
(5-31)
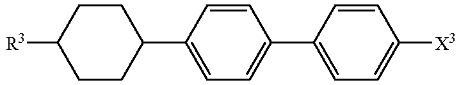
(5-32)
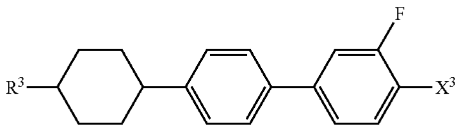
(5-33)
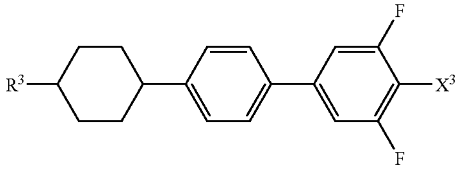
(5-34)
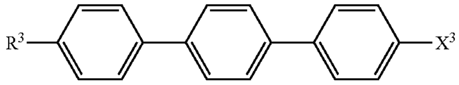
(5-35)
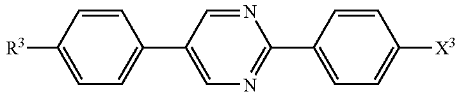
(5-36)
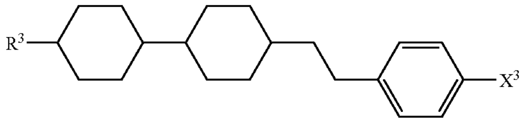
(5-37)
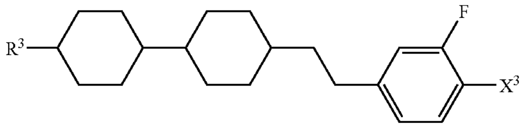
(5-38)
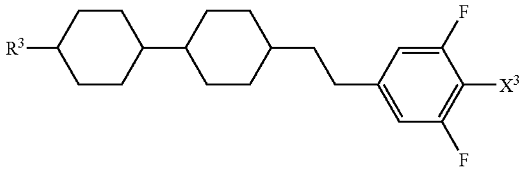
-continued
(5-39)
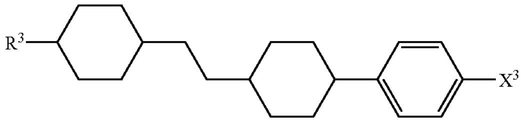
(5-40)
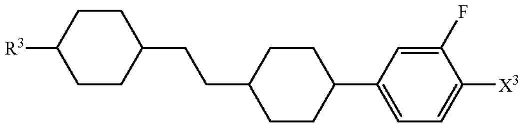
(5-41)
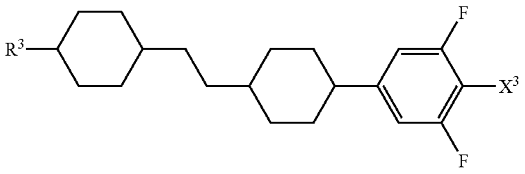
(5-42)
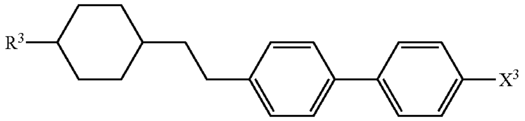
(5-43)
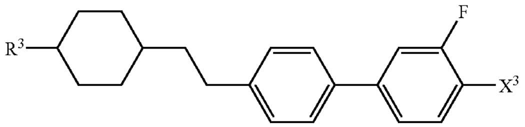
(5-44)
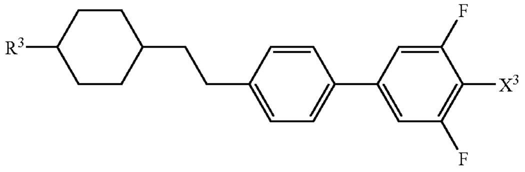
(5-45)
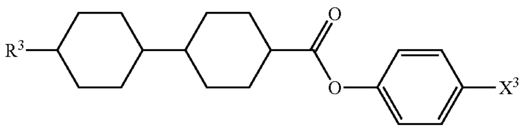
(5-46)
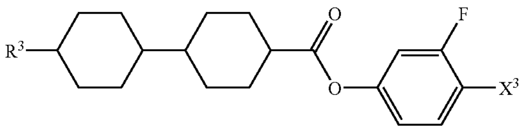
(5-47)
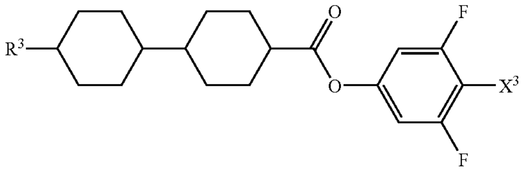

-continued (5-48)

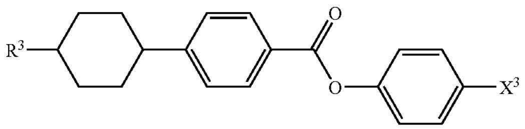

(5-49)

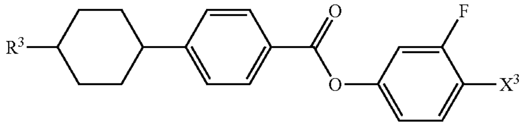

(5-50)

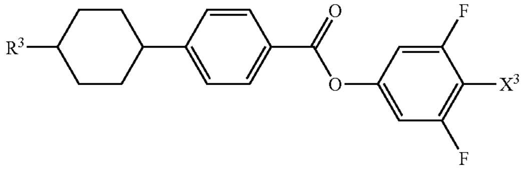

(5-51)

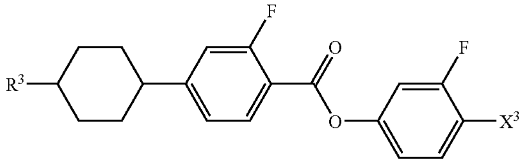

(5-52)

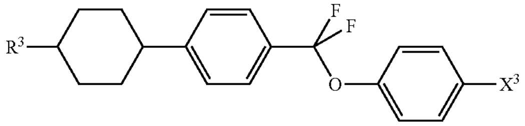

(5-53)

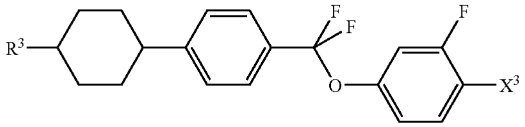

(5-54)

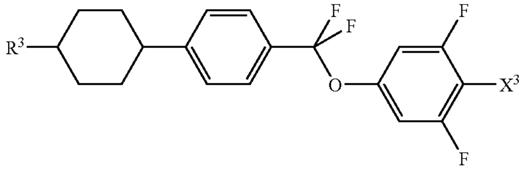

(5-55)

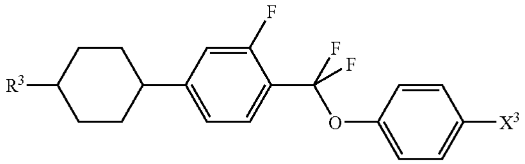

(5-56)

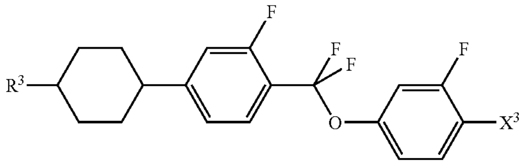

-continued (5-57)

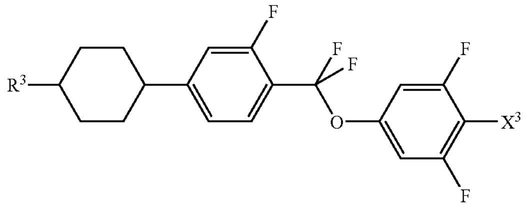

(5-58)

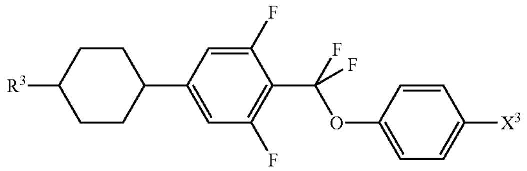

(5-59)

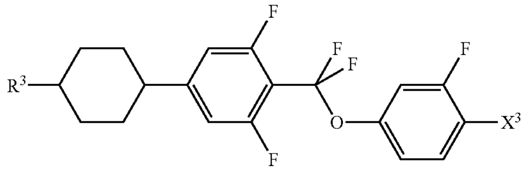

(5-60)

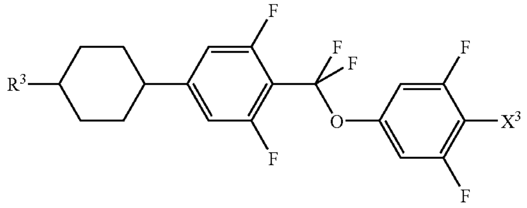

(5-61)

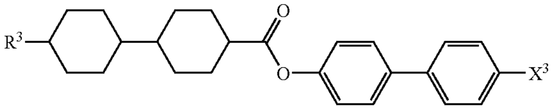

(5-62)

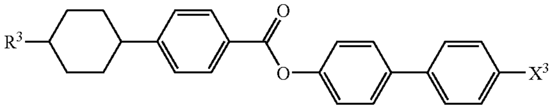

In these formulas, $R^3$ and $X^3$ have the meanings identical to those described above.

The compound (5), i.e. the component C, is used mainly to prepare a composition for STN and TN, because dielectric anisotropy is positive and its value is quite large. This component C can decrease the threshold voltage of the composition. This component C can adjust the viscosity and the optical anisotropy, and increase the temperature range of liquid crystal phases. Furthermore, the component C can also be used to improve steepness.

The component E may be added to adjust the threshold voltage, the temperature range of liquid crystal phases, optical anisotropy, dielectric anisotropy, viscosity, and so forth of this composition. When the composition is prepared for STN or TN, a suitable content of the component C is in the range of approximately 1% to approximately 99% by weight, preferably approximately 10% to approximately 97% by weight, and more preferably approximately 40% to approximately 95% by weight based on the total weight of the composition.

The component D is at least one compound selected from the group consisting of the compounds (6) to (10), and suitable to prepare a composition having a negative dielectric anisotropy for a VA device and so forth.
Examples of desirable compounds (6) to (10) are the compounds (6-1) to (6-5), the compounds (7-1) to (7-11), the compounds (8-1), and the compounds (10-1) to (10-11).
(6-1)
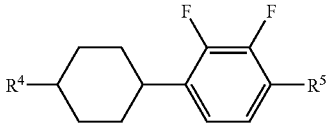
(6-2)
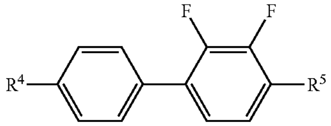
(6-3)
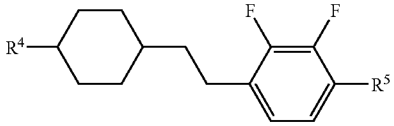
(6-4)
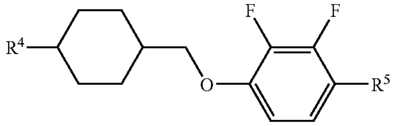
(6-5)
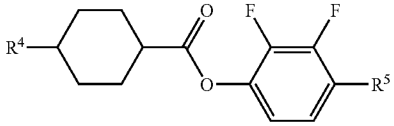
(7-1)
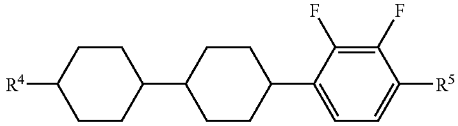
(7-2)
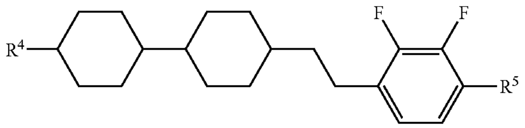
(7-3)
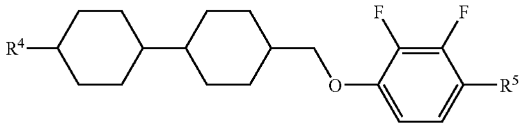
(7-4)
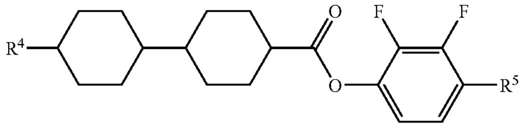
(7-5)
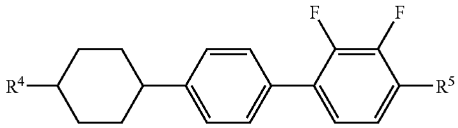
-continued
(7-6)
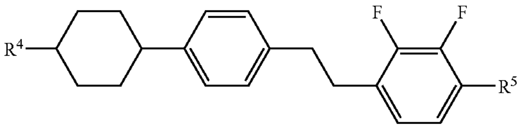
(7-7)
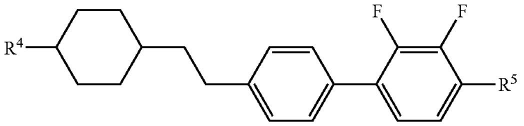
(7-8)
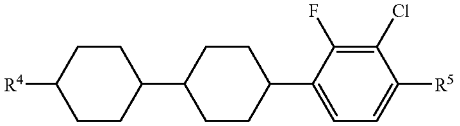
(7-9)
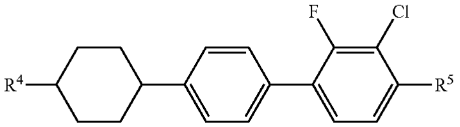
(7-10)
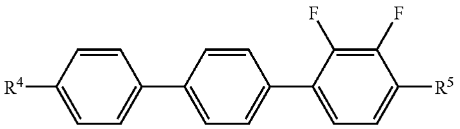
(7-11)
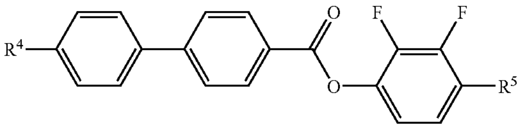
(8-1)
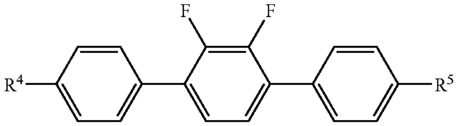
(10-1)
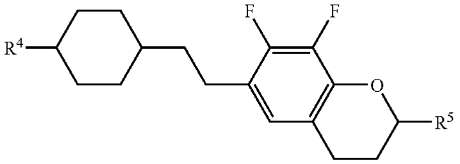
(10-2)
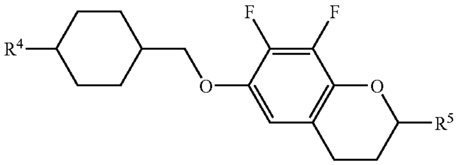
(10-3)
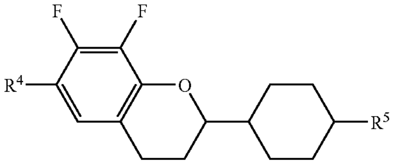

-continued (10-4)

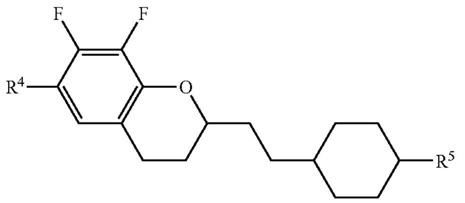

(10-5)

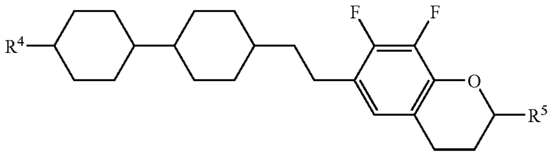

(10-6)

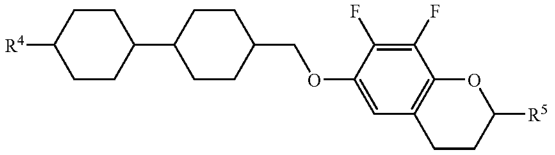

(10-7)

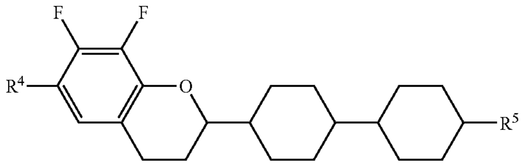

(10-8)

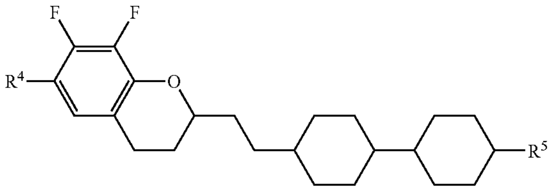

(10-9)

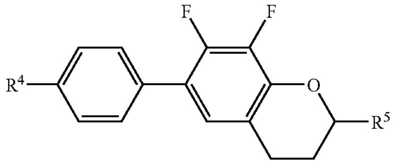

(10-10)

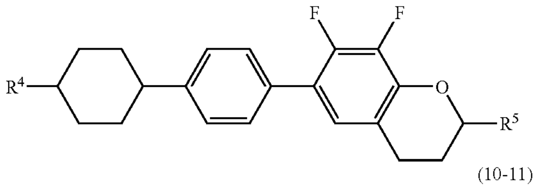

(10-11)

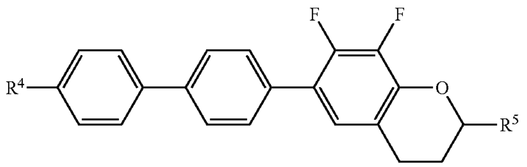

In these formulas, $R^4$ and $R^5$ have the meanings identical to those described above.

The component D is used mainly as a composition for a VA device in which dielectric anisotropy is negative. Decreasing the content of the component D is desirable as far as a required value of threshold voltage is satisfied, because the content of the component D increases with decreasing the threshold voltage, but increasing the viscosity of the composition. The content is desirably approximately 40% by weight or more for low-voltage driving, because the absolute value of the dielectric anisotropy is around 5.

In the component D, the compound (6) is a two-ring-containing compound and effective mainly in the adjustment of the threshold voltage, the adjustment of the viscosity, or the adjustment of the optical anisotropy. The compounds (7) and (8) are a three-ring-containing compound and effective in increasing a clearing point, broadening the range of a nematic phase, decreasing the threshold voltage, increasing the optical anisotropy, and so forth.

The content of the component D is preferably approximately 40% by weight or more, more preferably in the range of approximately 50% to approximately 95% by weight based on the total amount of the composition for preparing a composition for a VA device. The elastic constant or the voltage-transmission curve of the composition can be adjusted by mixing the component D. When the component D is mixed into a composition in which dielectric anisotropy is positive, its content is desirably approximately 30% by weight or less based on the total amount of the composition.

The component E is at least one compound selected from the group consisting of the compounds (11), (12), and (13). Examples of desirable compounds are the compounds (11-1) to (11-11), the compounds (12-1) to (12-18) and the compounds (13-1) to (13-6).

(11-1)

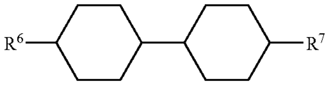

(11-2)

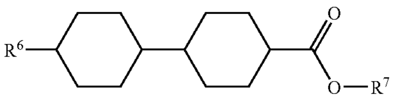

(11-3)

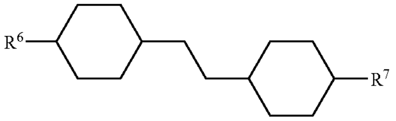

(11-4)

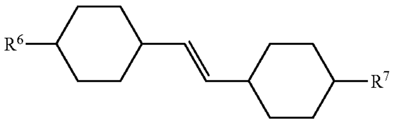

(11-5)

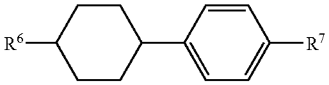

(11-6)

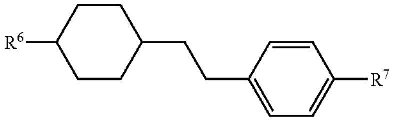

(11-7)

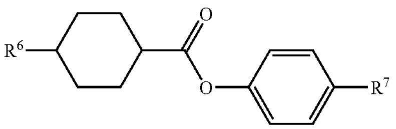

-continued
(11-8)
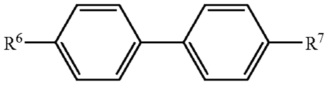
(11-9)
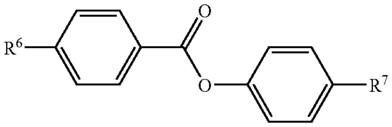
(11-10)
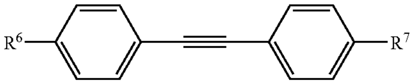
(11-11)
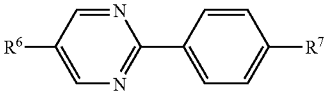
(12-1)
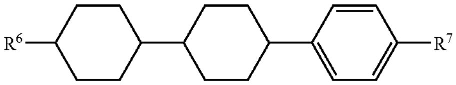
(12-2)
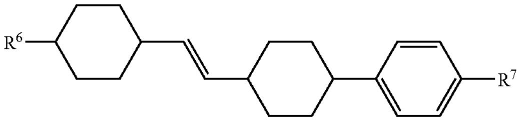
(12-3)
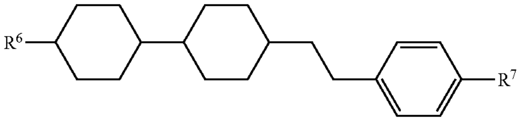
(12-4)
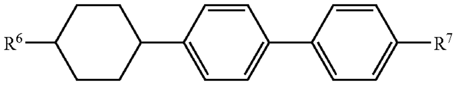
(12-5)
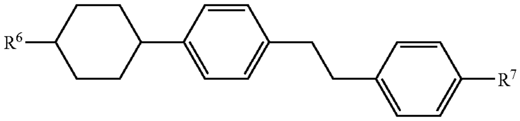
(12-6)
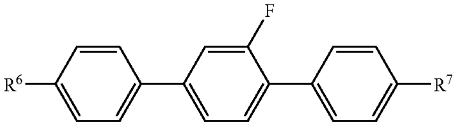
(12-7)
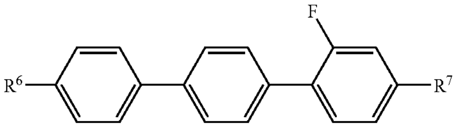
(12-8)
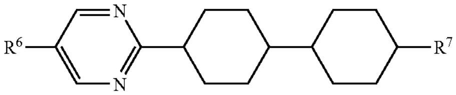
(12-9)
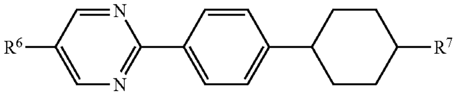
-continued
(12-10)
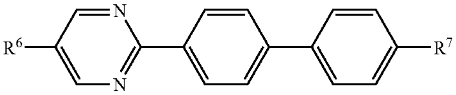
(12-11)
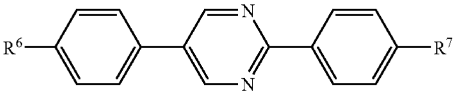
(12-12)
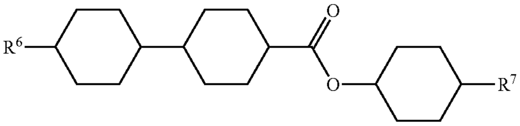
(12-13)
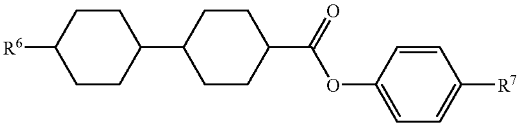
(12-14)
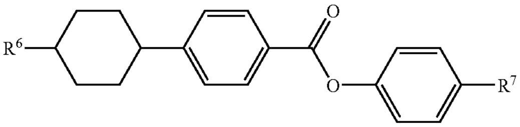
(12-15)
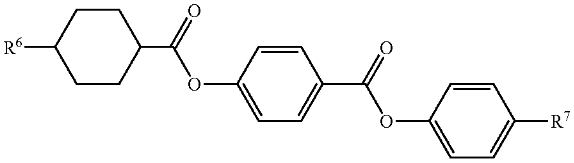
(12-16)
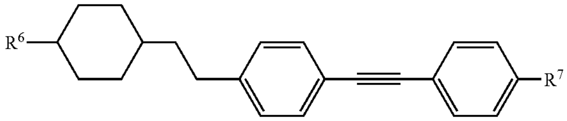
(12-17)
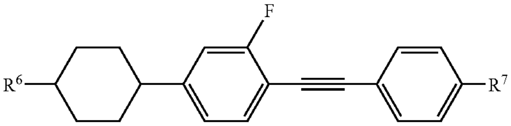
(12-18)
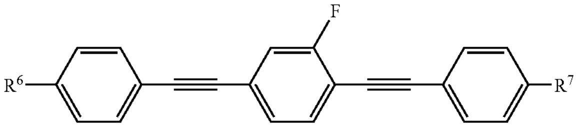
(13-1)
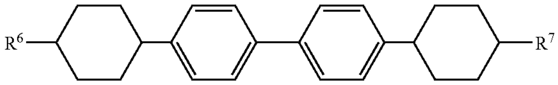
(13-2)
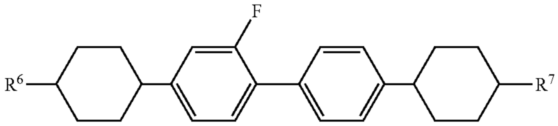

-continued (13-3)

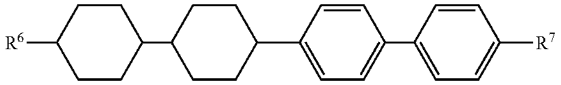

(13-4)

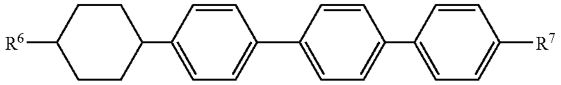

(13-5)

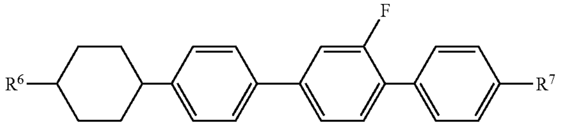

(13-6)

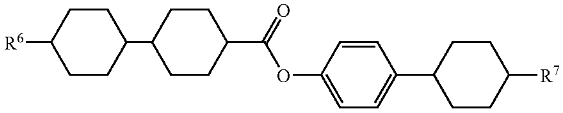

In these formulas, $R^6$ and $R^7$ have the meanings identical to those described above.

The compounds (11) to (13), i.e. the component E, are close to neutral because the absolute value of dielectric anisotropy is small. The compound (11) is effective mainly in adjusting the viscosity or the optical anisotropy. The compounds (12) and (13) are effective in broadening the range of a nematic phase such as increasing the clearing point, or effective in adjusting the optical anisotropy.

Increasing the content of the component E is desirable as far as a required value of threshold voltage is satisfied, because the content of the component E increases with increasing a threshold voltage, but decreasing the viscosity of the liquid crystal composition. When a composition for TFT is prepared, the content of the component E is preferably approximately 30% by weight or more, and more preferably approximately 50% by weight or more based on the total amount of the composition. When a composition for STN or TN is prepared, the content of the component E is preferably approximate 30% by weight or more, more preferably approximately 40% by weight or more based on the total amount of the composition.

The composition is generally prepared according to known methods such as a method for dissolving required components at a high temperature. An additive which is well known to a person skilled in the art may be added to the composition according to an intended use. It is possible to prepare, for example, a composition including an optically active compound described below and a composition for a GH mode to which a dye is added. The additive is well known to a person skilled in the art and described in the literature and so forth in detail.

The composition may further comprise at least one optically active compound. An example of the optically active compound is a well known chiral doping agent. The chiral doping agent is effective in inducing a helical structure of liquid crystals, adjusting a twist angle required and then preventing a reverse twist. Examples of the chiral doping agent are the optically active compounds (Op-1) to (Op-13) shown below.

(Op-1)

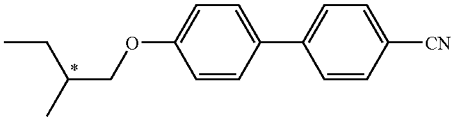

(Op-2)

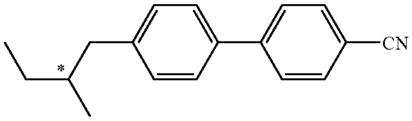

(Op-3)

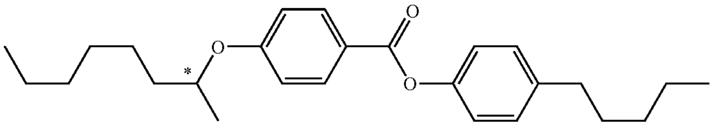

(Op-4)

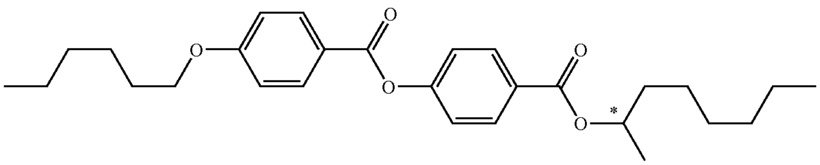

(Op-5)

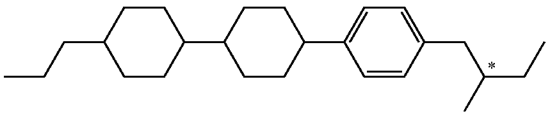

(Op-6)

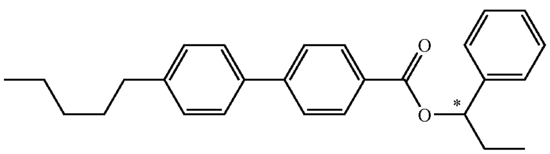

-continued (Op-7)

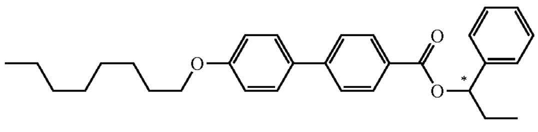

(Op-8)

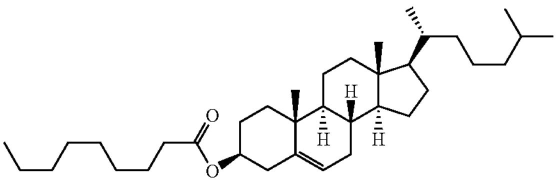

(Op-9)

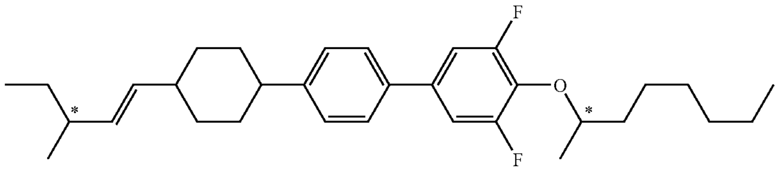

(Op-10)

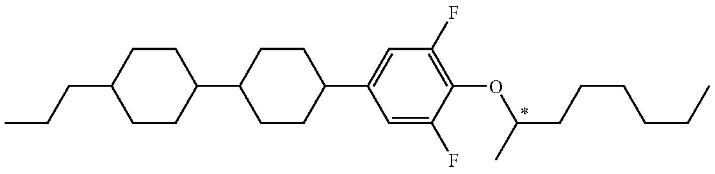

(Op-11)

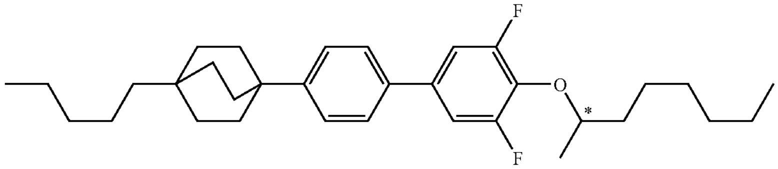

(Op-12)

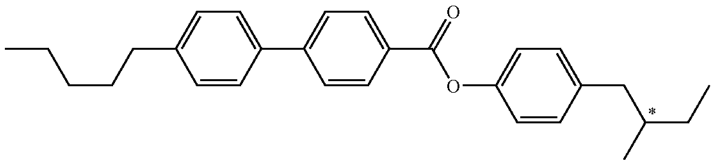

(Op-13)

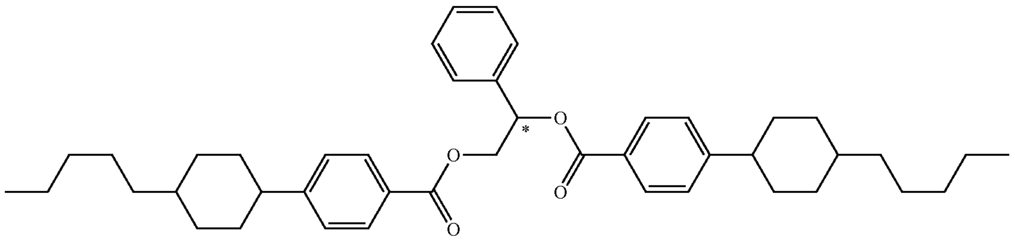

The optically active compounds added to the composition adjust the pitch of a twist. In compositions for TFT and TN, the pitch of the twist is desirably adjusted in the range of approximately 40 micrometers to approximately 200 micrometers. In a composition for STN, the pitch is desirably adjusted in the range of approximately 6 micrometers to approximately 20 micrometers. For a bistable TN device, the pitch is desirably adjusted in the range of approximately 1.5 micrometers to approximately 4 micrometers. At least two or more optically active compounds may be added for the purpose of adjusting the temperature dependence of the pitch.

The composition can also be used for a GH mode when a dichroic dye, such as a merocyanine compound, a styryl compound, an azo compound, an azomethine compound, an azoxy compound, a quinophthalone compound, an anthraquinone compound and a tetrazine compound, is added to the composition.

3. Device of the Invention

The third aspect of the invention is a liquid crystal display device using the composition comprising the compound (1). Examples of devices are those having operation modes described in the section of related art. Other examples are a nematic curvilinear aligned phase (NCAP) device made by microcapsulating liquid crystals and a polymer dispersed liquid crystal display device (PDLCD) in which a three-dimensional network polymer is formed in liquid crystals, such as a polymer network liquid crystal display device (PNLCD) Devices having relatively simple structures are shown in the following examples.

EXAMPLES

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention. The term of "%" means "% by weight" if not mentioned.

Compounds obtained were identified by means of nuclear magnetic resonance spectra obtained by using $^{1}$H-NMR analyses, gas chromatograms obtained by using gas chromatography (GC) analyses and so forth, and methods for analyses will be explained.

$^{1}$H-NMR analysis: A model DRX-500 apparatus (Bruker BioSpin Corporation) was used for measurement. Samples were dissolved in deuterated solvents such as $CDCl_3$ and so forth in which the samples were soluble, and measurement was carried out under the conditions of room temperature, twenty four times of accumulation and 500 MHz. In the explanation of NMR spectra, s, d, t, q, and m stand for singlet, doublet, triplet, quartet, and multiplet, respectively. Tetramethylsilane was used for the internal standard of chemical shift (δ values).

GC analysis: A Gas Chromatograph Model GC-14B made by Shimadzu Corporation was used for measurement. A capillary column CBP1-M25-025 (length 25 meters, bore 0.22 millimeters, film thickness micrometers, dimethylpolysiloxane as a stationary phase, non-polar) made by Shimadzu Corporation was used. The carrier gas was helium (1 ml per minute). The injector and the detector (FID) for samples were set up at 300° C.

A sample was dissolved in toluene preparing a 1% by weight solution, and 1 microliter of the solution was injected into the sample injector. The recorder used was a Chromatopac Model C-R6A made by Shimadzu Corporation or its equivalent. The resulting gas chromatogram recorded retention times of peaks and values of peak areas corresponding to component compounds.

Solvents for diluting the sample may also be chloroform, hexane, and so forth. The following capillary columns may also be used: DB-1 (length 30 meters, bore 0.32 millimeters, film thickness 0.25 micrometers) made by Agilent Technologies Inc., HP-1 (length 30 meters, bore 0.32 millimeters, film thickness 0.25 micrometers) made by Agilent Technologies Inc., Rtx-1 (length 30 meters, bore 0.32 millimeters, film thickness 0.25 micrometers) made by Restek Corporation, and BP-1 (length 30 meters, bore 0.32 millimeters, film thickness 0.25 micrometers) made by SGE International Pty. Ltd., and so forth.

The ratios of the amounts (% by weight) of the component compounds in compositions can be calculated based on values of each weight measured before a mixing. The ratios of the amount of component compounds in compositions once prepared can be obtained by means of gas chromatographic analyses. Although the internal and external standard methods using authentic samples are well known, the ratios of the amounts (% by weight) can also be calculated as described below. An area ratio of each peak in the gas chromatogram corresponds to the ratio of the amount of the component compound. Percentage by weight of the component compound is not completely identical to the area ratio of each peak. According to the invention, however, the ratio of the amounts (% by weight) of the component compound may be regarded as being identical to the area ratio of each peak, when the capillary columns described above are used, because there is no essential difference in the correction coefficient of the component compound.

[Samples of Compounds]

Two kinds of samples were used for measuring physical properties of compounds: one was a compound itself and the other was a mixture of the compound and mother liquid crystals.

When a sample was a mixture of the compound and the mother liquid crystals, measurement was carried out as follows. The sample was prepared by mixing 15% by weight of the compound obtained with 85% by weight of the mother liquid crystals. An extrapolated value was calculated from a measured value of the sample obtained, according to the method of extrapolation shown in the equation below, and described herein.

[Extrapolated Value]=(100×[Measured Value of Sample]−[% by Weight of Mother Liquid Crystals]×[Measured Value of Mother Liquid Crystals]/[% by Weight of Liquid Crystal Compound]

When a smectic phase (or crystals) separated out even at the ratio of the amount of the compound to the mother liquid crystals of (15% by weight/85% by weight) at 25° C., the ratio of the amount was changed step by step in the order of (10% by weight/90% by weight), (5% by weight/95% by weight), and (1% by weight/99% by weight). Measurement was carried out when the smectic phase (or the crystals) did not separate out at 25° C., and an extrapolated value was obtained according to the equation above.

There are a variety of mother liquid crystals for measurement and for example, the composition of the mother liquid crystals A (% by weight) is shown below.

Mother Liquid Crystals A:

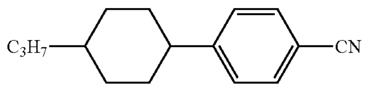

24%

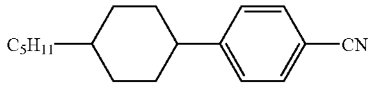

36%

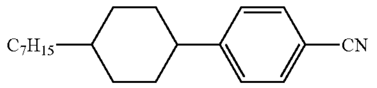

25%

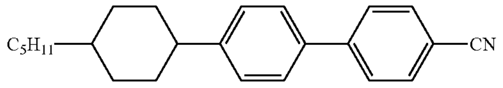

15%

[Measurement Method]

Measurement of the physical properties of compounds was carried out according to the following methods. Most methods are described in the Standard of Electric Industries Association of Japan, EIAJ·ED-2521 A or those with some modifications. No TFT was attached to a TN device used for measurement.

On values of physical properties, measured values were described as data when a sample was a liquid crystal compound itself. When the sample was a mixture of the compound and mother liquid crystals, values calculated from measured values by means of the extrapolating method were described as data. The compound itself was used for measurement of a phase structure and a phase transition temperature. The mixture of the compound and the mother liquid crystals A was used for other measurement.

Phase Structure: A sample (a compound) of a compound was placed on a hot plate in a melting point apparatus, a Hot Stage Model FP-52 made by Mettler Toledo International Inc., equipped with a polarizing microscope and was then heated at the rate of 3° C. per minute. The phase conditions and their changes were observed with the microscope and kinds of liquid crystal phases were determined.

Phase Transition Temperature (° C.): A sample (a compound) was heated and then cooled at the rate of 3° C. per minute using a Perkin-Elmer differential scanning calorimeter, a DSC-7 System or a Diamond DSC System. A starting point of an endothermic peak or an exothermic peak caused by a phase change of the sample was obtained by using the extrapolation and the phase transition temperature was determined.

In the following, the symbol C stand for crystals, which were expressed by $C_1$ and $C_2$ when kinds of the crystals were distinguishable. The symbols S, N and I stand for a smectic phase, a nematic phase and liquid (isotropic), respectively. When a smectic A phase, a smectic B phase, a smectic C phase, or a smectic F phase was distinguishable in the smectic phase, they were expressed as $S_A$, $S_B$, $S_C$, or $S_F$, respectively. Phase transition temperatures were expressed such as, for example, "C 50.0 N 100.0 I", which means that a phase transition temperature from crystals to a nematic phase (CN) was 50.0° C., a phase transition temperature from the nematic phase to liquid (NI) is 100.0° C.

Maximum Temperature of a Nematic Phase ($T_{NI}$ or NI; ° C.): A sample was placed on a hot plate in a melting point apparatus, a Hot Stage Model FP-52 made by Mettler Toledo International Inc., equipped with a polarizing microscope, and was observed during heating at the rate of 1° C. per minute. A temperature was measured when a part of the sample began to change from a nematic phase into liquid. A maximum temperature of a nematic phase may be abbreviated to "a maximum temperature."

Compatibility at Low Temperature: Samples were prepared by mixing a compound with mother liquid crystals so that the ratios of amounts of the compound became 20% by weight, 15% by weight, 5% by weight, 3% by weight, and 1% by weight, and placed in glass vials. After these glass vials had been kept in a freezer at −10° C. or −20° C. for a certain period, it was observed whether or not crystals or a smectic phase had been deposited.

Viscosity (η; measured at 20° C., mPa·s): Viscosity was measured by means of an E-type viscometer.

Optical Anisotropy (Δn; measured at 25° C.): Measurement was carried out with an Abbe refractometer equipped with a polarizing plate on an ocular, using light at a wavelength of 589 nm. The surface of a main prism was rubbed in one direction, and then a sample was dropped on the main prism. A refractive index (n‖) was measured when the direction of the polarized light was parallel to that of the rubbing. A refractive index (n⊥) was measured when the direction of the polarized light was perpendicular to that of the rubbing. The value of the optical anisotropy was calculated from the equation: Δn=n‖−n⊥.

Dielectric Anisotropy (Δ∈; measured at 25° C.): A sample was put in a TN device having a distance between two glass substrates (a cell gap) of 9 micrometers and a twist angle of 80 degrees. A voltage of 20 V was impressed onto the device, and a dielectric constant (∈‖) in a major axis direction of liquid crystal molecules was measured. A voltage of 0.5 was impressed onto the device, and a dielectric constant (∈⊥) in a minor axis direction of liquid crystal molecules was measured. The value of the dielectric anisotropy was calculated by using the equation: Δ∈=∈‖−∈⊥.

Example 1

Synthesis of 1-[difluoro(3,4,5-trifluorophenoxy)methyl]-4-[2-fluoro-4-(4'-pentyl-1,1'-bicyclohexane-4-yl)phenyl]cyclohexane (1-4-59)

No. 1-4-59

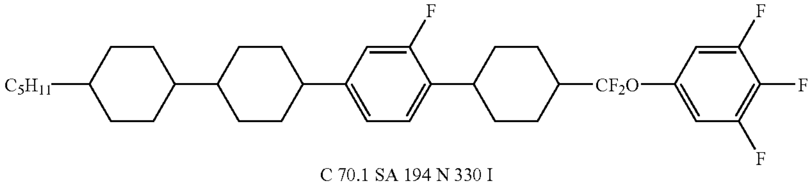

C 70.1 SA 194 N 330 I

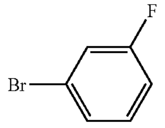

(T-1)

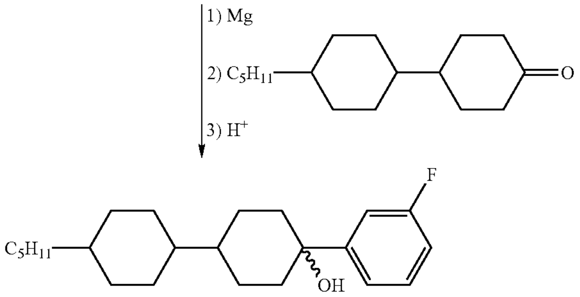

(T-2)

-continued
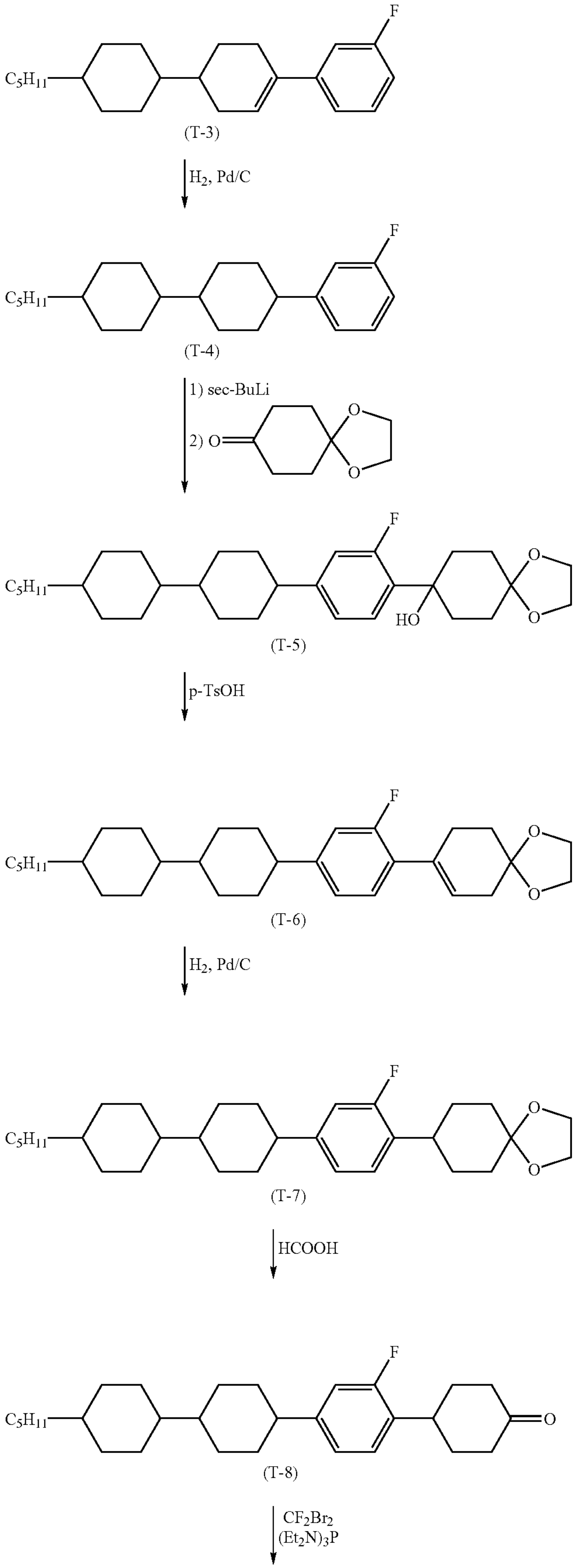

-continued

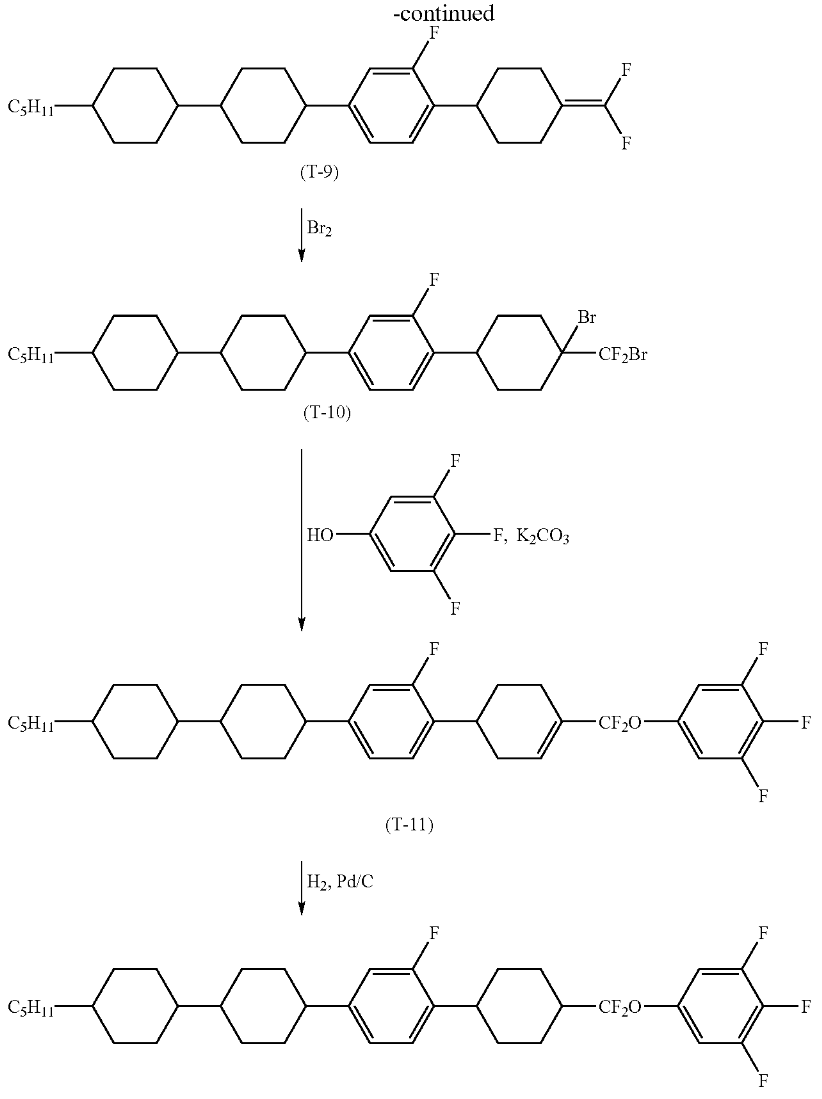

(T-9)

(T-10)

(T-11)

(No. 1-4-59)

[Synthesis of the Compound (T-2)]

Well-dried magnesium (8.34 g) and THF (10.0 ml) were placed in a reaction vessel under a nitrogen atmosphere and heated to 50° C. 3-Bromofluorobenzene (T-1) (50.0 g) dissolved in THF (50.0 ml) was slowly added dropwise to the vessel in the temperature range of 40° C. to 60° C., and the stirring was continued for another 60 minutes. To the Grignard reagent obtained, 4-(4-pentylcyclohexyl)cyclohexanone (85.9 g) in THF (180 ml) solution was added in the temperature range of 20° C. to 30° C., and the stirring was continued for another 180 minutes. After the reaction mixture had been poured into 1N-hydrochloric acid on an ice bath and mixed, organic and aqueous layers were separated by adding toluene (400 ml), and the aqueous layer was then extracted with toluene. The combined organic layers were washed with water and dried over anhydrous magnesium sulfate. Then, the solvent was distilled off under reduced pressure, leaving 1-(3-fluorophenyl)-4-(4-pentylcyclohexyl)cyclohexanol (T-2) (95.0 g).

[Synthesis of the Compound (T-3)]

The compound (T-2) (95.0 g), p-toluenesulfonic acid monohydrate (2.97 g) and toluene (300 ml) were put into a reaction vessel under a nitrogen atmosphere, and heated under reflux for 120 minutes while water being distilled was removed. After cooling to room temperature, toluene (120 ml) was added to the reaction mixture, which was washed sequentially with water, a saturated aqueous solution of sodium hydrogencarbonate and water, and then dried over anhydrous magnesium sulfate. The solution obtained was concentrated under reduced pressure and the residue was purified by means of column chromatography (silica gel; heptane), giving 1-(3-fluorophenyl)-4-(4-pentylcyclohexyl)cyclohexene (T-3) (66.4 g). The yield based on the compound (T-1) was 71%.

[Synthesis of the Compound (T-4)]

The compound (T-3) (66.4 g), palladium on carbon catalyst (NX type of 5% Pd/C (50% wet) made by N. E. Chemcat corp., which is referred to as Pd/C (NX type) hereinafter) (3.32 g), toluene (240 ml) and Solmix A-11 (240 ml) were put into a reaction vessel, and stirred under a hydrogen atmosphere at room temperature for 8 hours. After the catalyst had been removed by filtration, the reaction mixture was concentrated under reduced pressure. The residue was purified by means of column chromatography (silica gel; heptane) and then recrystallized from a mixed solvent of ethyl acetate/Solmix A-11, giving 4-(3-fluorophenyl)-4'-pentyl-1,1'-bicyclohexane(T-4) (39.8 g). The yield based on the compound (T-3) was 60%.

[Synthesis of the Compound (T-5)]

The compound (T-4) (20.0 g) and THF (450 ml) were put in a reaction vessel under a nitrogen atmosphere and cooled to −74° C. Sec-Butyl lithium (1.0 M, cyclohexane n-hexane solution) (64.0 ml) was added dropwise thereto in the temperature range of −74° C. to −68° C. and the stirring was continued for another 120 minutes. Then, 1,4-dioxaspiro[4,5]decane-8-one (11.3 g) in THF 120 ml) solution was added dropwise in the temperature range of −75° C. to −68° C., and allowed to react overnight while the reaction mixture was coming to room temperature. The reaction mixture thus obtained was poured into ice-water (600 ml) and mixed. Organic and aqueous layers were separated by adding toluene (600 ml), and the aqueous layer was extracted with toluene. The organic layers combined were washed sequentially with water, 1N-hydrochloric acid and water, and dried over anhydrous magnesium sulfate. Then, the solution obtained was concentrated under reduced pressure, giving 8-[2-fluoro-4-(4'-pentyl-1,1'-bicyclohexane-4-yl)phenyl]-1,4-dioxaspiro[4,5]decane-8-ol (T-5) (29.4 g).

[Synthesis of the Compound (T-6)]

The compound (T-5) (29.4g), p-toluenesulfonic acid monohydrate (1.47 g) and toluene (800 ml) were put in a reaction vessel under a nitrogen atmosphere, and heated under reflux for 120 minutes while water being distilled was removed. After cooling to room temperature, the reaction mixture was washed sequentially with water, a saturated aqueous solution of sodium hydrogencarbonate and water, and then dried over anhydrous magnesium sulfate. The solution obtained was concentrated under reduced pressure and the residue was purified by means of column chromatography (silica gel; toluene), giving 8-[2-fluoro-4-(4'-pentyl-1,1'-bicyclohexane-4-yl)phenyl]-1,4-dioxaspiro[4,5]decan-7-ene (T-6) (20.5 g). The yield based on the compound (T-4) was 72%.

[Synthesis of the Compound (T-7)]

The compound (T-6) (20.5 g), Pd/C (NX type) (1.03 g), toluene (200 ml) and IPA (200 ml) were put into a reaction vessel and stirred under hydrogen atmosphere for 8 hours. After the catalyst had been removed by filtration, the reaction mixture was concentrated under reduced pressure. The residue was purified by means of column chromatography (silica gel; heptane) and further recrystallized from a toluene/heptane mixed solvent, giving 8-[2-fluoro-4-(4'-pentyl-1,1'-bicyclohexane-4-yl)phenyl]-1,4-dioxaspiro[4,5]decane (T-7) (20.1 g). The yield based on the compound (T-6) was 99%.

[Synthesis of the Compound (T-8)]

The compound (T-7) (20.1 g), formic acid (100 ml) and toluene (400 ml) were put into a reaction vessel under a nitrogen atmosphere, and stirred under reflux for 3 hours. After the reaction mixture obtained had been allowed to come to 25° C., it was poured into ice-water (400 ml) and mixed. Organic and aqueous layers were separated by adding toluene (100 ml) and the aqueous layer was extracted with toluene. The organic layers combined were washed sequentially with water, a saturated aqueous solution of sodium hydrogencarbonate and water, and dried over anhydrous magnesium sulfate. The solution obtained was concentrated under reduced pressure and the residue was purified by means of column chromatography (silica gel; toluene/ethyl acetate), and then recrystallized from a mixed solvent of ethyl acetate/Solmix A-11, giving 4-[2-fluoro-4-(4'-pentyl-1,1'-bicyclohexane-4-yl)phenyl]cyclohexanone (T-8) (16.4 g). The yield based on the compound (T-7) was 88%.

[Synthesis of the Compound (T-9)]

Dibromodifluoromethane (16.2 g) and THF (30 ml) were put into a vessel under a nitrogen atmosphere and cooled to 10° C. Trisdiethylaminophosphine (38.2 g) in THF (50.0 ml) solution was added dropwise thereto and the stirring was continued for another 60 minutes. The compound (T-8) (16.5 g) in THF (400 ml) solution was then added dropwise in the temperature range of 20° C. to 35° C., and allowed to react overnight while the reaction mixture was coming to room temperature. The reaction mixture obtained was poured into ice-water (400 ml) and mixed. Organic and aqueous layers were separated by adding toluene (300 ml) and the aqueous layer was extracted with toluene. The organic layers combined were washed sequentially with water, 3N-hydrochloric acid and water, and dried over anhydrous magnesium sulfate. The solution was concentrated under reduced pressure and purified by means of column chromatography (silica gel; heptane/ethyl acetate), giving 4-[2-fluoro-4-(4'-pentyl-1,1'-bicyclohexane-4-yl)phenyl]difluoromethylenecyclohexane (T-9) (15.1 g). The yield based on the compound (T-8) was 85%.

[Synthesis of the Compound (T-10)]

The compound (T-9) (8.00 g) and chloroform (170 ml) were put into a reaction vessel under a nitrogen atmosphere and cooled to −10° C. Bromine (4.16 g) in chloroform (10.0 ml) solution was slowly added dropwise thereto and the stirring was continued for another 30 minutes. The reaction mixture obtained was washed sequentially with water, a saturated aqueous solution of sodium thiosulfate and water, and dried over anhydrous magnesium sulfate. The solution obtained was concentrated under reduced pressure and purified by means of column chromatography (silica gel; heptane/ethyl acetate), giving 1-bromo-1-bromodifluoromethyl-4-[2-fluoro-4-(4'-pentyl-1,1'-bicyclohexane-4-yl)phenyl]cyclohexane (T-10) (9.34 g). The yield based on the compound (T-9) was 86%.

[Synthesis of the Compound (T-11)]

3,4,5-Trifluorophenol (2.24 g), potassium carbonate (4.17 g), and N,N-dimethylformamide (DMF) (80.0 ml) were put into a reaction vessel under a nitrogen atmosphere and stirred at 115° C. for 30 minutes. Then, the compound (T-10) 9.34 g) in DMF (160 ml) solution was added dropwise and stirred for 2 hours at 115° C. After the reaction mixture had been allowed to come to 25° C., it was poured into ice-water (200 ml) and mixed. Organic and aqueous layers were separated by adding toluene (400 ml), and the aqueous layer was extracted with toluene. The organic layers combined were washed sequentially with water, 1N-hydrochloric acid and water, and dried over anhydrous magnesium sulfate. The obtained solution was concentrated under reduced pressure and the residue was purified by means of column chromatography (silica gel; a mixed solvent of heptane/Solmix A-11), giving 1-[difluoro(3,4,5-trifluorophenoxy)methyl]-4-[2-fluoro-4-(4'-pentyl-1,1'-bicyclohexane-4-yl)phenyl]cyclohexene (T-11) (3.44 g). The yield based on the compound (T-10) was 38%.

[Synthesis of the Compound (1-4-59)]

The compound (T-11) (3.00 g), palladium on carbon catalyst (5% Pd/C E type (50% wet) made by N. E. Chemcat corp., which is referred to as Pd/C (E type) hereinafter) (0.300 g), (toluene 30.0 ml) and IPA (30.0 ml) were put into a reaction vessel and stirred under a hydrogen atmosphere at 45° C., for 30 hours. After the catalyst had been removed by filtration, the reaction mixture was concentrated under reduced pressure. The residue was purified by means of column chromatography (silica gel; heptane), and further recrystallized from a mixed solvent of heptane/Solmix A-11, giving 1-[difluoro(3,4,5-trifluorophenoxy)methyl]-4-[2-fluoro-4-(4'-pentyl-1,1'-bicyclohexane-4-yl)phenyl]cyclohexane (1-4-59) (1.31 g). The yield based on the compound (T-11) was 44%.

Chemical shift δ (ppm) of $^1$H-NMR analysis was as follows and the obtained compound was identified as 1-[difluoro(3,4,5-trifluorophenoxy)methyl]-4-[2-fluoro-4-(4'-pentyl-1,1'-bicyclohexane-4-yl)phenyl]cyclohexane.

Chemical shift δ (ppm; $CDCl_3$); 7.11 (dd, J=7.95 Hz, J=7.95 Hz, 1H), 6.93 (dd, J=7.95 Hz, J=1.30 Hz, 1H), 6.90-6.82 (m, 3H), 2.88-2.79 (m, 1H), 2.41 (tt, J=12.2 Hz, J=3.20 Hz, 1H), 2.20-2.08 (m, 3H), 2.05-1.96 (m, 2H), 1.96-1.69 (m, 8H), 1.61-1.47 (m, 4H), 1.45-0.94 (m, 17H), 0.94-0.82 (m, 5H).

The phase transition temperature of the compound (1-4-59) obtained was as follows.

Phase transition temperature: C 70.1 $S_A$ 194 N 330 I.

Example 2

[Physical Properties of the Compound (1-4-59)]

Physical properties of the mother liquid crystals A described above were as follows.

Maximum temperature ($T_{NI}$)=71.7° C.; optical anisotropy (Δn)=0.137; dielectric anisotropy (Δ∈)=11.0.

The composition B consisting of 85% by weight of the mother liquid crystals A and 15% by weight of 1-[difluoro(3,4,5-trifluorophenoxy)methyl]-4-[2-fluoro-4-(4'-pentyl-1,1'-bicyclohexane-4-yl)phenyl]cyclohexane (1-4-59) obtained in Example 1 was prepared. Physical properties of the composition B were measured and the values of physical properties on the compound (1-4-59) were calculated by extrapolating the measured values. Results are as follows.

Maximum temperature ($T_{NI}$)=216° C.; optical anisotropy (Δn)=0.130; dielectric anisotropy (Δ∈)=6.77.

It was found from these results that the compound (1-4-59) had a relatively small optical anisotropy, a wide temperature range of liquid crystal phases was wide, and a quite high maximum temperature.

Example 3

Synthesis of 1-[difluoro(3,4,5-trifluorophenoxy)methyl]-4-(2-fluoro-4-[4-(5-pentyl-1,3-dioxane-2-yl)cyclohexyl]phenyl)cyclohexane (1-4-199)

No. 1-4-199

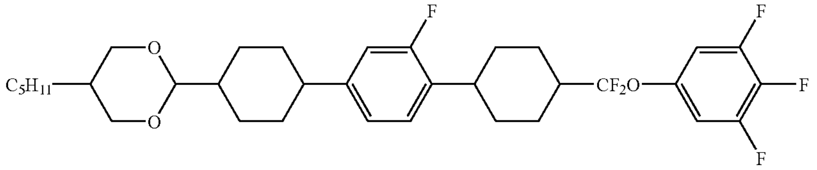

C 46.5 SA 222 N 301 I

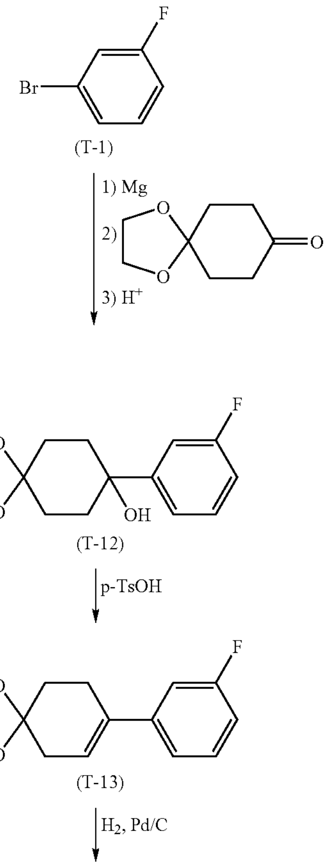

(T-1)

(T-12)

(T-13)

-continued
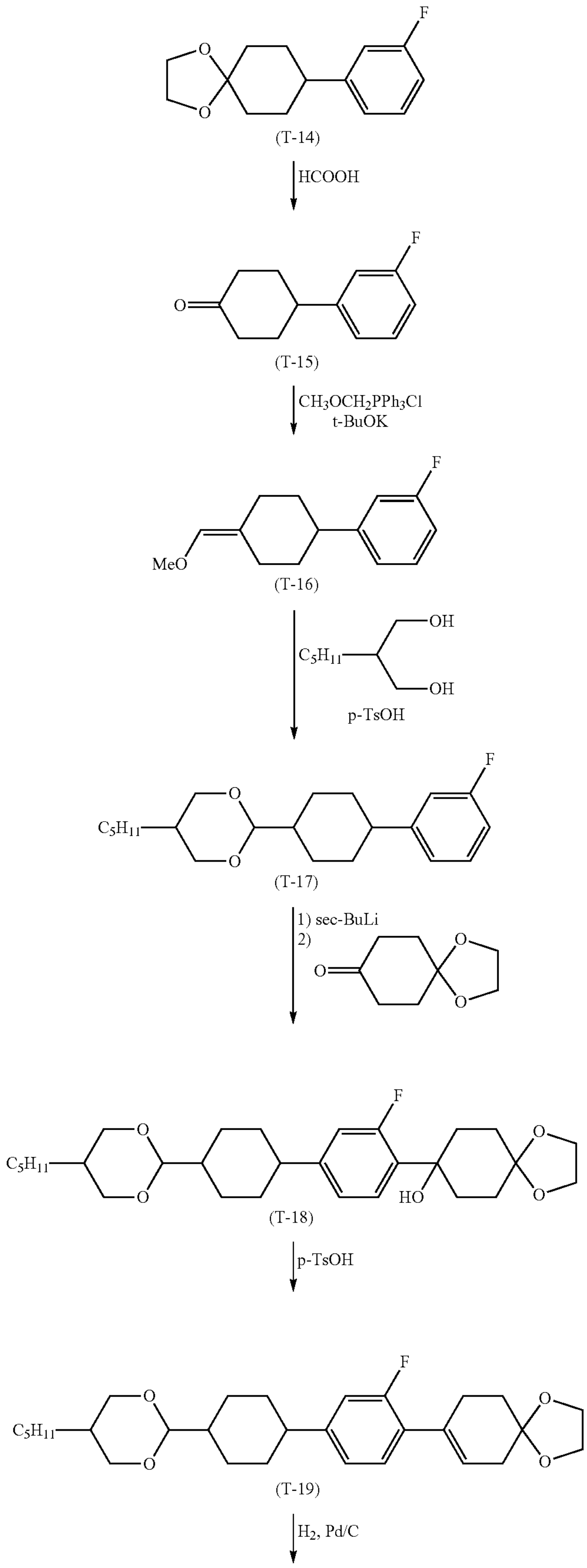

-continued

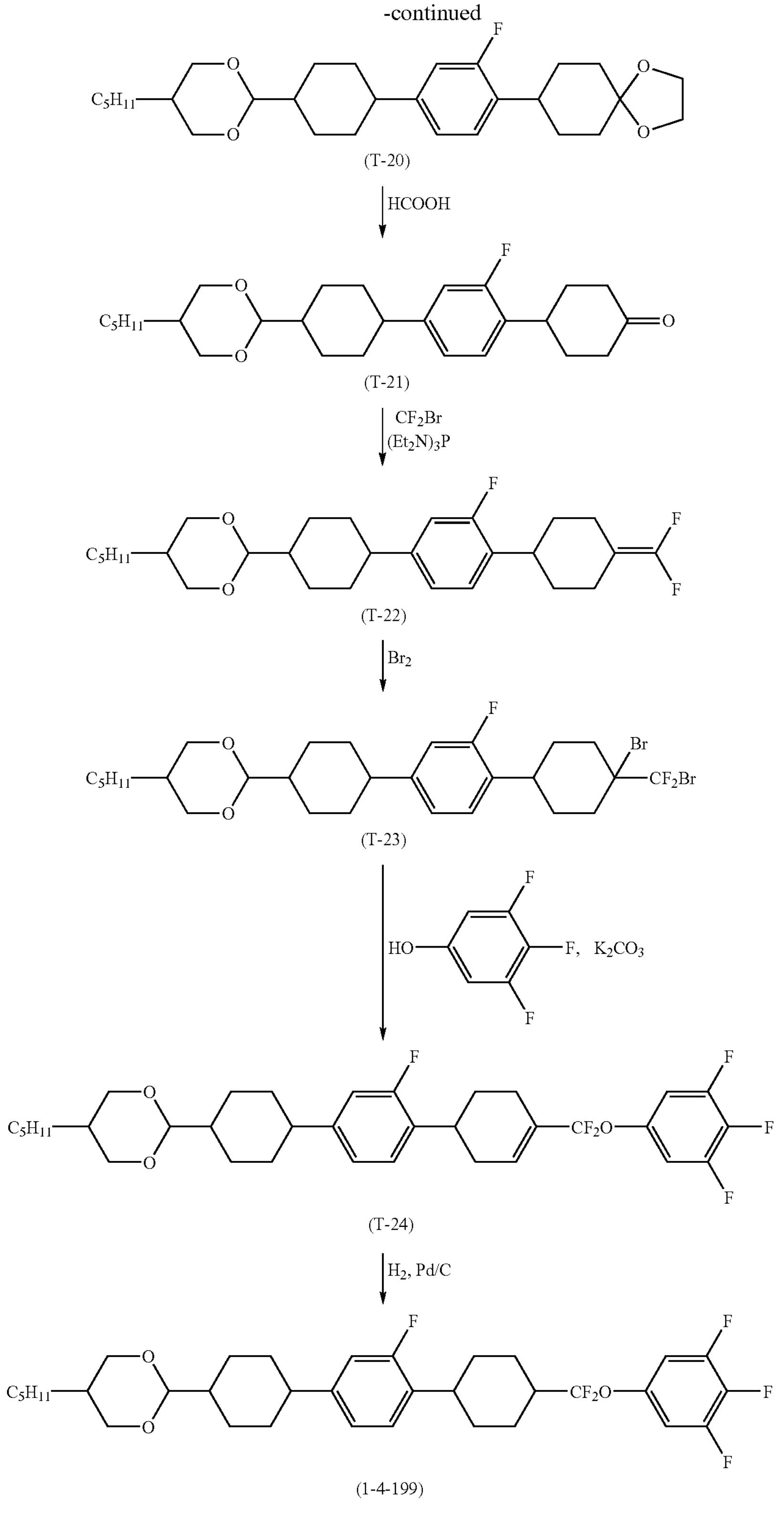

(T-20) (T-21) (T-22) (T-23) (T-24) (1-4-199)

[Synthesis of the Compound (T-12)]

Magnesium well dried (25.0 g) and THF (50.0 ml) were put into a reaction vessel under a nitrogen atmosphere, and heated up to 50° C. 3-Bromofluorobenzene (T-1) (150 g) dissolved in THF (150 ml) was slowly added dropwise thereto in the temperature range of 40° C. to 60° C. and the stirring was continued for another 60 minutes. To the obtained Grignard reagent, 1,4-dioxaspiro[4,5]decan-8-one (161 g) in THF (350 ml) solution was added dropwise in the temperature range of 20° C. to 30° C. and the stirring was continued for another 180 minutes. After the reaction mixture had been poured into 1N-hydrochloric acid on an ice bath and mixed, organic and aqueous layers were separated by adding toluene (600 ml). The aqueous layer was extracted with toluene. The organic layers were washed with water and dried over anhydrous magnesium sulfate. Then, the solvent was removed under reduced pressure, leaving 8-(3-fluorophenyl)-1,4-dioxaspiro[4,5]decan-8-ol (T-12) (210 g).

[Synthesis of the Compound (T-13)]

Using the compound (T-12) (210 g) above as a starting material, 8-(3-fluorophenyl)-1,4-dioxaspiro[4,5]decan-7-ene (T-13) (122 g) was obtained according to a method similar to that of the synthesis of the compound (T-3) in Example 1. The yield based on the compound (T-1) was 56%.

[Synthesis of the Compound (T-14)]

Using the compound (T-13) (100 g) above as a starting material, 8-(3-fluorophenyl)-1,4-dioxaspiro[4,5]decane (T-14) (99.5 g) was obtained according to a method similar to that of the synthesis of the compound (T-4) in Example 1. The yield based on the compound (T-13) was 99%.

[Synthesis of the Compound (T-15)]

The compound (T-14) (99.5 g), formic acid (500 ml) and toluene (500 ml) were put into a reaction vessel under a nitrogen atmosphere and heated to reflux for 3 hours. After the reaction mixture thus obtained had been allowed to come to 25° C., it was poured into ice-water (400 ml) and mixed. Organic and aqueous layers were separated by adding toluene (100 ml) and the aqueous layer was extracted with toluene. The organic layers obtained were washed sequentially with water, a saturated aqueous solution of sodium hydrogen carbonate and water, and dried over anhydrous magnesium sulfate. The obtained solution was concentrated under reduced pressure and purified by means of column chromatography (silica gel; toluene/ethyl acetate), giving 4-(3-fluorophenyl) cyclohexanone (T-15) (67.9 g). The yield based on the compound (T-14) was 84%.

[Synthesis of the Compound (T-16)]

Methoxymethyltriphenylphosphonium chloride (157 g) and THF (470 ml) were put into a reaction vessel under a nitrogen atmosphere and cooled to −30° C. Potassium t-butoxide (47.5 g) was added slowly thereto and the stirring was continued for 30 minutes. Then, the compound (T-15) (67.9 g) in THF (200 ml) solution was added dropwise in the temperature range of −30° C. to −25° C., and was allowed to react for 2 hours while the reaction mixture was coming to room temperature. The reaction mixture obtained was poured into ice-water (700 ml) and was mixed. Organic and aqueous layers were separated by adding toluene (700 ml). The aqueous layer was extracted with toluene and the organic layers combined were washed sequentially with water, 1N-hydrochloric acid, a saturated aqueous solution of sodium hydrogencarbonate and water and dried over anhydrous magnesium sulfate. The solution obtained was concentrated under reduced pressure and purified by means of column chromatography (silica gel; heptane/ethyl acetate), giving 4-(3-fluorophenyl)methoxymethylenecyclohexane (T-16) (77.1 g). The yield based on the compound (T-15) was 99%.

[Synthesis of the Compound (T-17)]

The compound (T-16) (72.1 g), 2-pentylpropane-1,3-diol (57.4 g), acetone (350 ml), and 6N-hydrochloric acid (70.0 ml) were put into a reaction vessel under a nitrogen atmosphere and heated to reflux for 4 hours. After the reaction mixture obtained had been allowed to come to 25° C., organic and aqueous layers were separated by adding toluene (300 ml) and the aqueous layer was extracted with toluene. The organic layers combined were washed sequentially with water, a saturated aqueous solution of sodium hydrogencarbonate and water, and dried over anhydrous magnesium sulfate. The solution thus obtained was concentrated under reduced pressure and the residue was purified by means of column chromatography (silica gel; heptane/ethyl acetate) and further recrystallized from a mixed solvent of heptane/Solmix A-11, giving 2-[4-(3-fluorophenyl)cyclohexyl]-5-pentyl-1,3-dioxane (T-17) (68.7 g). The yield based on the compound (T-16) was 63%.

[Synthesis of the Compound (T-18)]

Using the compound (T-17) (25.0 g) above as a starting material, 8-(2-fluoro-4-[4-(5-pentyl-1,3-dioxane-2-yl)cyclohexyl]phenyl)-1,4-dioxaspiro[4,5]decan-8-ol (T-18) (36.7 g) was obtained according to a method similar to that of the synthesis of the compound (T-5) in Example 1.

[Synthesis of the Compound (T-19)]

Using the compound (T-18) (36.7 g) above as a starting material, 8-(2-fluoro-4-[4-(5-pentyl-1,3-dioxane-2-yl)cyclohexyl]phenyl)-1,4-dioxaspiro[4,5]decan-7-ene (T-19) (25.7 g) was obtained according to a method similar to that of the synthesis of the compound (T-6) in Example 1. The yield based on the compound (T-17) was 73%.

[Synthesis of the Compound (T-20)]

Using the compound (T-19) (25.7 g) above as a starting material, 8-(2-fluoro-4-[4-(5-pentyl-1,3-dioxane-2-yl)cyclohexyl]phenyl)-1,4-dioxaspiro[4,5]decane (T-20) (22.8 g) was obtained according to a method similar to that of the synthesis of the compound (T-7) in Example 1. The yield based on the compound (T-19) was 89%.

[Synthesis of the Compound (T-21)]

The compound (T-20) (22.8 g), formic acid (68.0 ml) and toluene (680 ml) were put into a reaction vessel under a nitrogen atmosphere, and reacted at 40° C. for 5 hours. The reaction mixture obtained was poured into ice-water (500 ml) and mixed. Organic and aqueous layers were separated by adding toluene (300 ml) and the aqueous layer was extracted with toluene. The organic layers combined were washed sequentially with water, a saturated aqueous solution of sodium hydrogencarbonate and water, and dried over anhydrous magnesium sulfate. The solution thus obtained was concentrated under reduced pressure and the residue was purified by means of column chromatography (silica gel; heptane/ethyl acetate) and further recrystallized from a mixed solvent of heptane/Solmix A-11, giving 4-(2-fluoro-4-[4-(5-pentyl-1,3-dioxane-2-yl)cyclohexyl]phenyl)cyclohexanone (T-21) (12.6 g). The yield based on the compound (T-20) was 61%.

[Synthesis of the Compound (T-22)]

Using the compound (T-21) (12.6 g) above as a starting material, 4-(2-fluoro-4-[4-(5-pentyl-1,3-dioxane-2-yl)cyclohexyl]phenyl)difluoromethylenecyclohexane (T-22) (12.5 g) was obtained according to a method similar to that of the synthesis of the compound (T-9) in Example 1. The yield based on the compound (T-21) was 92%.

[Synthesis of the Compound (T-23)]

Using the compound (T-22) (12.5 g) above as a starting material, 1-bromo-1-bromodifluoromethyl-4-(2-fluoro-4-[4-(5-pentyl-1,3-dioxane-2-yl)cyclohexyl]phenyl)cyclohexane (T-23) (14.8 g) was obtained according to a method similar to that of the synthesis of the compound (T-10) in Example 1. The yield based on the compound (T-22) was 88%.

[Synthesis of the Compound (T-24)]

Using the compound (T-23) (14.8 g) above as a starting material, 1-[difluoro(3,4,5-trifluorophenoxy)methyl]-4-(2-fluoro-4-[4-(5-pentyl-1,3-dioxane-2-yl)cyclohexyl]phenyl) cyclohexene(T-24) (6.96 g) was obtained according to a method similar to that of the synthesis of the compound (T-11) in Example 1. The yield based on the compound (T-23) was 48%.

[Synthesis of the Compound (1-4-199)]

Using the compound (T-24) (3.00 g) obtained above as a starting material, 1-[difluoro(3,4,5-trifluorophenoxy)methyl]-4-(2-fluoro-4-[4-(5-pentyl-1,3-dioxane-2-yl)cyclohexyl]phenyl)cyclohexane (1-4-199) (1.01 g) was obtained according to a method similar to that of the synthesis of the compound (1-4-59) in Example 1. The yield based on the compound (T-24) was 34%.

Chemical shift δ (ppm) of $^1$H-NMR analysis was as follows and the compound obtained was identified as 1-[difluoro(3,4,5-trifluorophenoxy)methyl]-4-(2-fluoro-4-[4-(5-pentyl-1,3-dioxane-2-yl)cyclohexyl]phenyl)cyclohexane.

Chemical shift δ (ppm; $CDCl_3$); 7.10 (dd, J=7.95 Hz, J=7.95 Hz, 1H), 6.93 (dd, J=7.90 Hz, J=1.35 Hz, 1H), 6.90-6.82 (m, 3H), 4.21 (d, J=5.20 Hz, 1H), 4.09 (dd, J=11.5 Hz, J=4.50 Hz, 2H), 3.30 (dd, J=11.4 Hz, J=11.4 Hz, 2H), 2.88-2.77 (m, 1H), 2.44 (tt, J=12.0, J=2.95 Hz, 1H), 2.20-2.07 (m, 3H), 2.04-1.89 (m, 7H), 1.63-1.46 (m, 5H), 1.46-1.35 (m, 2H), 1.35-1.18 (m, 8H), 1.07-0.98 (m, 2H), 0.88 (t, J=7.05 Hz, 3H).

The phase transition temperature of the compound (1-4-199) obtained was as follows.

Phase transition temperature: C 46.5 $S_A$ 222 N 301 I.

Example 4

[Physical Properties of the Compound (1-4-199)]

The composition C consisting of 85% by weight of the mother liquid crystals A and 15% by weight of 1-[difluoro(3,4,5-trifluorophenoxy)methyl]-4-(2-fluoro-4-[4-(5-pentyl-1,3-dioxane-2-yl)cyclohexyl]phenyl)cyclohexane (1-4-199) obtained in Example 3 was prepared. Physical properties of the composition C obtained were measured and the values of physical properties on the compound (1-4-199) were calculated by extrapolating the measured values. The results were as follows.

Maximum temperature ($T_{NI}$)=192° C.; optical anisotropy (Δn)=0.124; dielectric anisotropy (Δ∈)=16.8.

From these results, it was found that the compound (1-4-199) had a relatively small optical anisotropy, a wide temperature range of liquid crystal phases, a high maximum temperature, and a large dielectric anisotropy.

Example 5

Synthesis of 1-[difluoro(3-fluoro-4-[trifluoromethoxy]phenoxy)methyl]-4-[2-fluoro-4-(4'-pentyl-1,1'-bicyclohexane-4-yl)phenyl]cyclohexane (1-4-66)

No. 1-4-66

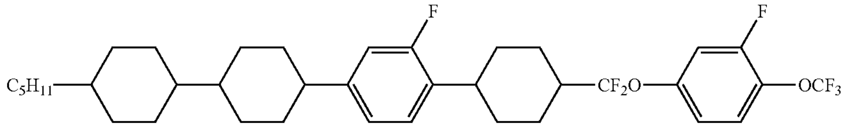

C 59.0 SA 245 N 343 I

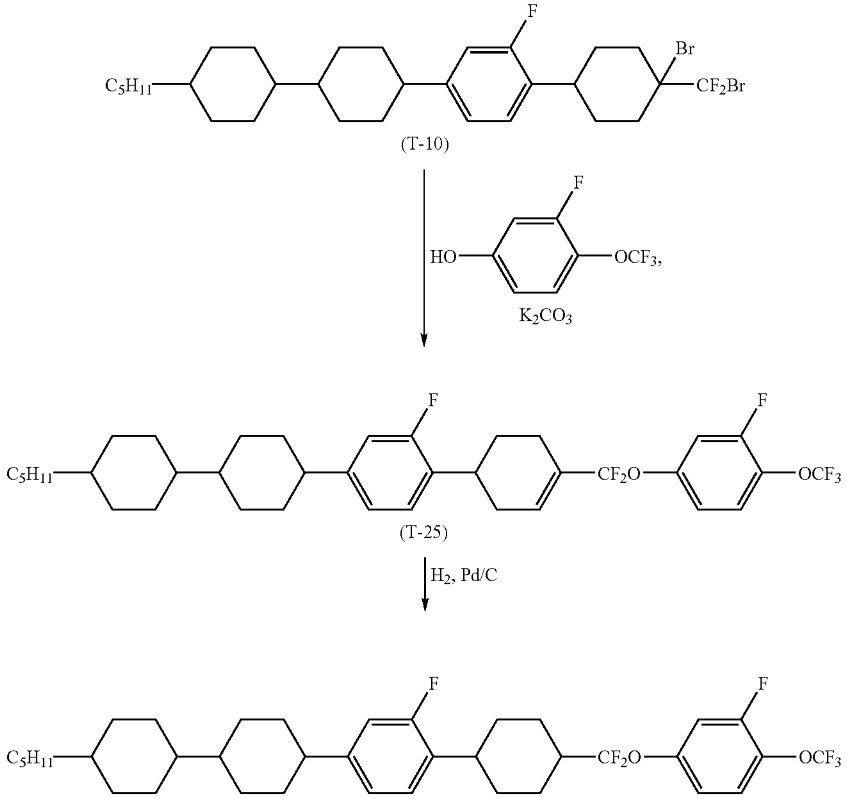

[Synthesis of the Compound (T-25)]

3-Fluoro-4-(trifluoromethoxy)phenol (3.04 g), potassium carbonate (3.57 g), and N,N-dimethylformamide (DMF) (30.0 ml) were poured into a reaction vessel under a nitrogen atmosphere and stirred at 100° C. for 30 minutes. Then, the compound (T-10) (8.00 g) in DMF (130 ml) solution was added dropwise and stirred at 100° C. for 2 hours. After the reaction mixture had been allowed to come to 25° C., it was added to ice-water (200 ml) and organic and aqueous layers were separated by adding toluene (400 ml). The organic layer obtained was washed sequentially with water, a saturated aqueous solution of sodium thiosulfate and water, and dried over anhydrous magnesium sulfate. The solution obtained was concentrated under reduced pressure and the residue was purified by means of column chromatography (silica gel; heptane), and further recrystallized from a mixed solvent of heptane/Solmix A-11, giving 1-[difluoro(3-fluoro-4-[trifluoromethoxy]phenoxy)methyl]-4-[2-fluoro-4-(4'-pentyl-1,1'-bicyclohexane-4-yl)phenyl]cyclohexene (T-25) (4.28 g). The yield based on the compound (T-10) was 51%.

[Synthesis of the Compound (1-4-66)]

Using the compound (T-25) (4.28 g) obtained above as a starting material, 1-[difluoro(3-fluoro-4-[trifluoromethoxy]phenoxy)methyl]-4-[2-fluoro-4-(4'-pentyl-1,1'-bicyclohexane-4-yl)phenyl]cyclohexane (1-4-66) (2.38 g) was obtained by a method similar to that of the synthesis of the compound (1-4-59) in Example 1. The yield based on the compound (T-25) was 55%.

Chemical shift δ (ppm) of $^{1}H$-NMR analysis was as follows and the obtained compound was identified as 1-[difluoro(3-fluoro-4-[trifluoromethoxy]phenoxy)methyl]-4-[2-fluoro-4-(4'-pentyl-1,1'-bicyclohexane-4-yl)phenyl]cyclohexane.

Chemical shift δ (ppm; $CDCl_3$); 7.32-7.23 (m, 1H), 7.14-7.06 (m, 2H), 6.99(d, J=9.05 Hz, 1H), 6.93 (dd, J=7.75 Hz, J=1.25 Hz, 1H), 6.86 (dd, J=12.0 Hz, J=1.30 Hz, 1H), 2.88-2.79 (m, 1H), 2.41 (tt, J=12.2 Hz, J=3.20 Hz, 1H), 2.20-2.08 (m, 3H), 2.05-1.96 (m, 2H), 1.96-1.69 (m, 8H), 1.64-1.47 (m, 4H), 1.45-0.94 (m, 17H), 0.94-0.82 (m, 5H).

The phase transition temperature of the compound (1-4-66) obtained was as follows.

Phase transition temperature: C 59.0 $S_A$ 245 N 343 I.

Example 6

[Physical Properties of the Compound (1-4-66)]

The composition F consisting of 85% by weight of the mother liquid crystals A and 15% by weight of 1-[difluoro(3-fluoro-4-[trifluoromethoxy]phenoxy)methyl]-4-[2-fluoro-4-(4'-pentyl-1,1'-bicyclohexane-4-yl)phenyl]cyclohexane (1-4-66) obtained in Example 5 was prepared. Physical properties of the composition F obtained were measured and extrapolated values of the compound (1-4-66) were calculated by extrapolating the measured values. The results were as follows.

Maximum temperature ($T_{NI}$)=214° C.; optical anisotropy (Δn)=0.130; dielectric anisotropy (Δ∈)=2.37.

From these results, it was found that the compound (1-4-66) had a relatively small optical anisotropy, a quite wide temperature range of liquid crystal phases and a high maximum temperature.

Example 7

Synthesis of 1-[difluoro[(2,3',4',5'-tetrafluoro-1,1'-biphenyl-4-yl)oxy]methyl]-4-[2-fluoro-4-(4-pentyl-cyclohexyl)phenyl]cyclohexane (1-3-171)

No. 1-3-171

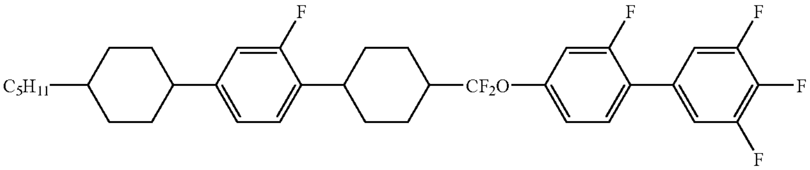

C 70.1 N. 287 I

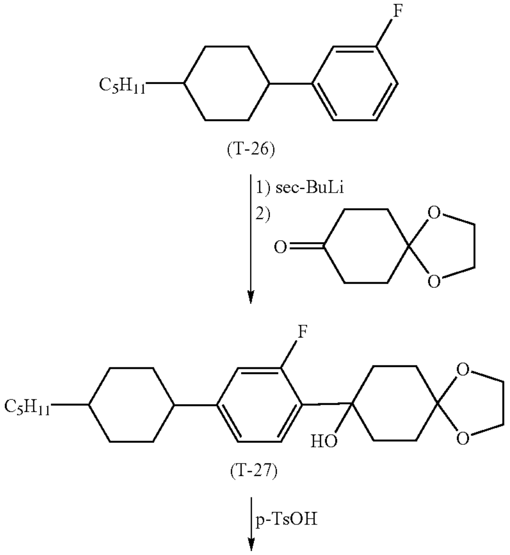

(T-26)

(T-27)

-continued
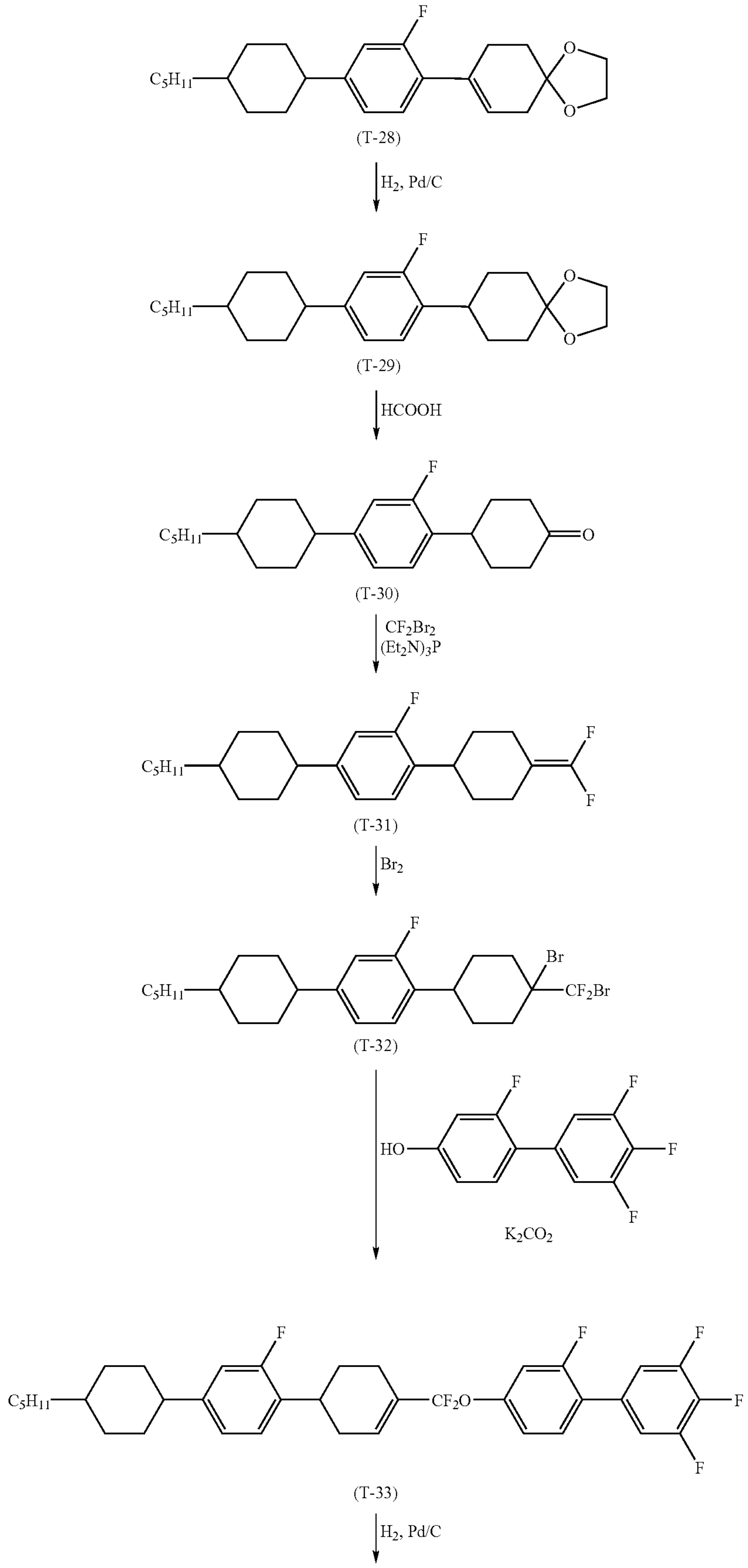

-continued

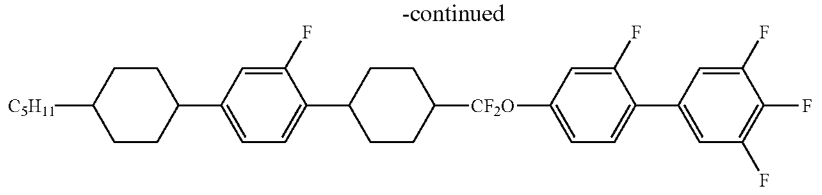

(No. 1-3-171)

[Synthesis of the Compound (T-27)]

Using 4-(3-fluorophenyl)pentylcyclohexane (T-26) (30.0 g) as a starting material, 8-[2-fluoro-4-(4-pentylcyclohexyl) phenyl]-1,4-dioxospiro[4,5]decan-8-ol (T-27) (49.0 g) was obtained by a method similar to that of the synthesis of the compound (T-5) in Example 1.

[Synthesis of the Compound (T-28)]

Using the compound (T-27) (49.0 g) obtained above as a starting material, 8-[2-fluoro-4-(4-pentylcyclohexyl)phenyl]-1,4-dioxaspiro[4,5]decan-7-ene (T-28) (40.2 g) was obtained by a method similar to that of the synthesis of the compound (T-6) in Example 1. The yield based on the compound (T-26) was 86%.

[Synthesis of the Compound (T-29)]

Using the compound (T-28) (40.2 g) obtained above as a starting material, 8-[2-fluoro-4-(4-pentylcyclohexyl)phenyl]-1,4-dioxaspiro[4,5]decane (T-29) (34.8 g) was obtained by a method similar to that of the synthesis of the compound (T-7) in Example 1. The yield based on the compound (T-28) was 86%.

[Synthesis of the Compound (T-30)]

Using the compound (T-29) (34.8 g) obtained above as a starting material, 4-[2-fluoro-4-(4-pentylcyclohexyl)phenyl] cyclohexanone (T-30) (19.4 g) was obtained by a method similar to that of the synthesis of the compound (T-8) in Example 1. The yield based on the compound (T-29) was 63%.

[Synthesis of the Compound (T-31)]

Using the compound (T-30) (15.0 g) obtained above as a starting material, 4-[2-fluoro-4-(4-pentylcyclohexyl)phenyl] difluoromethylenecyclohexane (T-31) 15.6 g) was obtained by a method similar to that of the synthesis of the compound (T-9) in Example 1. The yield based on the compound (T-30) was 95%.

[Synthesis of the Compound (T-32)]

Using the compound (T-31) (15.6 g) obtained above as a starting material, 1-bromo-1-bromodifluoromethyl-4-[2-fluoro-4-(4-pentylcyclohexyl)phenyl]cyclohexane (T-32) (18.8 g) was obtained by a method similar to that of the synthesis of the compound (T-10) in Example 1. The yield based on the compound (T-31) was 85%.

[Synthesis of the Compound (T-33)]

4-Hydroxy-2,3',4',5'-tetrafluoro-1,1'-biphenyl (3.98 g), potassium carbonate (3.79 g), N,N-dimethylformamide (DMF; 50.0 ml) were put into a reaction vessel under a nitrogen atmosphere and stirred at 100° C. for 30 minutes. Then, the compound (T-32) (7.37 g) in DMF (100 ml) solution was added dropwise and the stirring was continued for 2 hours at 100° C. After the reaction mixture had been allowed to come to 25° C., it was added to ice-water (150 ml) and mixed. Organic and aqueous layers were separated by adding toluene (300 ml), and the aqueous layer was extracted with toluene. The organic layers combined were washed sequentially with water, a saturated aqueous solution of sodium thiosulfate and water, and dried over anhydrous magnesium sulfate. The obtained solution was concentrated under reduced pressure and the residue was purified by means of column chromatography (silica gel; heptane), and further recrystallized from a mixed solvent of ethyl acetate/Solmix A-11, giving 1-[difluoro[(2,3',4',5'-tetrafluoro-1,1'-biphenyl-4-yl)oxy]methyl]-4-[2-fluoro-4-(4-pentylcyclohexyl)phenyl]cyclohexene (T-33) (5.33 g). The yield based on the compound (T-32) was 63%.

[Synthesis of the Compound (1-3-171)]

Using the compound (T-33) (5.33 g) obtained above as a starting material, 1-[difluoro[(2,3',4',5'-tetrafluoro-1,1'-biphenyl-4-yl)oxy]methyl]-4-[2-fluoro-4-(4-pentylcyclohexyl)phenyl]cyclohexane (1-3-171) (2.87 g) was obtained by a method similar to that of the synthesis of the compound (1-4-59) in example 1. The yield based on the compound (T-33) was 54%.

Chemical shift δ (ppm) of $^1$H-NMR analysis was as follows and the obtained compound was identified as 1-[difluoro[(2,3',4',5'-tetrafluoro-1,1'-biphenyl-4-yl)oxy]methyl]-4-[2-fluoro-4-(4-pentylcyclohexyl)phenyl]cyclohexane.

Chemical shift δ (ppm; $CDCl_3$); 7.38-7.30 (m, 1H), 7.19-7.03 (m, 5H), 6.94 (dd, J=8.10 Hz, J=1.50 Hz, 1H), 6.87 (dd, J=12.0 Hz, J=1.20 Hz, 1H), 2.85 (tt, J=11.6 Hz, J=3.45 Hz, 1H), 2.43 (tt, J=12.2 Hz, J=3.05 Hz, 1H), 2.25-2.11 (m, 3H), 2.05-1.97 (m, 2H), 1.92-1.82 (m, 4H), 1.66-1.50 (m, 4H), 1.46-1.18 ( m, 11H), 1.09-0.98 (m, 2H), 0.90 (t, J=7.15 Hz, 3H).

The phase transition temperature of the compound (1-3-171) obtained was as follows.

Phase transition temperature: C 70.1 N 287 I.

Example 8

[Physical Properties of the Compound (1-3-171)]

The composition G consisting of 85% by weight and the mother liquid crystals A and 15% by weight of 1-[difluoro[(2,3',4',5'-tetrafluoro-1,1'-biphenyl-4-yl)oxy]methyl]-4-[2-fluoro-4-(4-pentylcyclohexyl)phenyl]cyclohexane (1-3-171) obtained in Example 7 was prepared. Physical properties of the composition G were measured and the values obtained were extrapolated giving an extrapolated value of the compound (1-3-171). The results were as follows.

Maximum temperature ($T_{NI}$)=180° C.; optical anisotropy (Δn)=0.150; dielectric anisotropy (Δ∈)=18.3.

From these results, it was found that the compound (1-3-171) had a wide temperature range of liquid crystal phases and a large dielectric anisotropy.

Example 9
Synthesis of 1-[difluoro[(3',3",4",5"-tetrafluoro[1,1',4',1"-terphenyl]-4-yl)oxy]methyl]-4-(5-pentyl-1,3-dioxane-2-yl)cyclohexane (1-2-8)
No. 1-2-8
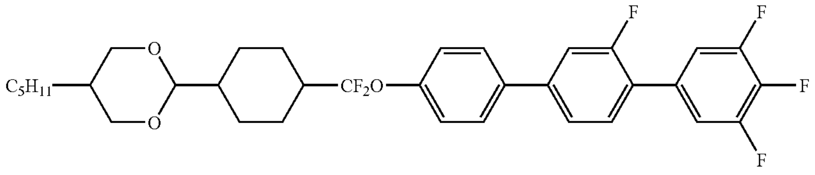
C 860.0 SA 140 N 263 I
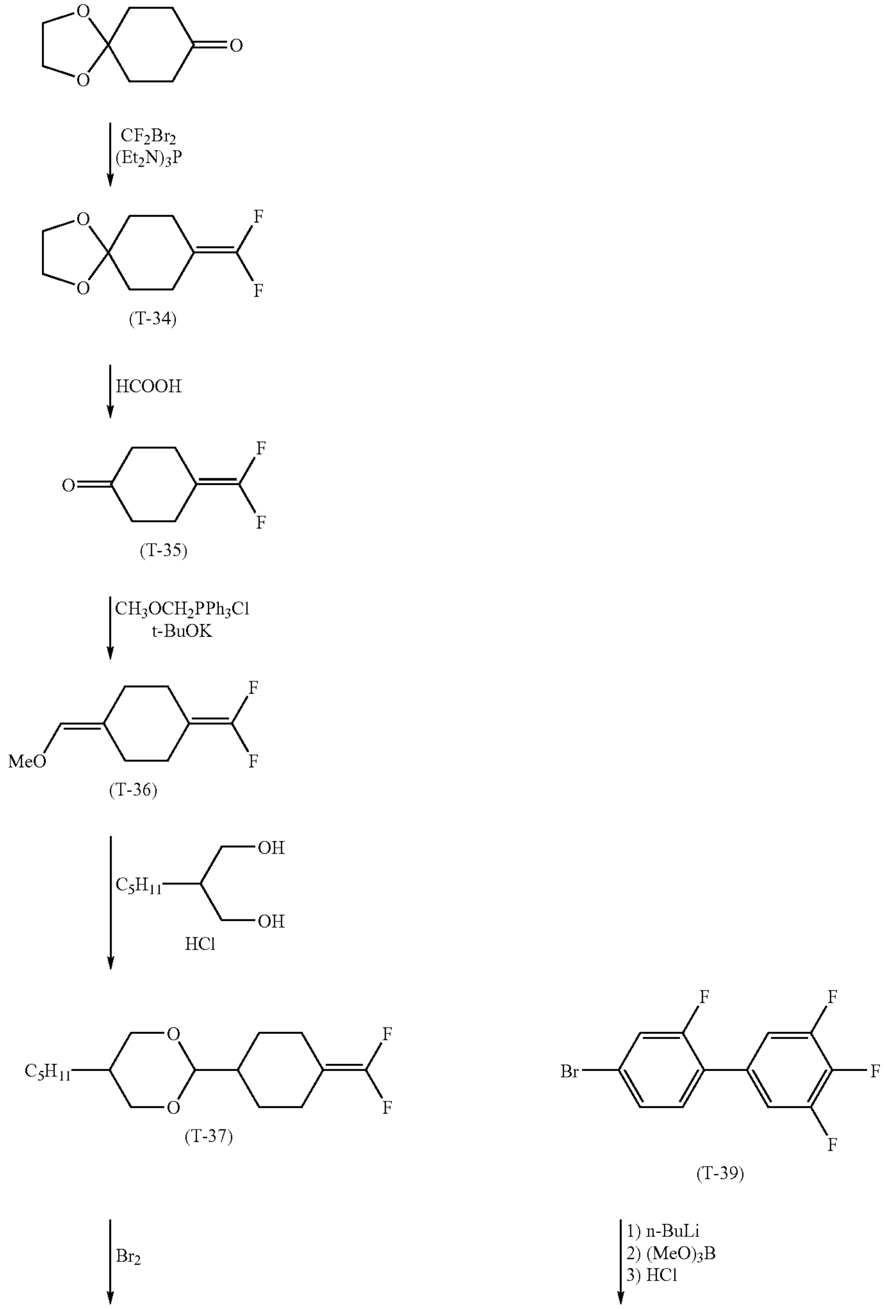

-continued

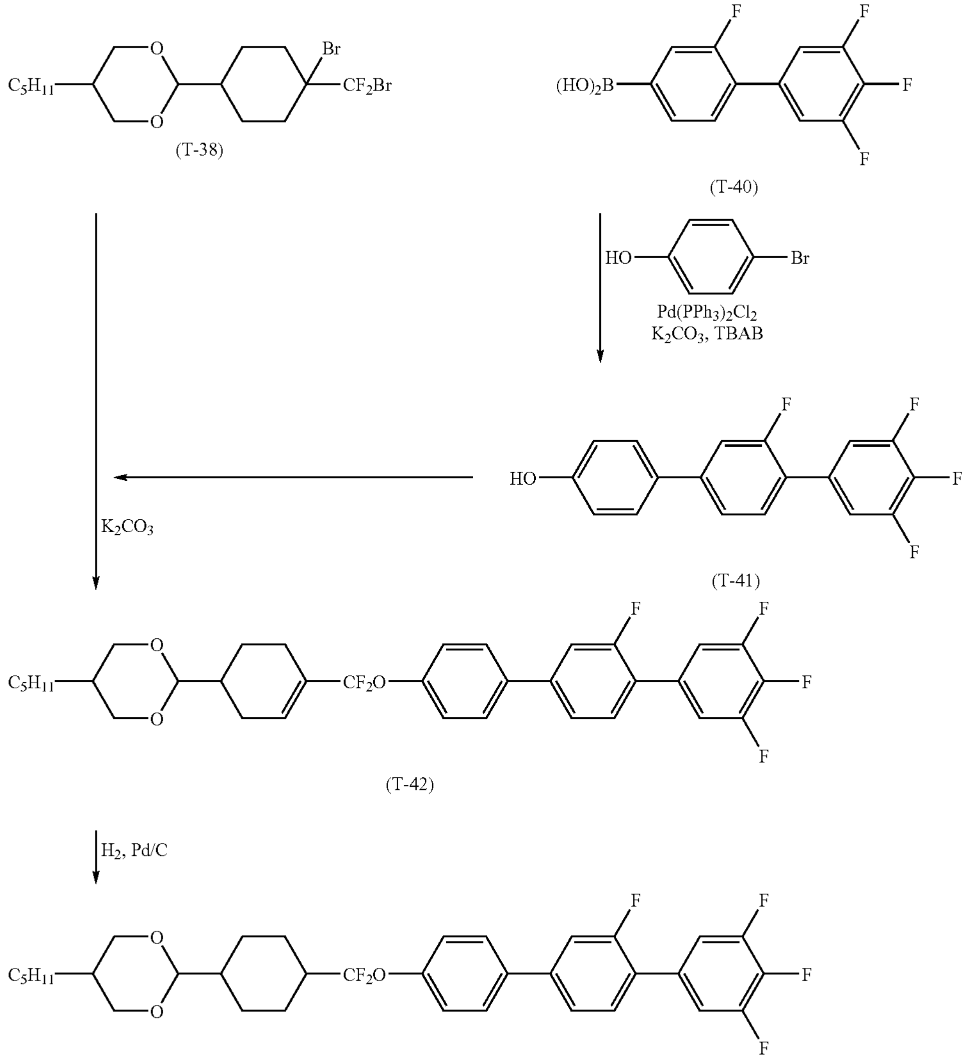

(T-38)

(T-40)

(T-41)

(T-42)

(No. 1-2-8)

[Synthesis of the Compound (T-34)]

Using 1,4-dioxaspiro[4,5]decan-8-one (50.0 g) as a starting material, 8-difluoromethylene-1,4-dioxaspiro[4,5]decane (T-34) (49.3 g) was obtained by a method similar to that of the synthesis of the compound (T-9) in Example 1. The yield based on 1,4-dioxaspiro[4,5]decan-8-one was 81%.

[Synthesis of the Compound (T-35)]

Using the compound (T-34) (49.3 g) obtained above as a starting material, 4-difluoromethylenecyclohexanode (T-35) (37.8 g) was obtained by a method similar to that of the synthesis of the compound (T-15) in Example 3.

[Synthesis of the Compound (T-36)]

Using the compound (T-35) (37.8 g) obtained above as a starting material, 4-difluoromethylene-1-methoxymethylenecyclohexane (T-36) (40.6 g) was obtained by a method similar to that of the synthesis of the compound (T-16) in Example 3. The yield based on the compound (T-34) was 90%.

[Synthesis of the Compound (T-37)]

Using the compound (T-36) (12.0 g) obtained above as a starting material, 2-(4-difluoromethylenecyclohexyl)-5-pentyl-1,3-dioxane (T-37) (9.57 g) was obtained by a method similar to that of the synthesis of the compound (T-17) in Example 3. The yield based on the compound (T-36) was 48%.

[Synthesis of the Compound (T-38)]

Using the compound (T-37) (9.57 g) obtained above as a starting material, 1-bromo-1-bromodifluoromethyl-4-(5-pentyl-1,3-dioxane-2-yl)cyclohexane (T-38) (13.5 g) was obtained by a method similar to that of the synthesis of the compound (T-10) in Example 1. The yield based on the compound (T-37) was 91%.

[Synthesis of the Compound (T-40)]

4-Bromo-2,3',4',5'-tetrafluoro-1,1'-biphenyl (T-39) (12.0 g) and diethyl ether (220 ml) were put into a reaction vessel under a nitrogen atmosphere and cooled to −74° C. 1.57M of n-butyl lithium in n-hexane solution (31.5 ml) was added dropwise thereto in the temperature range of −74° C. to −68° C. and stirred another 120 minutes. Then, trimethyl borate (6.70 ml) in THF (20 ml) solution was added dropwise in the temperature range of −75° C. to −68° C. and the stirring was continued for another 180 minutes while the reaction mixture was allowed to come to 25° C. Then, the reaction mixture was cooled to −30° C. and 6N-hydrochloric acid (40 ml) was slowly added dropwise thereto, and the mixture was stirred for another 180 minutes. After the reaction thus obtained had been allowed to come to 25° C., it was poured into ice-water (200 ml) and mixed. Organic and aqueous layers were separated by adding ethyl acetate 200 ml). The aqueous layer was extracted with toluene. The organic layers combined were washed sequentially with water, a saturated aqueous solution of sodium hydrogencarbonate and brine, and dried over anhydrous magnesium sulfate. Then, the solvent was distilled off under reduced pressure and 2,3',4',5'-tetrafluoro-1,1'-biphenylboronic acid (T-40) (8.91 g) was obtained. The yield based on the compound (T-39) was 85%.

[Synthesis of the Compound (T-41)]

4-Bromophenol (5.56 g), 2,3',4',5'-tetrafluoro-1,1'-biphenylboronic acid (T-40) (5.00 g), potassium carbonate (8.13 g), $Pd(Ph_3P)_2Cl_2$ (0.413 g), and 2-propanol (100 ml) were put in a reaction vessel under a nitrogen atmosphere and heated under reflux for 5 hours. After the reaction mixture had been allowed to come to 25° C., it was poured into water (100 ml) and toluene (100 ml) and mixed. Then, the mixture was allowed to stand, separating into two of organic and aqueous layers, and the aqueous layer was extracted with toluene. The organic layers combined were washed with water and dried over anhydrous magnesium sulfate. The solution obtained was concentrated under reduced pressure and the residue was purified by means of column chromatography (silica gel; toluene), and further recrystallized from a mixed solvent of heptane/Solmix A-11, giving 4-hydroxy-3',3",4",5"-tetrafluoro-1,1',4',1"-terphenyl (T-41) (4.00 g). The yield based on the compound (T-40) was 56%.

[Synthesis of the Compound (T-42)]

The compound (T-41) (4.00 g) obtained above, potassium carbonate (4.34 g), N,N-dimethylformamide (DMF; 50.0 ml) were put into a reaction vessel under a nitrogen atmosphere, and stirred at 90° C. for 30 minutes. Then, the compound (T-38) (4.71 g) in DMF (30 ml) solution was added dropwise and stirred at 90° C. for 3 hours. After the reaction mixture had been allowed to come to 25° C., it was added to ice-water (100 ml) and mixed. Organic and aqueous layers were separated by adding toluene (200 ml), and the aqueous layer was extracted with toluene. The organic layers combined were washed sequentially with water, a saturated aqueous solution of sodium thiosulfate and water, and dried over anhydrous magnesium sulfate. The obtained solution was concentrated under reduced pressure and the residue was purified by means of column chromatography (silica gel; heptane), and further recrystallized from a mixed solvent of ethyl acetate/Solmix A-11, giving 1-[difluoro[(3',3",4",5"-tetrafluoro[1,1',4',1"-terphenyl]-4-yl)oxy]methyl]-4-(5-pentyl-1,3-dioxane-2-yl) cyclohexene (T-42) (2.20 g). The yield based on the compound (T-38) was 35%.

[Synthesis of the Compound (1-2-8)]

Using the compound (T-42) (2.20 g) obtained above as a starting material, 1-[difluoro[(3',3",4",5"-tetrafluoro[1,1',4',1"-terphenyl]-4-yl)oxy]methyl]-4-(5-pentyl-1,3-dioxane-2-yl)cyclohexane (1-2-8) (0.91 g) was obtained by a method similar to that of the synthesis of the compound (1-4-59) in Example 1. The yield based on the compound (T-42) was 41%.

Chemical shift δ (ppm) of $^1$H-NMR analysis was as follows and the obtained compound was identified as 1-[difluoro[(3',3",4",5"-tetrafluoro[1,1',4',1"-terphenyl]-4-yl)oxy]methyl]-4-(5-pentyl-1,3-dioxane-2-yl)cyclohexane.

Chemical shift δ (ppm; $CDCl_3$); 7.60-7.53 (m, 2H), 7.47-7.40 (m, 2H), 7.37 (d, J=12.5 Hz, 1H), 7.29-7.19 (m, 4H), 4.21 (d, J=5.15 Hz, 1H), 4.09 (dd, J=11.5 Hz, J=4.50 Hz, 2H), 3.29 (dd, J=11.3 Hz, J=11.3 Hz, 2H), 2.15-1.91 (m, 6H), 1.63-1.51 (m, 1H), 1.46-1.34 (m, 2H), 1.34-1.22 (m, 6H), 1.21-1, 10 (m, 2H), 1.07-0.98 (m, 2H), 0.88 (t, J=6.80 Hz, 3H).

The phase transition temperature of the compound (1-2-8) obtained was as follows.

Phase transition temperature: C 86.0 $S_A$ 140 N 263 I.

Example 10

[Physical Properties of the Compound (1-2-8)]

The composition H consisting of 85% by weight of the mother liquid crystals A and 15% by weight of 1-[difluoro[(3',3",4",5"-tetrafluoro[1,1',4',1"-terphenyl]-4-yl)oxy]methyl]-4-(5-pentyl-1,3-dioxane-2-yl)cyclohexane(1-2-8) obtained in Example 9 was prepared. Physical properties of the composition H obtained were measured and extrapolated values of the compound (1-2-8) were calculated from the measured values by means of extrapolation. The values were as follows.

A maximum temperature ($T_{NI}$)=207° C.; optical anisotropy (Δn)=0.190; dielectric anisotropy (Δ∈)=22.8.

It was found from these results that the compound (1-2-8) had a relatively large optical anisotropy, the temperature range of liquid crystal phases was wide, the maximum temperature was quite high, while the dielectric anisotropy was large.

Example 11

The compounds (1-1-1) to (1-1-19), (1-2-1) to (1-2-25), (1-3-1) to (1-3-312), and (1-4-1) to (1-4-499) shown below can be synthesized based on Examples 1, 3, 5, 7, and 9, and moreover synthetic methods described herein. The data herein were obtained according to the methods described above. Phase transition temperatures were described by using the measured values of compounds themselves. The maximum temperatures ($T_{NI}$), dielectric anisotropy (Δ∈) and optical anisotropy (Δn) were described by using extrapolated values calculated by extrapolating measured values of samples which were prepared by mixing the compounds into the mother liquid crystals A, as described in Examples 2, 4, 6, 8, and 10.

| No. | |
|---|---|
| 1-1-1 | 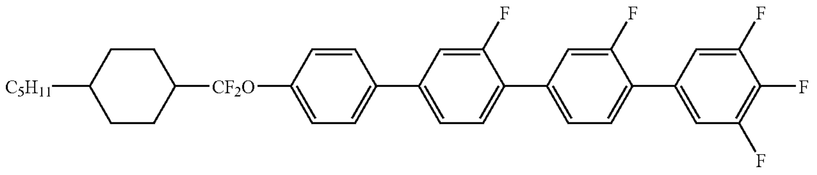 |

-continued
| No. | |
|---|---|
| 1-1-2 | 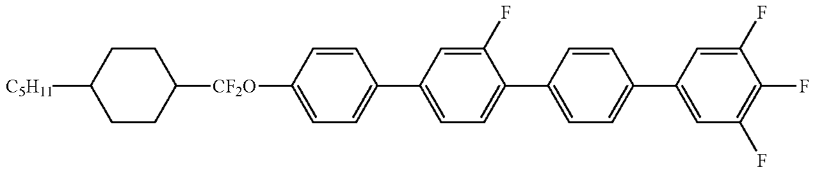 |
| 1-1-3 | 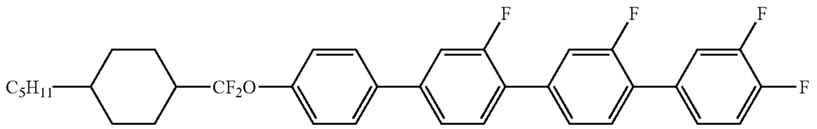 |
| 1-1-4 | 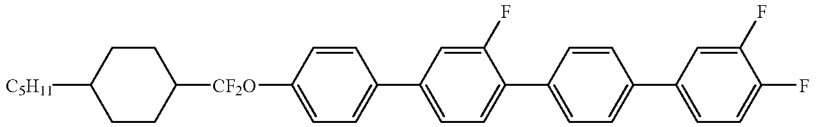 |
| 1-1-5 | 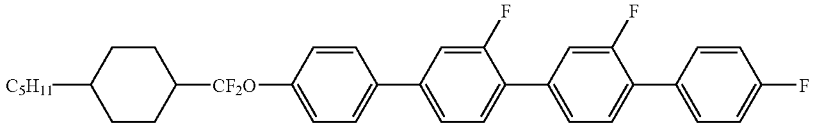 |
| 1-1-6 | 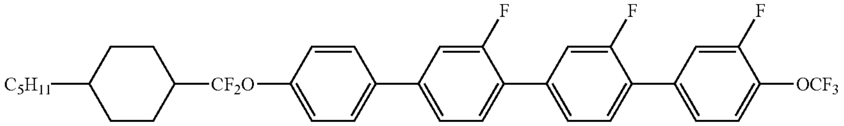 |
| 1-1-7 | 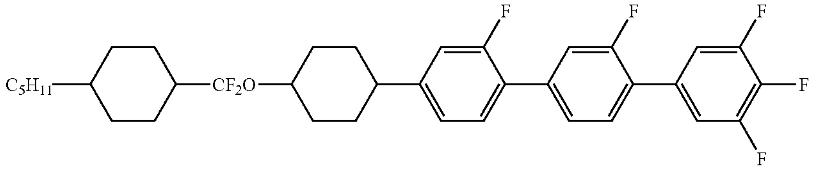 |
| 1-1-8 | 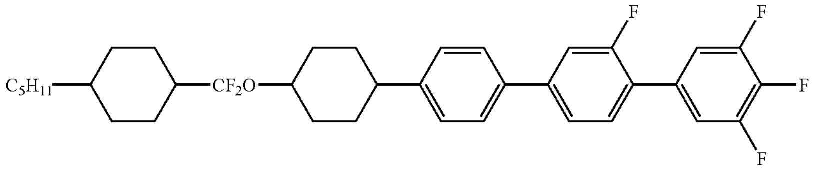 |
| 1-1-9 | 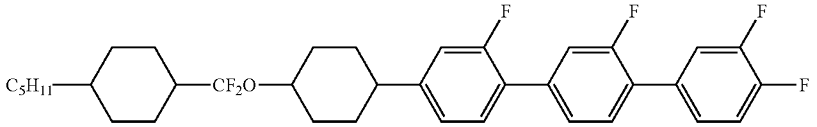 |
| 1-1-10 | 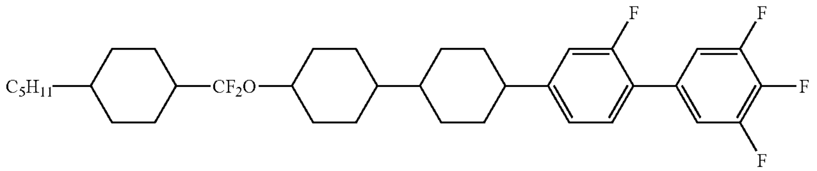 |
| 1-1-11 | 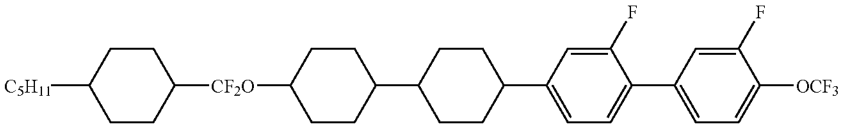 |

-continued
| No. | |
|---|---|
| 1-1-12 | 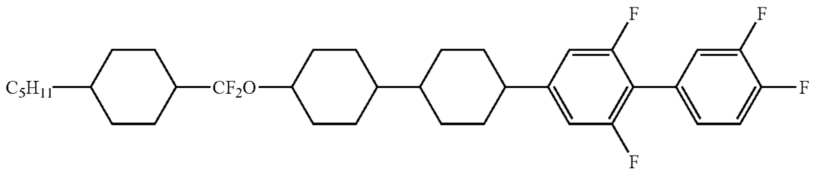 |
| 1-1-13 | 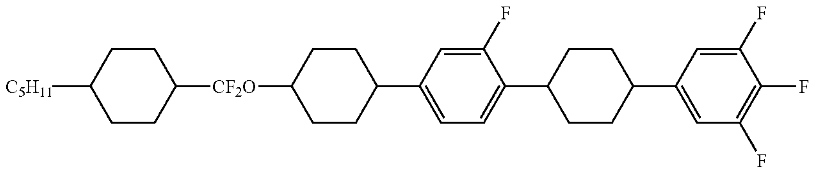 |
| 1-1-14 | 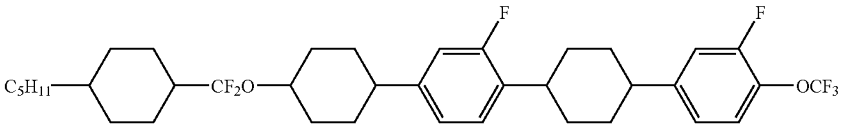 |
| 1-1-15 | 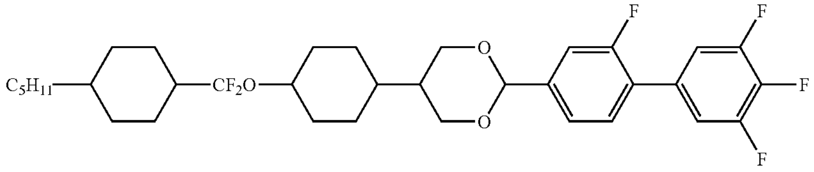 |
| 1-1-16 | 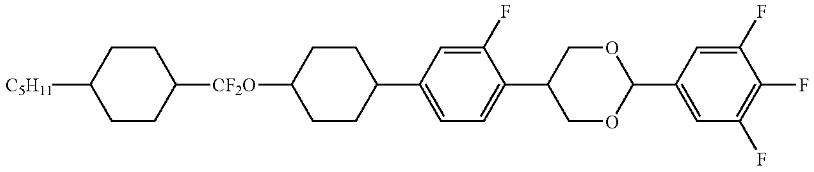 |
| 1-1-17 | 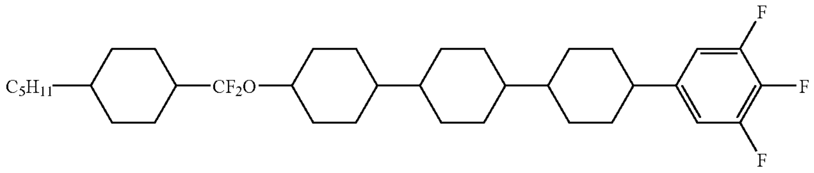 |
| 1-1-18 | 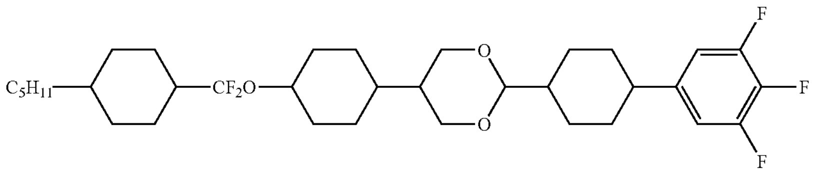 |
| 1-1-19 | 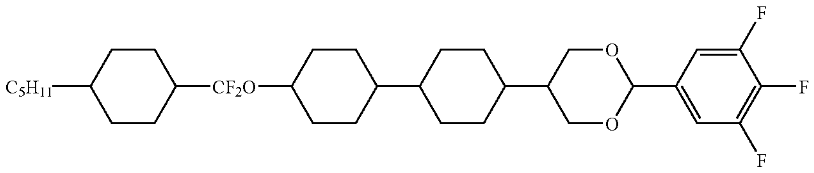 |
| 1-2-1 | 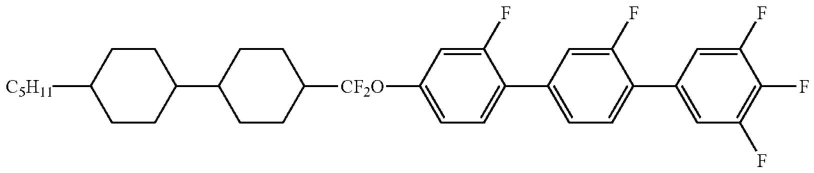 |

-continued
| No. |
| --- |
1-2-2
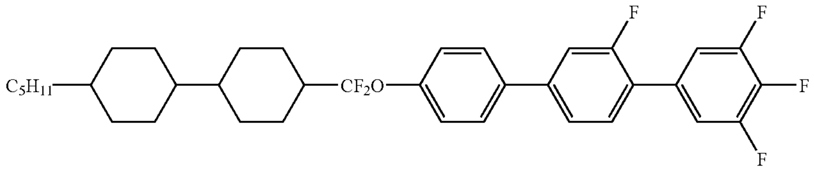
1-2-3
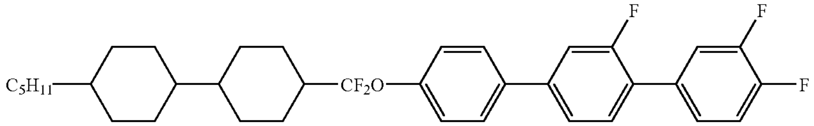
1-2-4
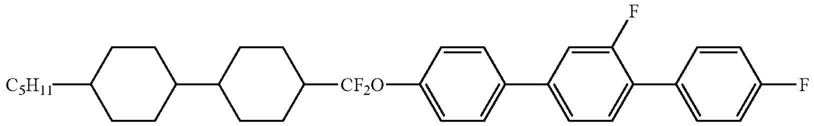
1-2-5
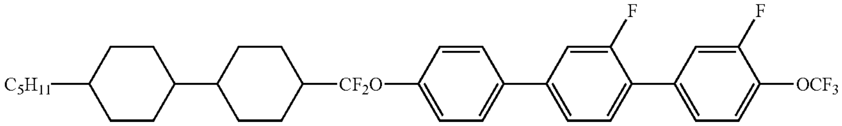
1-2-6
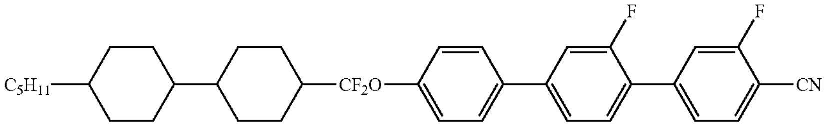
1-2-7
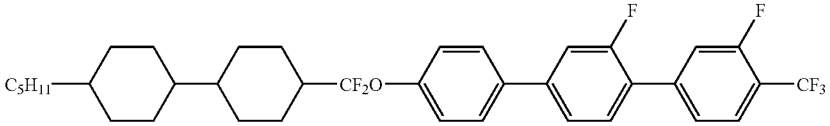
1-2-8
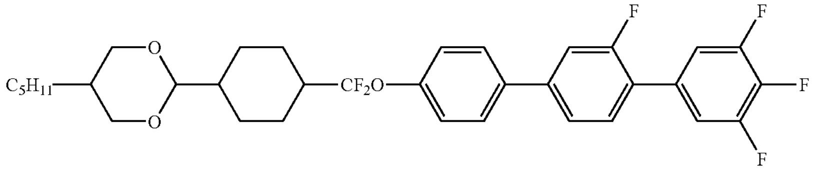
$T_{NI}$ = 207° C., Δ n = 0.190, Δ ∈ = 22.8
1-2-9
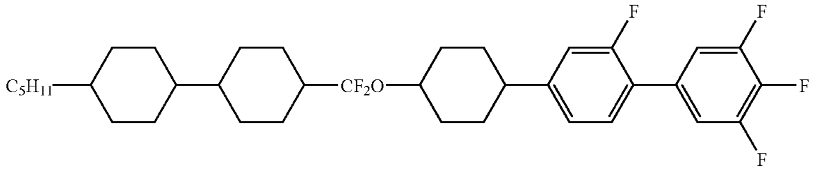
1-2-10
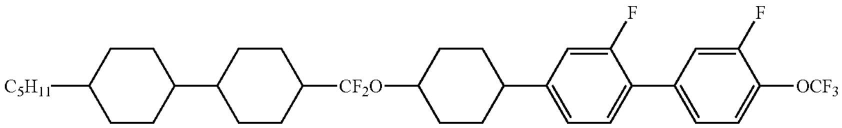

-continued
| No. | |
|---|---|
| 1-2-11 | 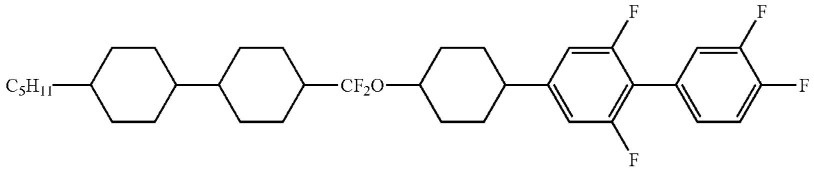 |
| 1-2-12 | 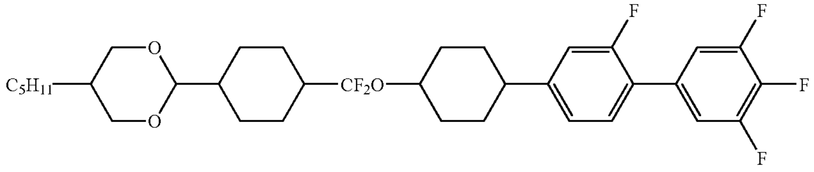 |
| 1-2-13 | 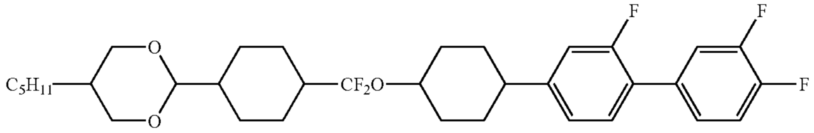 |
| 1-2-14 | 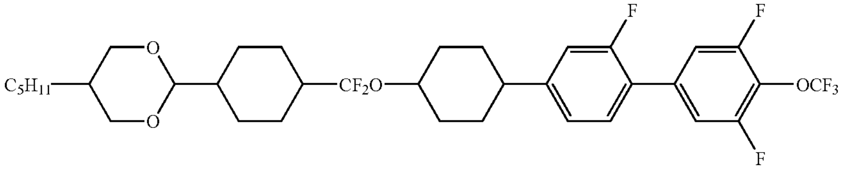 |
| 1-2-15 | 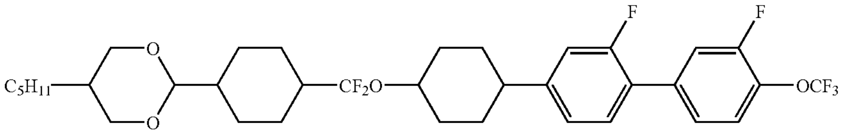 |
| 1-2-16 | 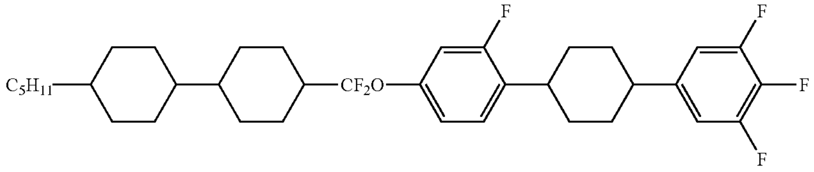 |
| 1-2-17 | 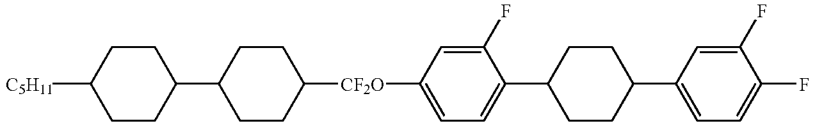 |
| 1-2-18 | 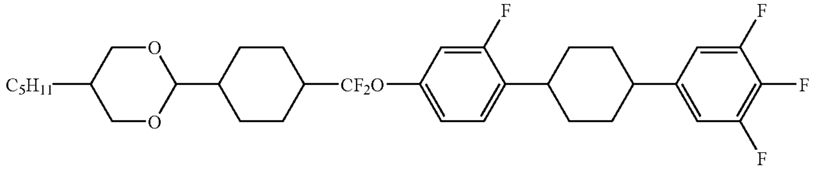 |
| 1-2-19 | 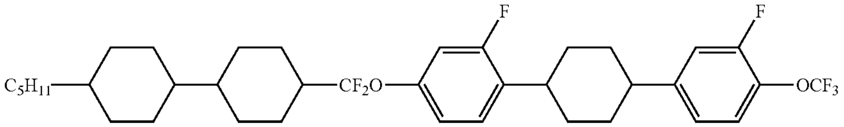 |

-continued
| No. | |
|---|---|
| 1-2-20 | 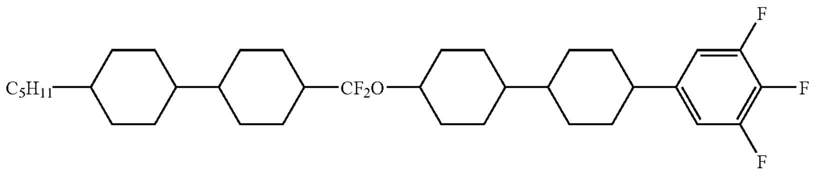 |
| 1-2-21 | 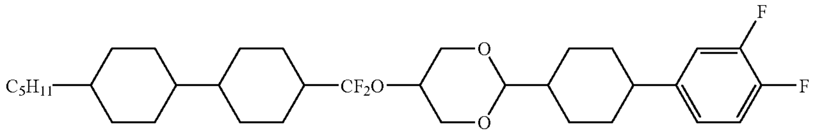 |
| 1-2-22 | 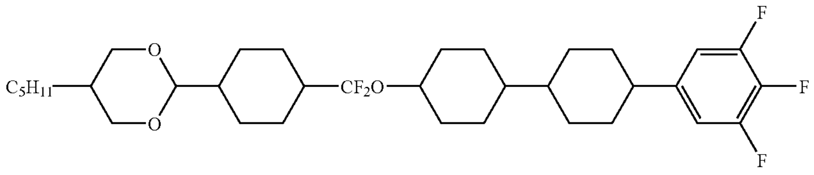 |
| 1-2-23 | 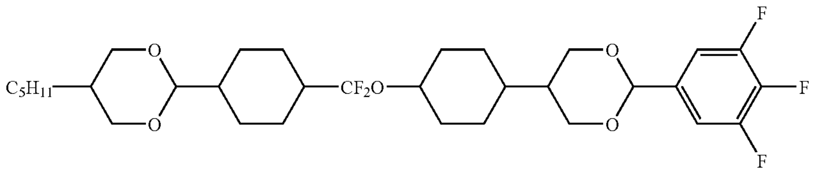 |
| 1-2-24 | 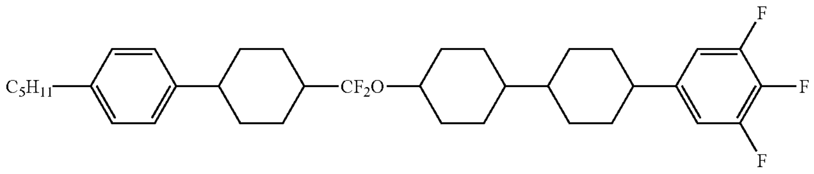 |
| 1-2-25 | 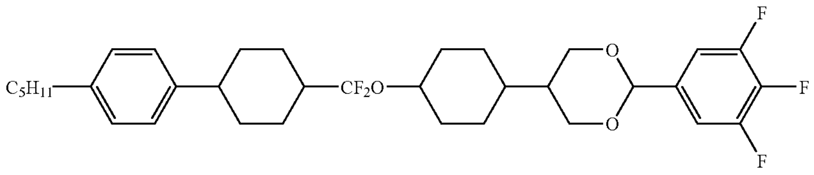 |
| 1-3-1 | 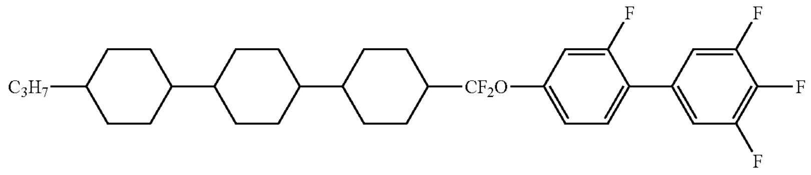 |
| 1-3-2 | 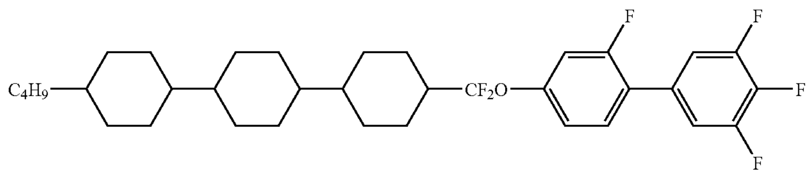 |

-continued
| No. | |
|---|---|
| 1-3-3 | 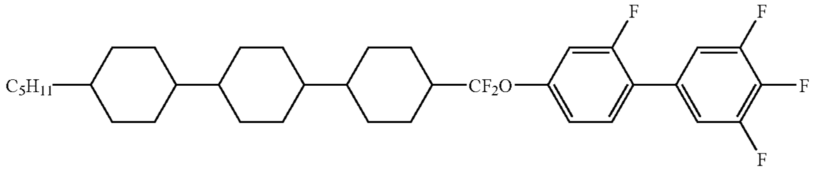 |
| 1-3-4 | 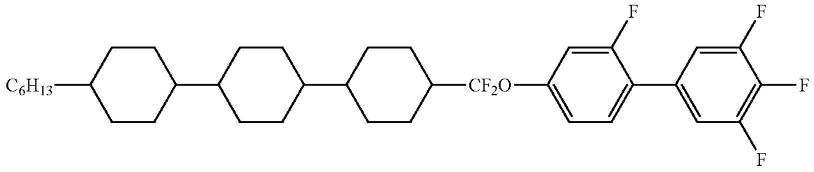 |
| 1-3-5 | 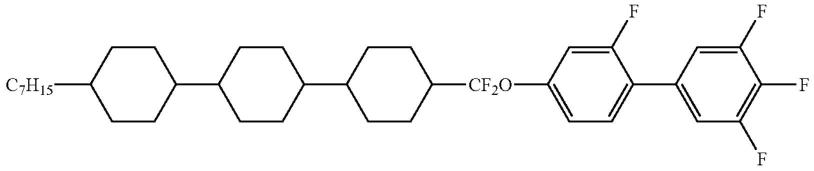 |
| 1-3-6 | 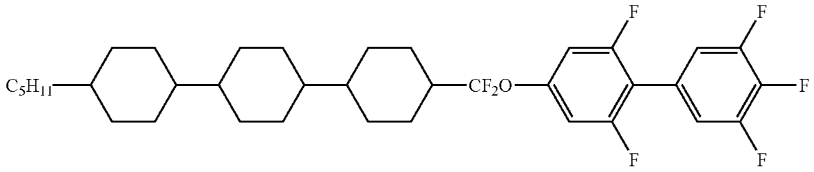 |
| 1-3-7 | 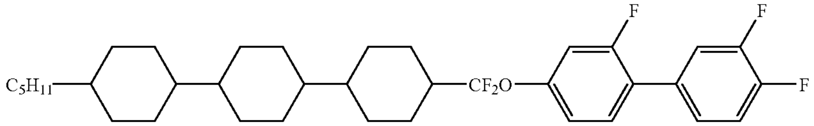 |
| 1-3-8 | 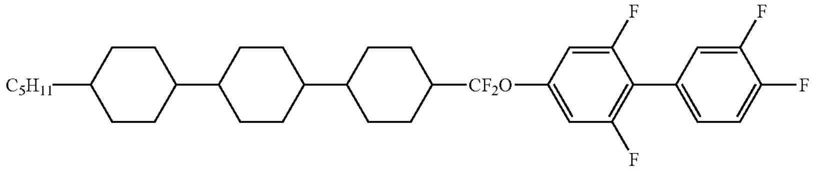 |
| 1-3-9 | 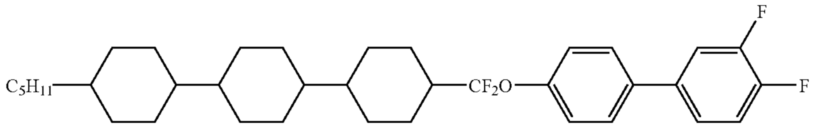 |
| 1-3-10 | 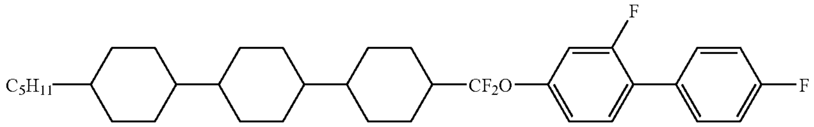 |
| 1-3-11 | 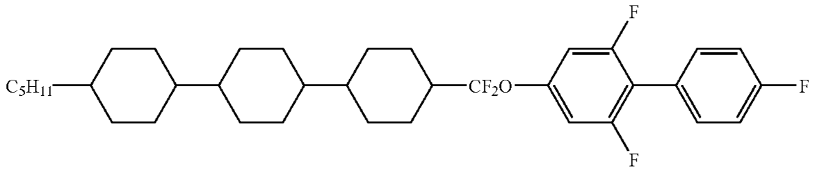 |

-continued
| No. | |
|---|---|
| 1-3-12 | 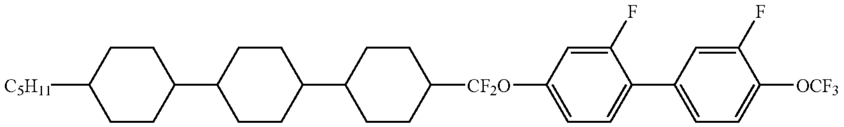 |
| 1-3-13 | 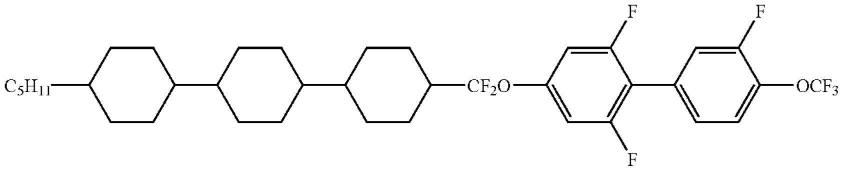 |
| 1-3-14 | 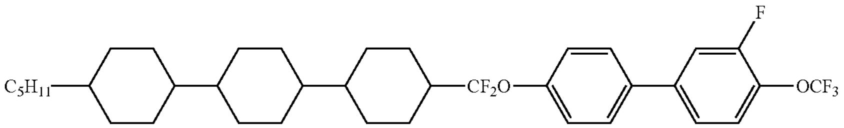 |
| 1-3-15 | 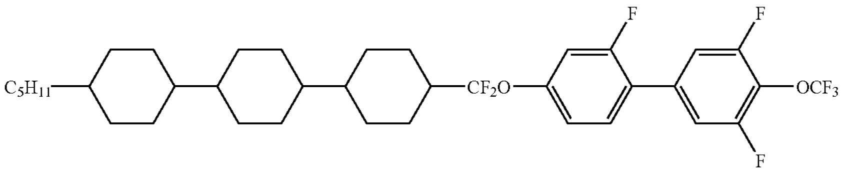 |
| 1-3-16 | 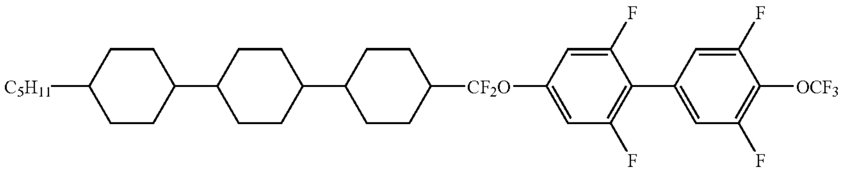 |
| 1-3-17 | 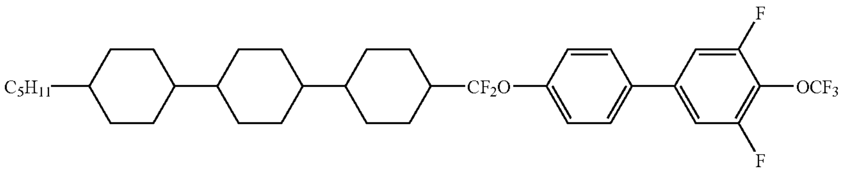 |
| 1-3-18 | 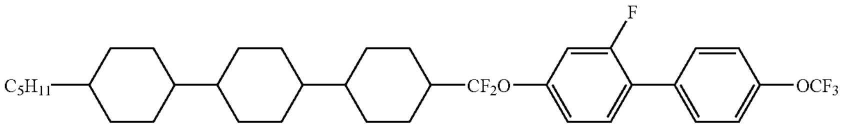 |
| 1-3-19 | 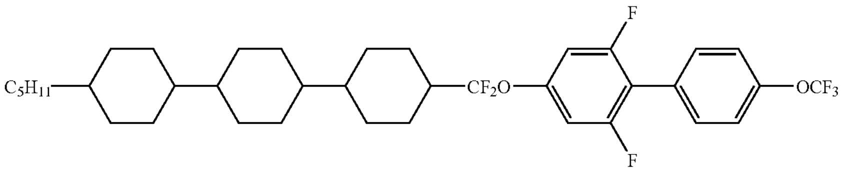 |
| 1-3-20 | 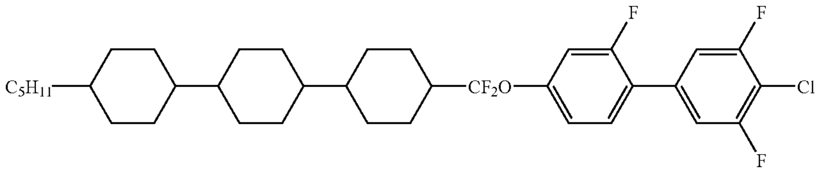 |

-continued
| No. | |
|---|---|
| 1-3-21 | 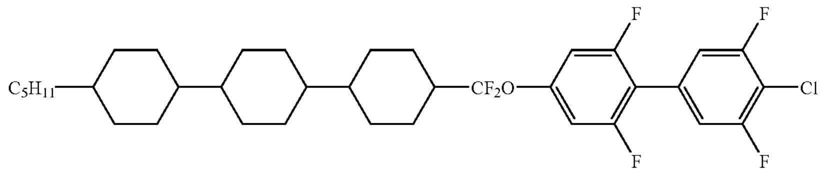 |
| 1-3-22 | 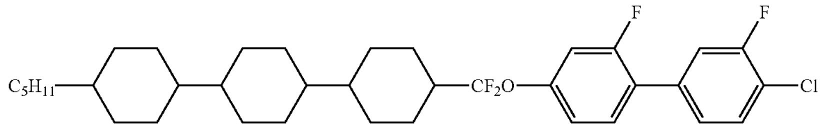 |
| 1-3-23 | 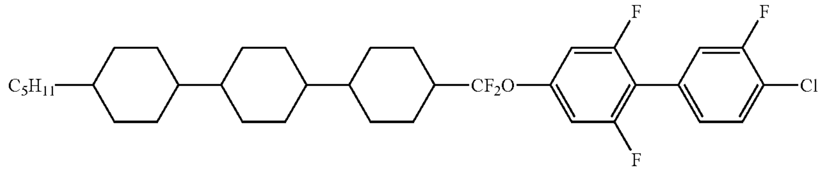 |
| 1-3-24 | 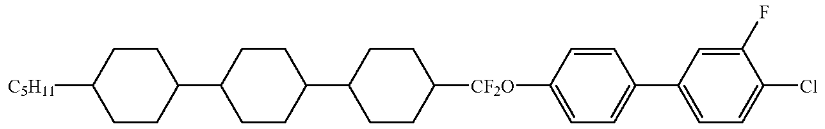 |
| 1-3-25 | 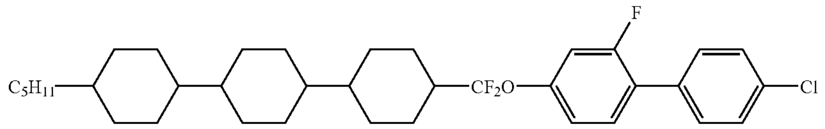 |
| 1-3-26 | 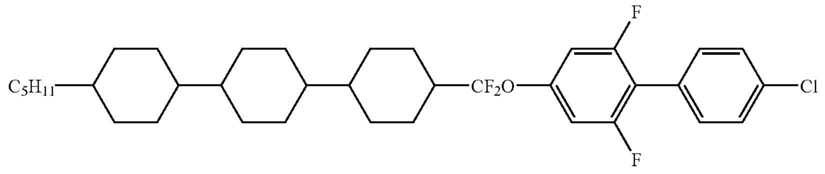 |
| 1-3-27 | 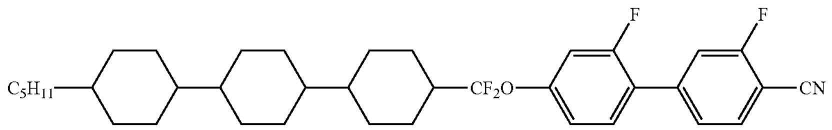 |
| 1-3-28 | 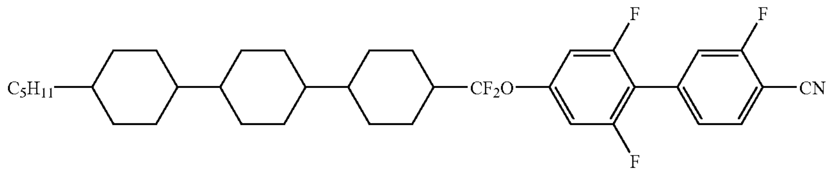 |
| 1-3-29 | 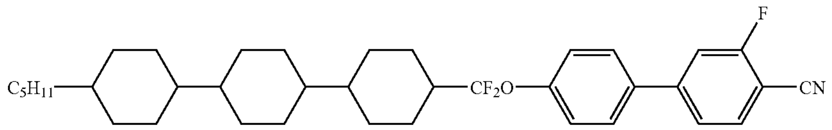 |

-continued
| No. | |
|---|---|
| 1-3-30 | 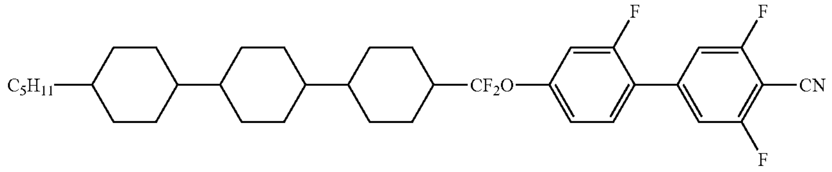 |
| 1-3-31 | 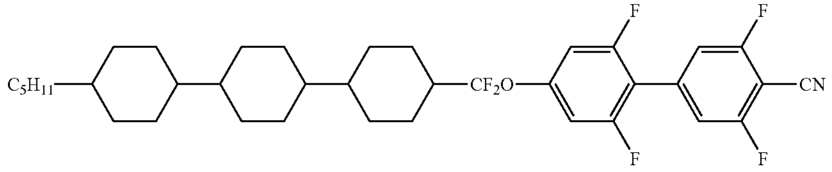 |
| 1-3-32 | 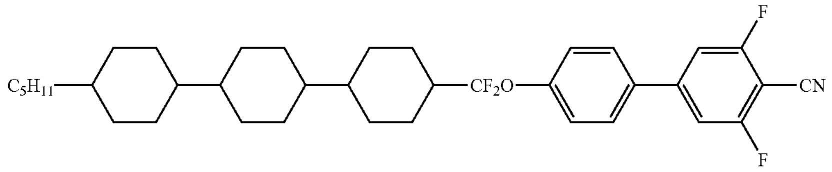 |
| 1-3-33 | 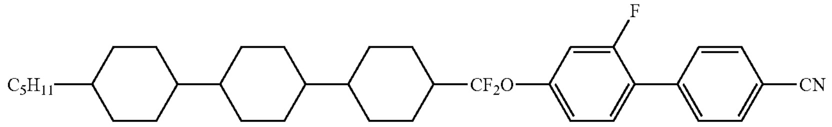 |
| 1-3-34 | 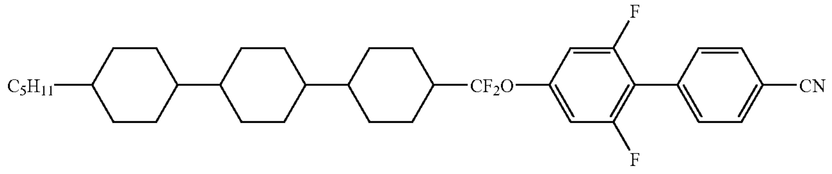 |
| 1-3-35 | 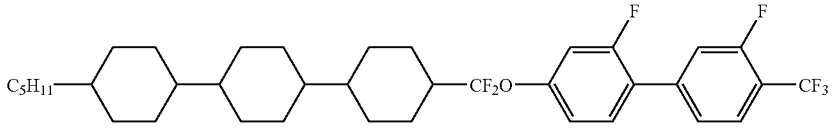 |
| 1-3-36 | 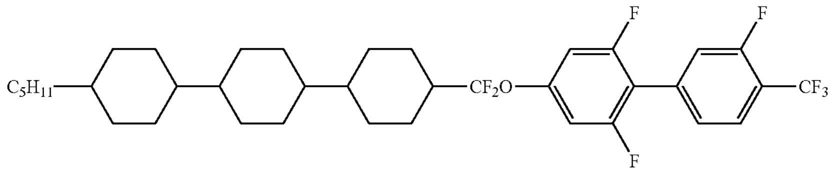 |
| 1-3-37 | 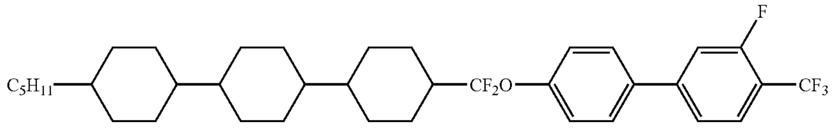 |
| 1-3-38 | 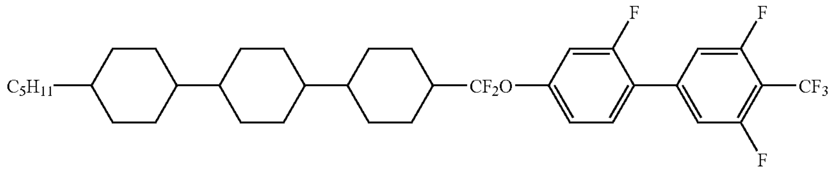 |

-continued
| No. | |
|---|---|
| 1-3-39 | 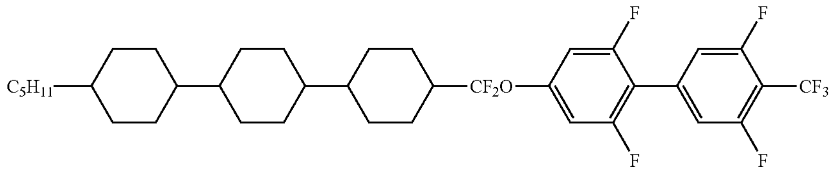 |
| 1-3-40 | 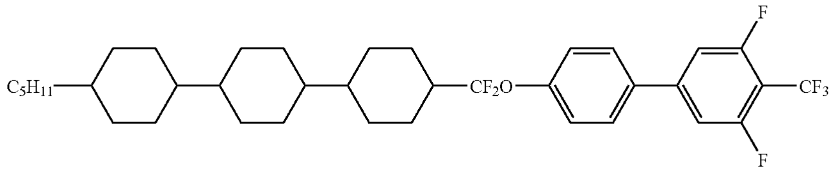 |
| 1-3-41 | 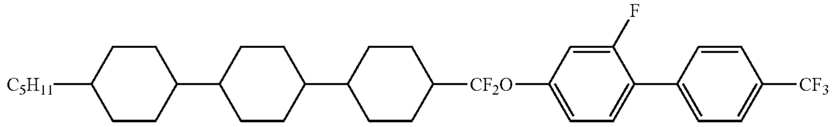 |
| 1-3-42 | 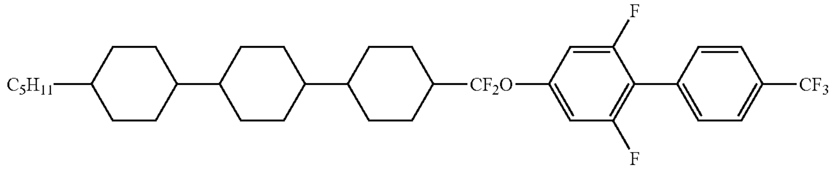 |
| 1-3-43 | 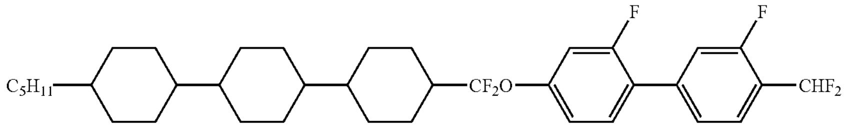 |
| 1-3-44 | 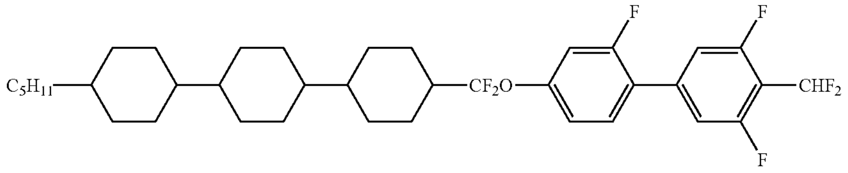 |
| 1-3-45 | 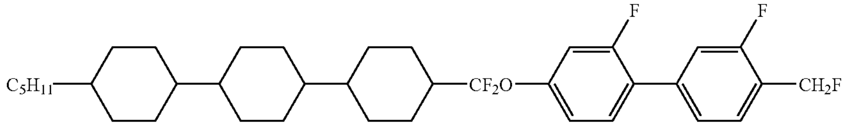 |
| 1-3-46 | 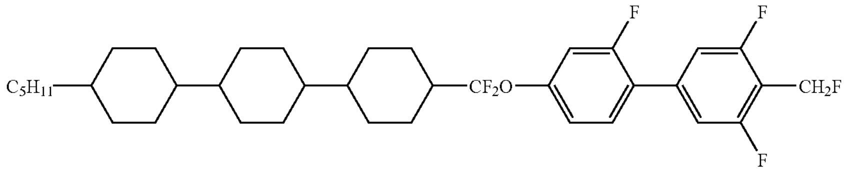 |
| 1-3-47 | 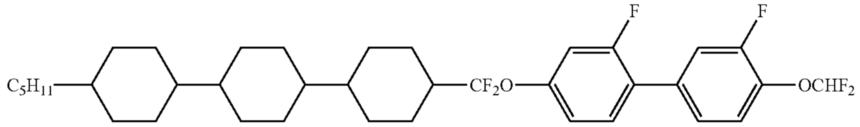 |

-continued
| No. | |
|---|---|
| 1-3-48 | 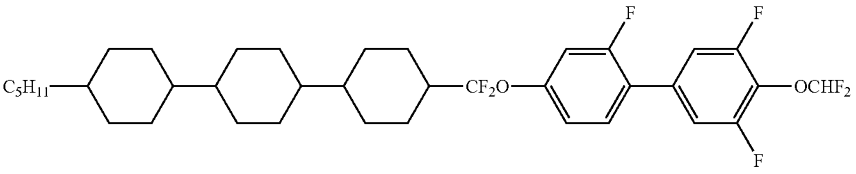 |
| 1-3-49 | 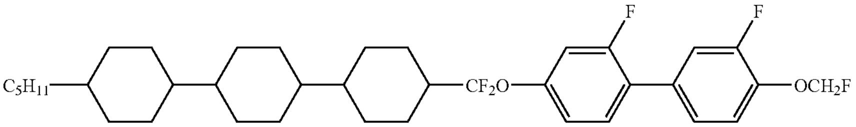 |
| 1-3-50 | 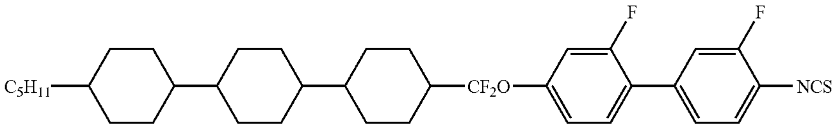 |
| 1-3-51 | 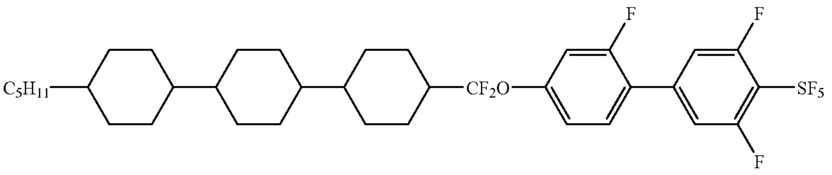 |
| 1-3-52 | 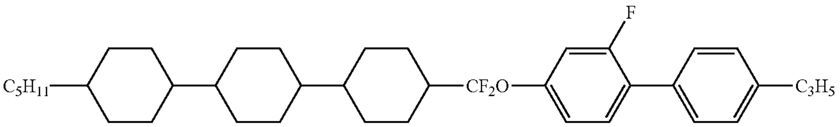 |
| 1-3-53 | 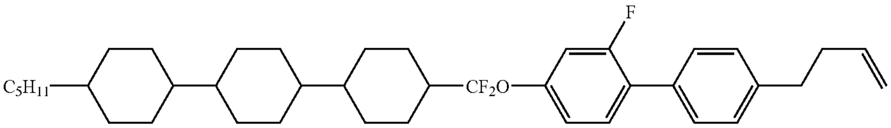 |
| 1-3-54 | 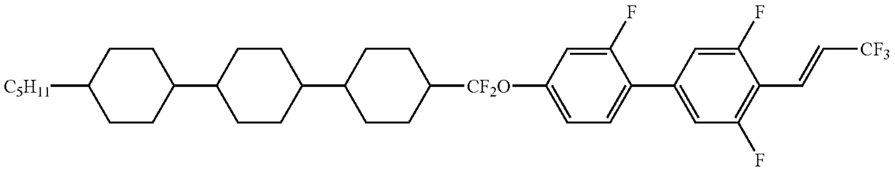 |
| 1-3-55 | 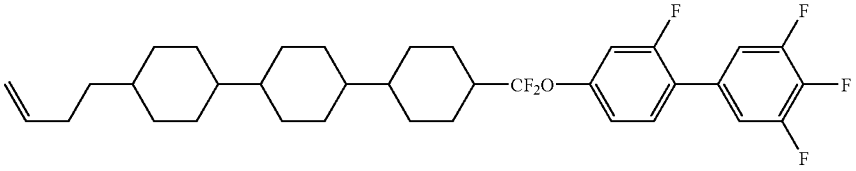 |
| 1-3-56 | 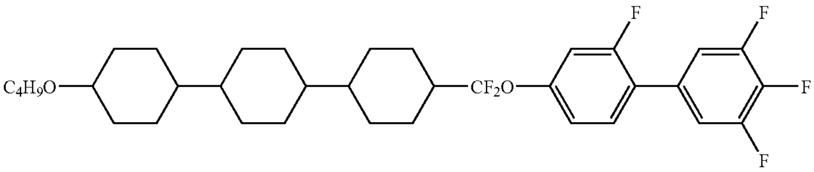 |

-continued
| No. | |
|---|---|
| 1-3-57 | 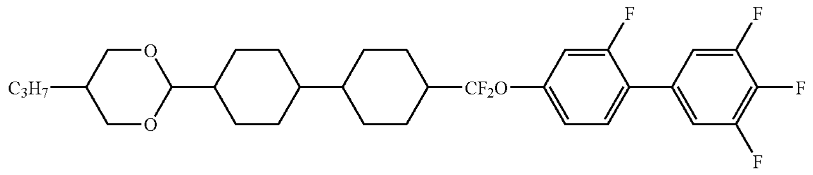 |
| 1-3-58 | 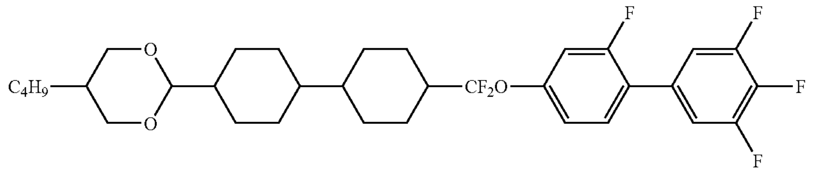 |
| 1-3-59 | 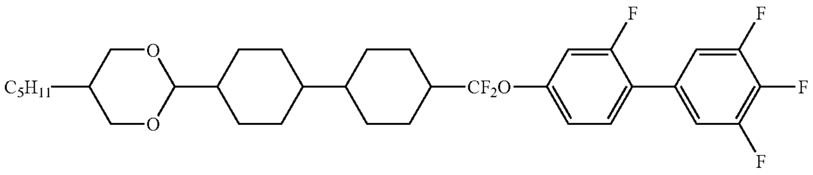 |
| 1-3-60 | 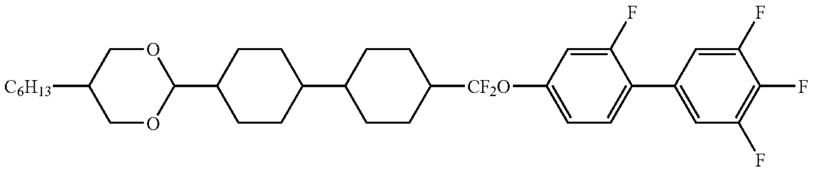 |
| 1-3-61 | 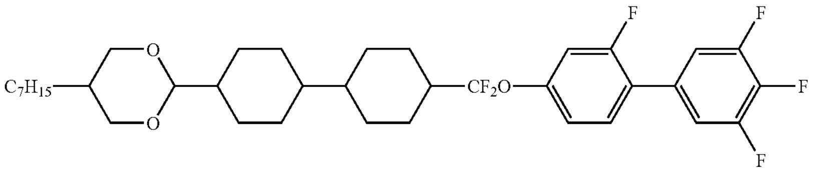 |
| 1-3-62 | 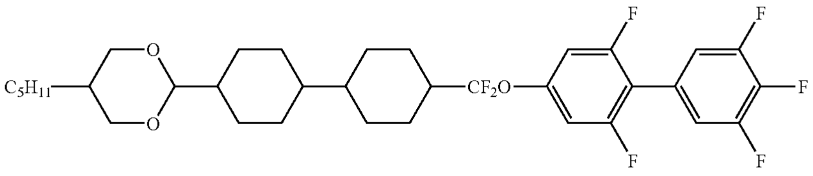 |
| 1-3-63 | 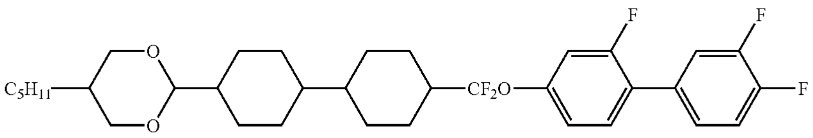 |
| 1-3-64 | 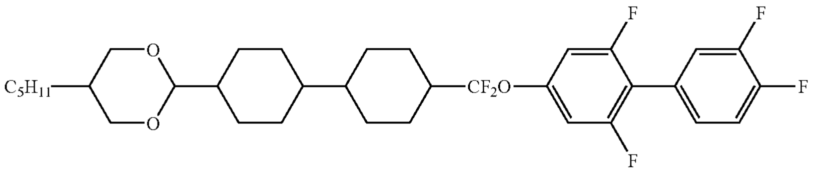 |
| 1-3-65 | 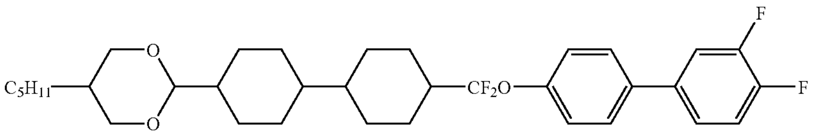 |

-continued
| No. |
|---|
1-3-66
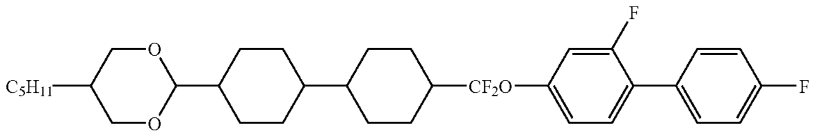
1-3-67
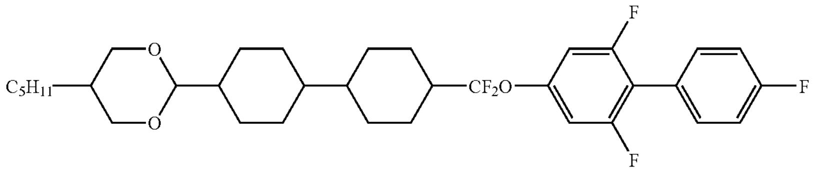
1-3-68
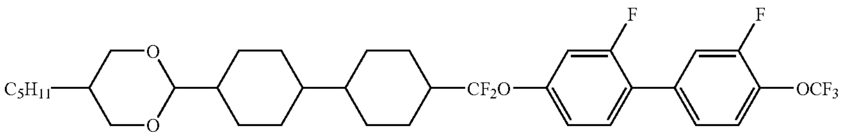
1-3-69
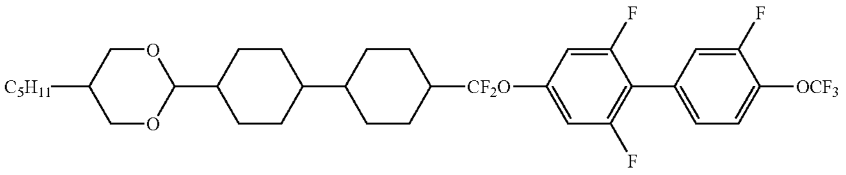
1-3-70
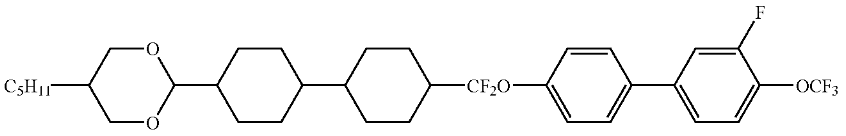
1-3-71
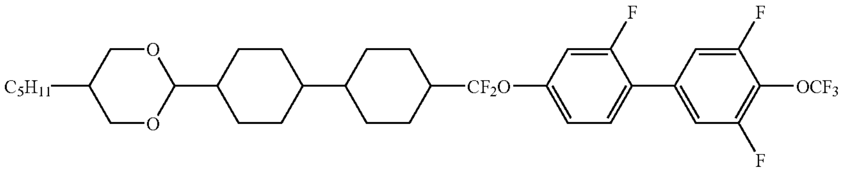
1-3-72
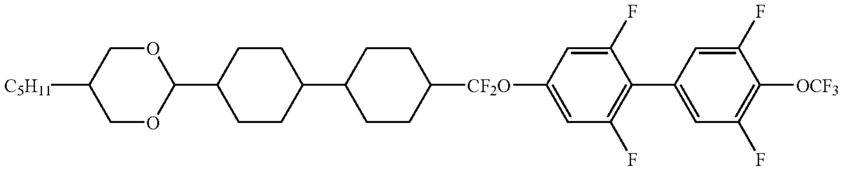
1-3-73
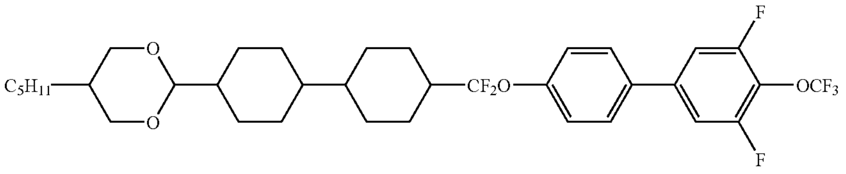
1-3-74
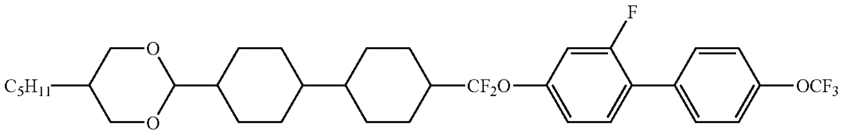

-continued
No.
1-3-75
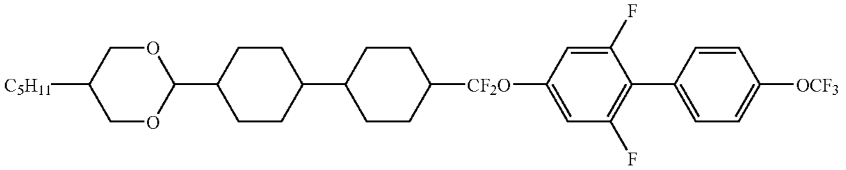
1-3-76
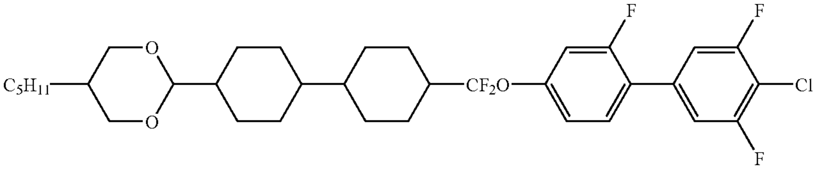
1-3-77
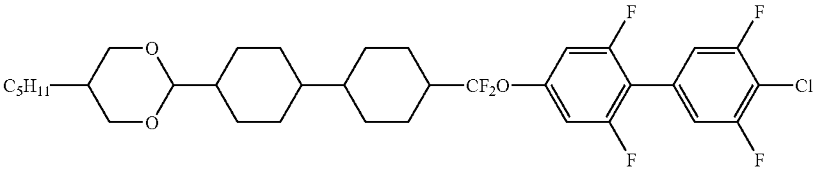
1-3-78
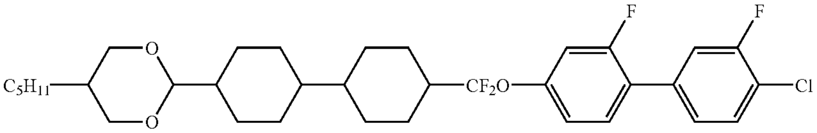
1-3-79
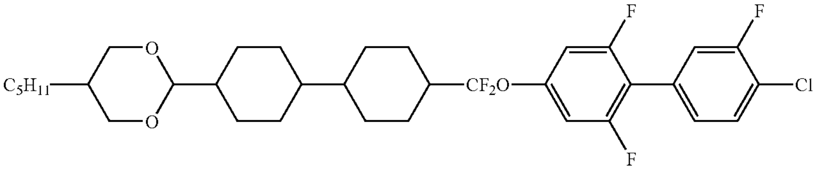
1-3-80
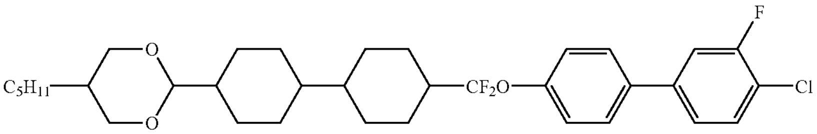
1-3-81
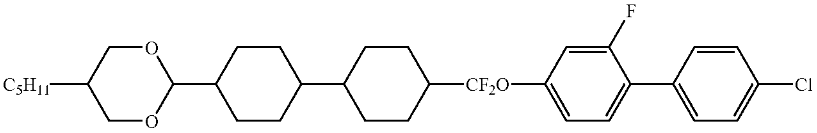
1-3-82
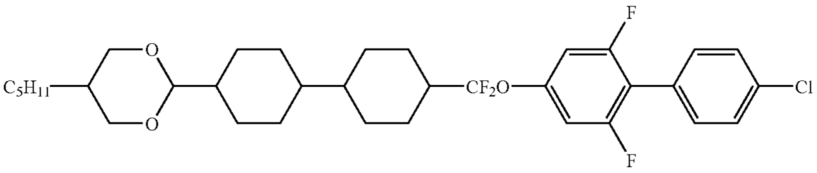
1-3-83
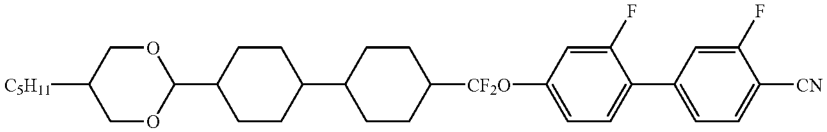

-continued
No.
1-3-84
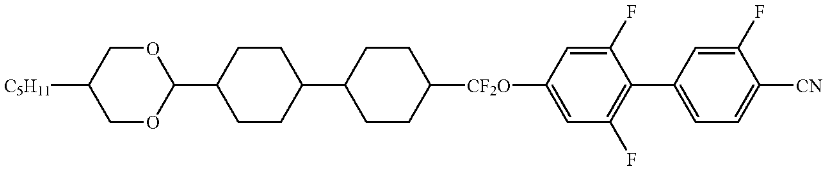
1-3-85
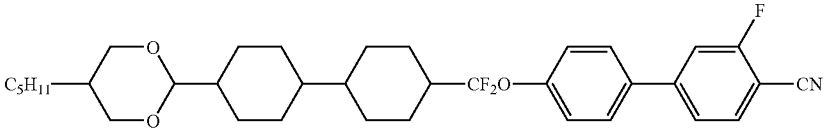
1-3-86
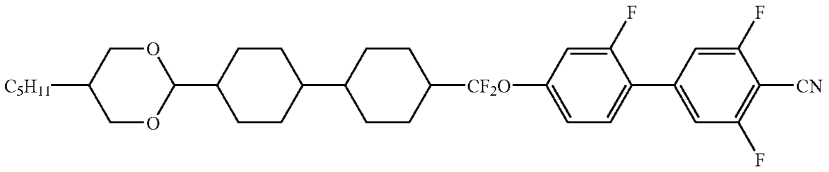
1-3-87
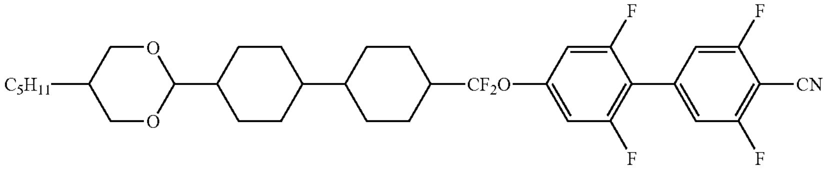
1-3-88
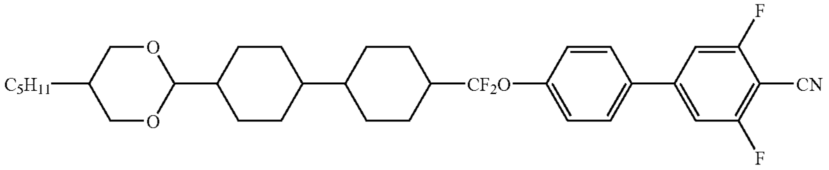
1-3-89
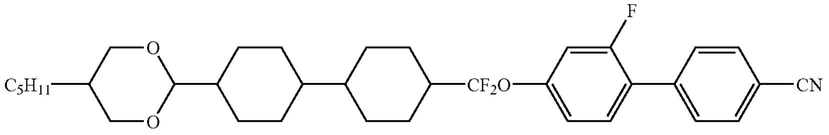
1-3-90
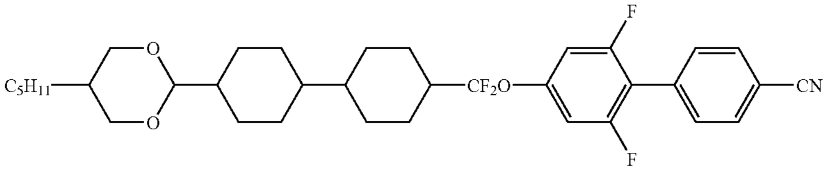
1-3-91
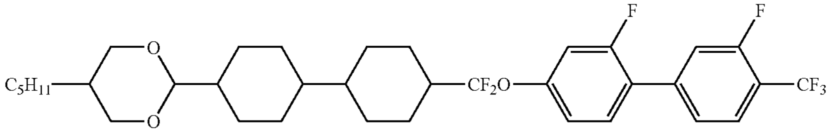
1-3-92
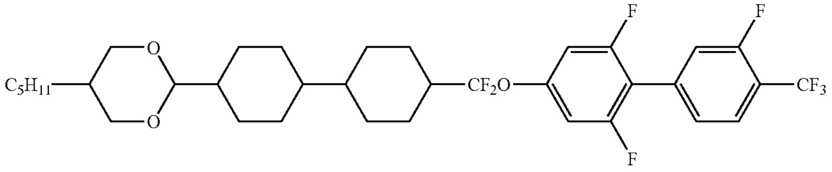

-continued
| No. | |
|---|---|
| 1-3-93 | 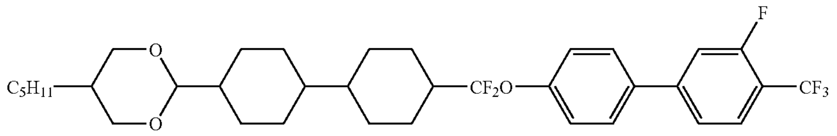 |
| 1-3-94 | 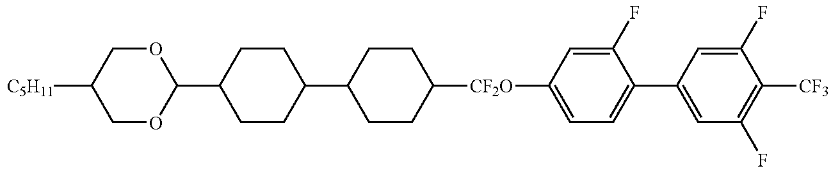 |
| 1-3-95 | 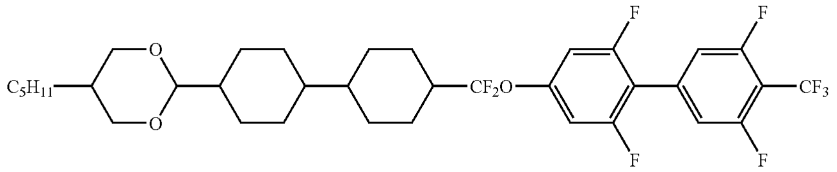 |
| 1-3-96 | 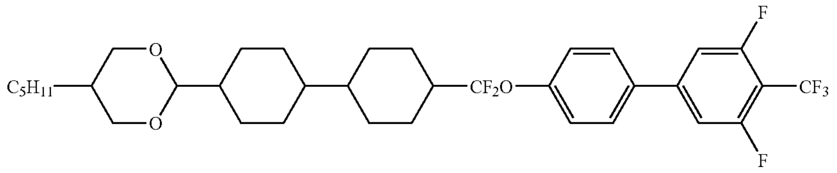 |
| 1-3-97 | 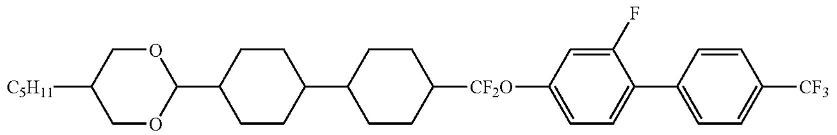 |
| 1-3-98 | 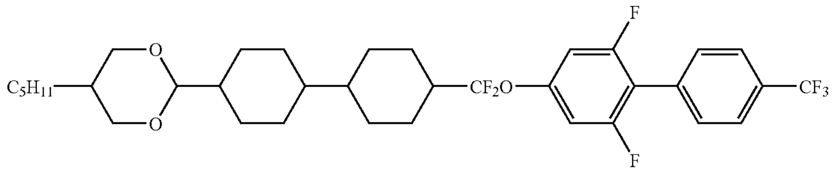 |
| 1-3-99 | 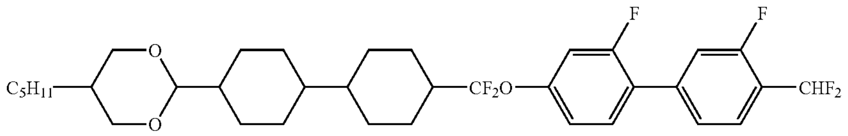 |
| 1-3-100 | 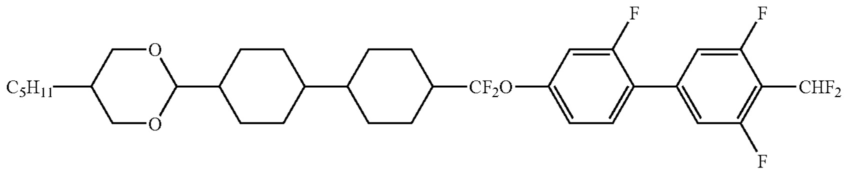 |
| 1-3-101 | 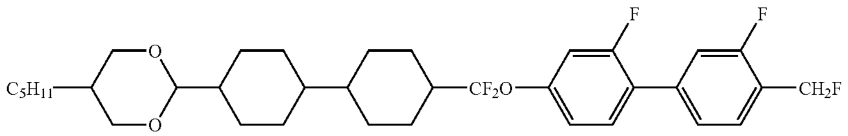 |

-continued
| No. | |
|---|---|
| 1-3-102 | 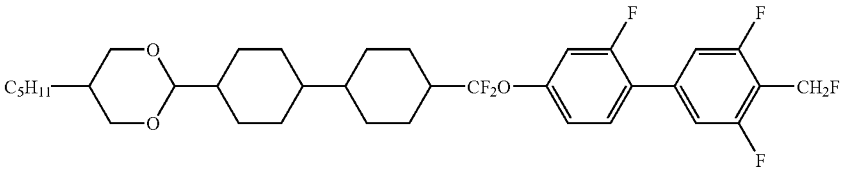 |
| 1-3-103 | 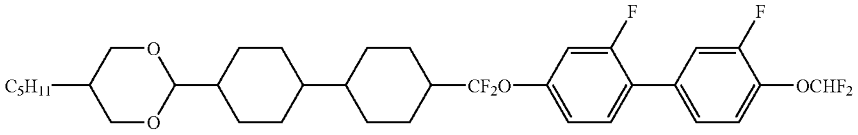 |
| 1-3-104 | 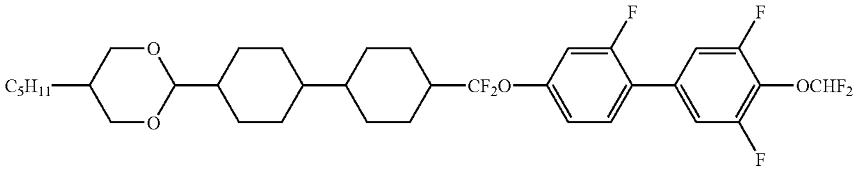 |
| 1-3-105 | 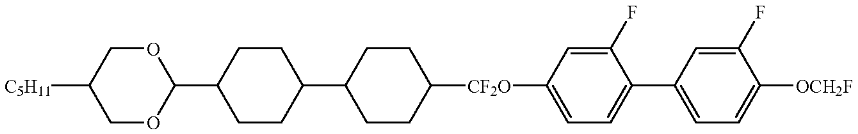 |
| 1-3-106 | 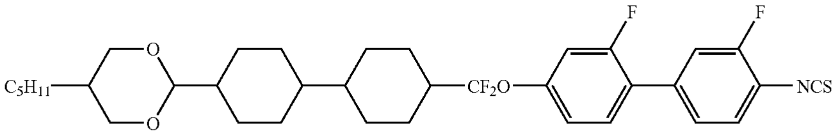 |
| 1-3-107 | 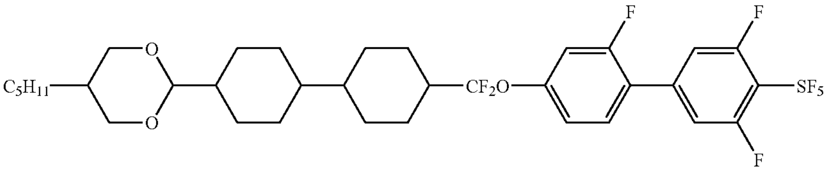 |
| 1-3-108 | 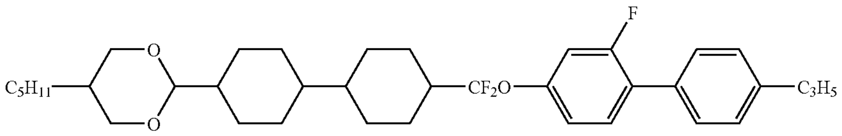 |
| 1-3-109 | 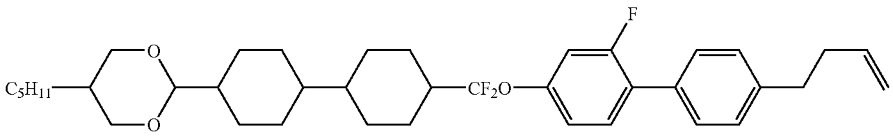 |
| 1-3-110 | 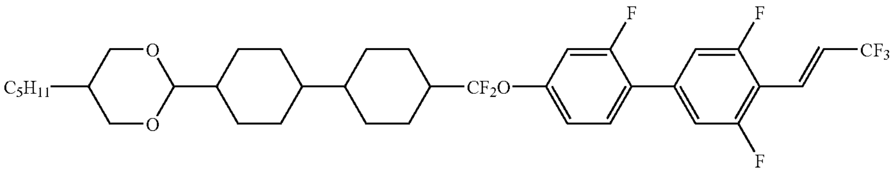 |

-continued
No.
1-3-111
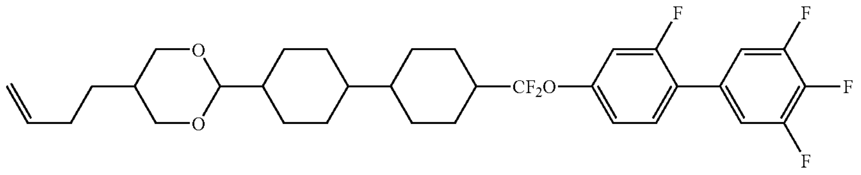
1-3-112
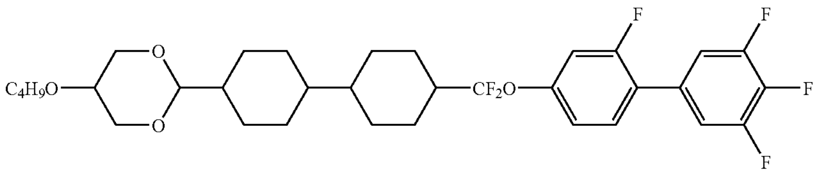
1-3-113
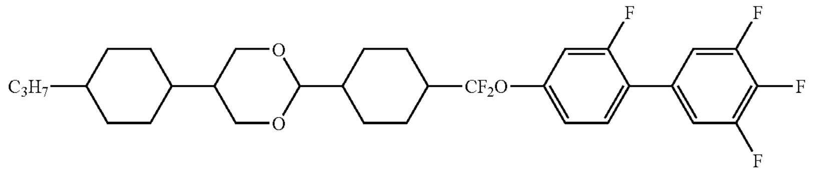
1-3-114
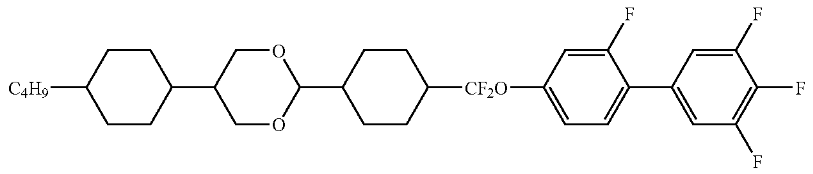
1-3-115
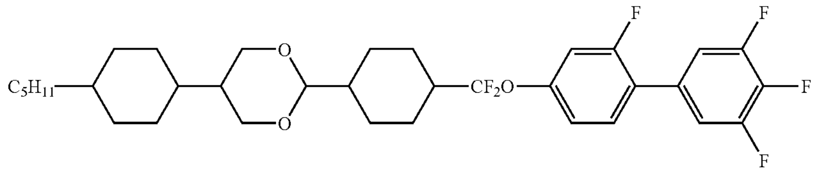
1-3-116
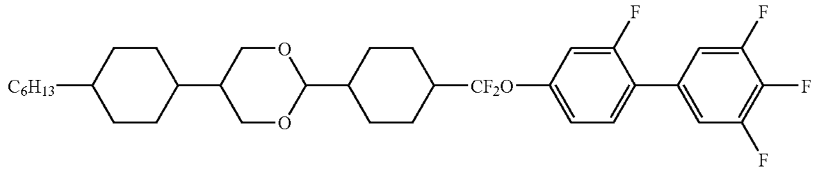
1-3-117
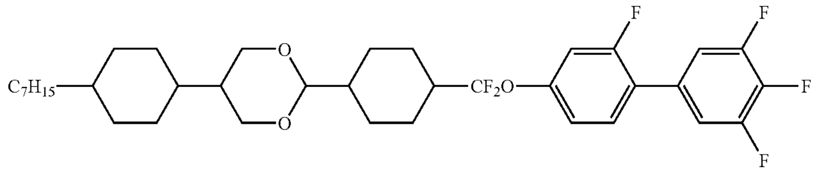
1-3-118
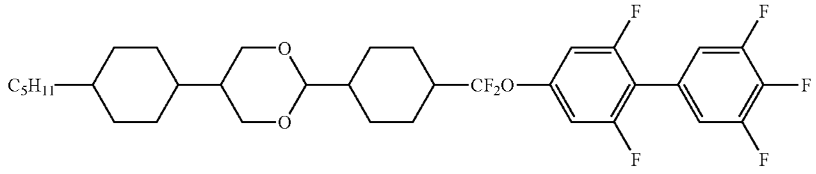
1-3-119
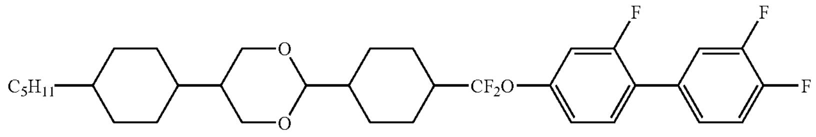

-continued
No.
1-3-120
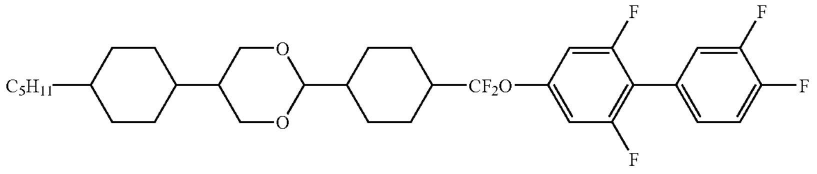
1-3-121
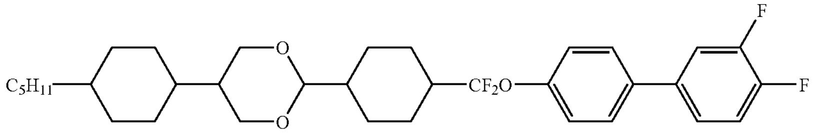
1-3-122
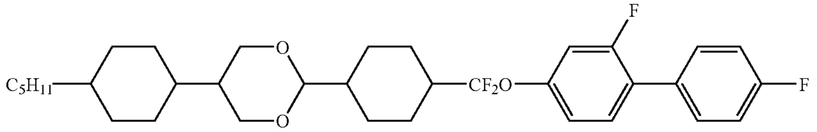
1-3-123
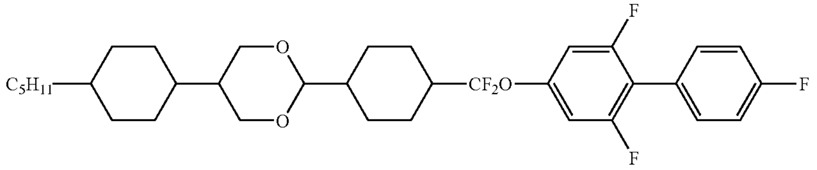
1-3-124
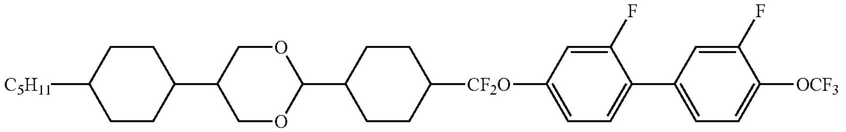
1-3-125
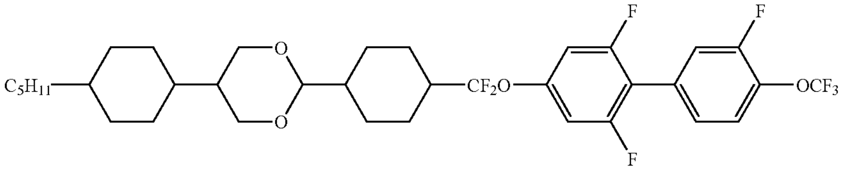
1-3-126
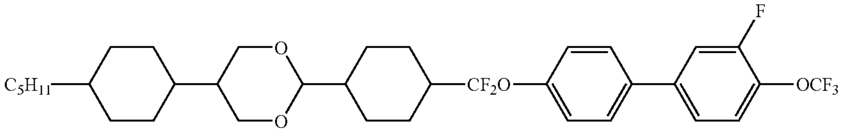
1-3-127
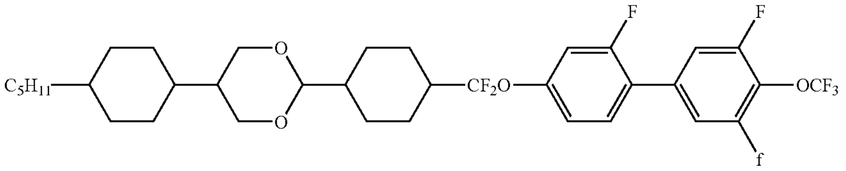
1-3-128
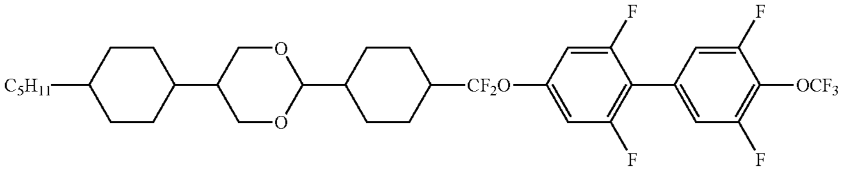

-continued
| No. | |
|---|---|
| 1-3-129 | 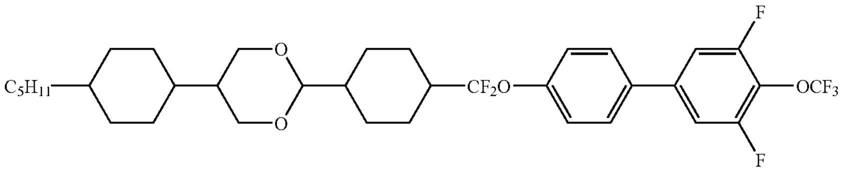 |
| 1-3-130 | 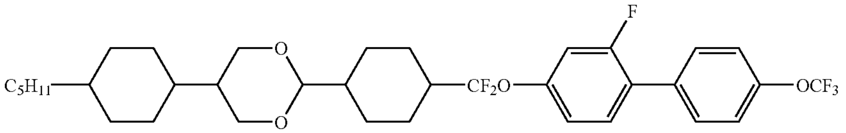 |
| 1-3-131 | 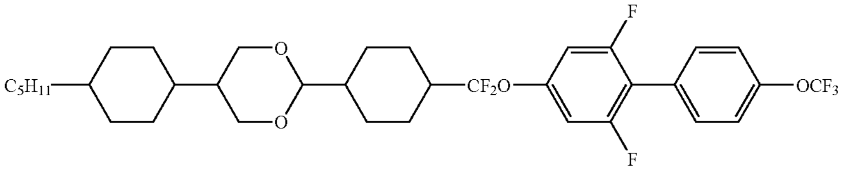 |
| 1-3-132 | 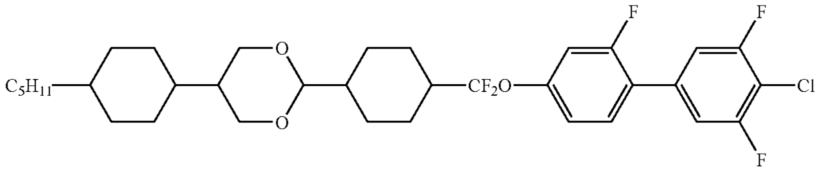 |
| 1-3-133 | 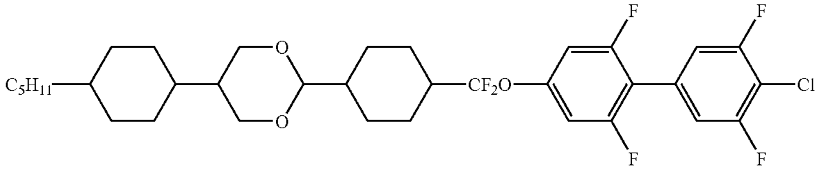 |
| 1-3-134 | 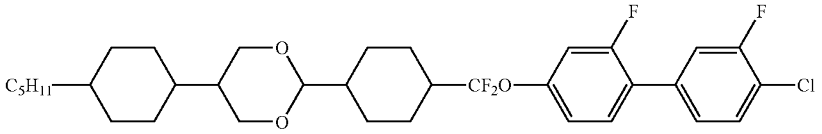 |
| 1-3-135 | 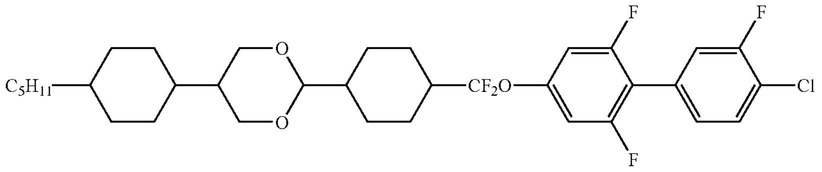 |
| 1-3-136 | 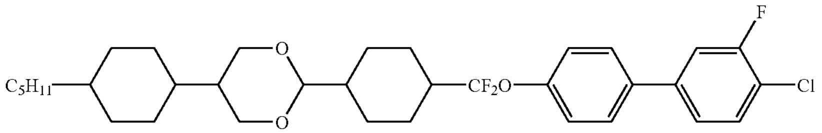 |
| 1-3-137 | 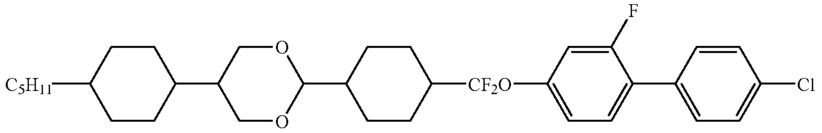 |

-continued
| No. | |
|---|---|
| 1-3-138 | 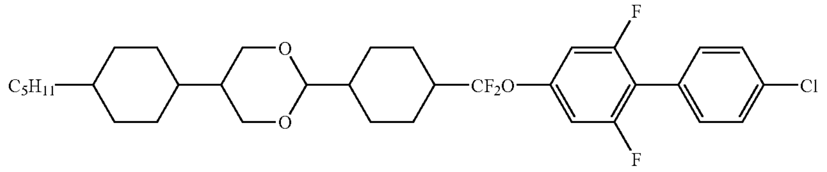 |
| 1-3-139 | 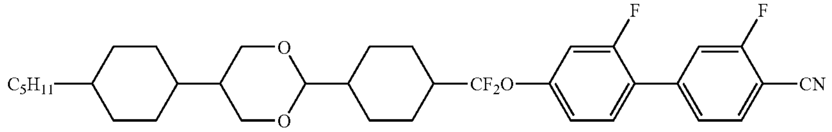 |
| 1-3-140 | 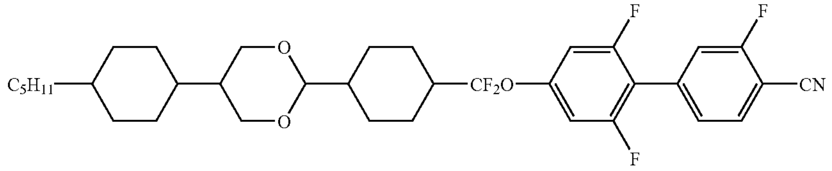 |
| 1-3-141 | 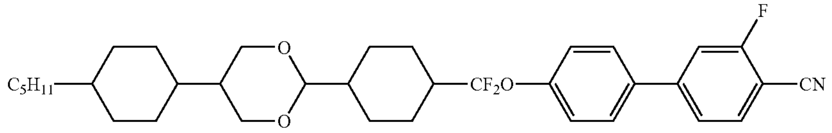 |
| 1-3-142 | 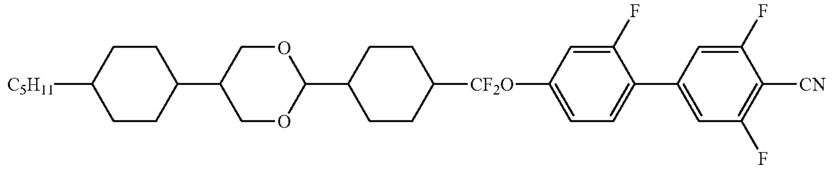 |
| 1-3-143 | 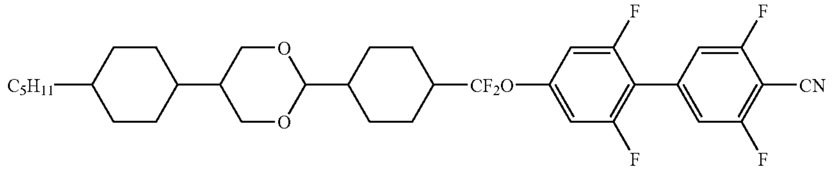 |
| 1-3-144 | 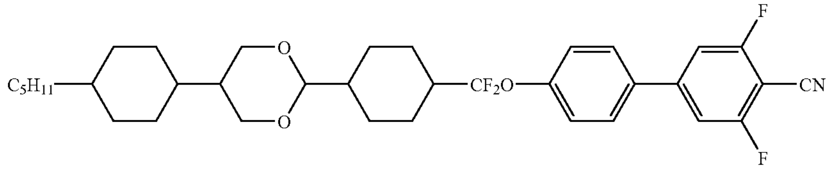 |
| 1-3-145 | 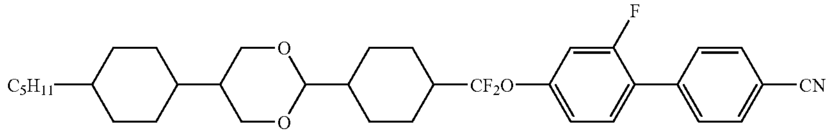 |
| 1-3-146 | 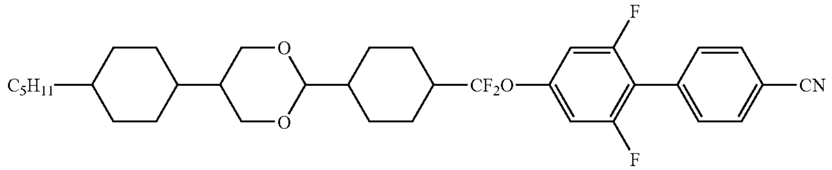 |

-continued
| No. | |
|---|---|
| 1-3-147 | 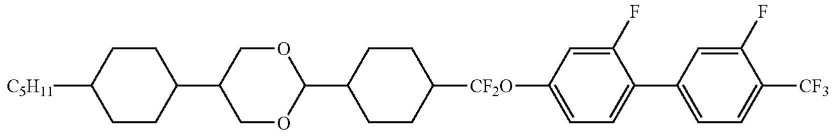 |
| 1-3-148 | 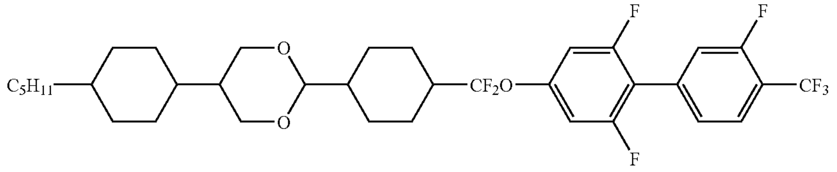 |
| 1-3-149 | 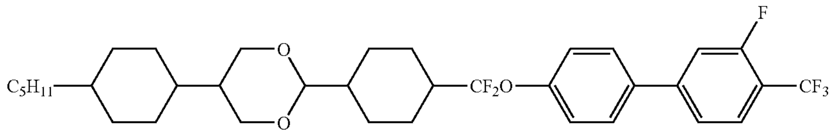 |
| 1-3-150 | 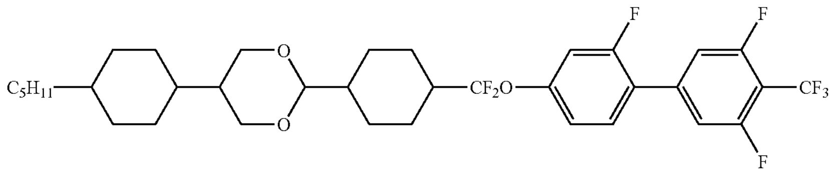 |
| 1-3-151 | 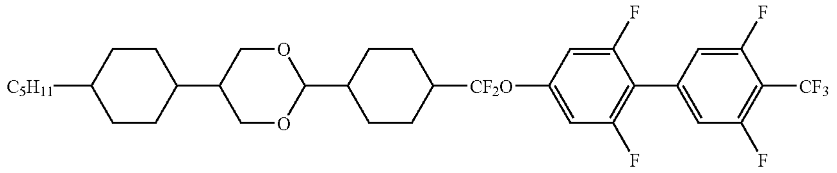 |
| 1-3-152 | 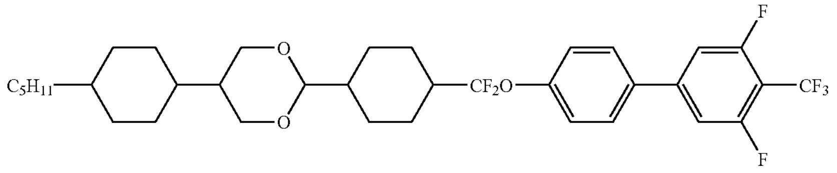 |
| 1-3-153 | 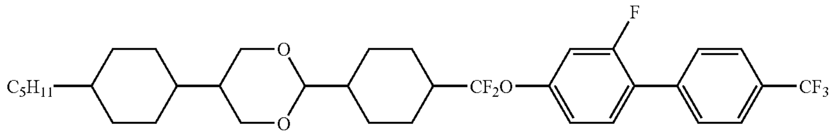 |
| 1-3-154 | 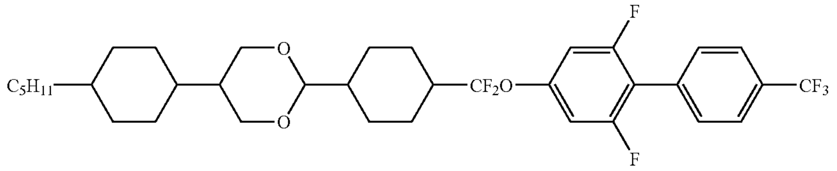 |
| 1-3-155 | 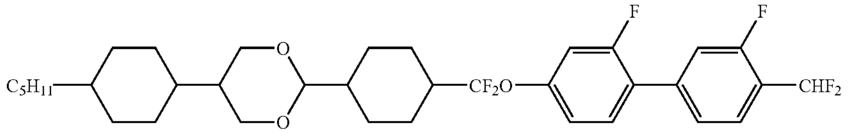 |

-continued
| No. | |
|---|---|
| 1-3-156 | 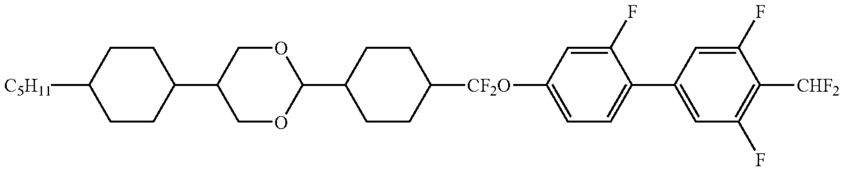 |
| 1-3-157 | 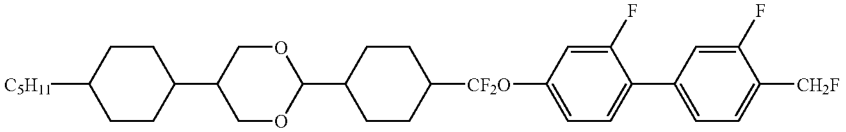 |
| 1-3-158 | 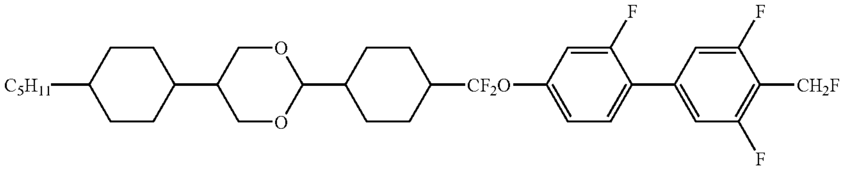 |
| 1-3-159 | 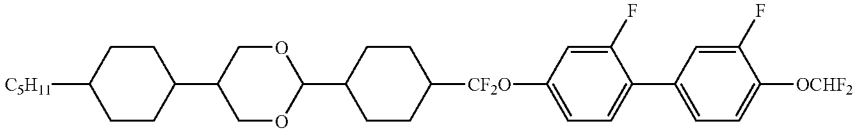 |
| 1-3-160 | 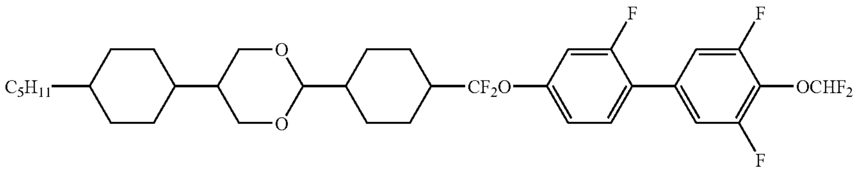 |
| 1-3-161 | 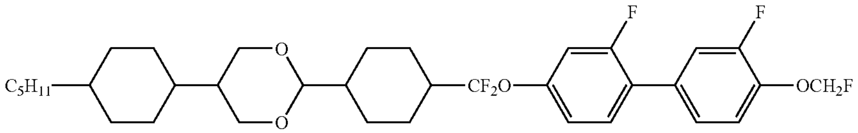 |
| 1-3-162 | 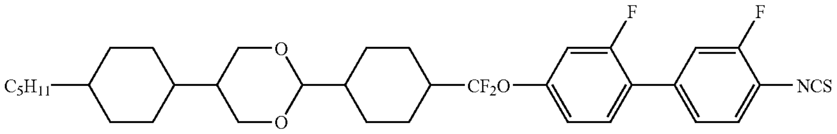 |
| 1-3-163 | 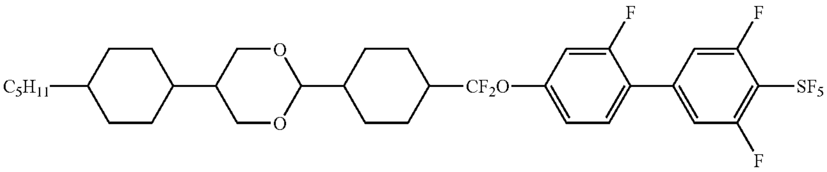 |
| 1-3-164 | 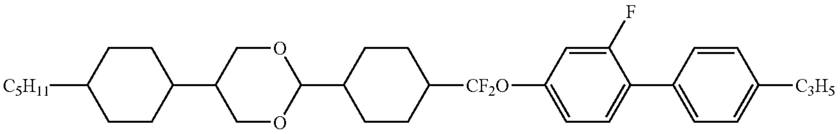 |

-continued
| No. |
|---|
| 1-3-165 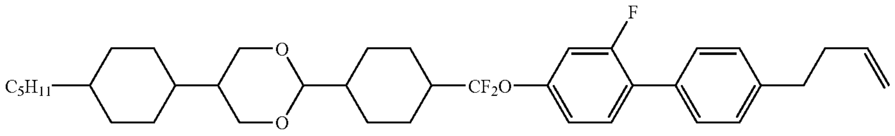 |
| 1-3-166 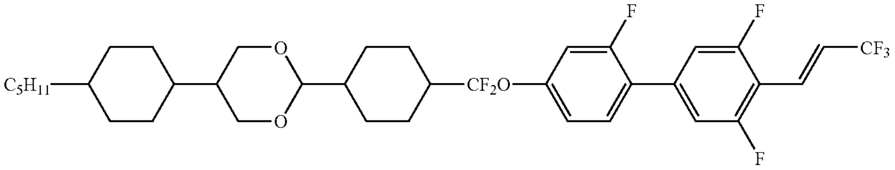 |
| 1-3-167 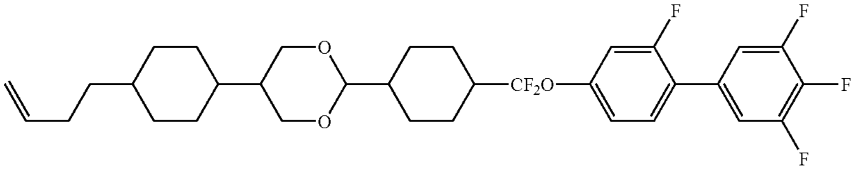 |
| 1-3-168 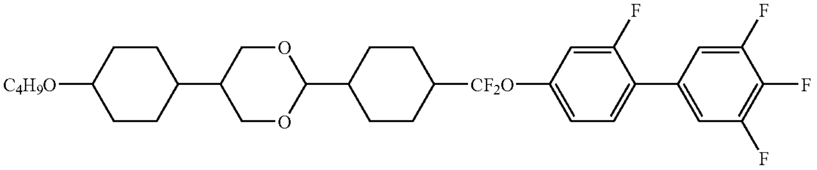 |
| 1-3-169 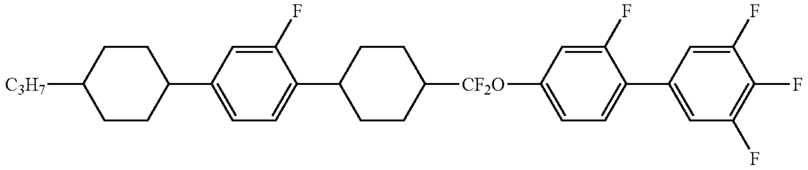 |
| 1-3-170 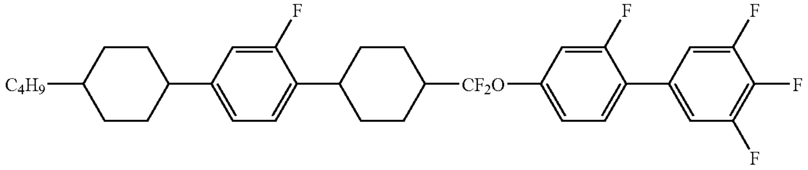 |
| 1-3-171 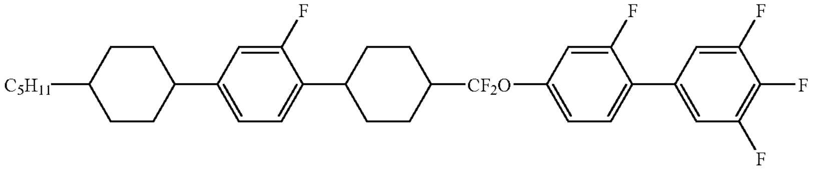 $T_{NI}$ = 180° C., Δ n = 0.150, Δ ∈ = 18.3 |
| 1-3-172 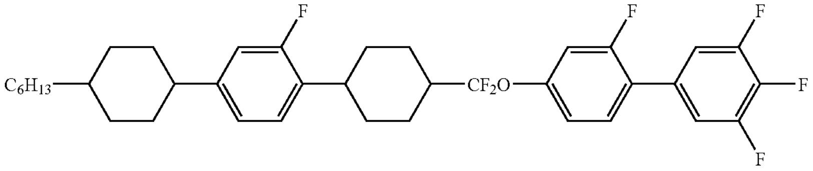 |

-continued
| No. | |
|---|---|
| 1-3-173 | 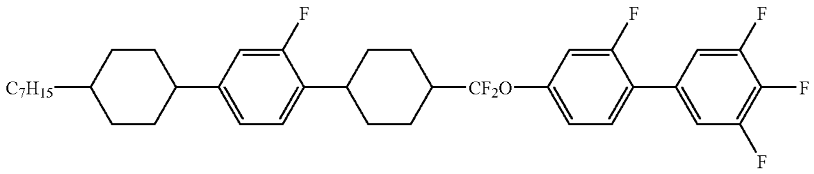 |
| 1-3-174 | 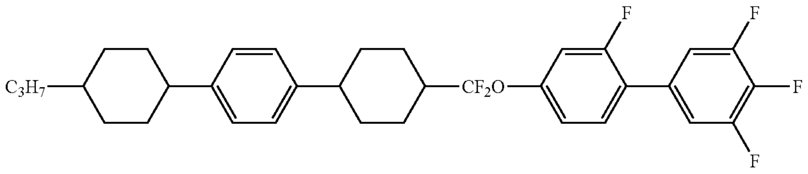 |
| 1-3-175 | 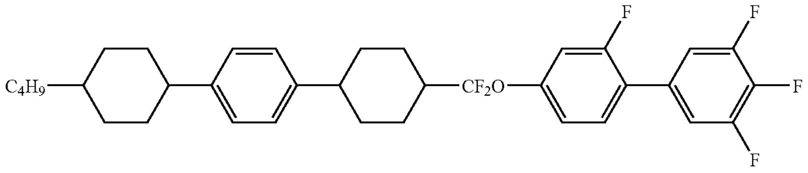 |
| 1-3-176 | 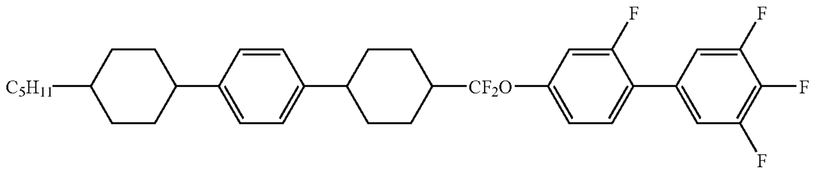 |
| 1-3-177 | 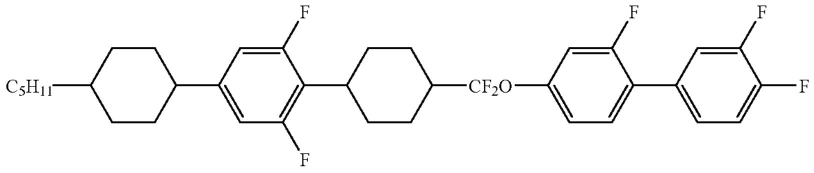 |
| 1-3-178 | 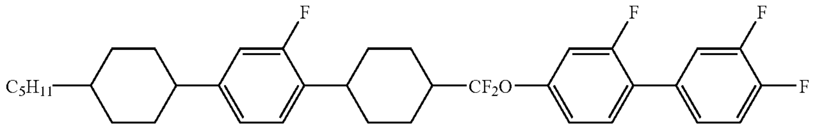 |
| 1-3-179 | 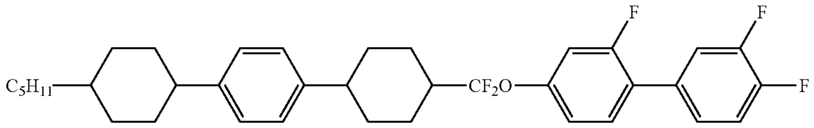 |
| 1-3-180 | 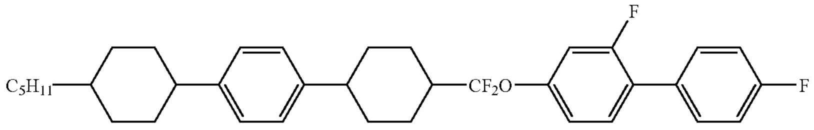 |
| 1-3-181 | 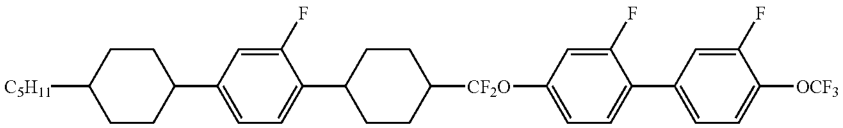 |

-continued
No.
1-3-182
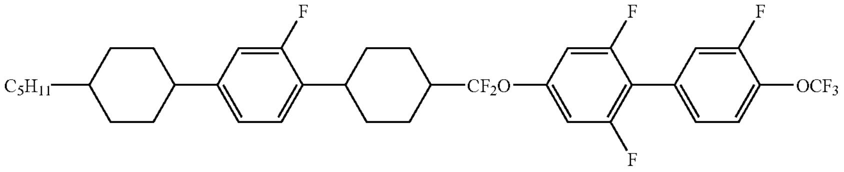
1-3-183
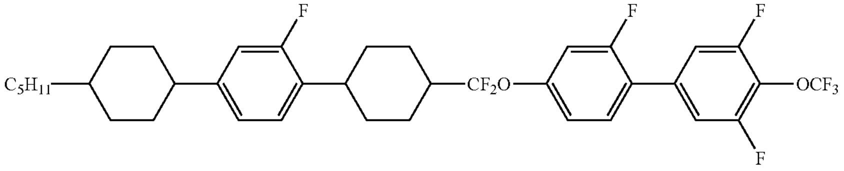
1-3-184
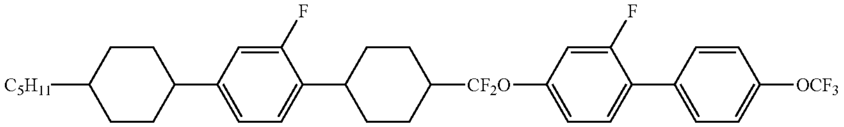
1-3-185
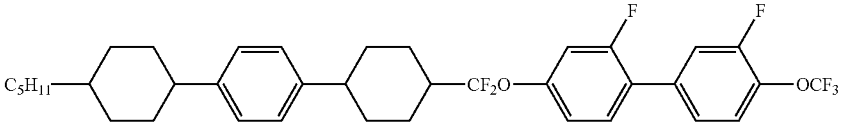
1-3-186
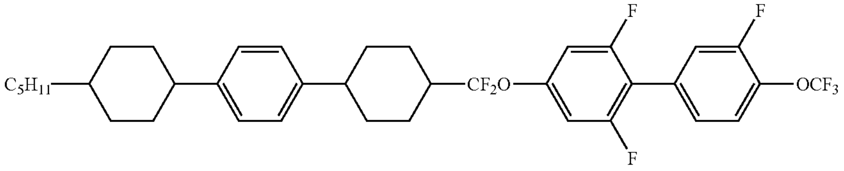
1-3-187
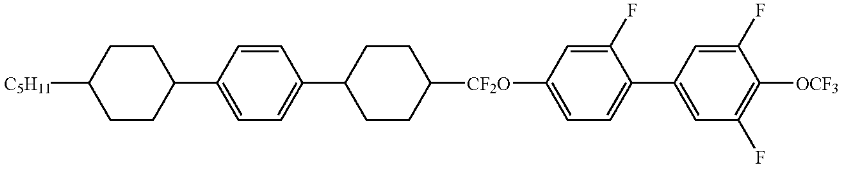
1-3-188
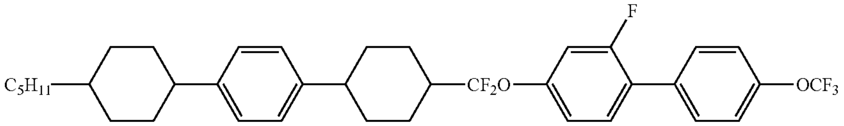
1-3-189
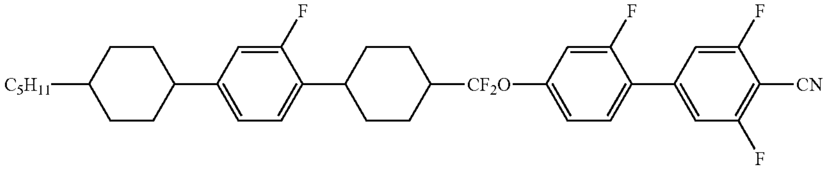
1-3-190
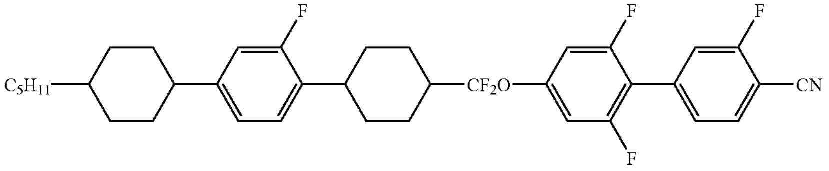

-continued
| No. | |
|---|---|
| 1-3-191 | 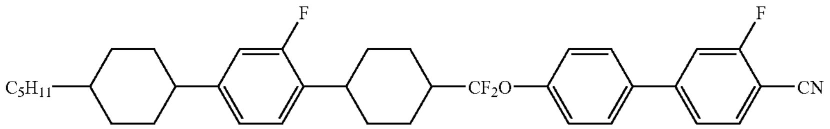 |
| 1-3-192 | 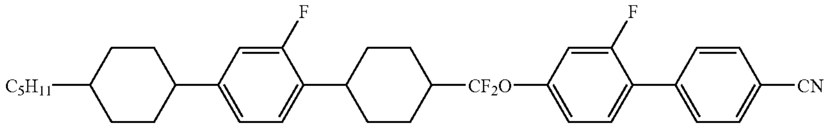 |
| 1-3-193 | 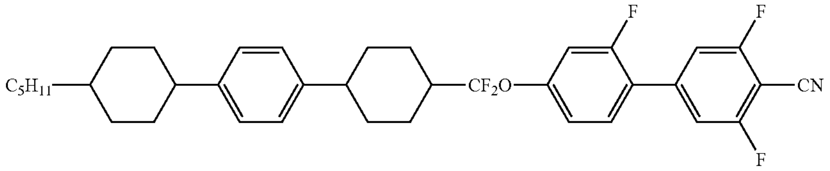 |
| 1-3-194 | 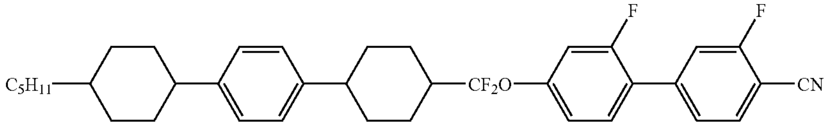 |
| 1-3-195 | 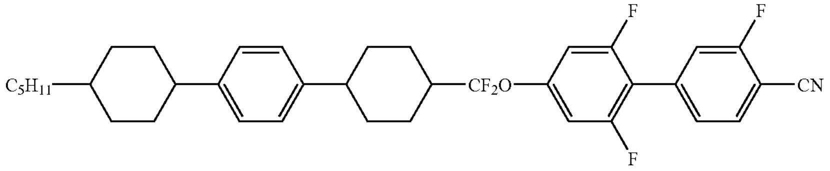 |
| 1-3-196 | 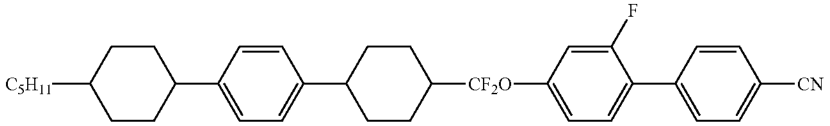 |
| 1-3-197 | 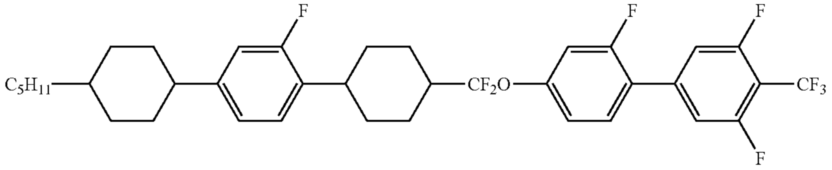 |
| 1-3-198 | 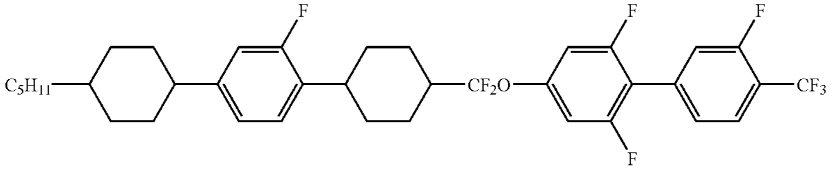 |
| 1-3-199 | 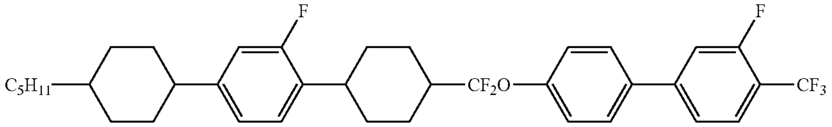 |
| 1-3-200 | 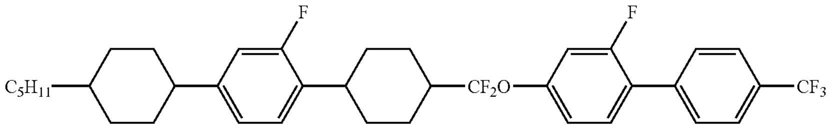 |

-continued
No.
1-3-201
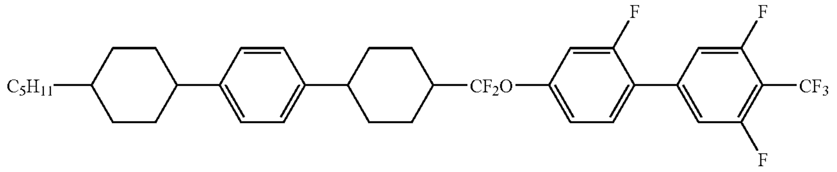
1-3-202
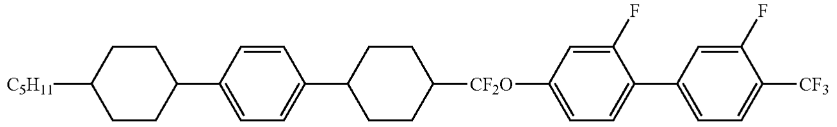
1-3-203
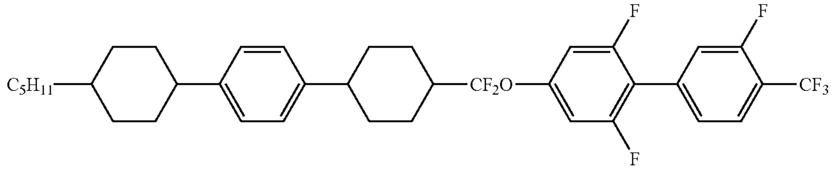
1-3-204
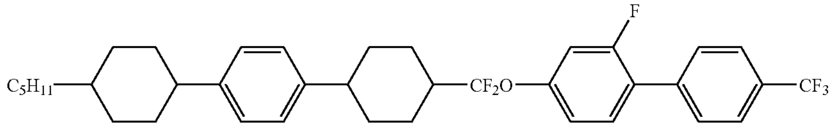
1-3-205
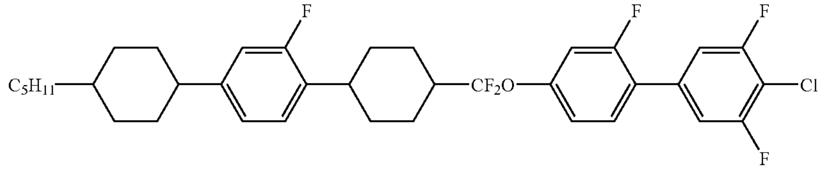
1-3-206
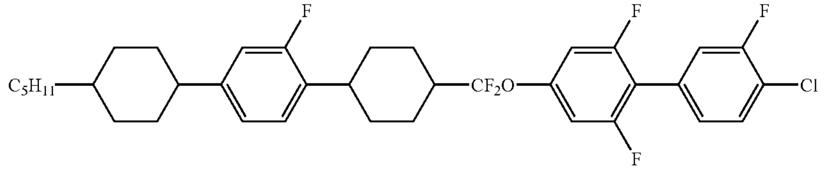
1-3-207
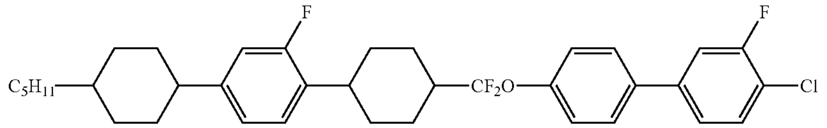
1-3-208
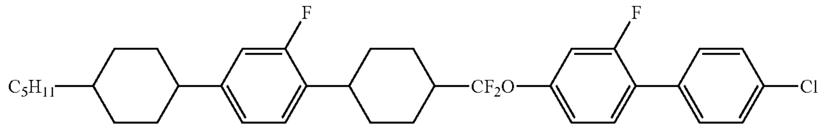
1-3-209
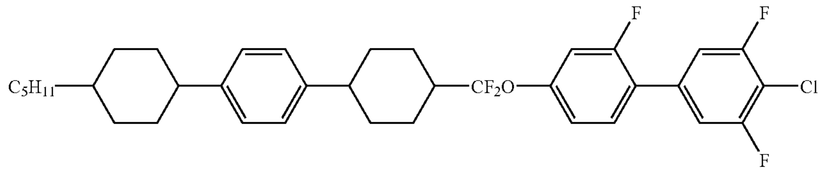

-continued
| No. | |
|---|---|
| 1-3-210 | 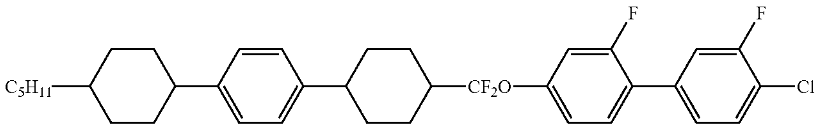 |
| 1-3-211 | 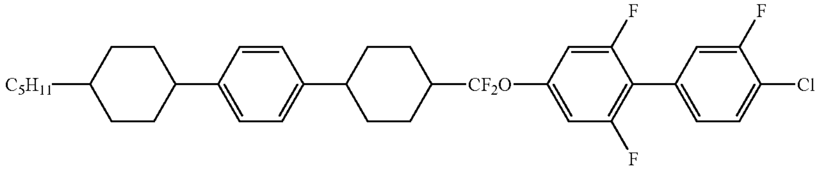 |
| 1-3-212 | 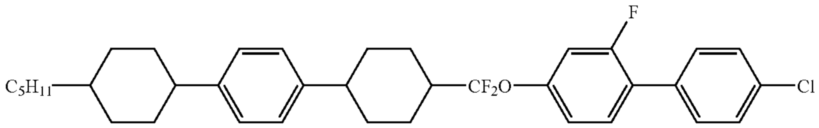 |
| 1-3-213 | 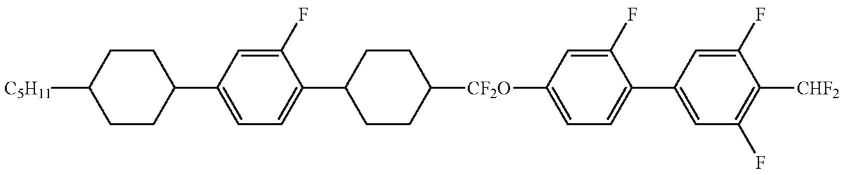 |
| 1-3-214 | 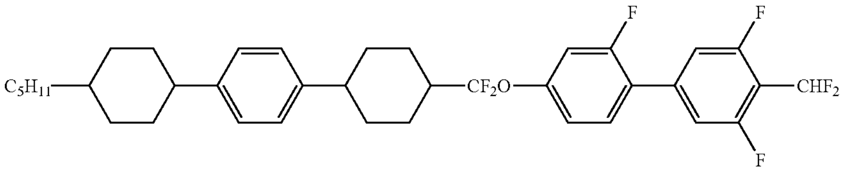 |
| 1-3-215 | 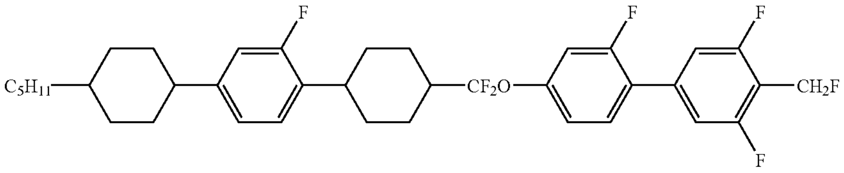 |
| 1-3-216 | 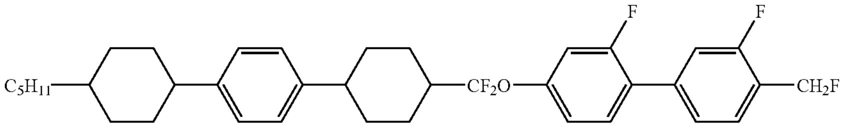 |
| 1-3-217 | 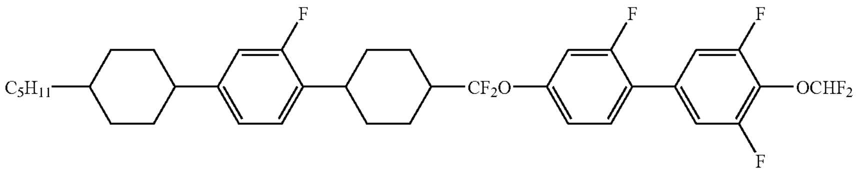 |
| 1-3-218 | 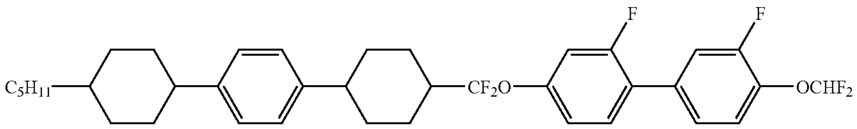 |

-continued
| No. | |
|---|---|
| 1-3-219 | 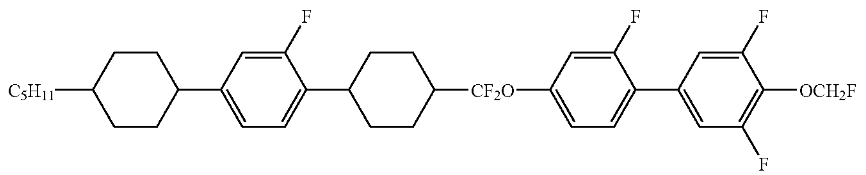 |
| 1-3-220 | 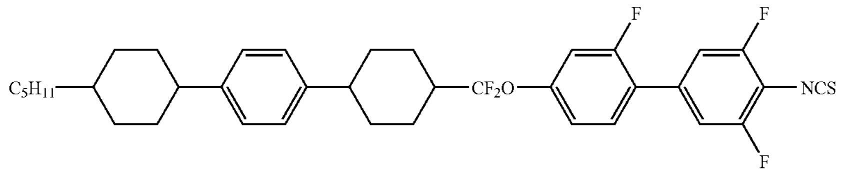 |
| 1-3-221 | 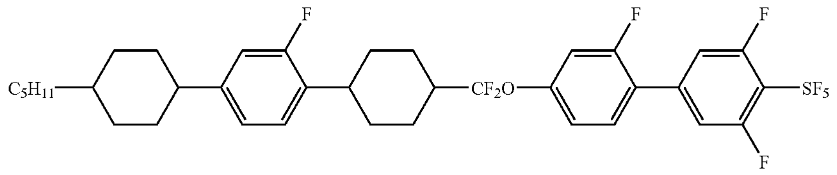 |
| 1-3-222 | 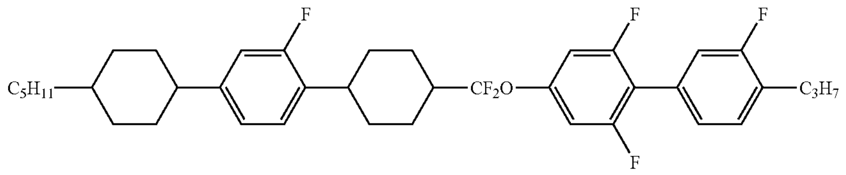 |
| 1-3-223 | 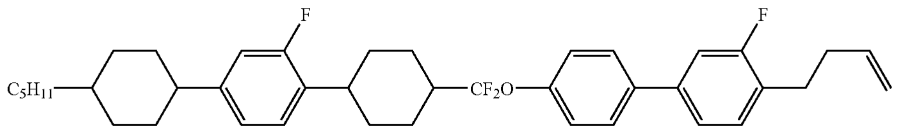 |
| 1-3-224 | 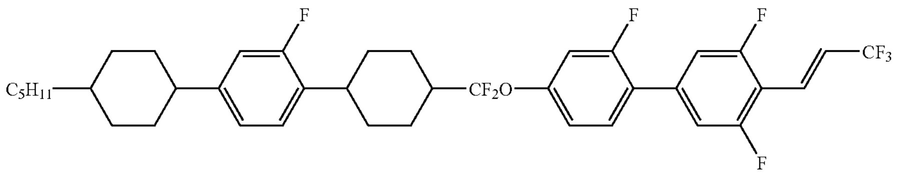 |
| 1-3-225 | 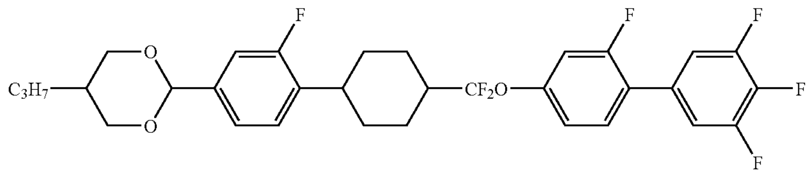 |
| 1-3-226 | 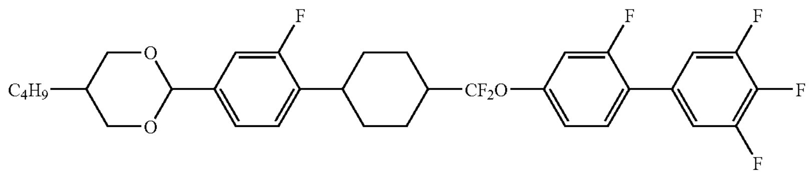 |
| 1-3-227 | 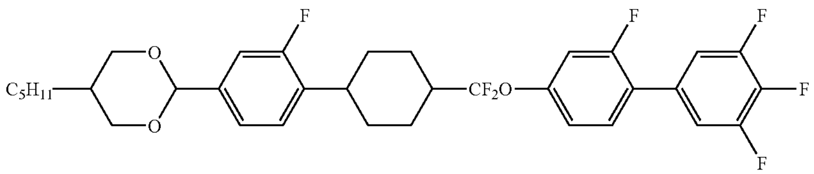 |

-continued
No.
1-3-228
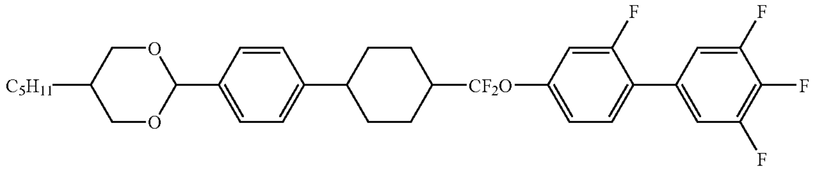
1-3-229
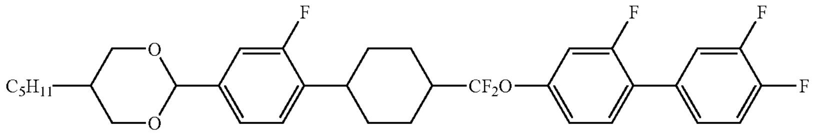
1-3-230
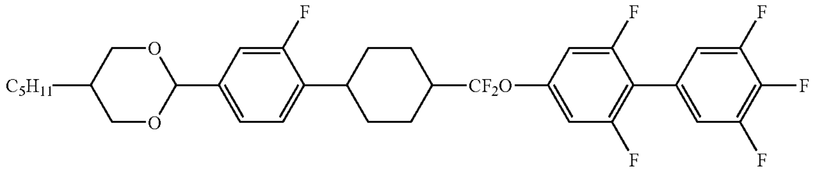
1-3-231
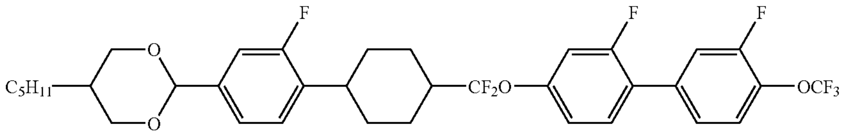
1-3-232
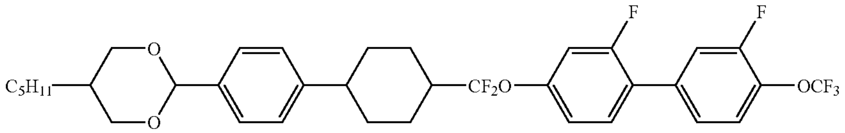
1-3-233
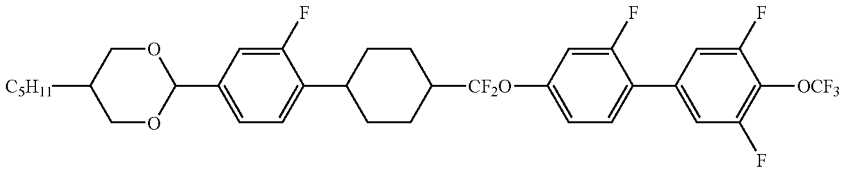
1-3-234
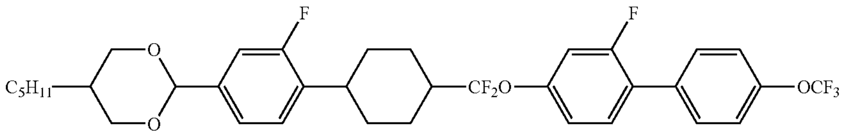
1-3-235
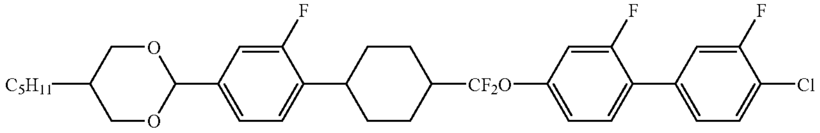
1-3-236
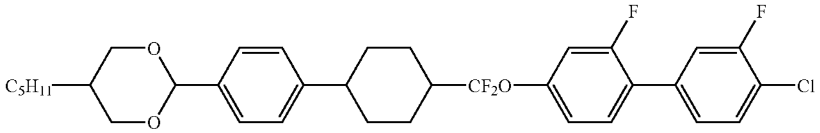

-continued
| No. | |
|---|---|
| 1-3-237 | 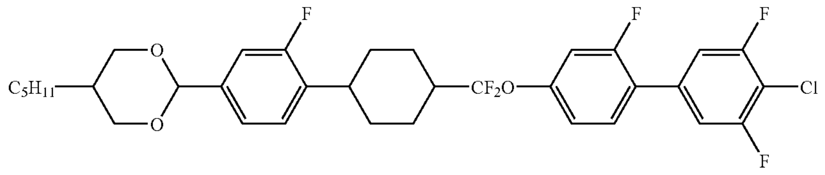 |
| 1-3-238 | 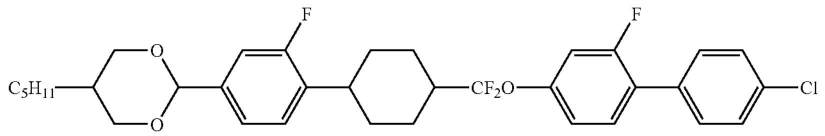 |
| 1-3-239 | 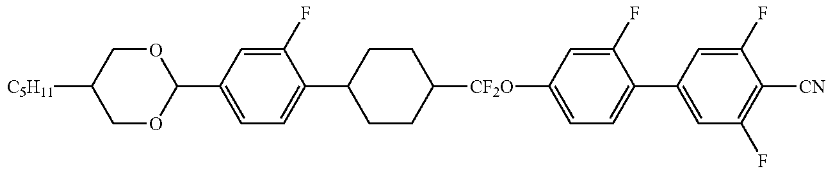 |
| 1-3-240 | 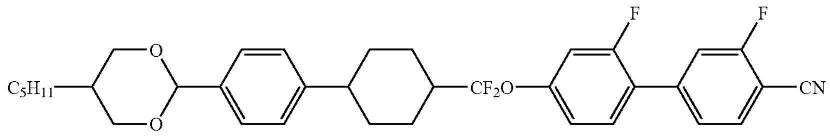 |
| 1-3-241 | 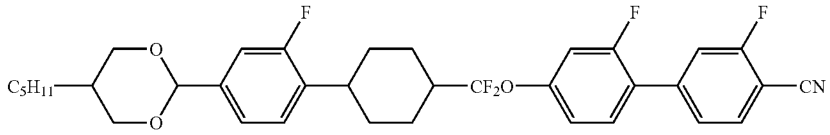 |
| 1-3-242 | 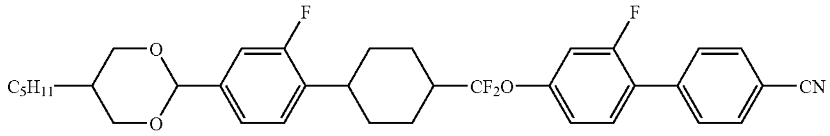 |
| 1-3-243 | 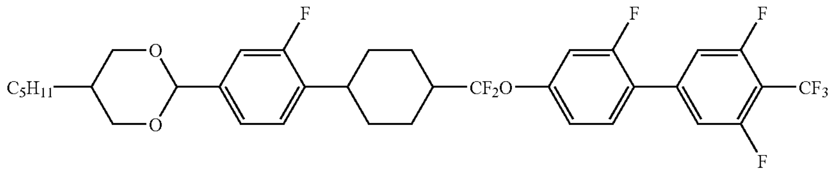 |
| 1-3-244 | 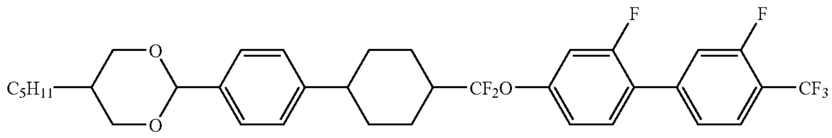 |
| 1-3-245 | 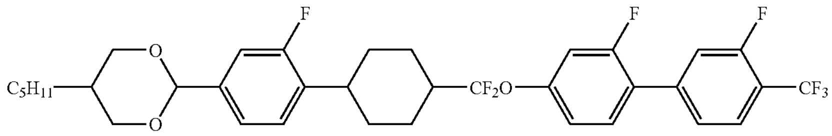 |
| 1-3-246 | 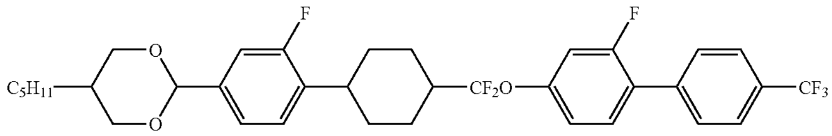 |

-continued
| No. | |
|---|---|
| 1-3-247 | 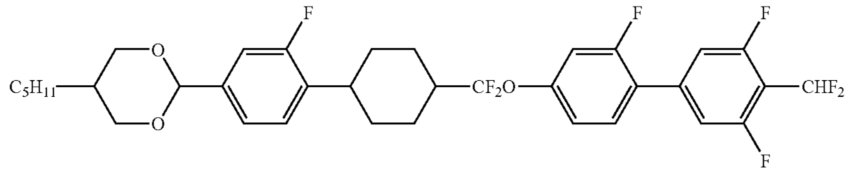 |
| 1-3-248 | 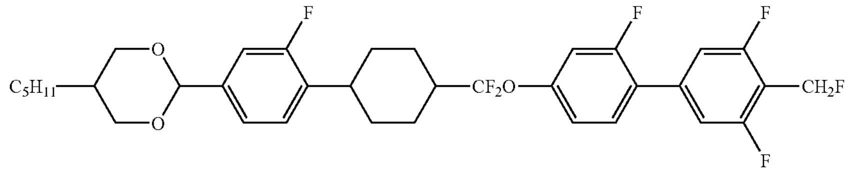 |
| 1-3-249 | 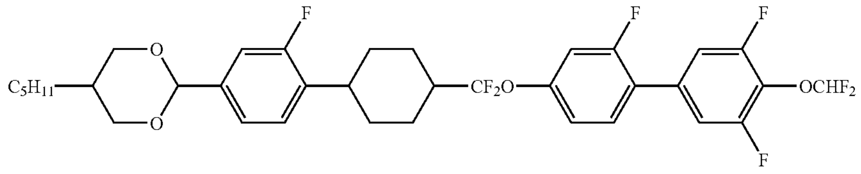 |
| 1-3-250 | 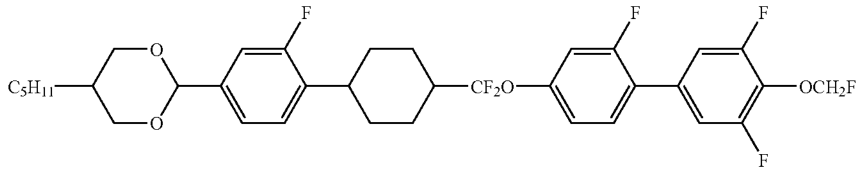 |
| 1-3-251 | 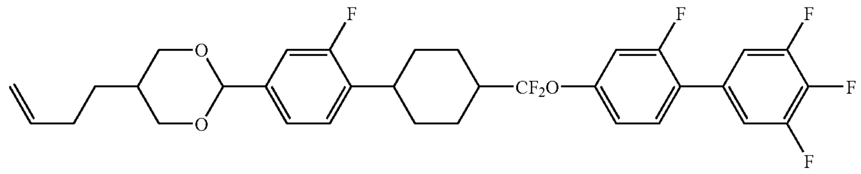 |
| 1-3-252 | 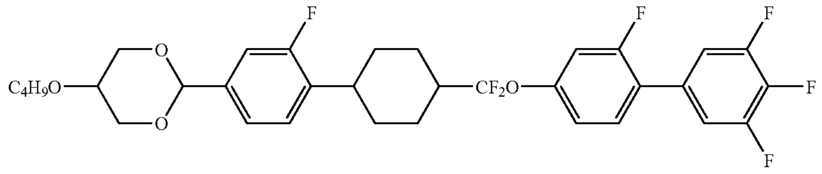 |
| 1-3-253 | 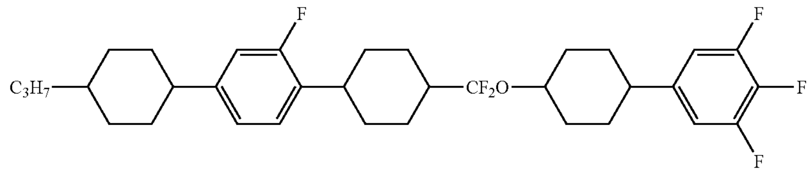 |
| 1-3-254 | 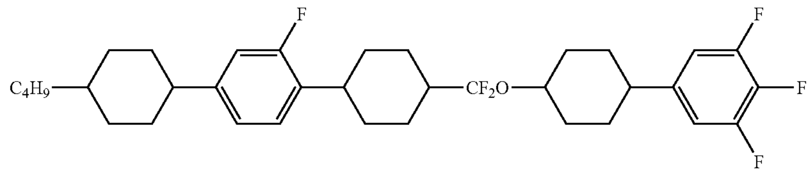 |

-continued
| No. | |
|---|---|
| 1-3-255 | 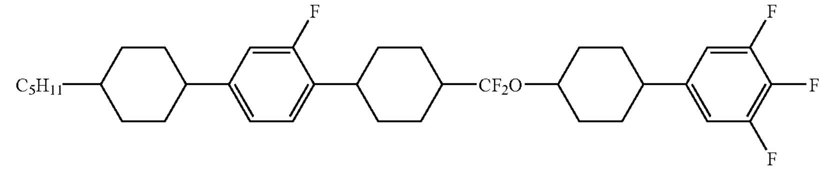 |
| 1-3-256 | 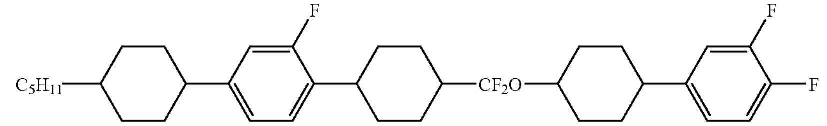 |
| 1-3-257 | 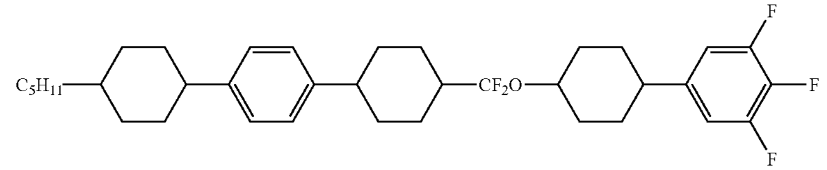 |
| 1-3-258 | 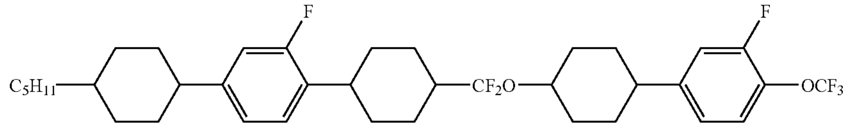 |
| 1-3-259 | 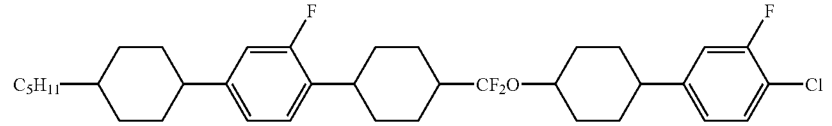 |
| 1-3-260 | 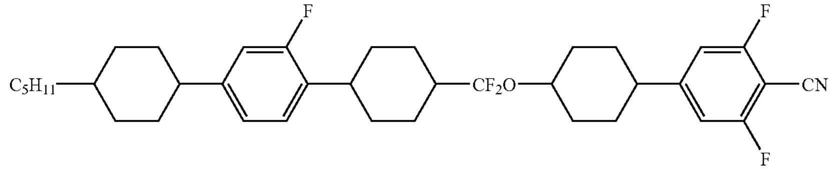 |
| 1-3-261 | 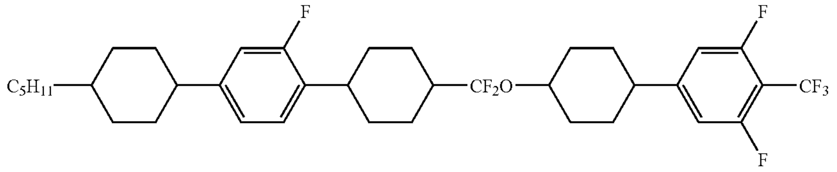 |
| 1-3-262 | 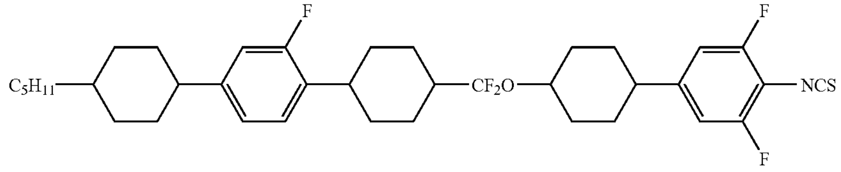 |
| 1-3-263 | 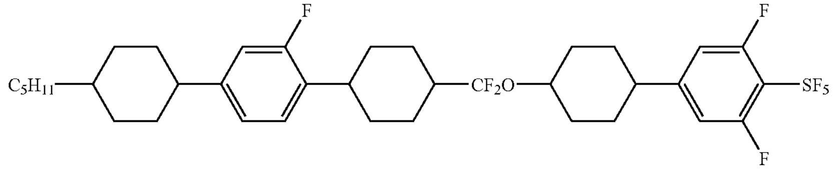 |

-continued
| No. | |
|---|---|
| 1-3-264 | 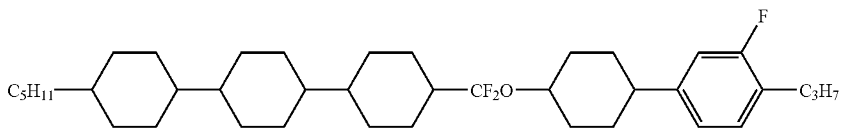 |
| 1-3-265 | 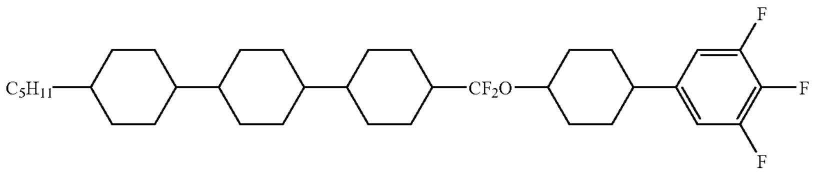 |
| 1-3-266 | 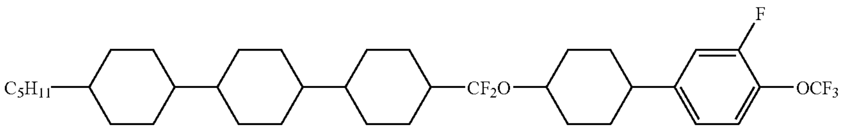 |
| 1-3-267 | 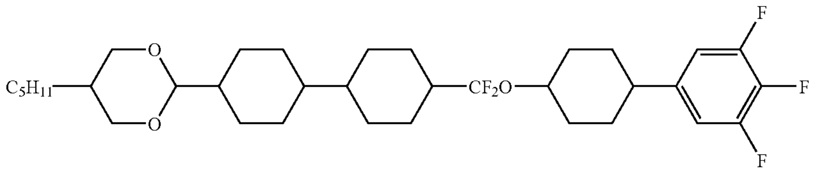 |
| 1-3-268 | 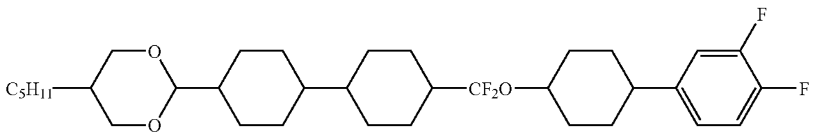 |
| 1-3-269 | 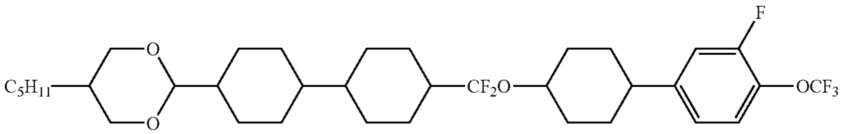 |
| 1-3-270 | 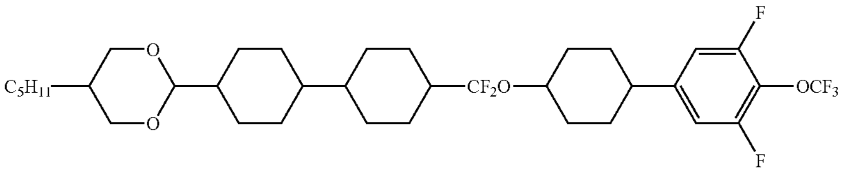 |
| 1-3-271 | 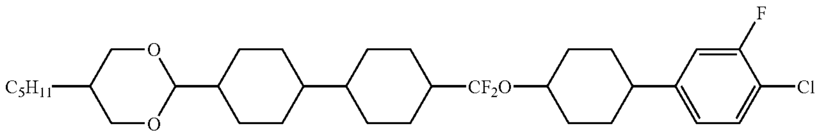 |
| 1-3-272 | 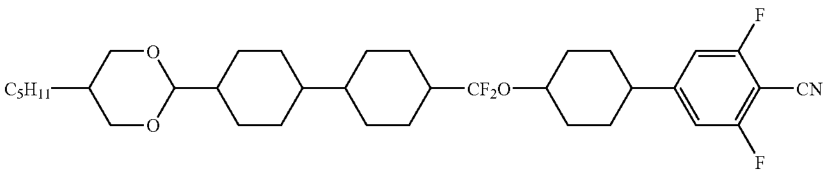 |

-continued
| No. | |
|---|---|
| 1-3-273 | 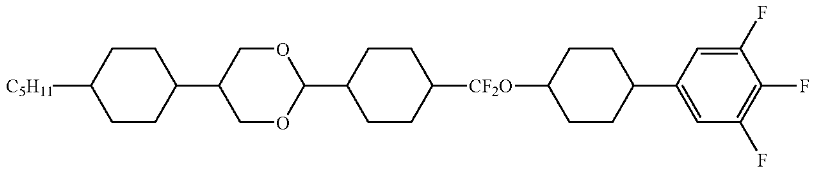 |
| 1-3-274 | 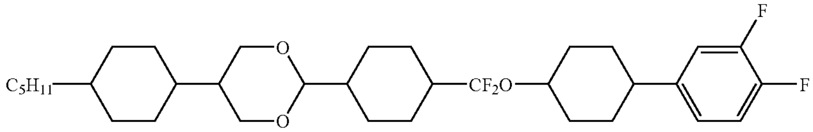 |
| 1-3-275 | 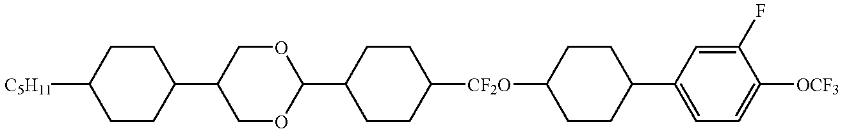 |
| 1-3-276 | 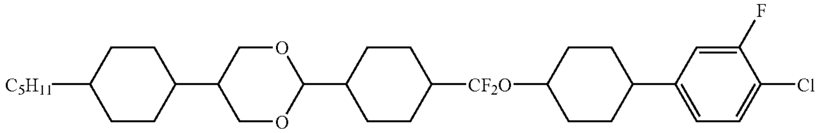 |
| 1-3-277 | 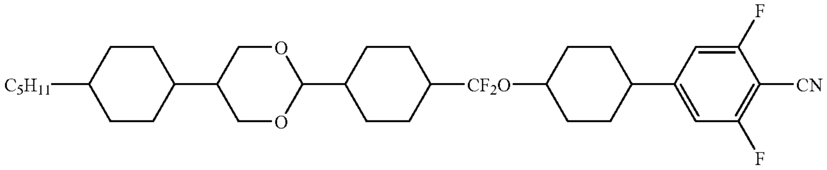 |
| 1-3-278 | 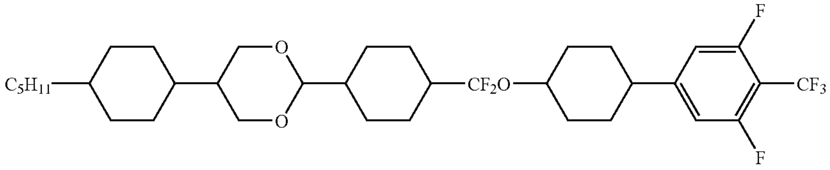 |
| 1-3-279 | 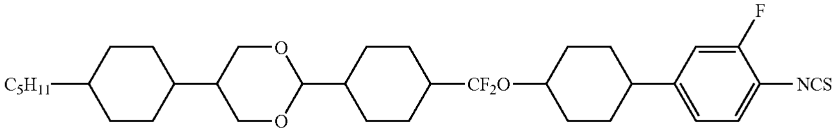 |
| 1-3-280 | 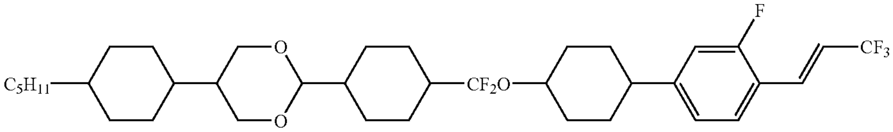 |
| 1-3-281 | 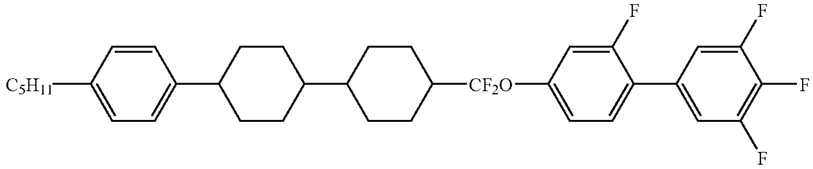 |

-continued
No.
1-3-282
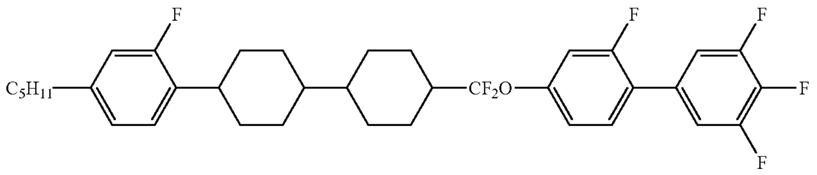
1-3-283
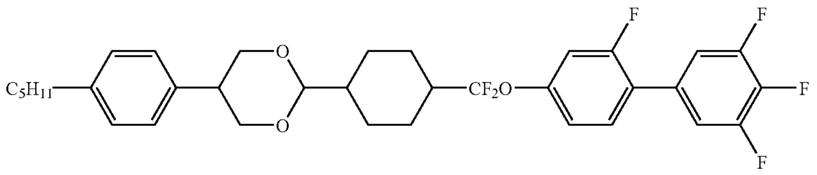
1-3-284
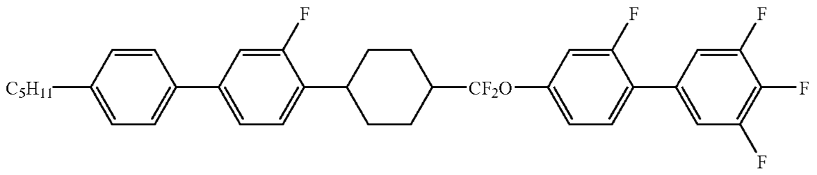
1-3-285
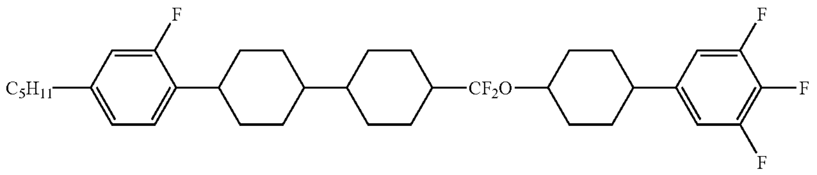
1-3-286
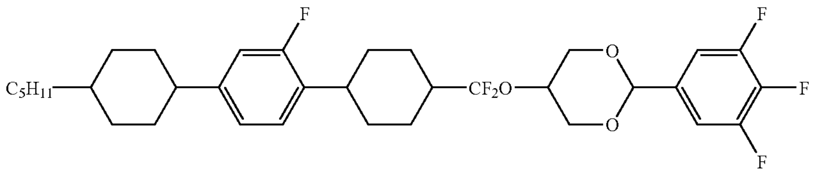
1-3-287
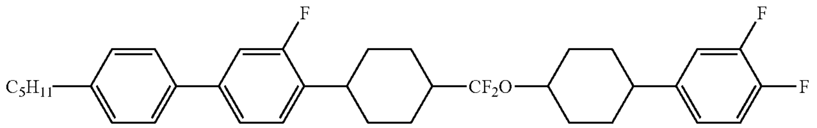
1-3-288
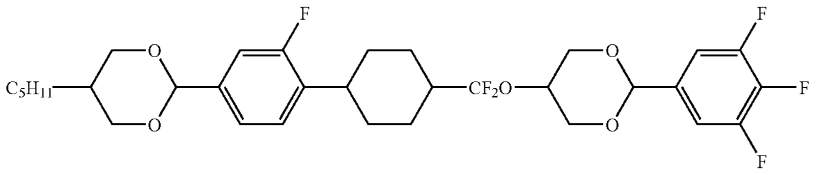
1-3-289
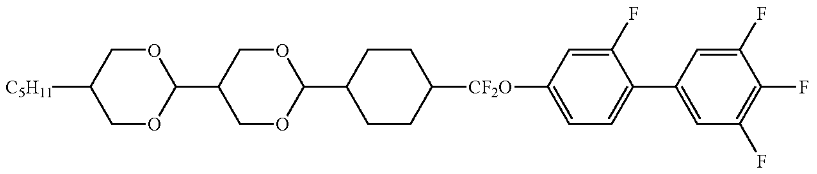
1-3-290
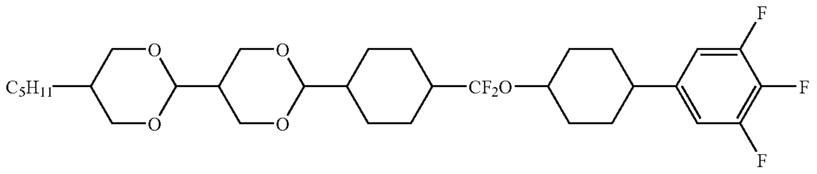

-continued
| No. | |
|---|---|
| 1-3-291 | 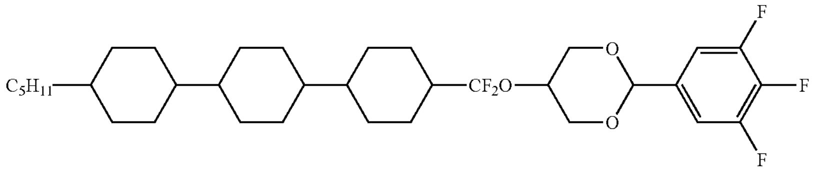 |
| 1-3-292 | 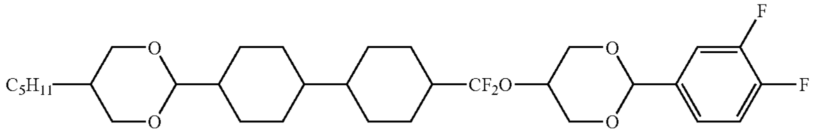 |
| 1-3-293 | 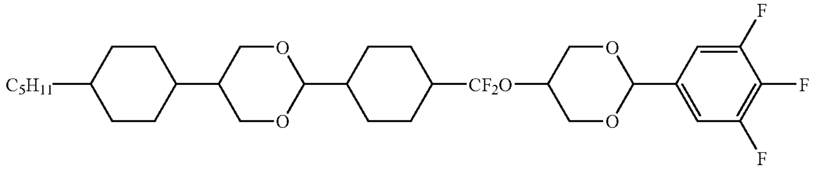 |
| 1-3-294 | 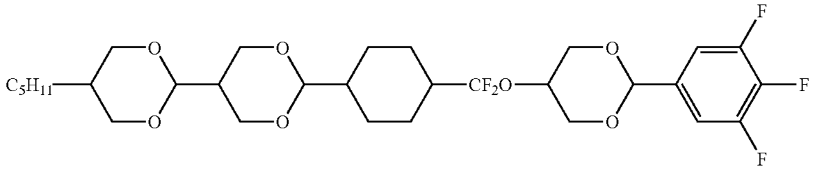 |
| 1-3-295 | 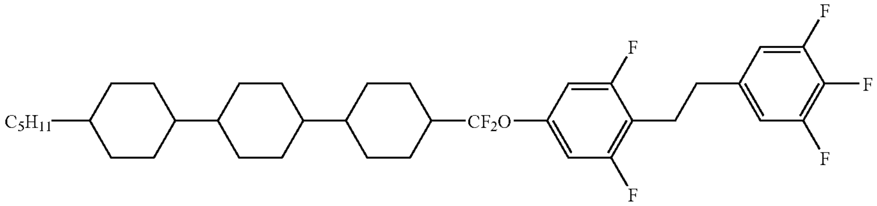 |
| 1-3-296 | 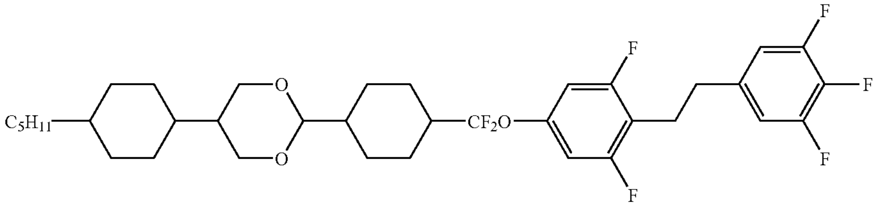 |
| 1-3-297 | 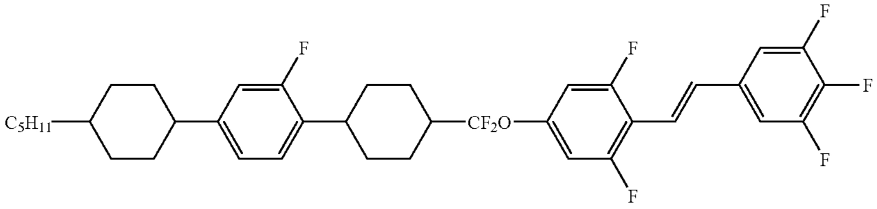 |
| 1-3-298 | 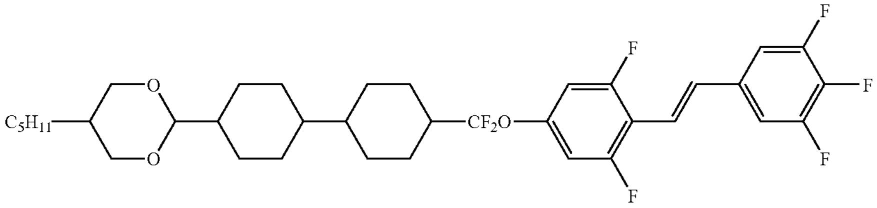 |

-continued
No.
1-3-299
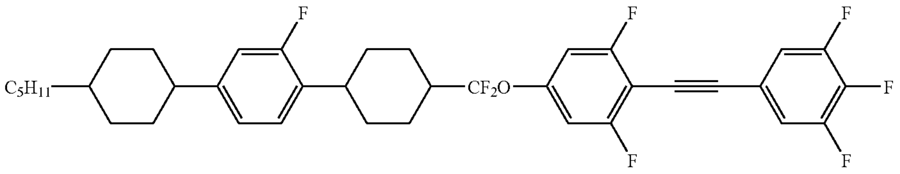
1-3-300
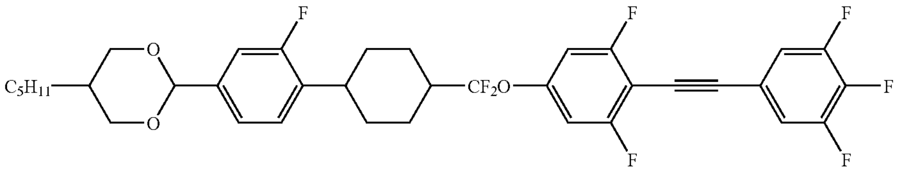
1-3-301
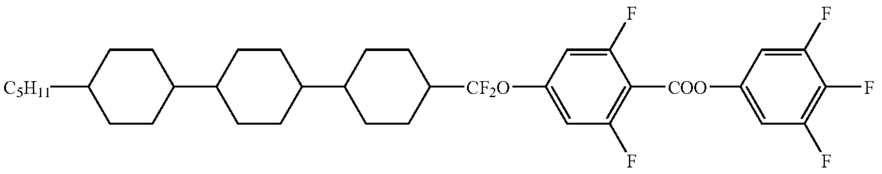
1-3-302
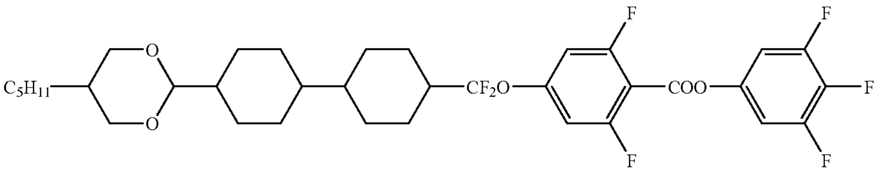
1-3-303
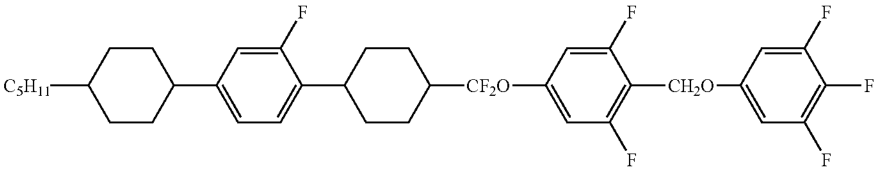
1-3-304
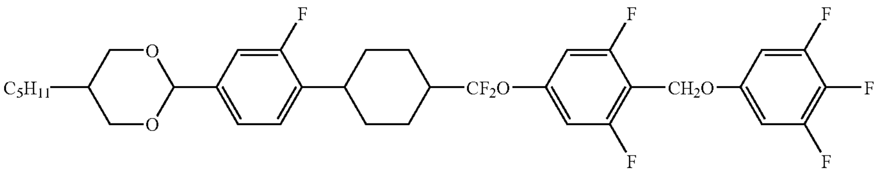
1-3-305
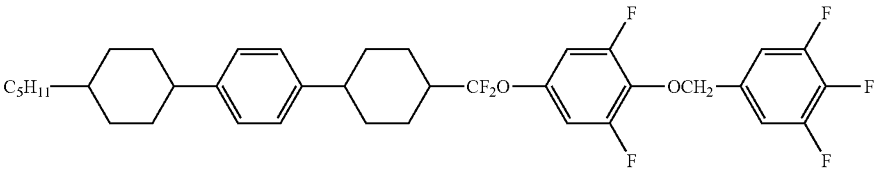
1-3-306
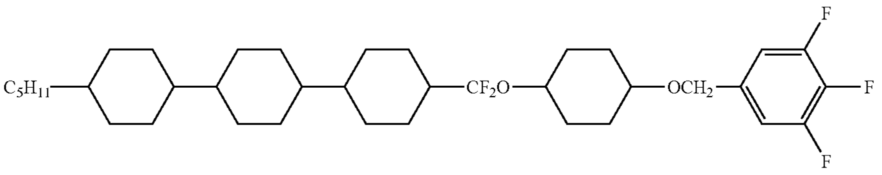

-continued
| No. | |
|---|---|
| 1-3-307 | 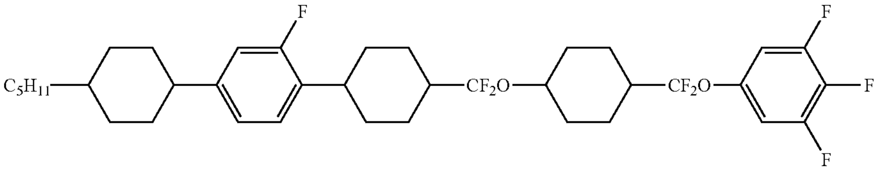 |
| 1-3-308 | 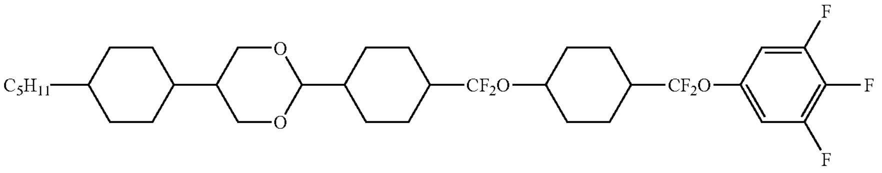 |
| 1-3-309 | 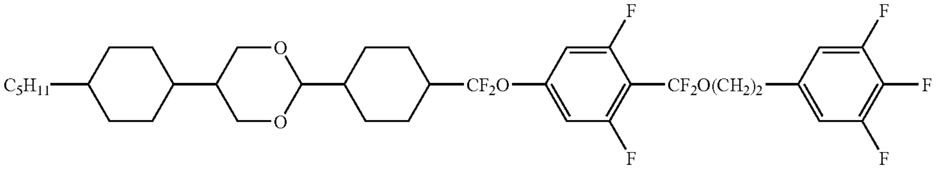 |
| 1-3-310 | 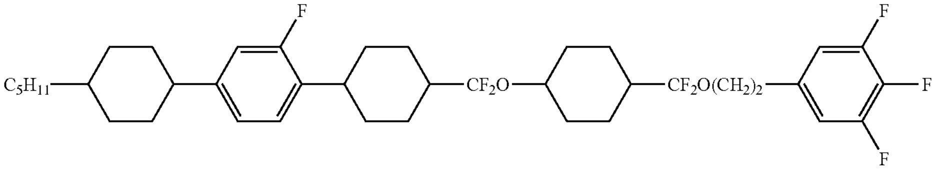 |
| 1-3-311 | 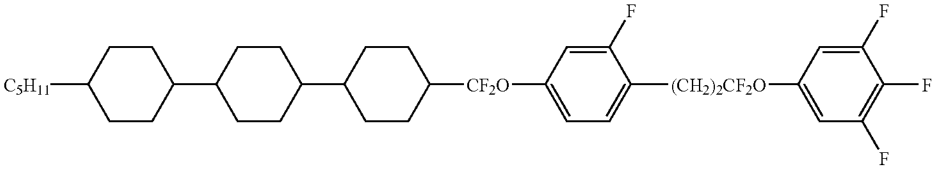 |
| 1-3-312 | 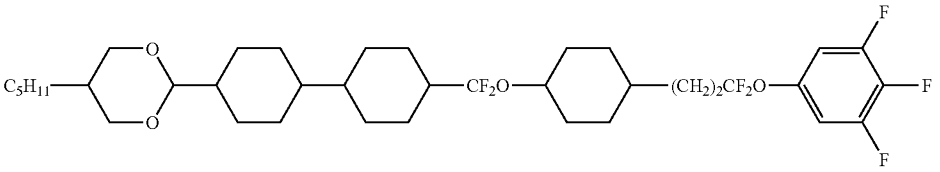 |
| 1-4-1 | 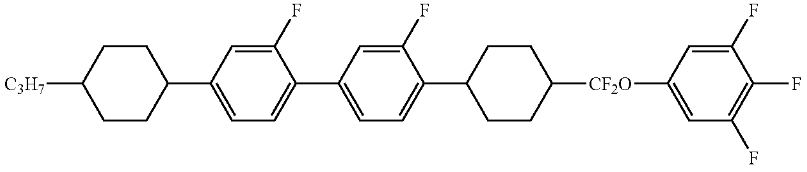 |
| 1-4-2 | 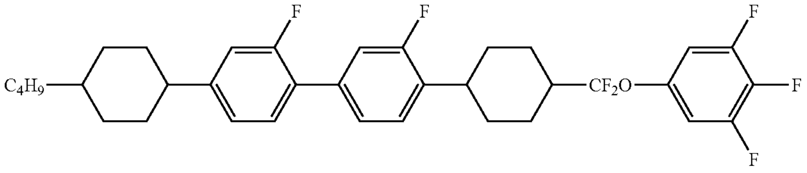 |

-continued
| No. | |
|---|---|
| 1-4-3 | 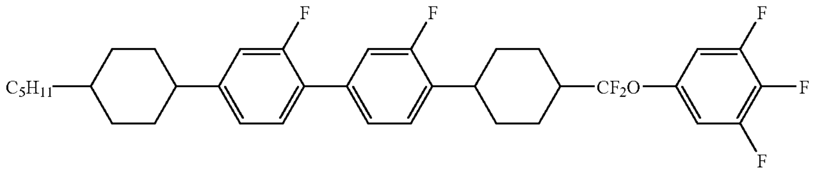 |
| 1-4-4 | 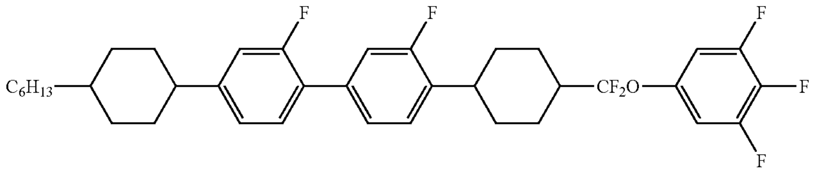 |
| 1-4-5 | 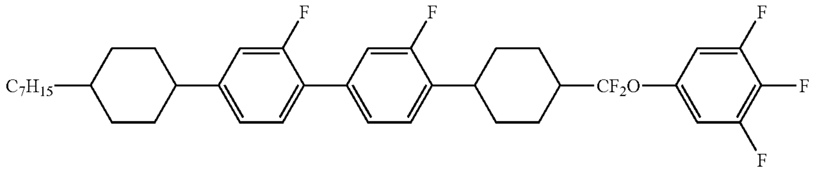 |
| 1-4-6 | 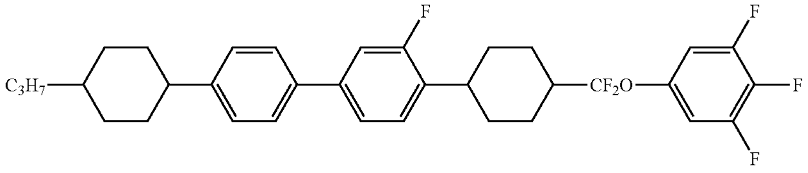 |
| 1-4-7 | 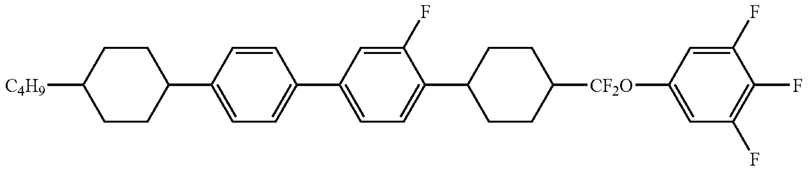 |
| 1-4-8 | 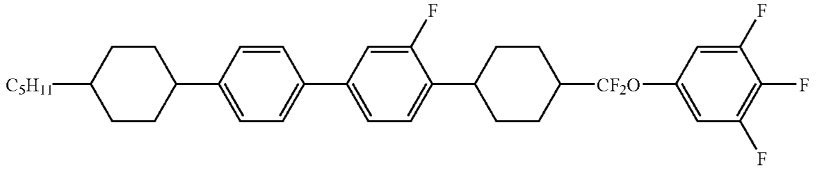 |
| 1-4-9 | 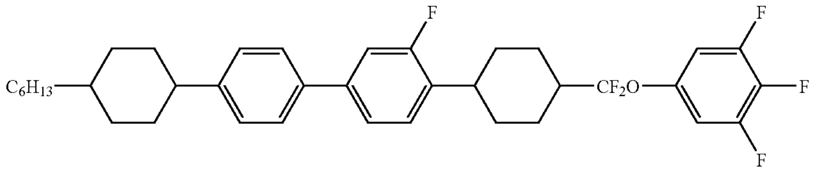 |
| 1-4-10 | 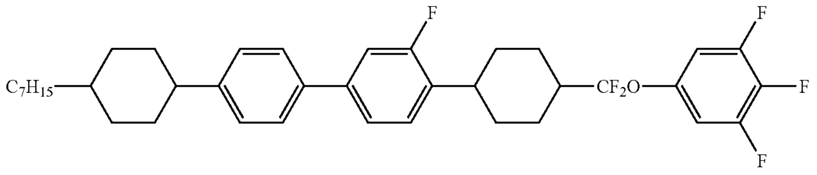 |

-continued
| No. | |
|---|---|
| 1-4-11 | 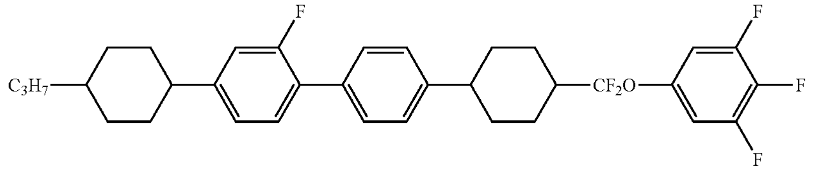 |
| 1-4-12 | 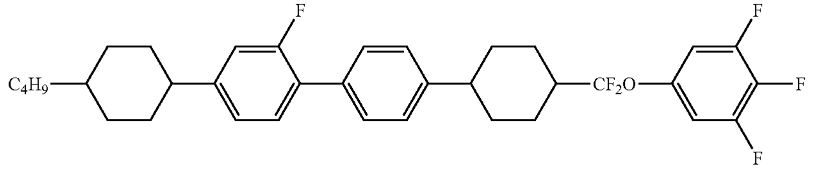 |
| 1-4-13 | 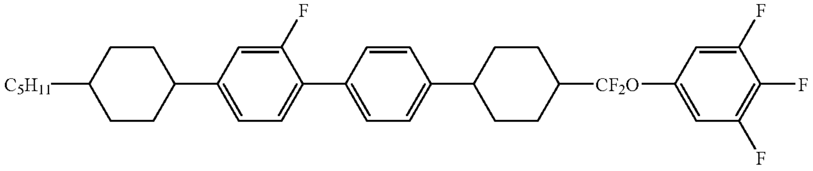 |
| 1-4-14 | 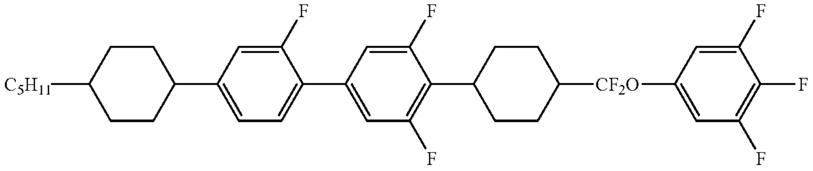 |
| 1-4-15 | 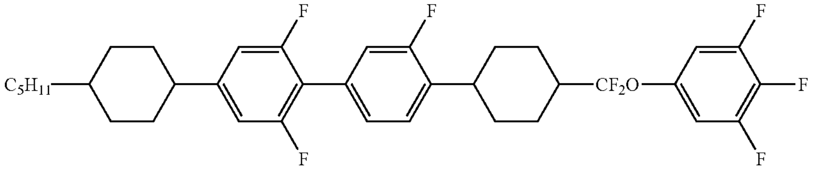 |
| 1-4-16 | 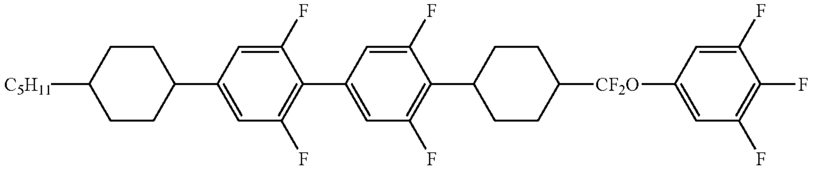 |
| 1-4-17 | 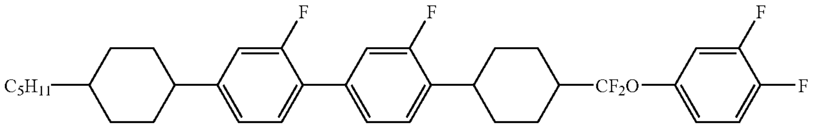 |
| 1-4-18 | 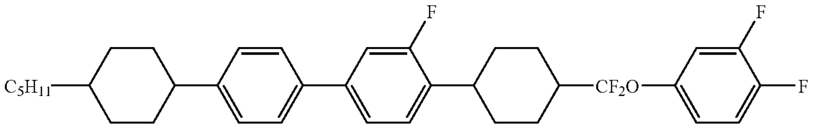 |
| 1-4-19 | 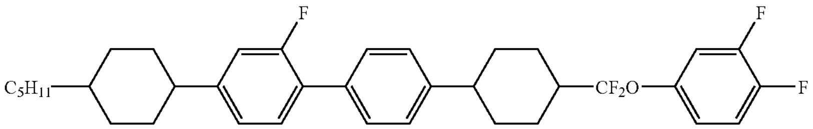 |

-continued
| No. | |
|---|---|
| 1-4-20 | 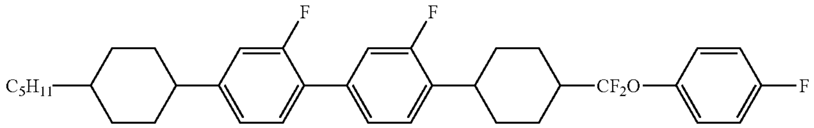 |
| 1-4-21 | 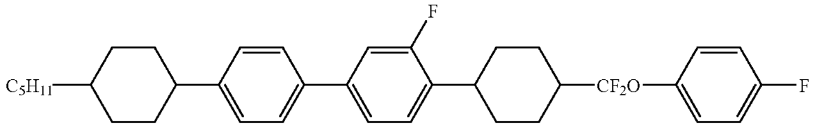 |
| 1-4-22 | 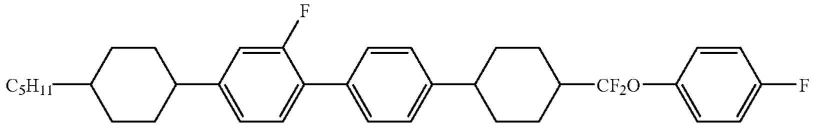 |
| 1-4-23 | 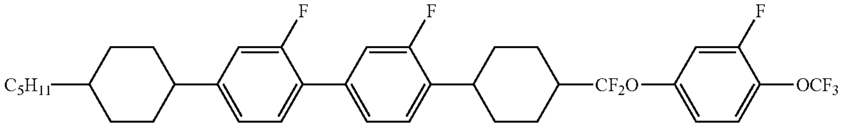 |
| 1-4-24 | 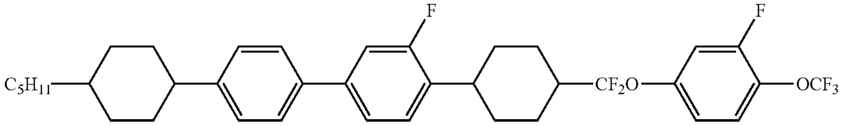 |
| 1-4-25 | 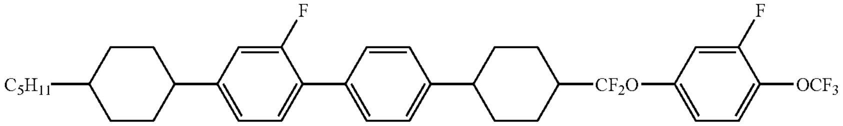 |
| 1-4-26 | 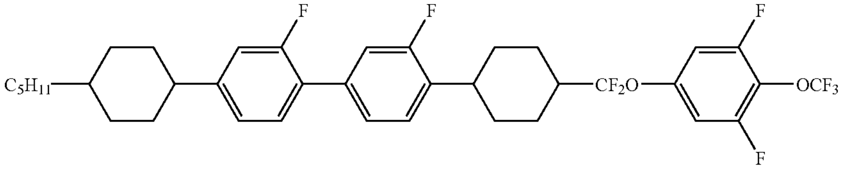 |
| 1-4-27 | 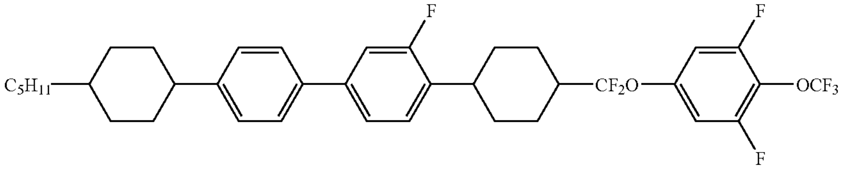 |
| 1-4-28 | 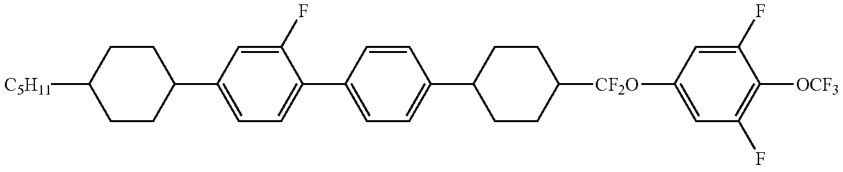 |
| 1-4-29 | 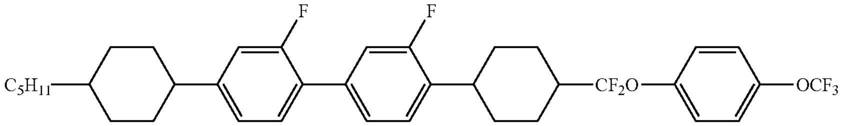 |

-continued
| No. | |
|---|---|
| 1-4-30 | 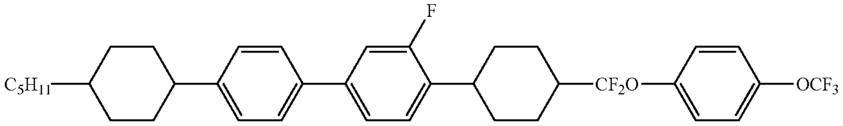 |
| 1-4-31 | 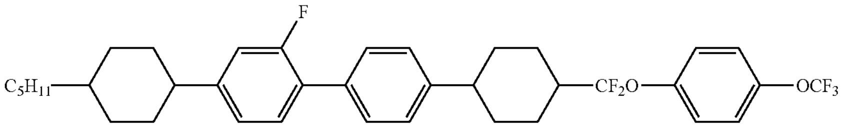 |
| 1-4-32 | 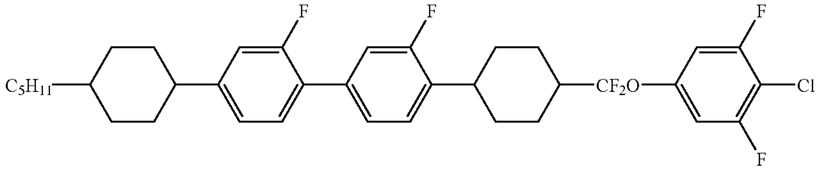 |
| 1-4-33 | 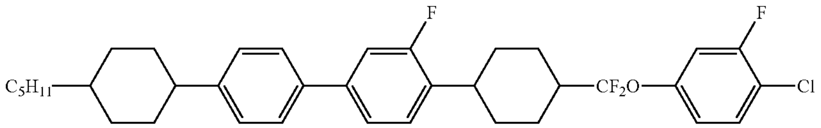 |
| 1-4-34 | 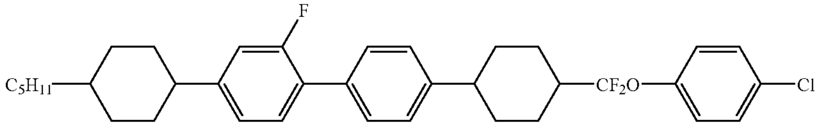 |
| 1-4-35 | 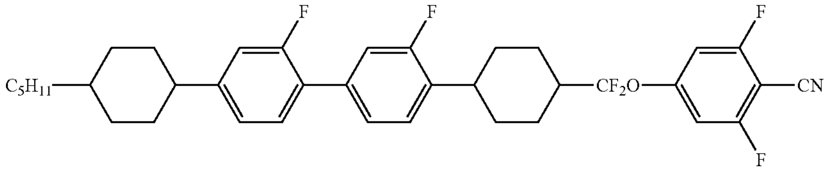 |
| 1-4-36 | 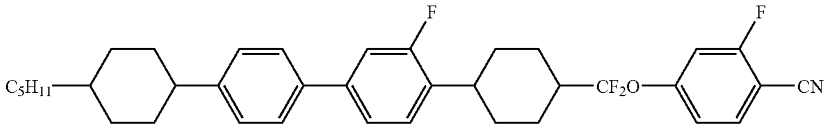 |
| 1-4-37 | 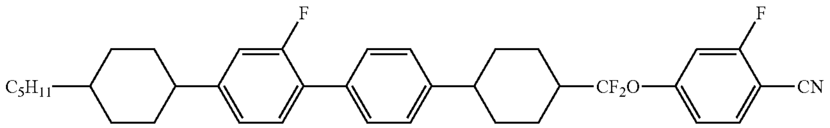 |
| 1-4-38 | 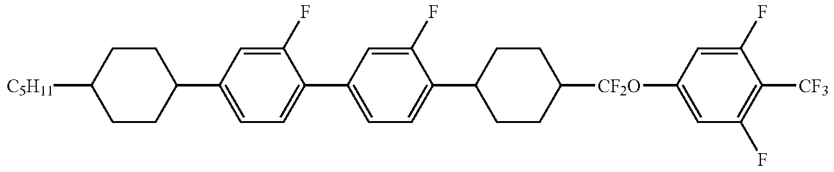 |
| 1-4-39 | 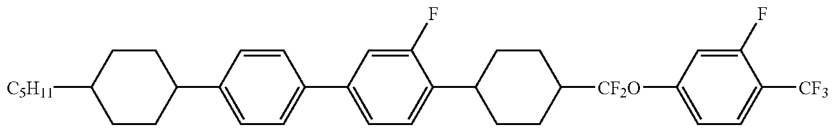 |

-continued
| No. | |
|---|---|
| 1-4-40 | 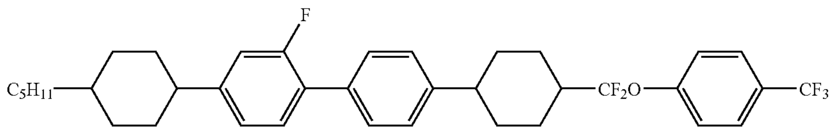 |
| 1-4-41 | 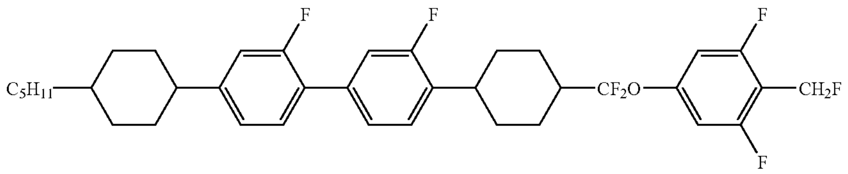 |
| 1-4-42 | 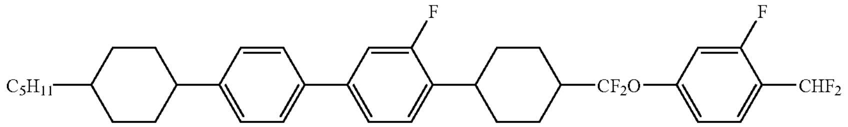 |
| 1-4-43 | 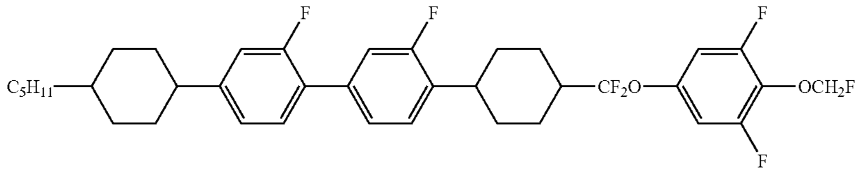 |
| 1-4-44 | 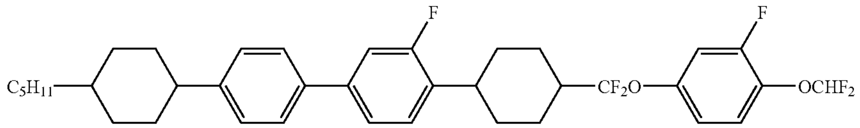 |
| 1-4-45 | 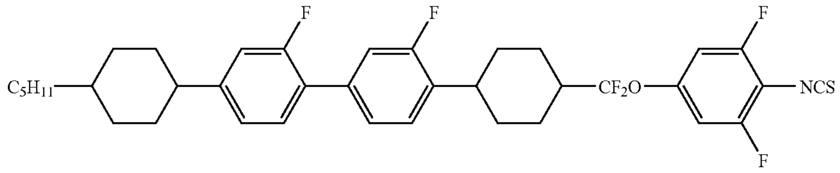 |
| 1-4-46 | 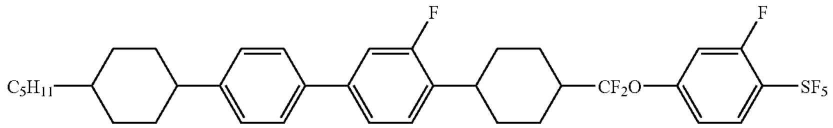 |
| 1-4-47 | 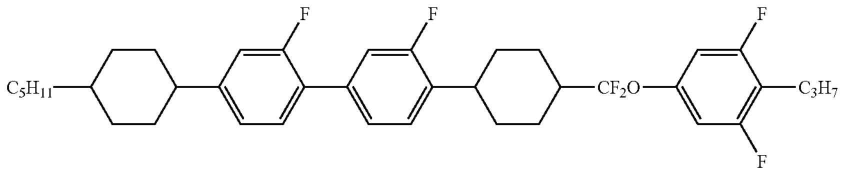 |
| 1-4-48 | 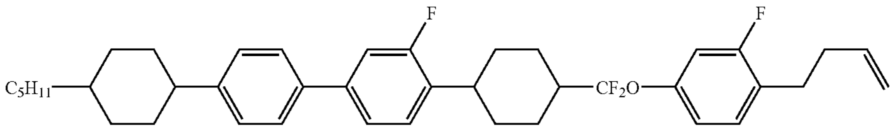 |

-continued
| No. | |
|---|---|
| 1-4-49 | 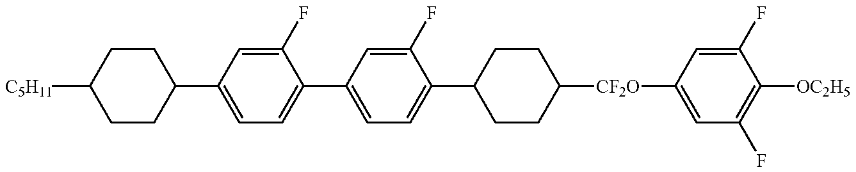 |
| 1-4-50 | 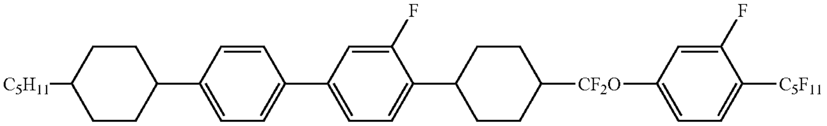 |
| 1-4-51 | 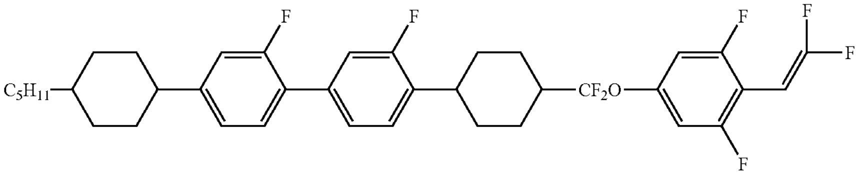 |
| 1-4-52 | 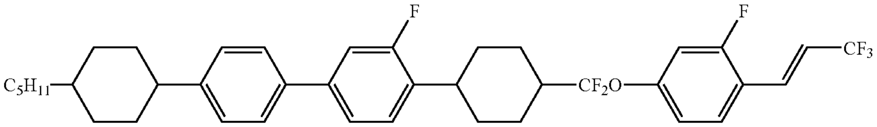 |
| 1-4-53 | 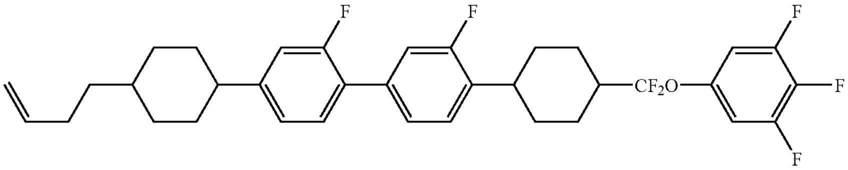 |
| 1-4-54 | 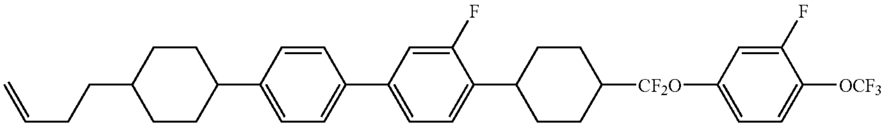 |
| 1-4-55 | 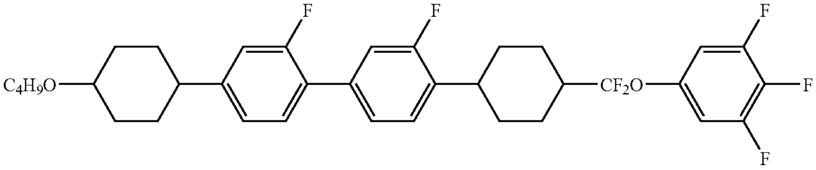 |
| 1-4-56 | 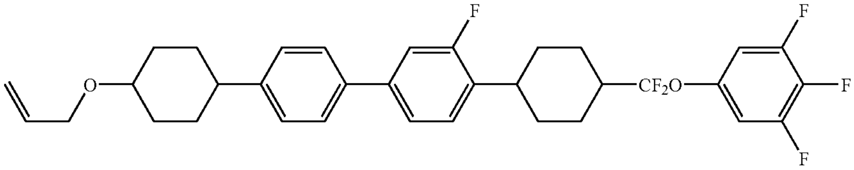 |
| 1-4-57 | 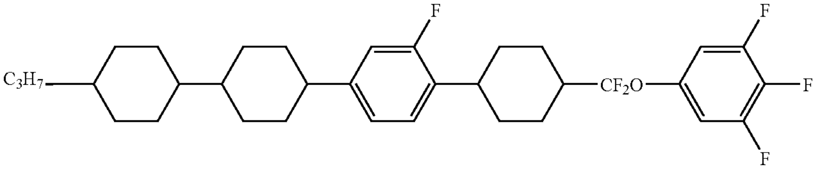 |

-continued
| No. | |
|---|---|
| 1-4-58 | 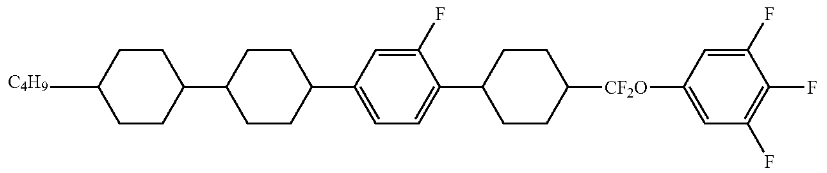 |
| 1-4-59 | 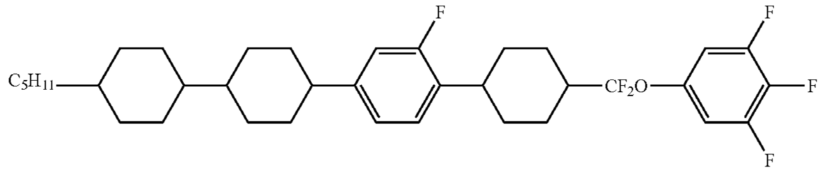<br>$T_{NI}$ = 216° C., Δ n = 0.130, Δ ∈ = 6.77 |
| 1-4-60 | 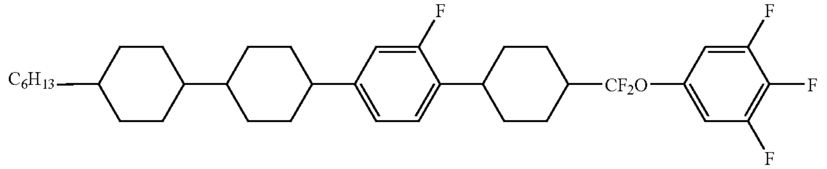 |
| 1-4-61 | 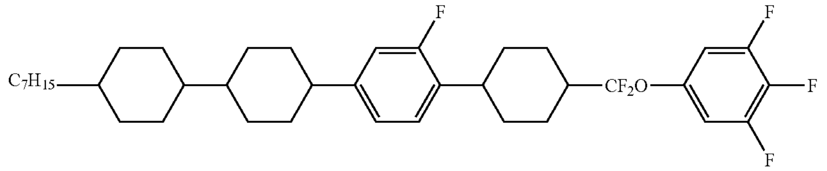 |
| 1-4-62 | 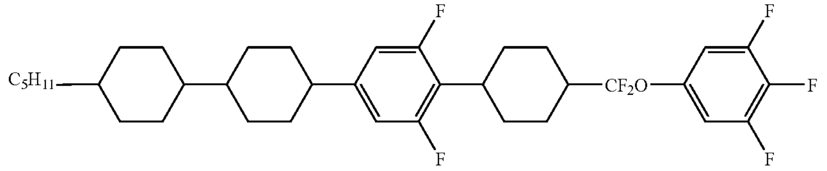 |
| 1-4-63 | 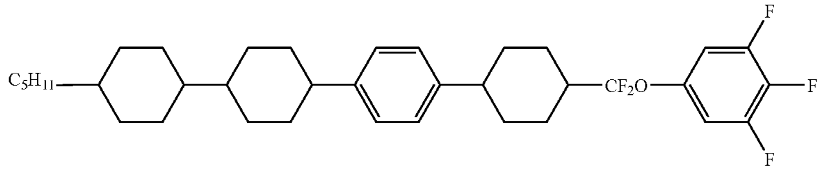 |
| 1-4-64 | 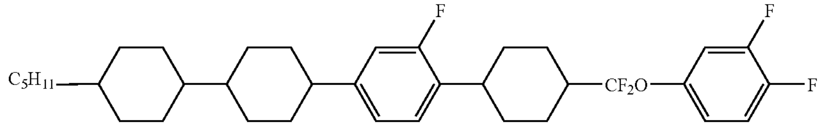 |
| 1-4-65 | 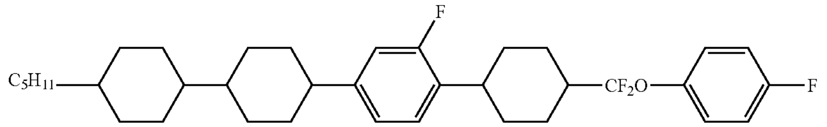 |
| 1-4-66 | 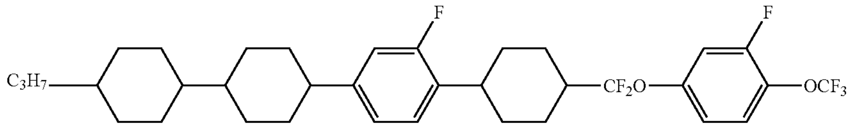<br>$T_{NI}$ = 214° C., Δ n = 0.130, Δ ∈ = 2.37 |

-continued
| No. | |
|---|---|
| 1-4-67 | 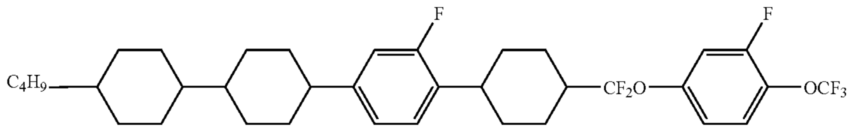 |
| 1-4-68 | 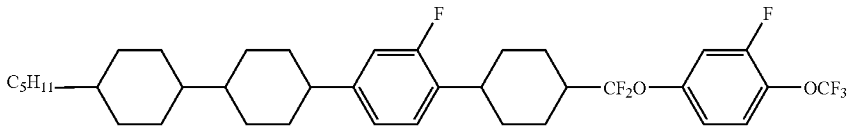 |
| 1-4-69 | 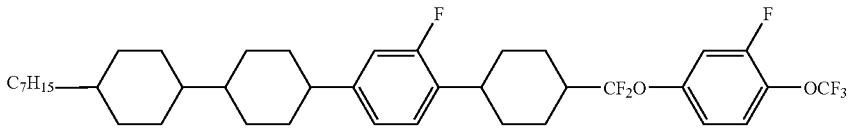 |
| 1-4-70 | 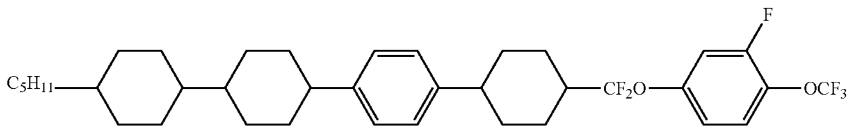 |
| 1-4-71 | 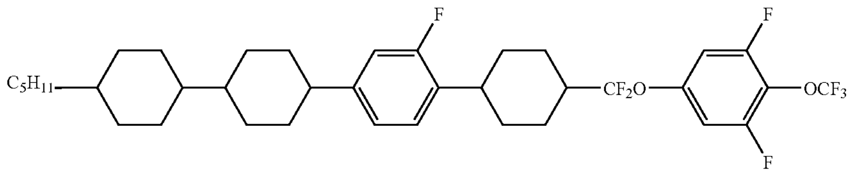 |
| 1-4-72 | 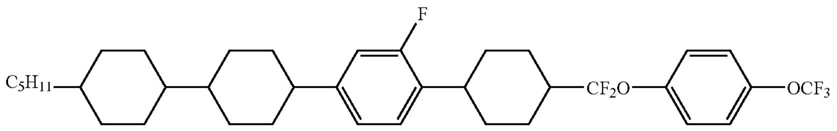 |
| 1-4-73 | 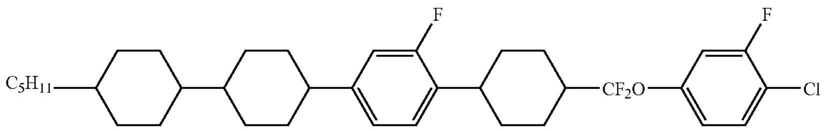 |
| 1-4-74 | 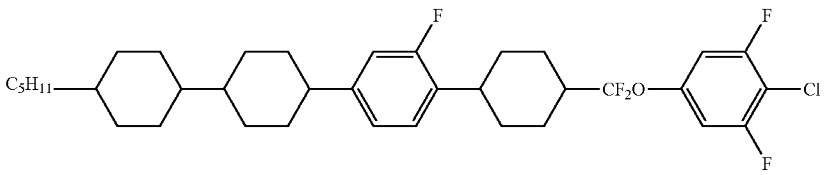 |
| 1-4-75 | 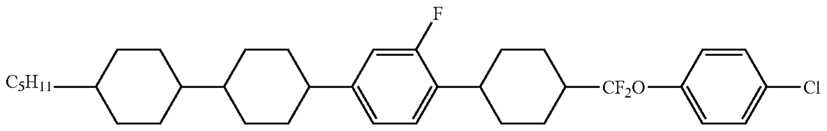 |
| 1-4-76 | 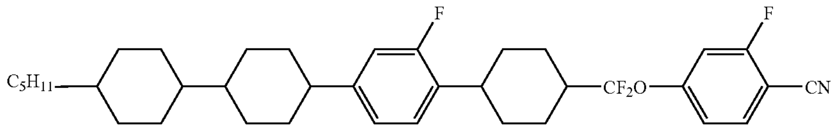 |

-continued
| No. | |
|---|---|
| 1-4-77 | 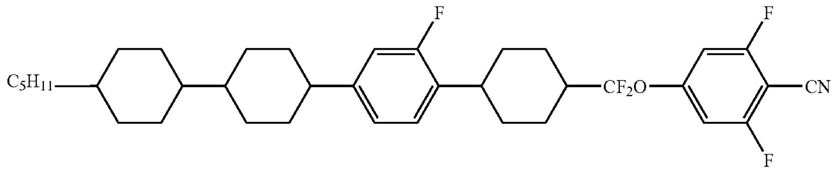 |
| 1-4-78 | 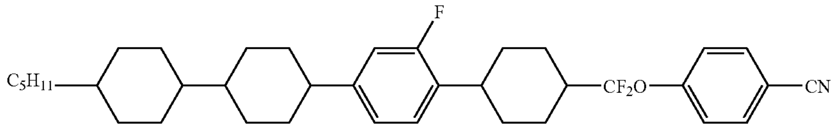 |
| 1-4-79 | 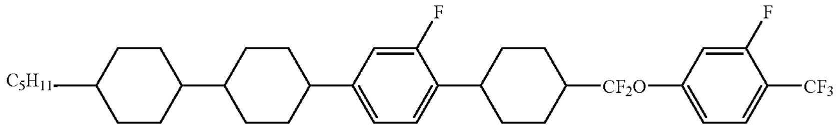 |
| 1-4-80 | 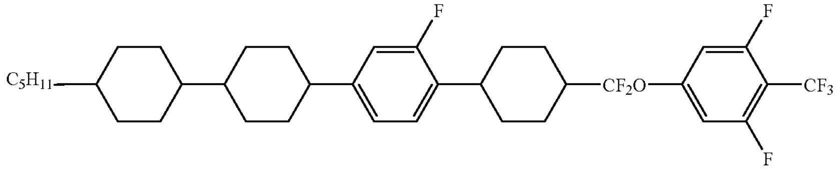 |
| 1-4-81 | 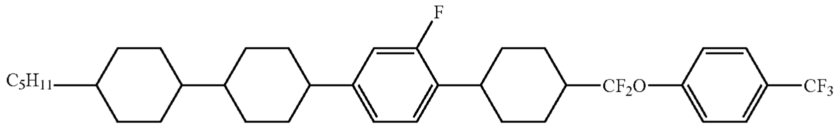 |
| 1-4-82 | 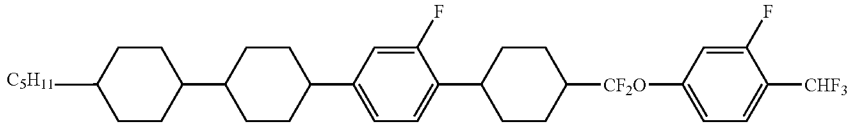 |
| 1-4-83 | 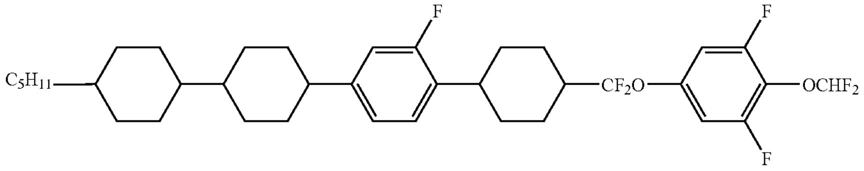 |
| 1-4-84 | 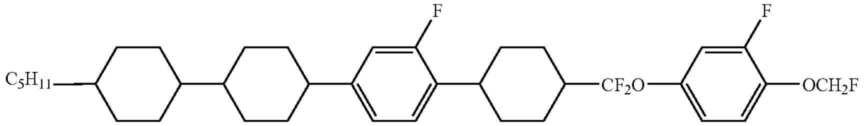 |
| 1-4-85 | 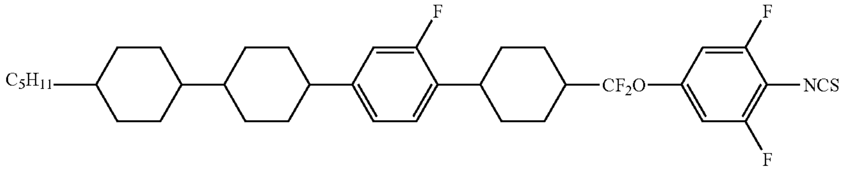 |

-continued
| No. | |
|---|---|
| 1-4-86 | 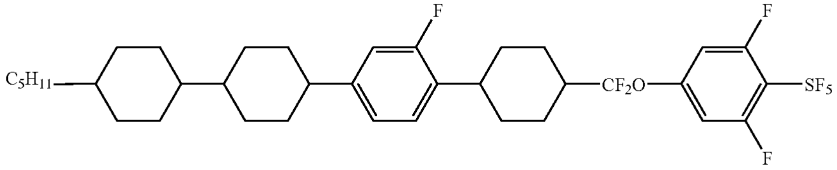 |
| 1-4-87 | 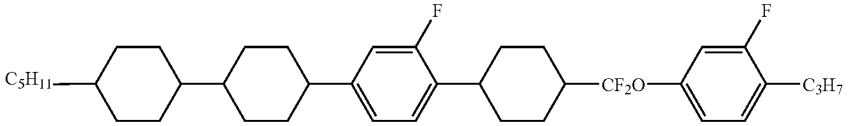 |
| 1-4-88 | 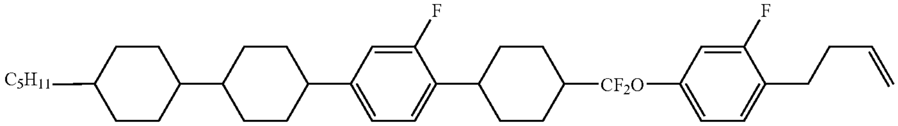 |
| 1-4-89 | 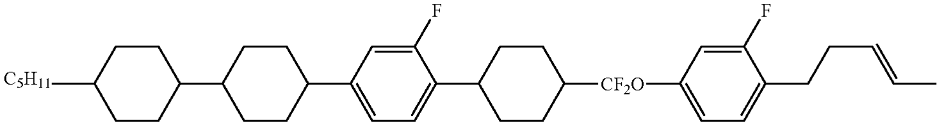 |
| 1-4-90 | 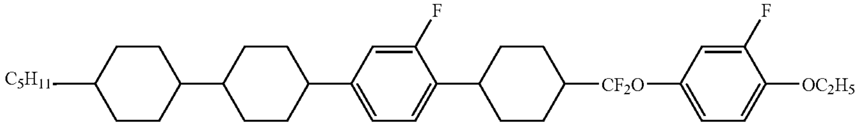 |
| 1-4-91 | 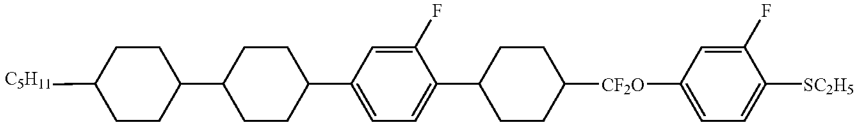 |
| 1-4-92 | 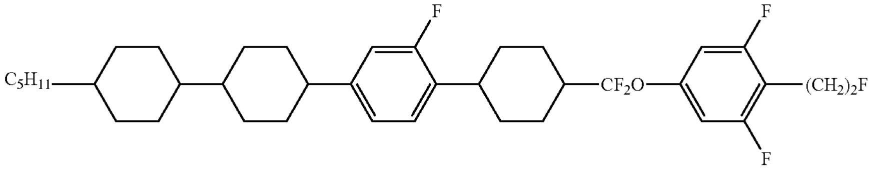 |
| 1-4-93 | 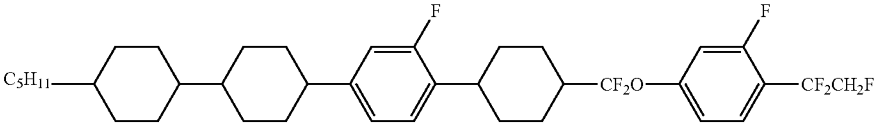 |
| 1-4-94 | 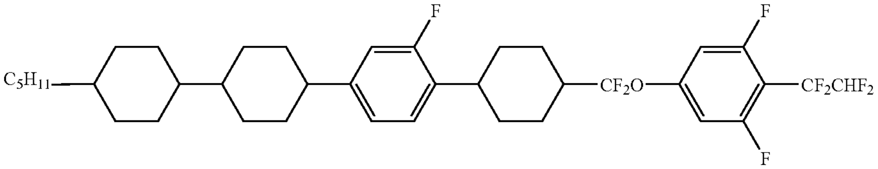 |
| 1-4-95 | 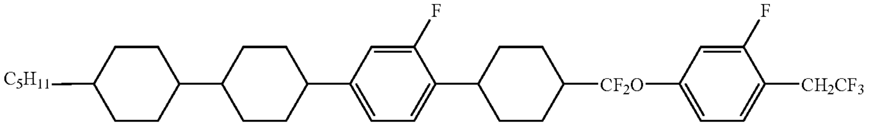 |

-continued
No.
1-4-96
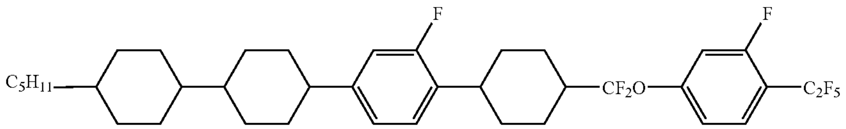
1-4-97
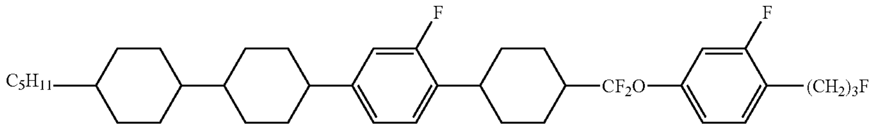
1-4-98
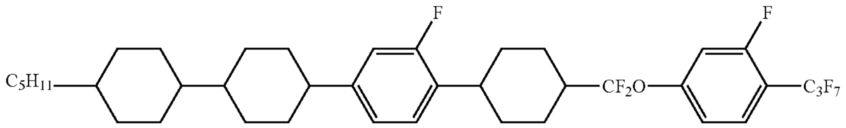
1-4-99
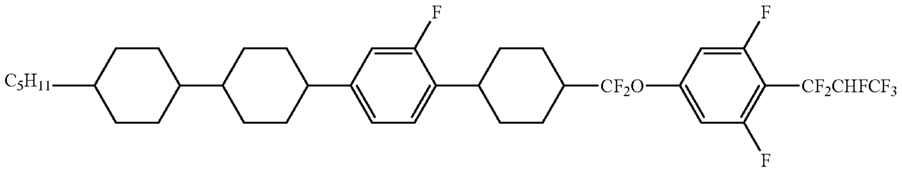
1-4-100
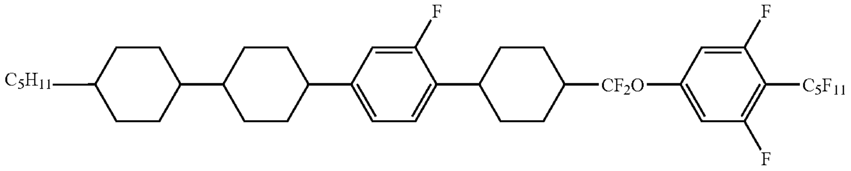
1-4-101
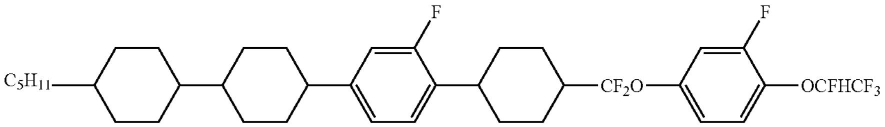
1-4-102
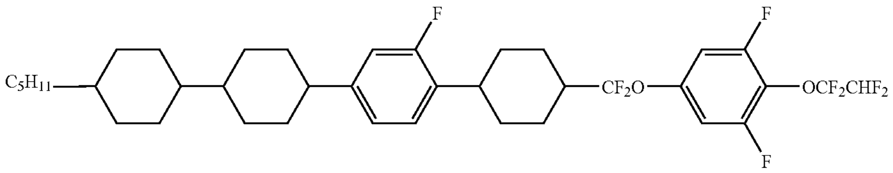
1-4-103
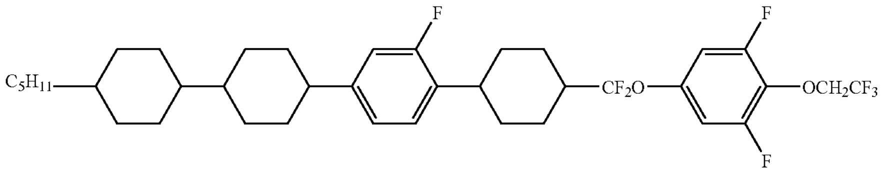
1-4-104
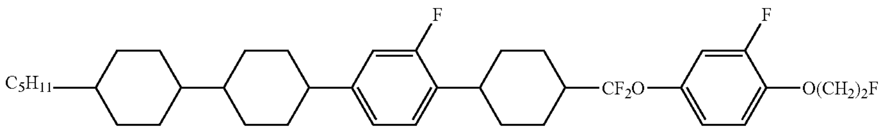
1-4-105
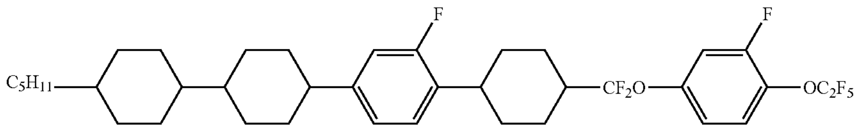

-continued
No.
1-4-106
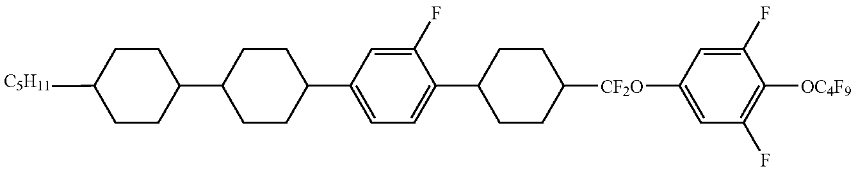
1-4-107
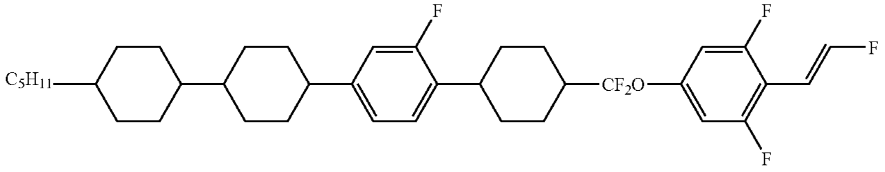
1-4-108
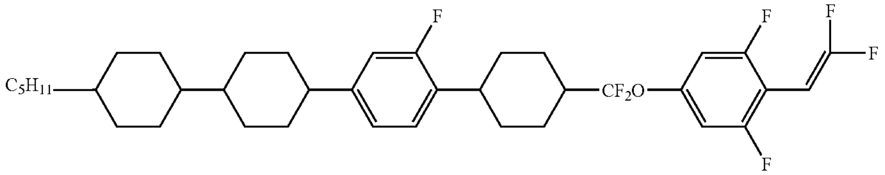
1-4-109
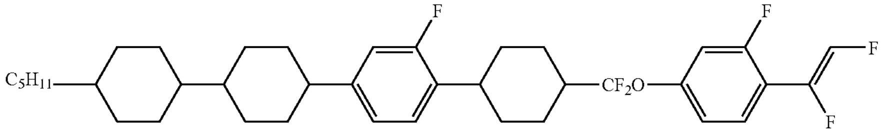
1-4-110
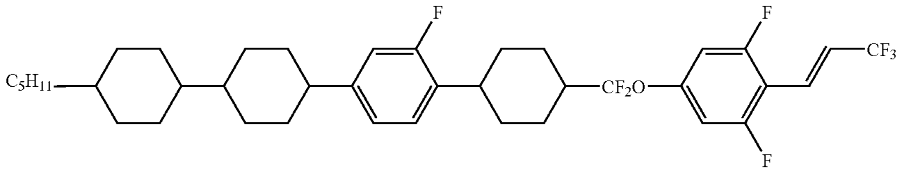
1-4-111
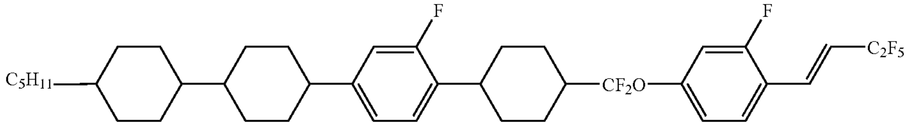
1-4-112
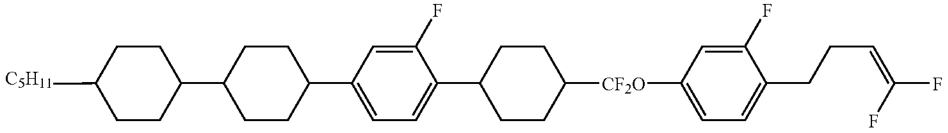
1-4-113
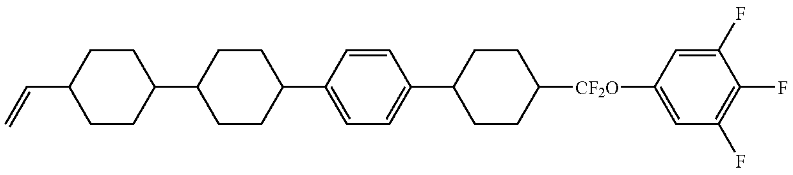
1-4-114
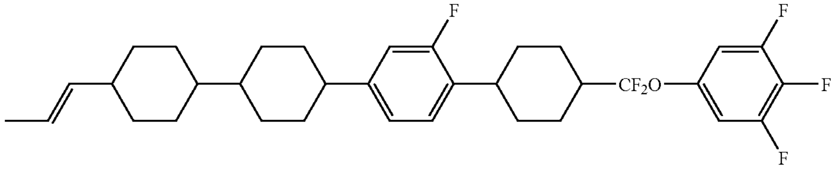

-continued
| No. | |
|---|---|
| 1-4-115 | 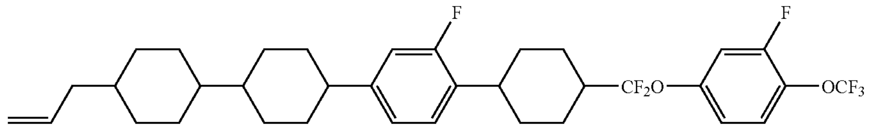 |
| 1-4-116 | 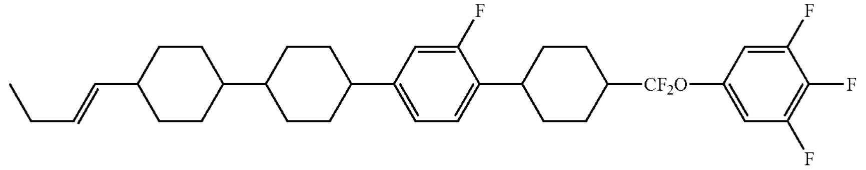 |
| 1-4-117 | 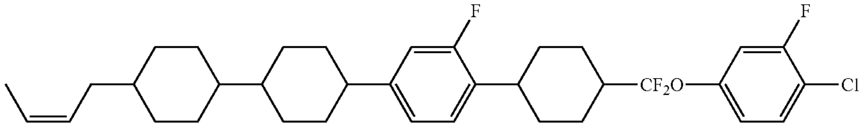 |
| 1-4-118 | 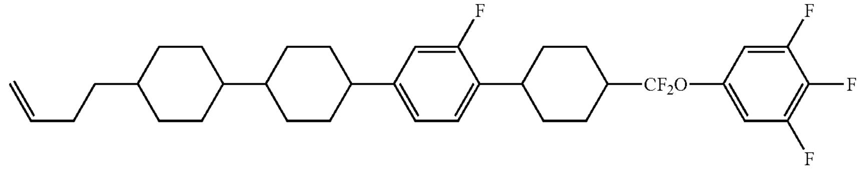 |
| 1-4-119 | 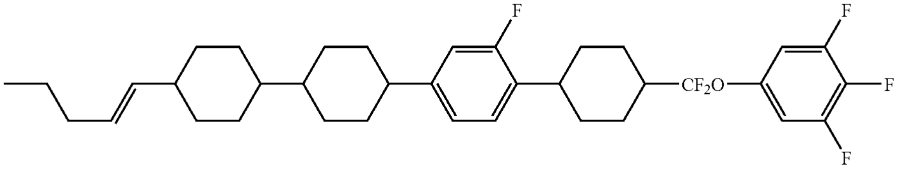 |
| 1-4-120 | 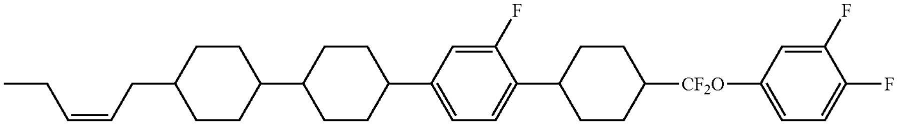 |
| 1-4-121 | 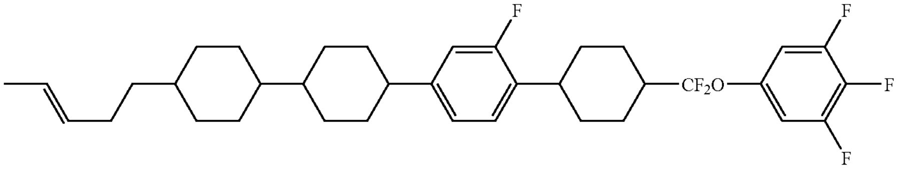 |
| 1-4-122 | 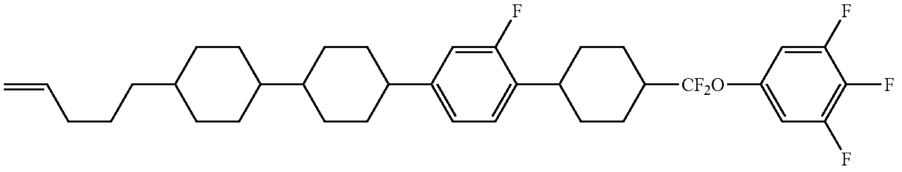 |
| 1-4-123 | 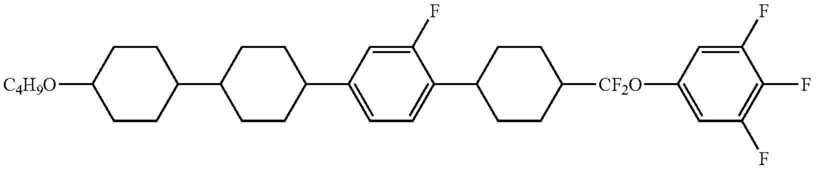 |

-continued
| No. | |
|---|---|
| 1-4-124 | 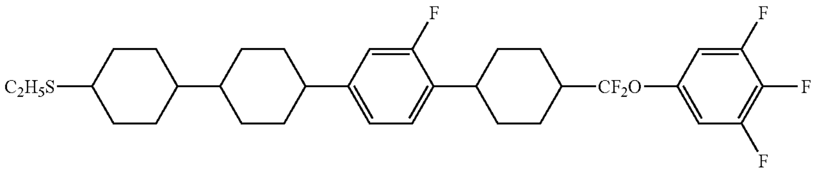 |
| 1-4-125 | 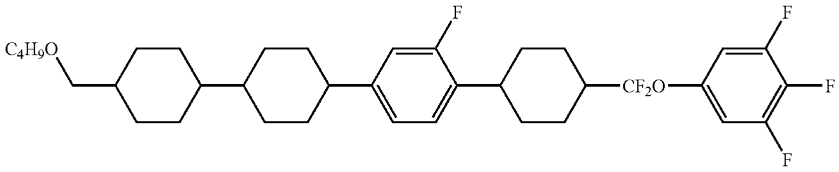 |
| 1-4-126 | 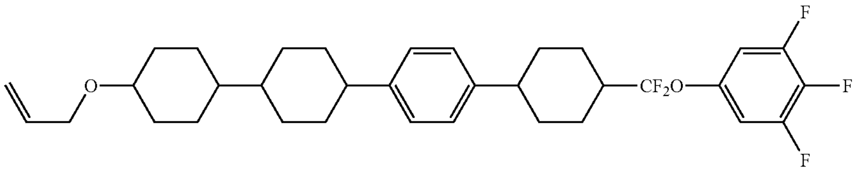 |
| 1-4-127 | 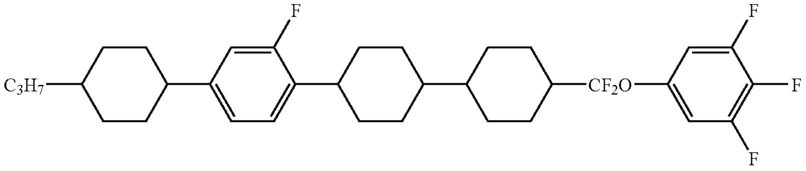 |
| 1-4-128 | 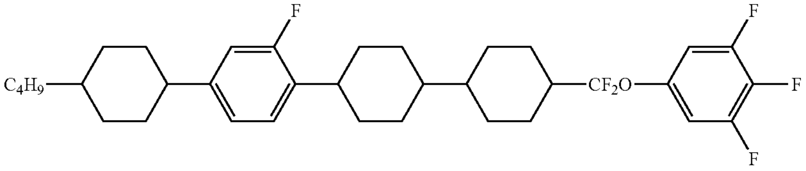 |
| 1-4-129 | 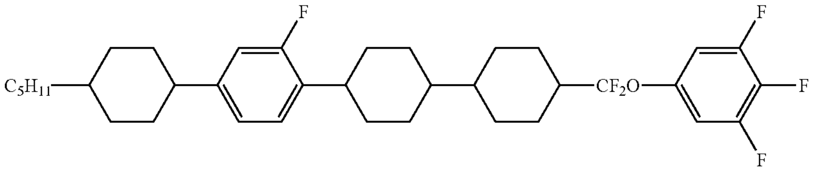 |
| 1-4-130 | 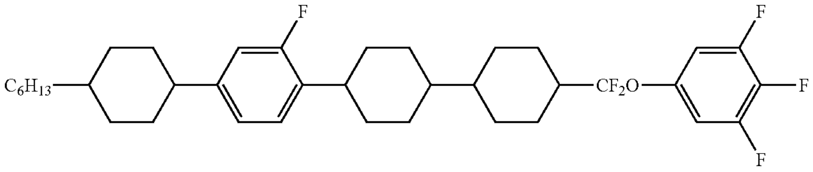 |
| 1-4-131 | 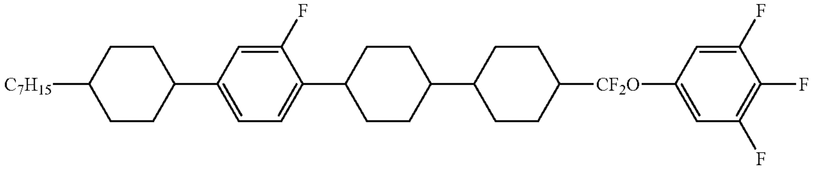 |

-continued
| No. | |
|---|---|
| 1-4-132 | 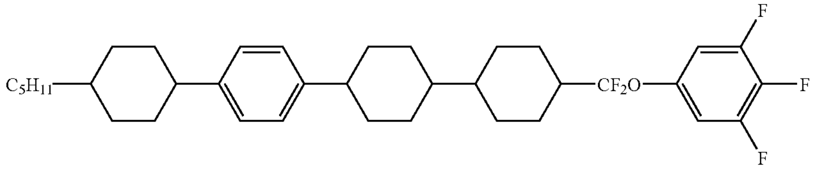 |
| 1-4-133 | 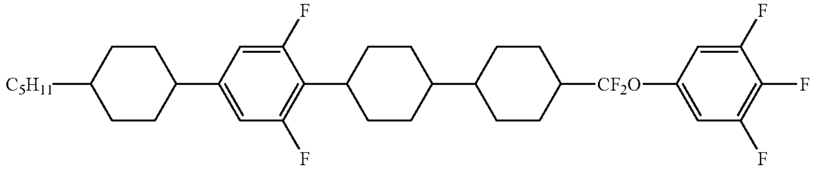 |
| 1-4-134 | 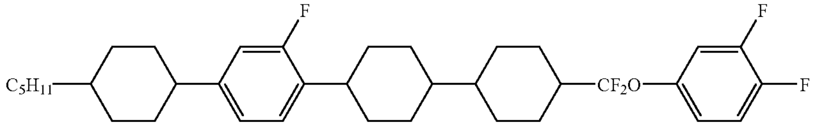 |
| 1-4-135 | 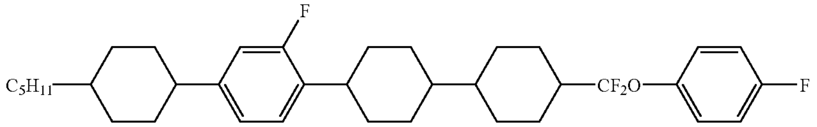 |
| 1-4-136 | 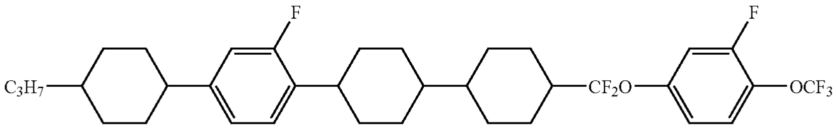 |
| 1-4-137 | 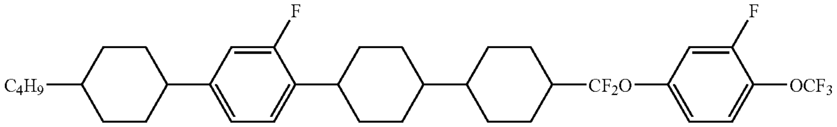 |
| 1-4-138 | 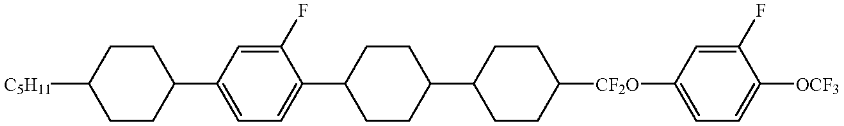 |
| 1-4-139 | 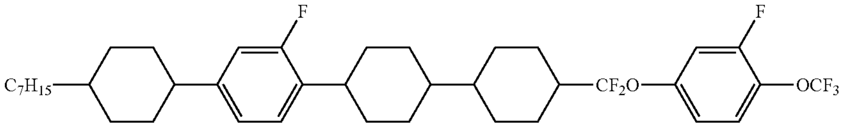 |
| 1-4-140 | 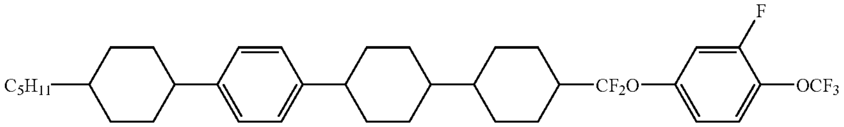 |
| 1-4-141 | 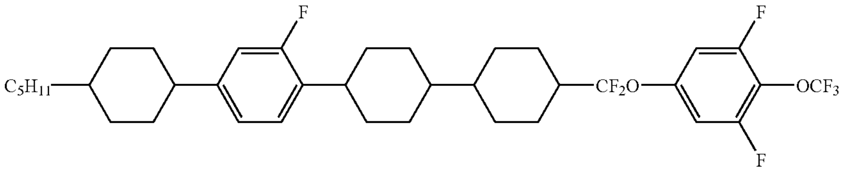 |

-continued
| No. | |
|---|---|
| 1-4-142 | 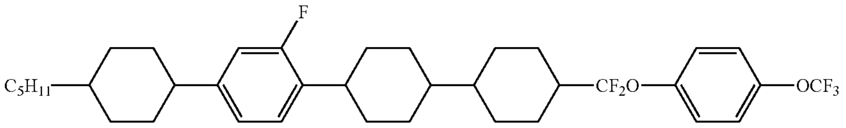 |
| 1-4-143 | 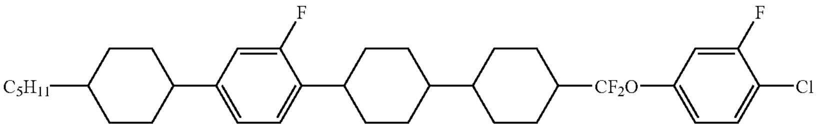 |
| 1-4-144 | 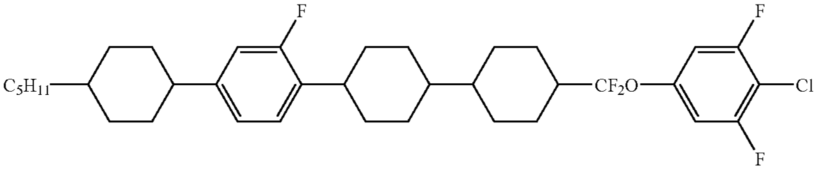 |
| 1-4-145 | 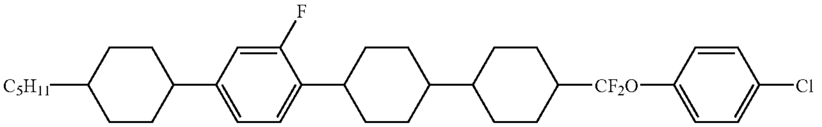 |
| 1-4-146 | 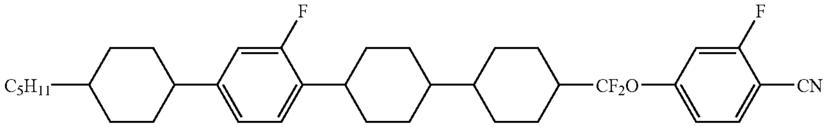 |
| 1-4-147 | 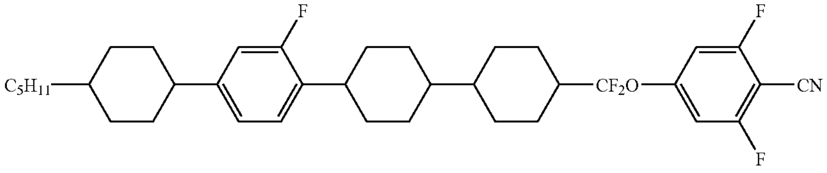 |
| 1-4-148 | 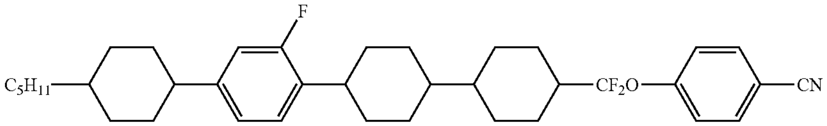 |
| 1-4-149 | 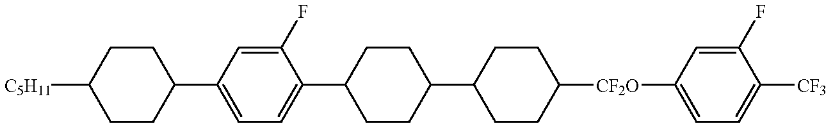 |
| 1-4-150 | 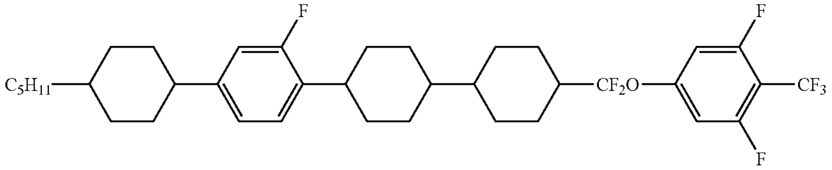 |
| 1-4-151 | 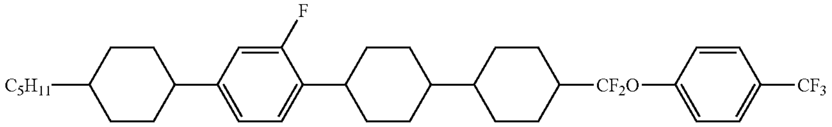 |

-continued
No.
1-4-152
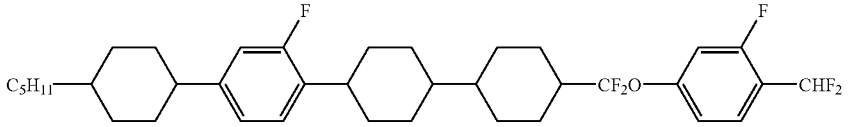
1-4-153
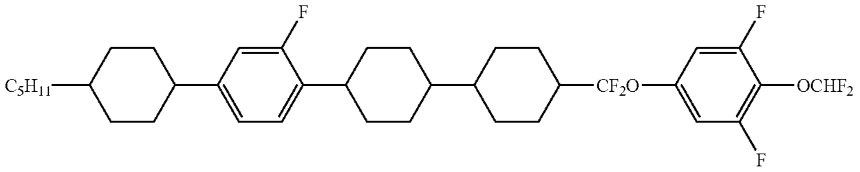
1-4-154
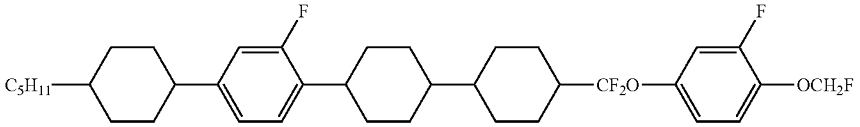
1-4-155
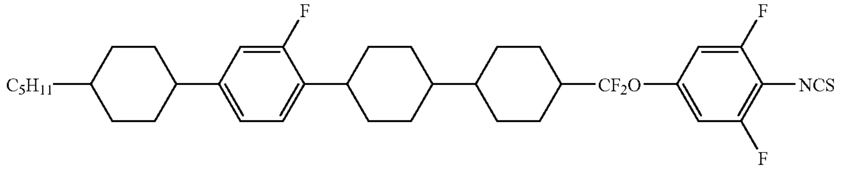
1-4-156
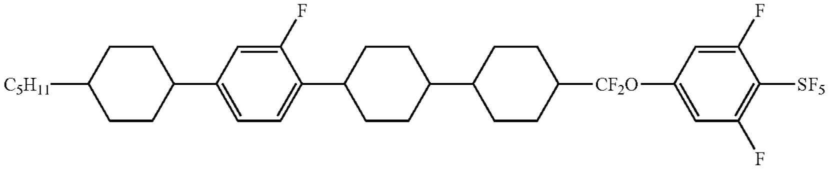
1-4-157
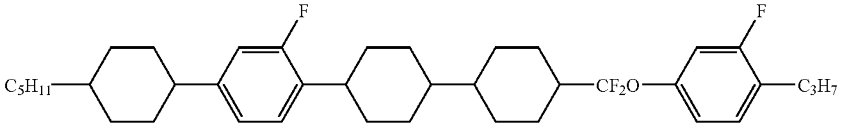
1-4-158
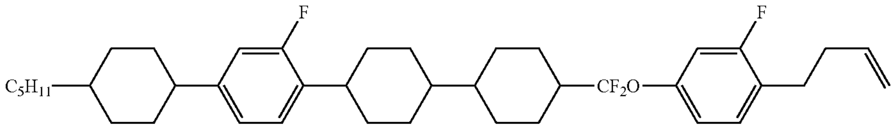
1-4-159
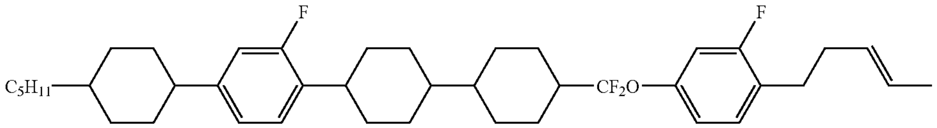
1-4-160
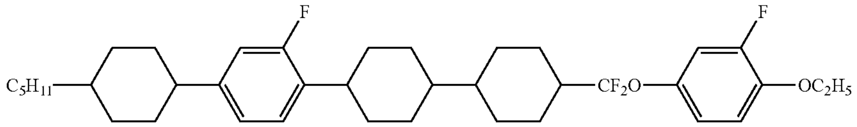
1-4-161
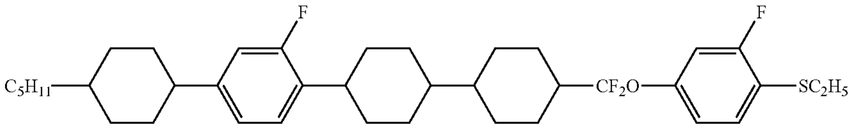

-continued
| No. | |
|---|---|
| 1-4-162 | 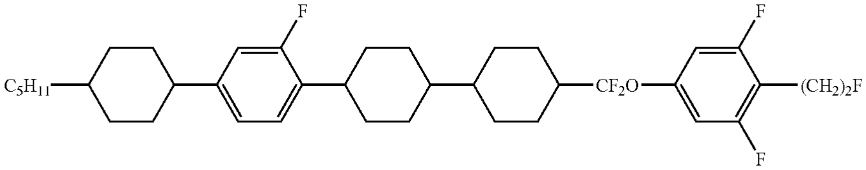 |
| 1-4-163 | 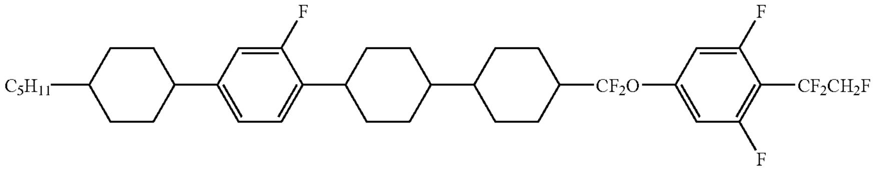 |
| 1-4-164 | 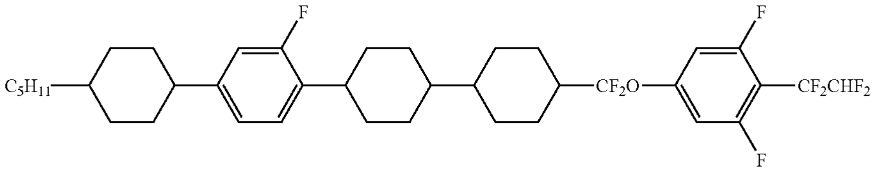 |
| 1-4-165 | 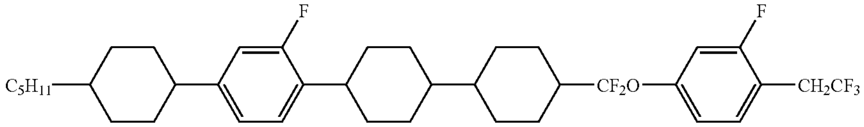 |
| 1-4-166 | 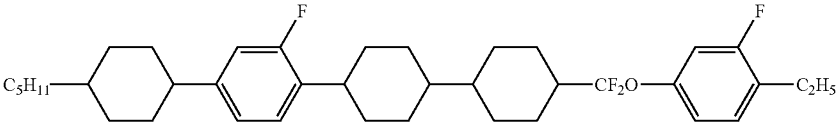 |
| 1-4-167 | 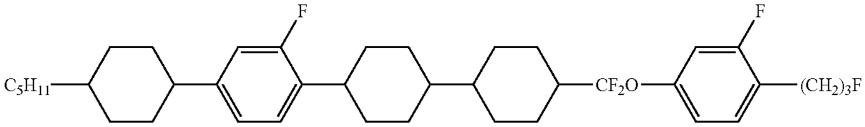 |
| 1-4-168 | 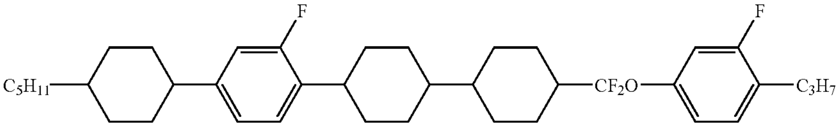 |
| 1-4-169 | 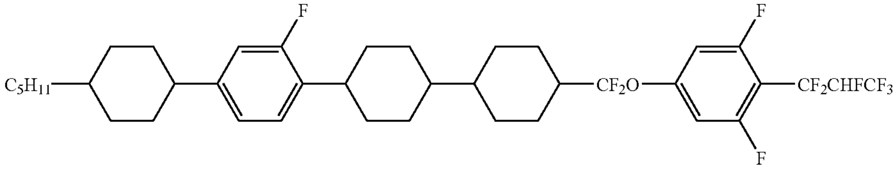 |
| 1-4-170 | 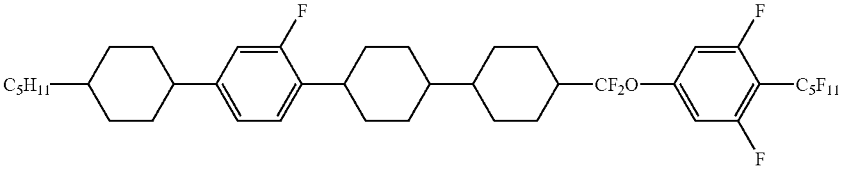 |

-continued
| No. | |
|---|---|
| 1-4-171 | 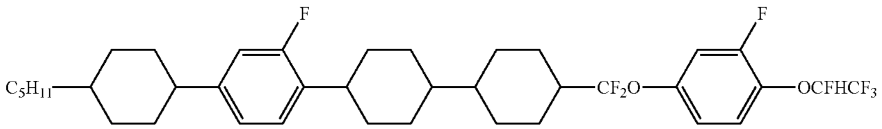 |
| 1-4-172 | 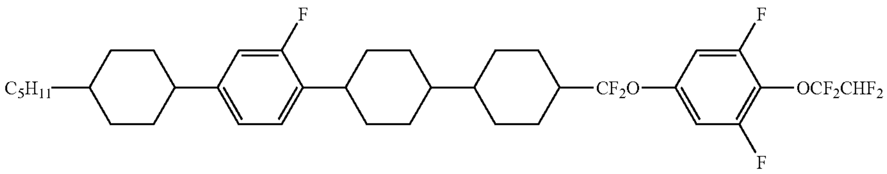 |
| 1-4-173 | 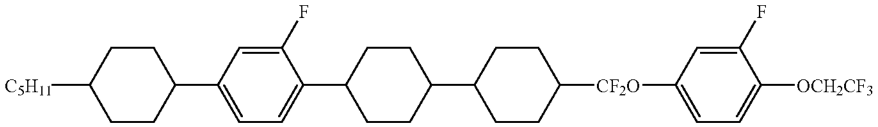 |
| 1-4-174 | 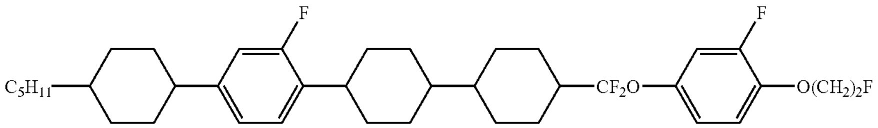 |
| 1-4-175 | 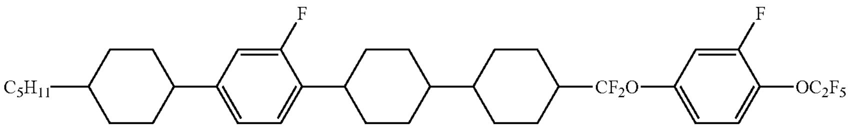 |
| 1-4-176 | 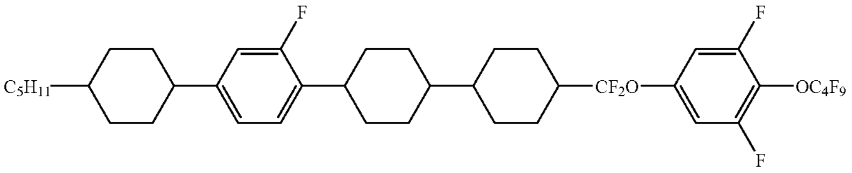 |
| 1-4-177 | 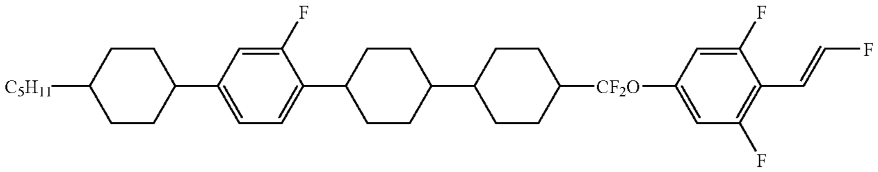 |
| 1-4-178 | 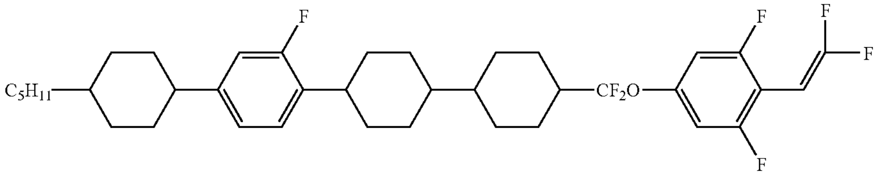 |
| 1-4-179 | 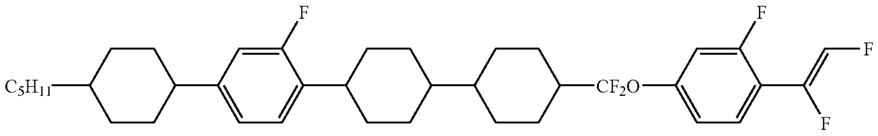 |

-continued
No.
1-4-180
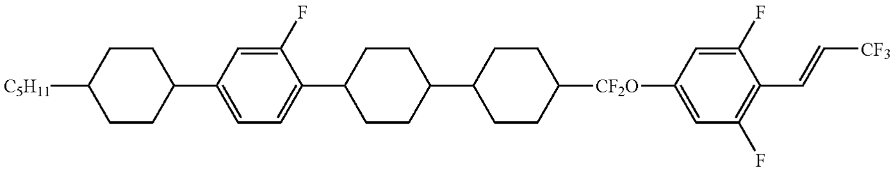
1-4-181
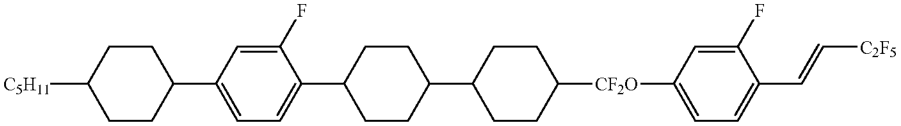
1-4-182
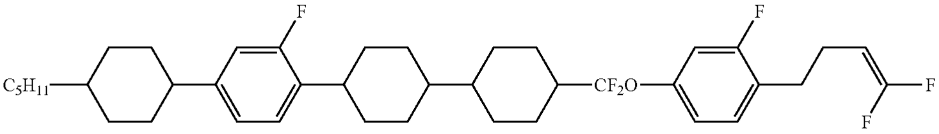
1-4-183
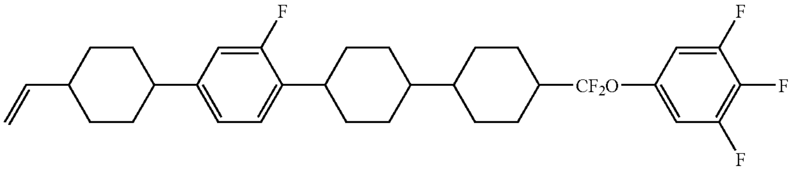
1-4-184
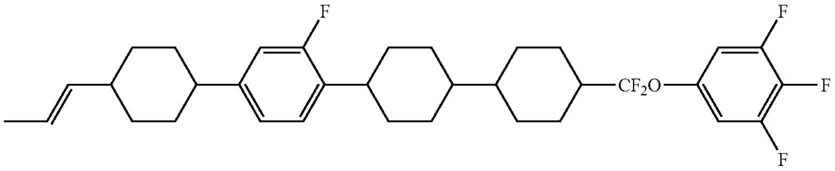
1-4-185
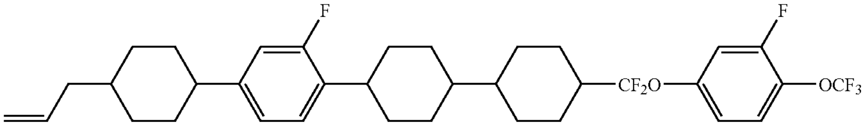
1-4-186
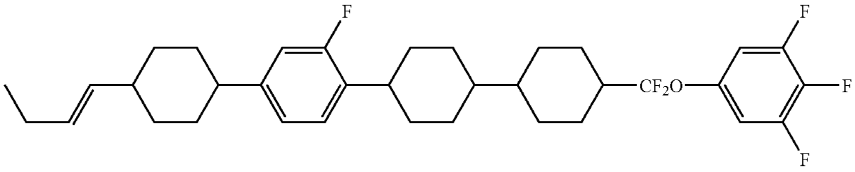
1-4-187
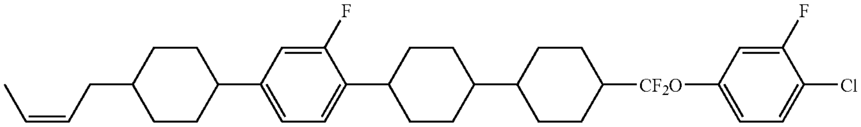
1-4-188
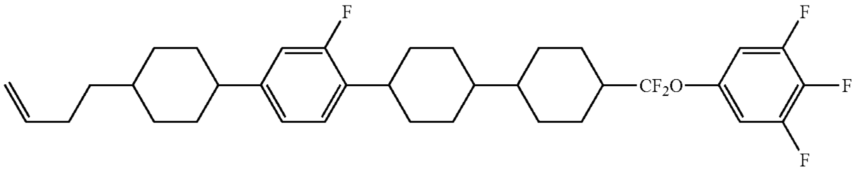

-continued
| No. | |
|---|---|
| 1-4-189 | 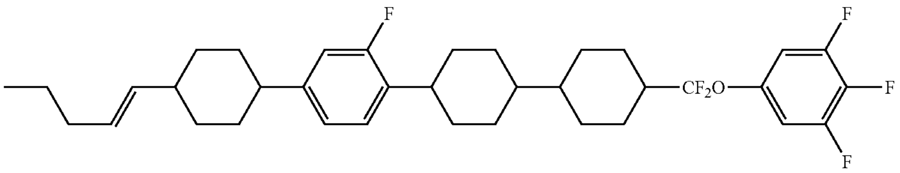 |
| 1-4-190 | 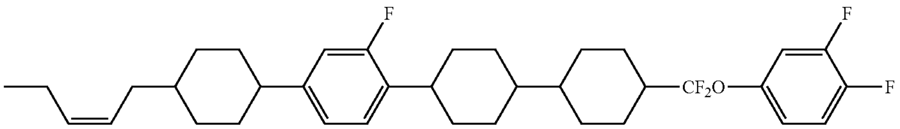 |
| 1-4-191 | 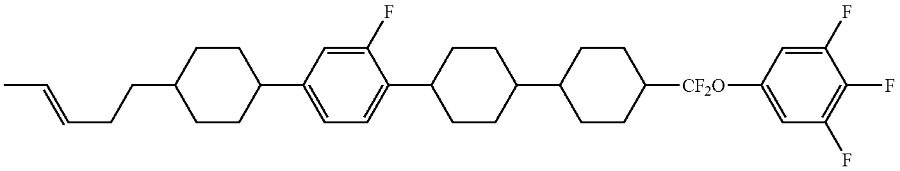 |
| 1-4-192 | 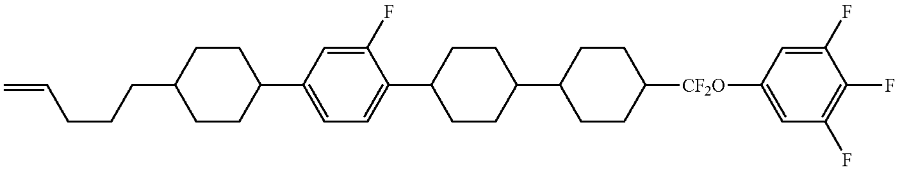 |
| 1-4-193 | 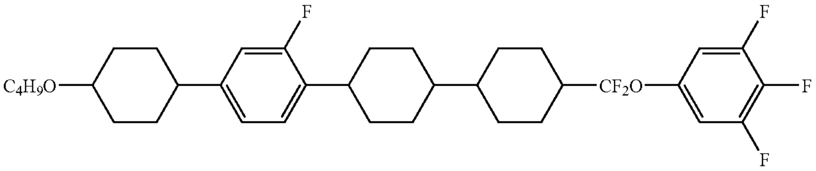 |
| 1-4-194 | 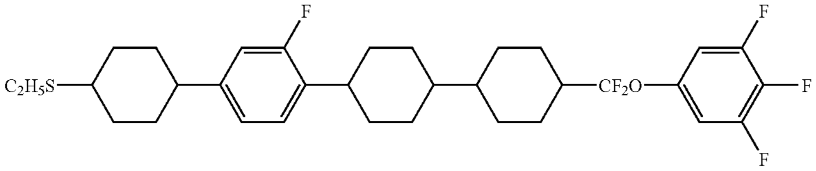 |
| 1-4-195 | 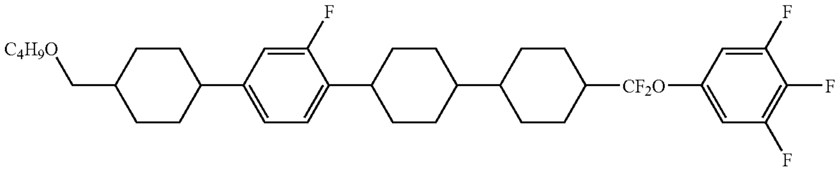 |
| 1-4-196 | 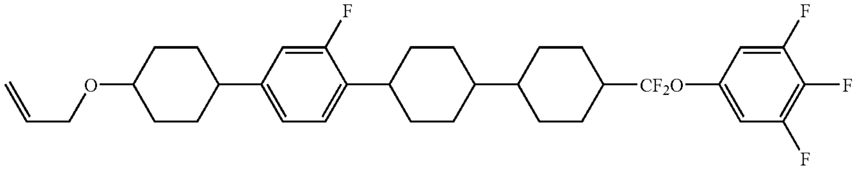 |
| 1-4-197 | 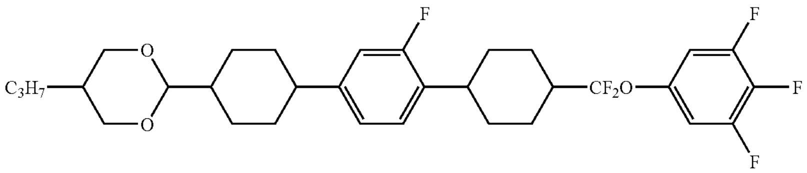 |

-continued
| No. | |
|---|---|
| 1-4-198 | 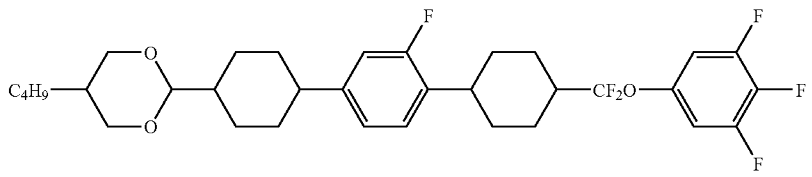 |
| 1-4-199 | 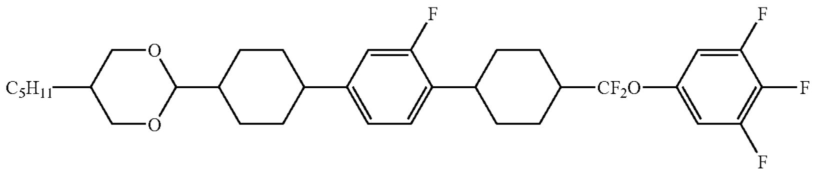 $T_{NI}$ = 192° C., Δ n = 0.124, Δ ∈ = 16.8 |
| 1-4-200 | 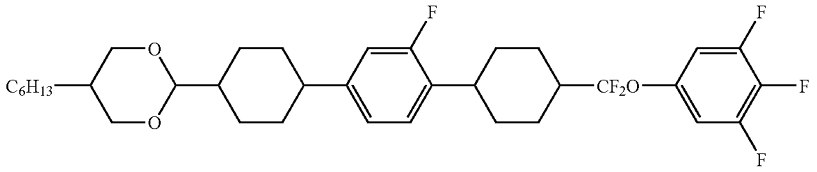 |
| 1-4-201 | 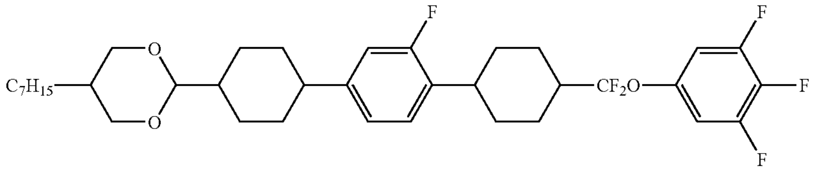 |
| 1-4-202 | 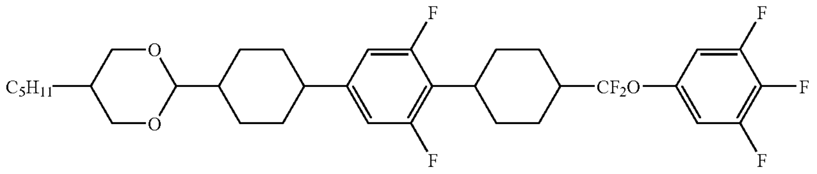 |
| 1-4-203 | 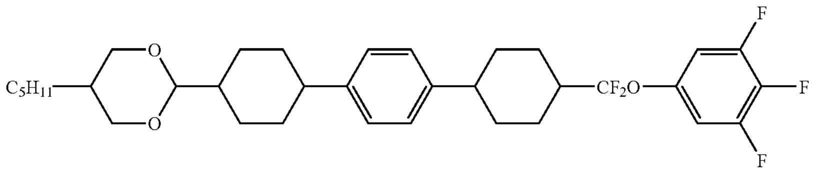 |
| 1-4-204 | 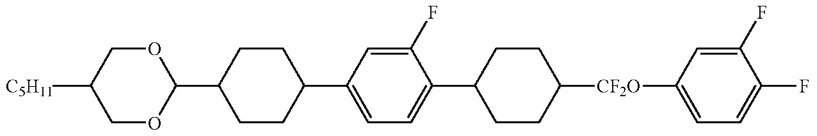 |
| 1-4-205 | 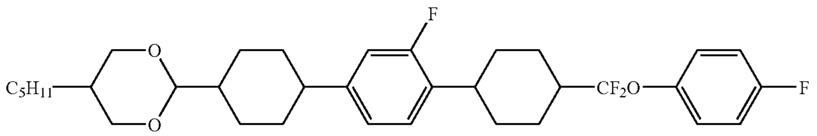 |
| 1-4-206 | 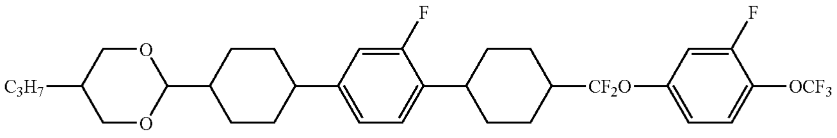 |

-continued
| No. | |
|---|---|
| 1-4-207 | 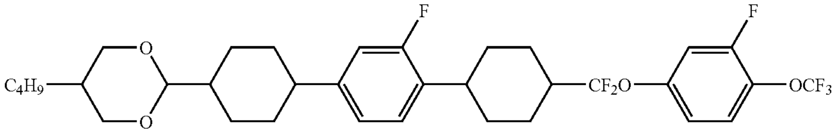 |
| 1-4-208 | 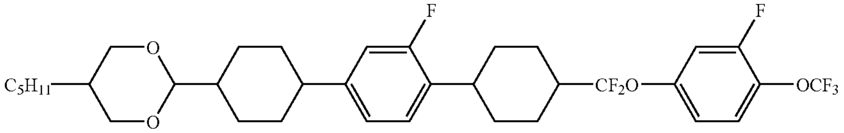 |
| 1-4-209 | 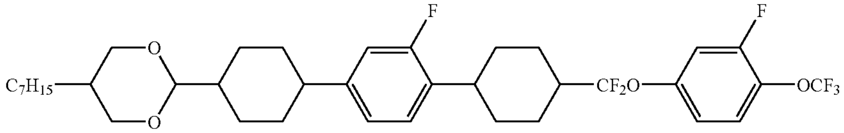 |
| 1-4-210 | 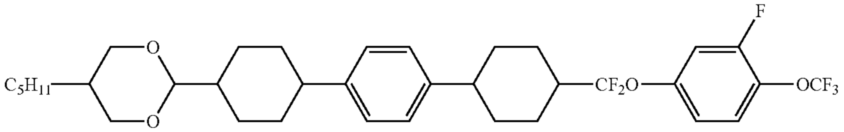 |
| 1-4-211 | 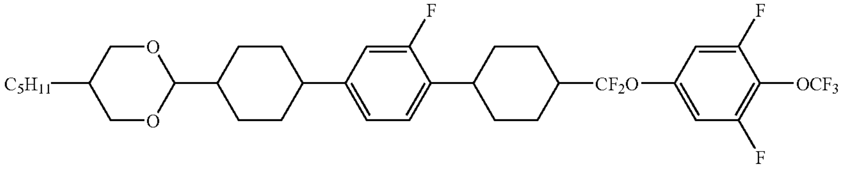 |
| 1-4-212 | 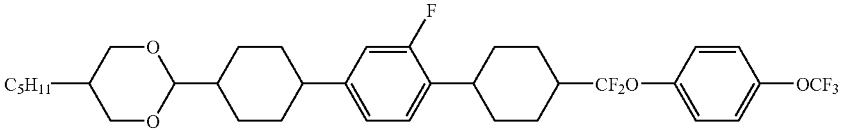 |
| 1-4-213 | 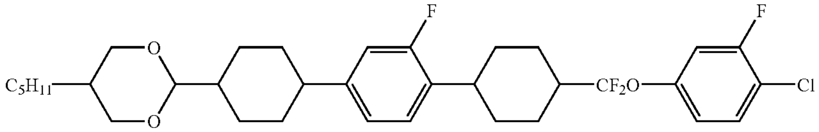 |
| 1-4-214 | 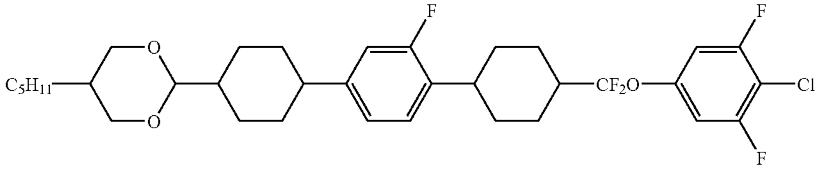 |
| 1-4-215 | 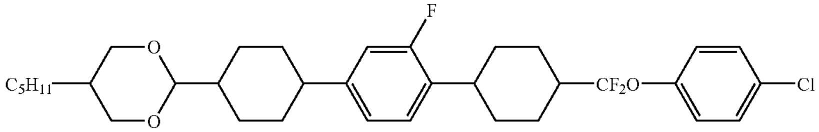 |
| 1-4-216 | 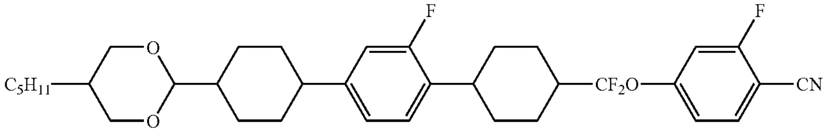 |

-continued
No.
1-4-217
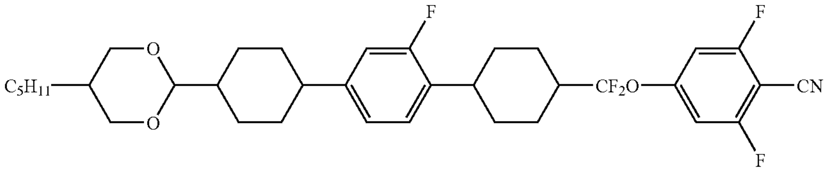
1-4-218
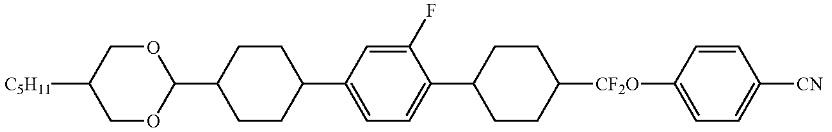
1-4-219
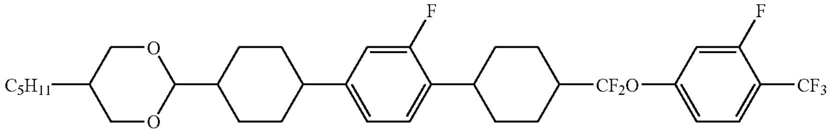
1-4-220
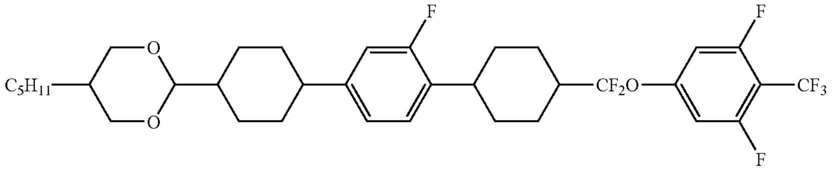
1-4-221
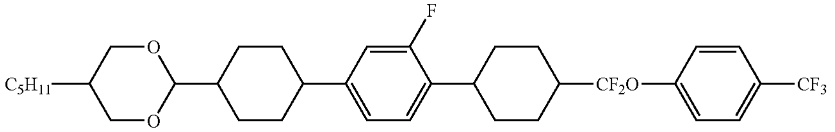
1-4-222
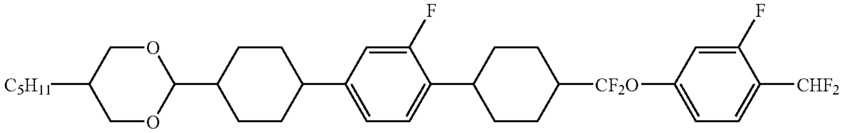
1-4-223
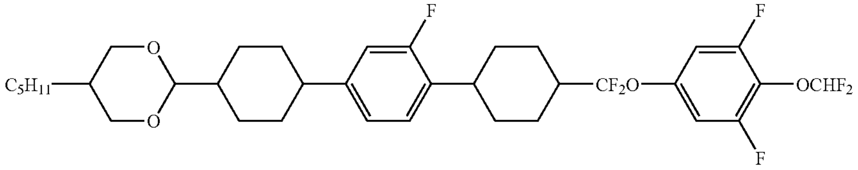
1-4-224
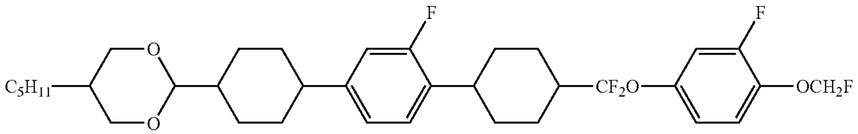
1-4-225
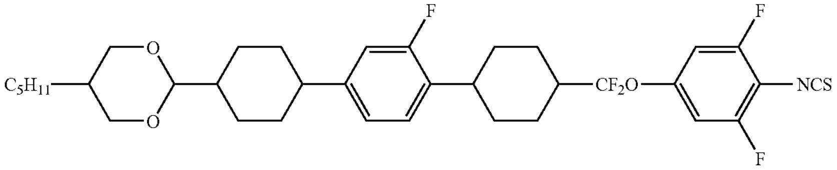

-continued
| No. | |
|---|---|
| 1-4-226 | 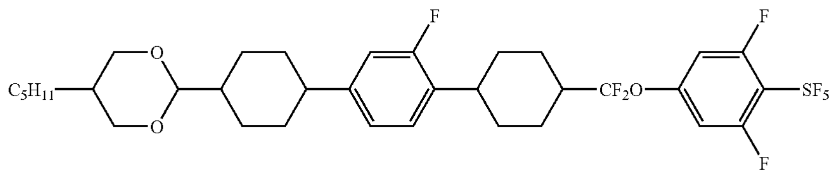 |
| 1-4-227 | 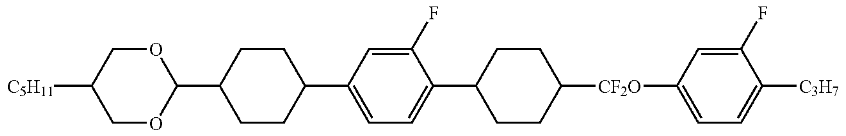 |
| 1-4-228 | 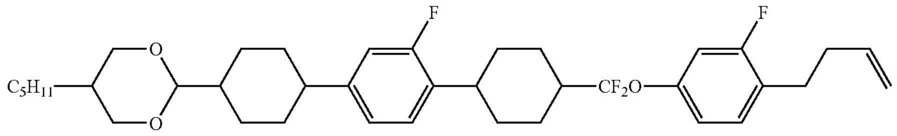 |
| 1-4-229 | 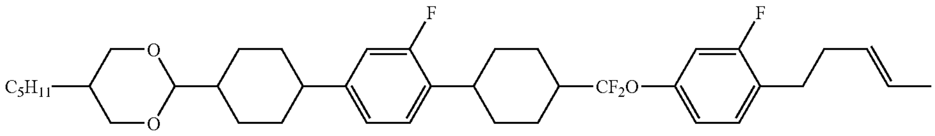 |
| 1-4-230 | 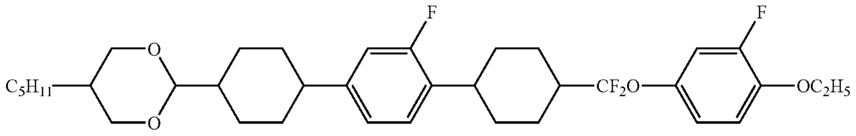 |
| 1-4-231 | 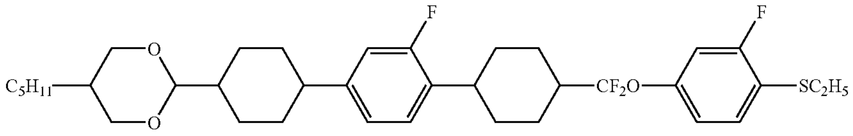 |
| 1-4-232 | 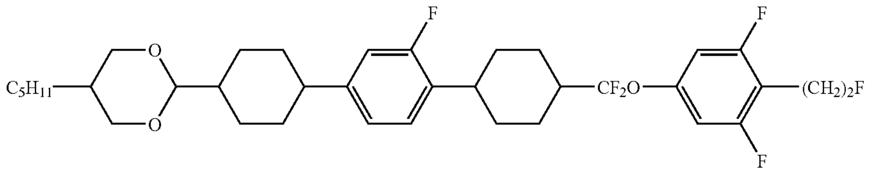 |
| 1-4-233 | 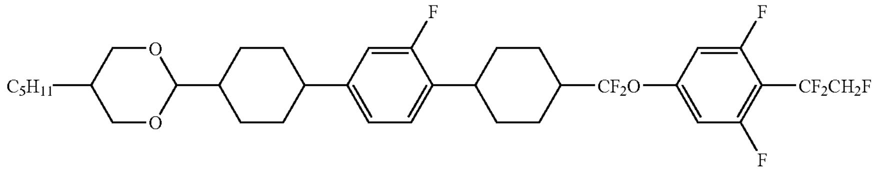 |
| 1-4-234 | 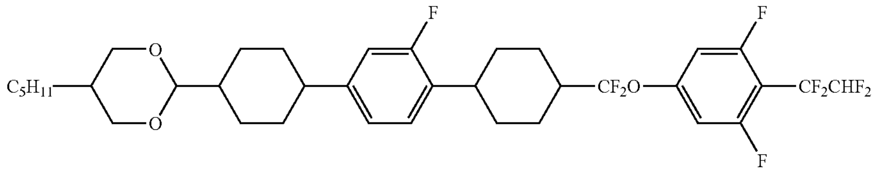 |

-continued
| No. | |
|---|---|
| 1-4-235 | 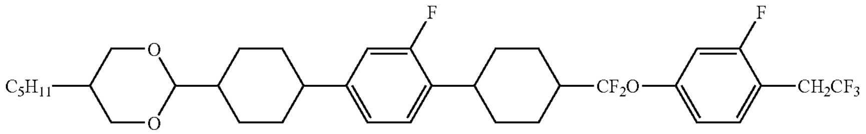 |
| 1-4-236 | 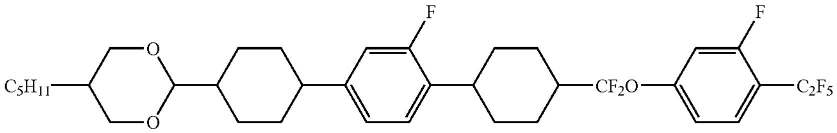 |
| 1-4-237 | 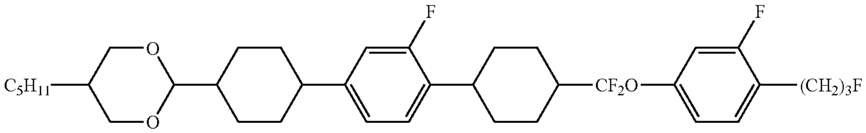 |
| 1-4-238 | 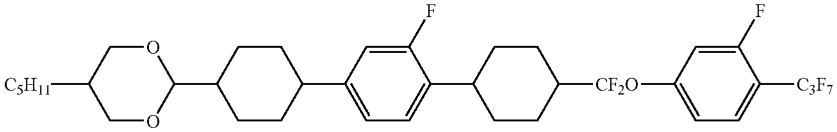 |
| 1-4-239 | 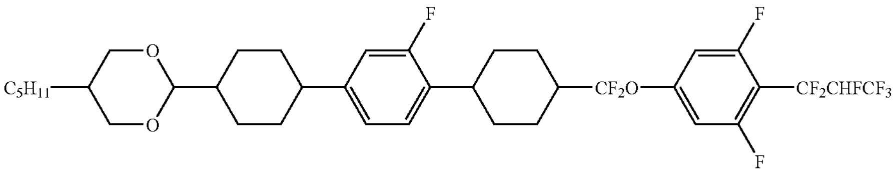 |
| 1-4-240 | 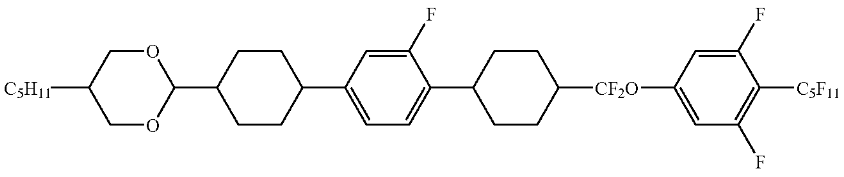 |
| 1-4-241 | 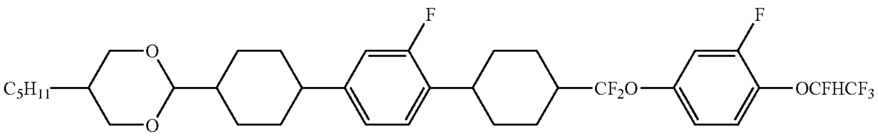 |
| 1-4-242 | 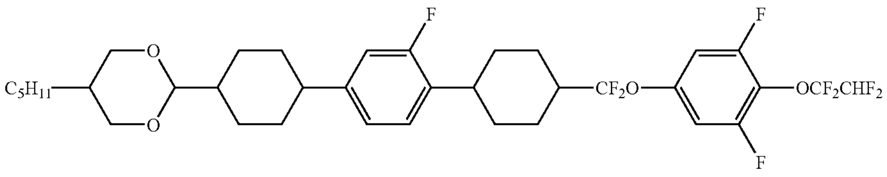 |
| 1-4-243 | 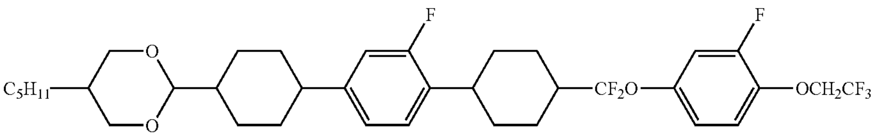 |
| 1-4-244 | 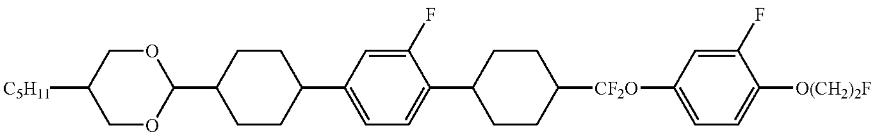 |

-continued
| No. | |
|---|---|
| 1-4-245 | 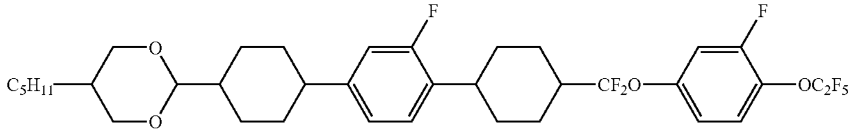 |
| 1-4-246 | 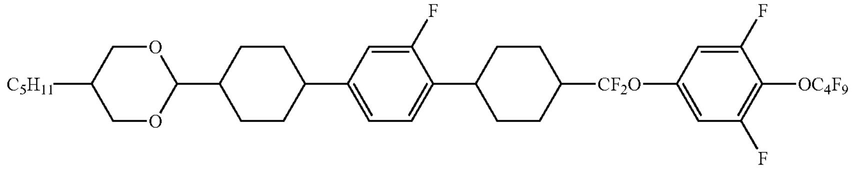 |
| 1-4-247 | 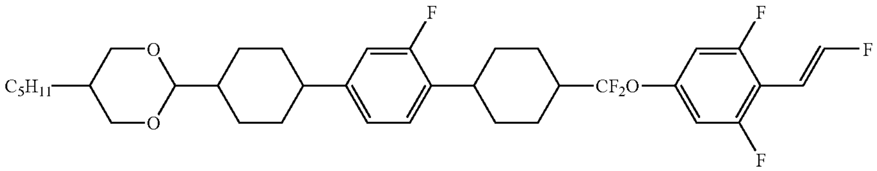 |
| 1-4-248 | 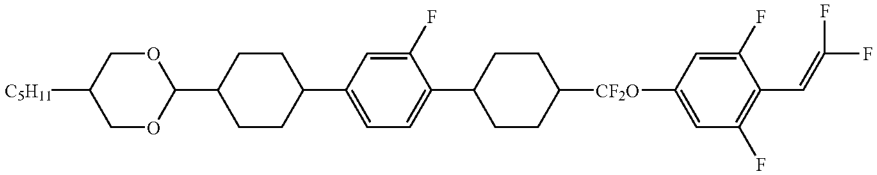 |
| 1-4-249 | 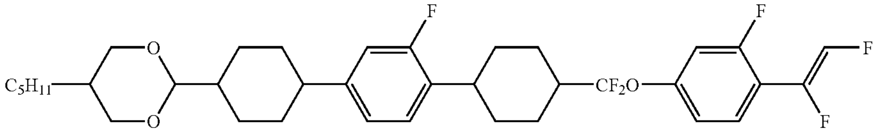 |
| 1-4-250 | 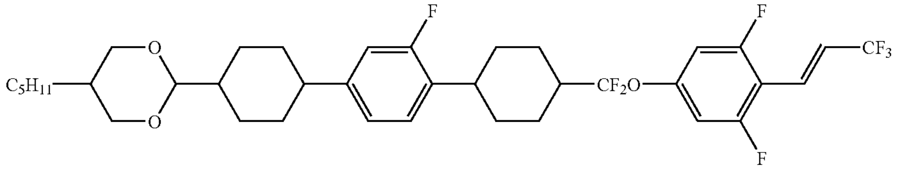 |
| 1-4-251 | 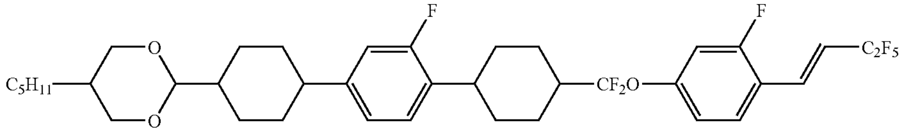 |
| 1-4-252 | 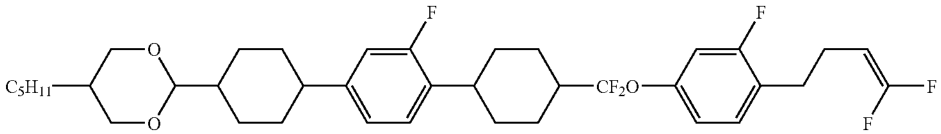 |
| 1-4-253 | 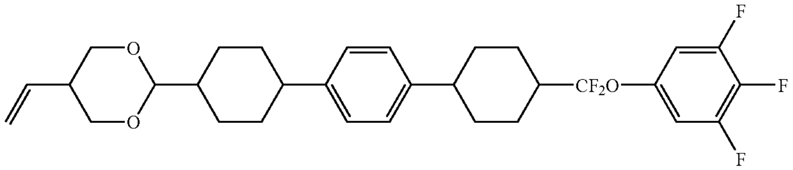 |

-continued
| No. | |
|---|---|
| 1-4-254 | 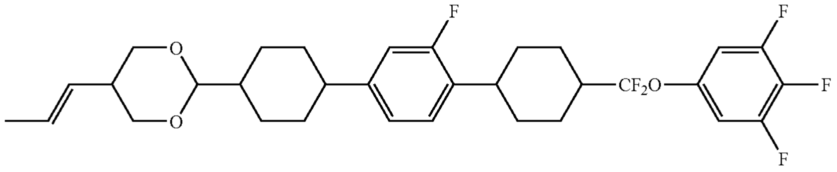 |
| 1-4-255 | 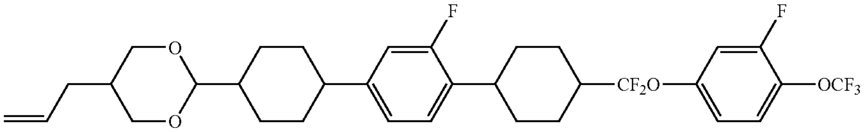 |
| 1-4-256 | 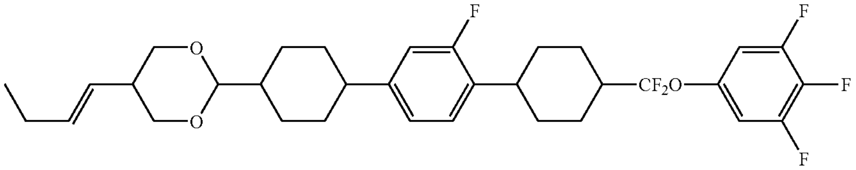 |
| 1-4-257 | 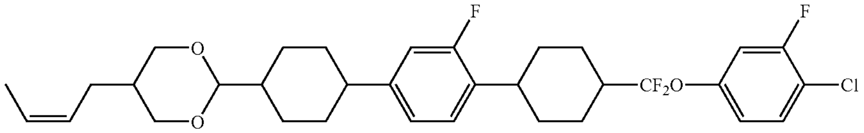 |
| 1-4-258 | 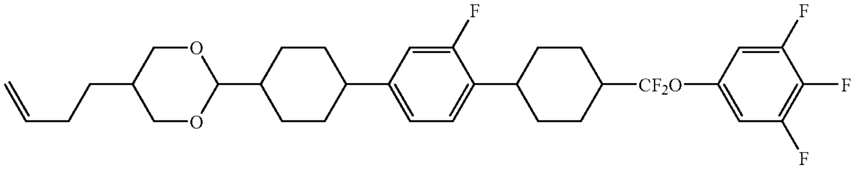 |
| 1-4-259 | 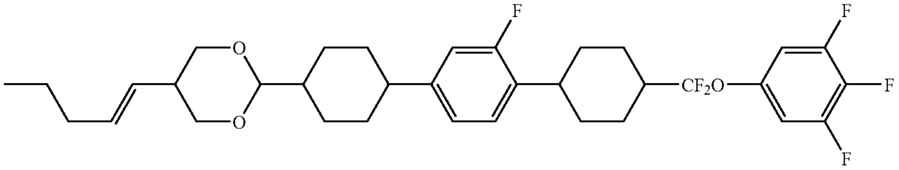 |
| 1-4-260 | 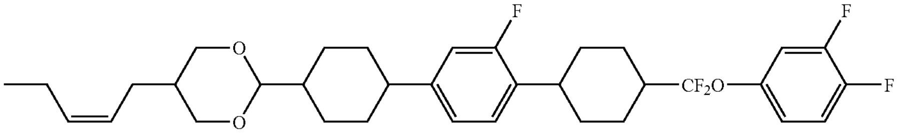 |
| 1-4-261 | 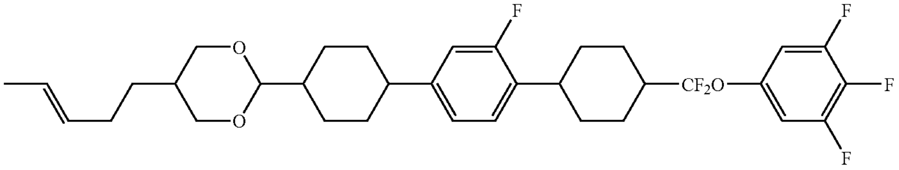 |
| 1-4-262 | 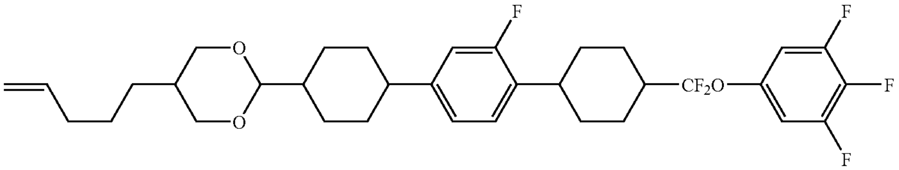 |

-continued
| No. | |
|---|---|
| 1-4-263 | 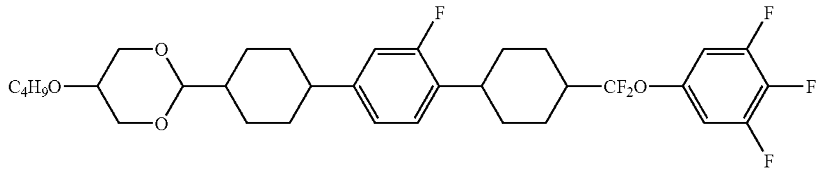 |
| 1-4-264 | 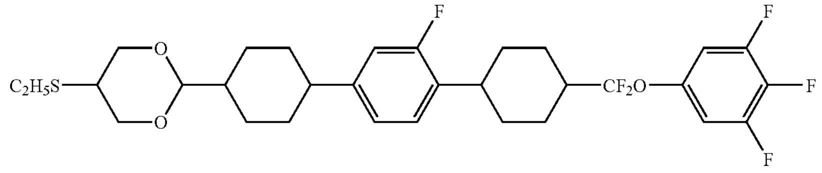 |
| 1-4-265 | 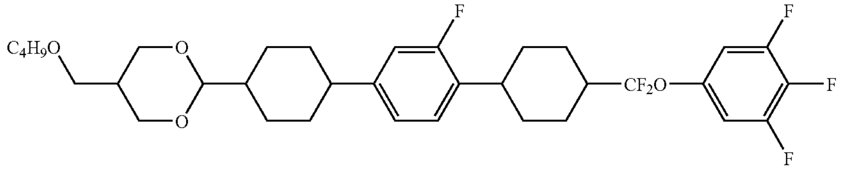 |
| 1-4-266 | 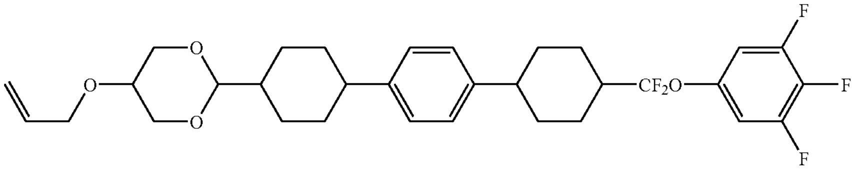 |
| 1-4-267 | 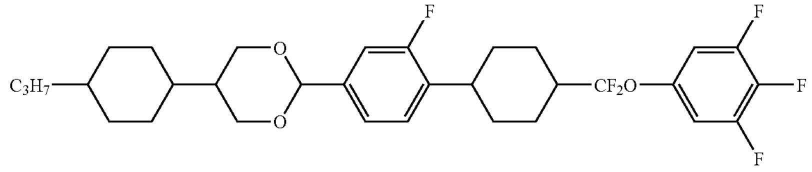 |
| 1-4-268 | 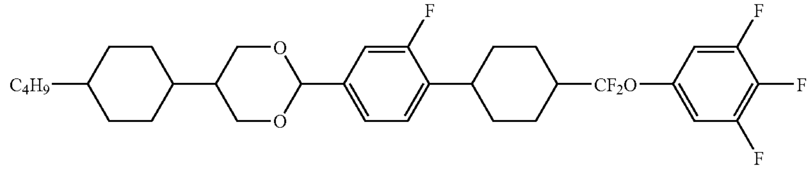 |
| 1-4-269 | 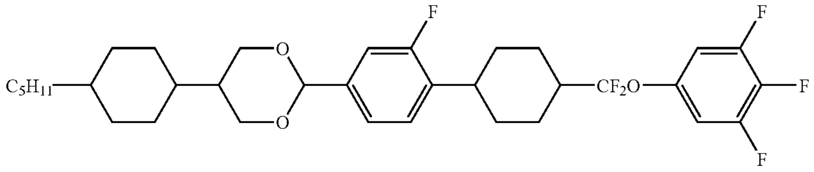 |
| 1-4-270 | 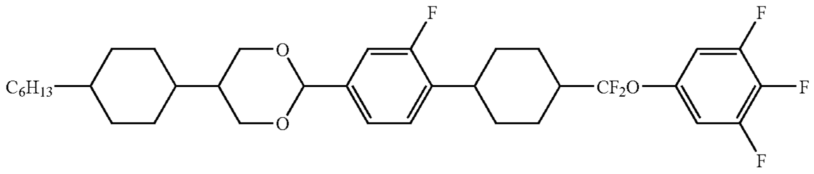 |

-continued
| No. | |
|---|---|
| 1-4-271 | 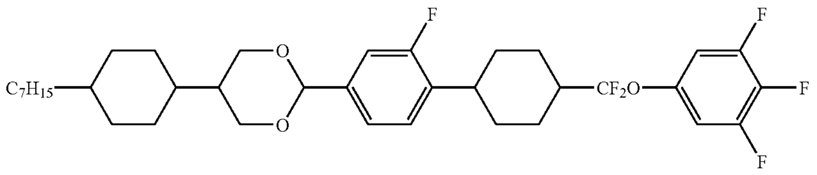 |
| 1-4-272 | 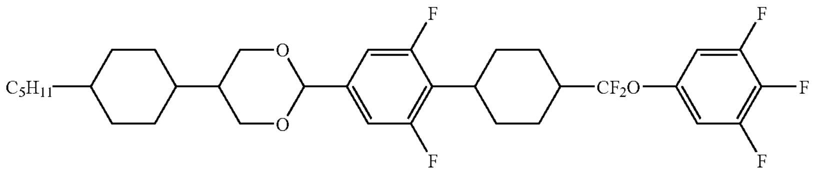 |
| 1-4-273 | 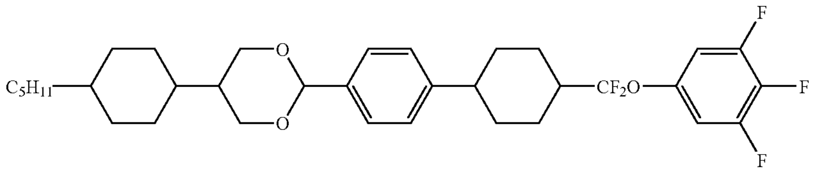 |
| 1-4-274 | 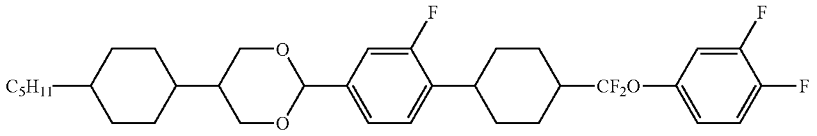 |
| 1-4-275 | 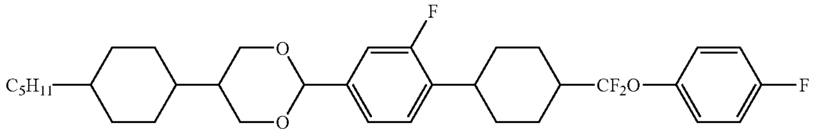 |
| 1-4-276 | 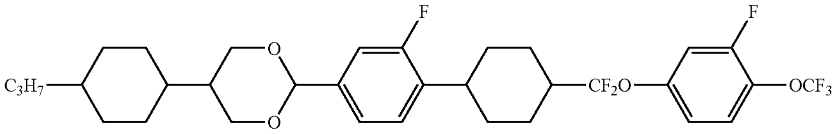 |
| 1-4-277 | 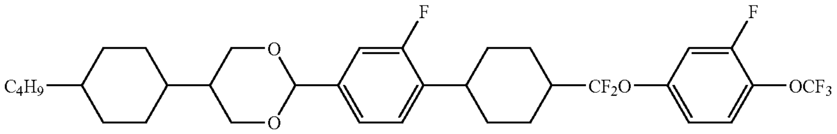 |
| 1-4-278 | 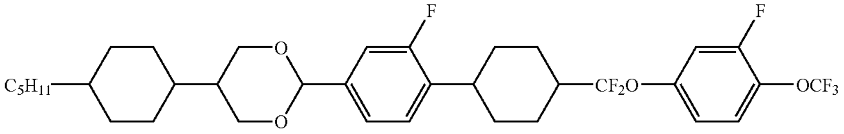 |
| 1-4-279 | 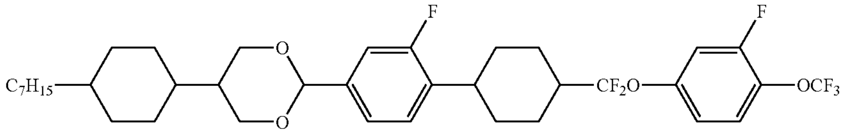 |
| 1-4-280 | 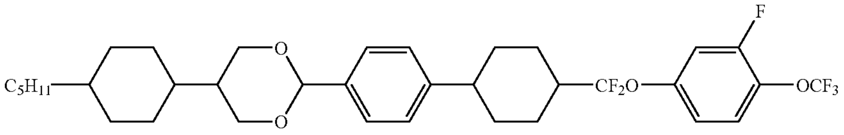 |

-continued
| No. | |
|---|---|
| 1-4-281 | 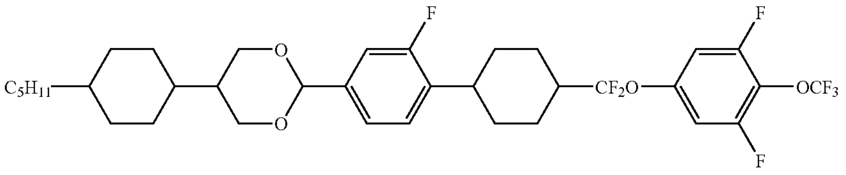 |
| 1-4-282 | 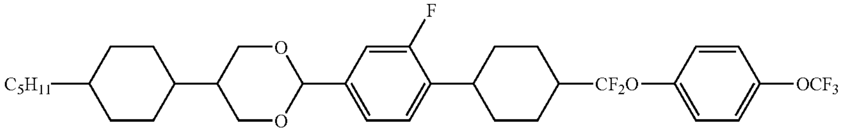 |
| 1-4-283 | 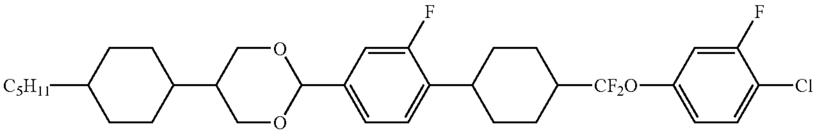 |
| 1-4-284 | 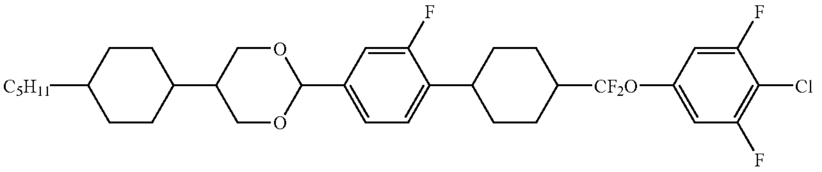 |
| 1-4-285 | 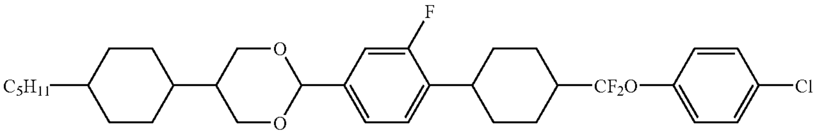 |
| 1-4-286 | 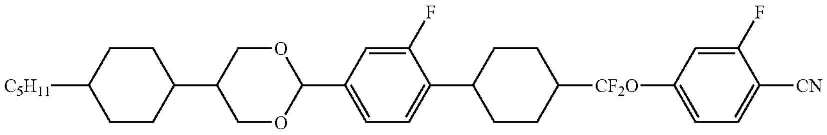 |
| 1-4-287 | 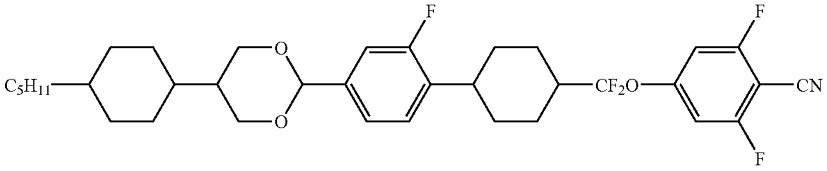 |
| 1-4-288 | 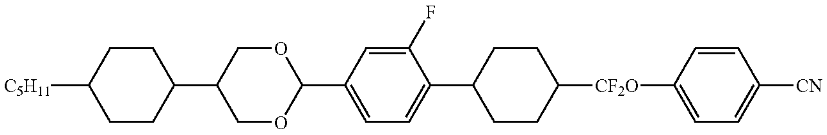 |
| 1-4-289 | 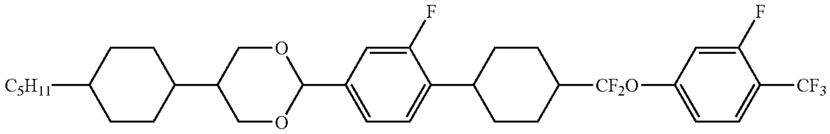 |

-continued
| No. | |
|---|---|
| 1-4-290 | 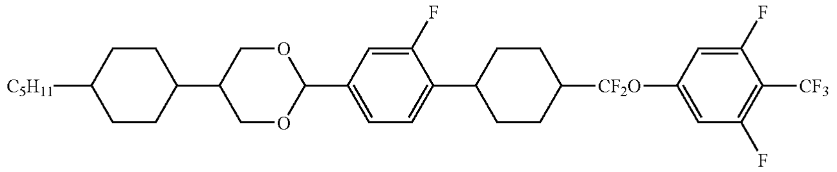 |
| 1-4-291 | 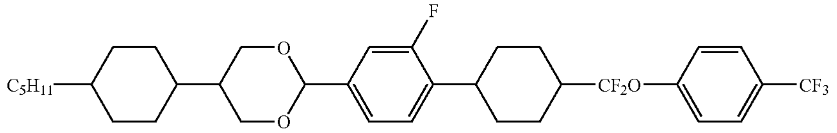 |
| 1-4-292 | 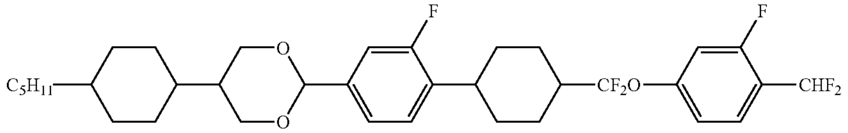 |
| 1-4-293 | 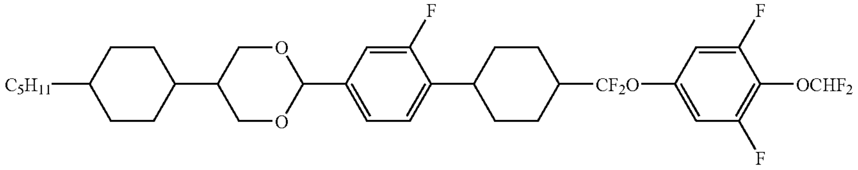 |
| 1-4-294 | 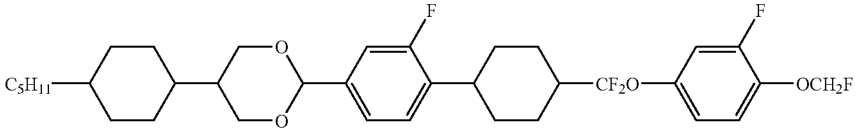 |
| 1-4-295 | 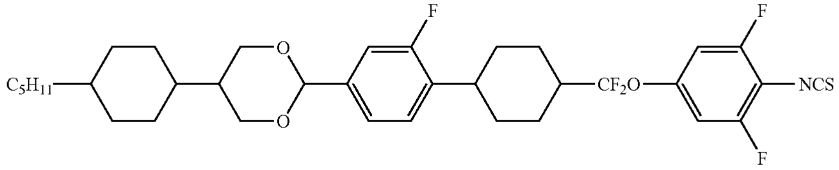 |
| 1-4-296 | 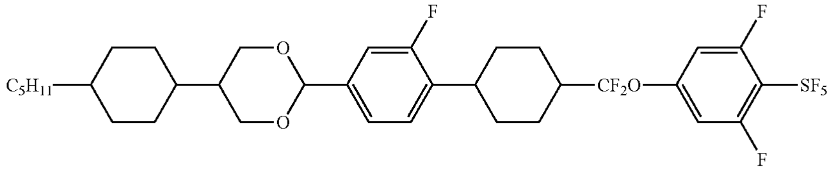 |
| 1-4-297 | 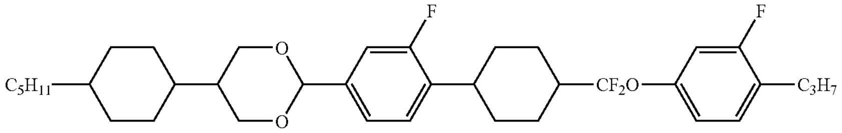 |
| 1-4-298 | 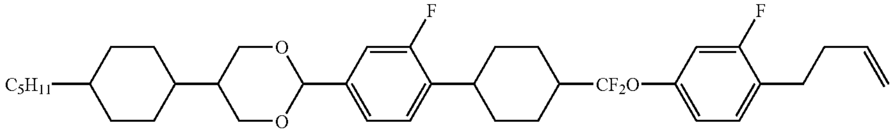 |

-continued
No.
1-4-299
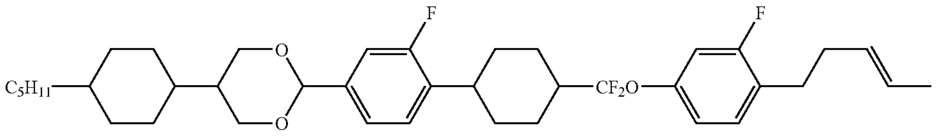
1-4-300
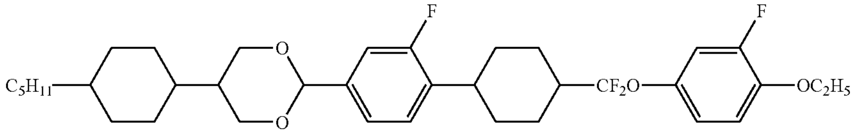
1-4-301
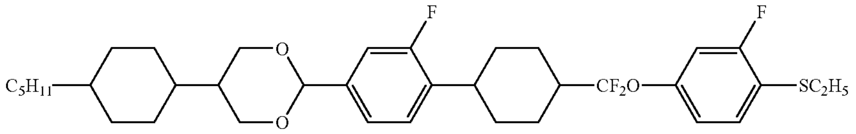
1-4-302
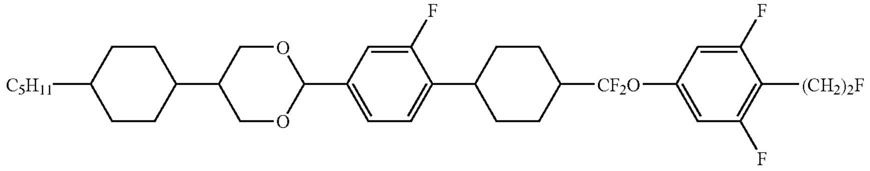
1-4-303
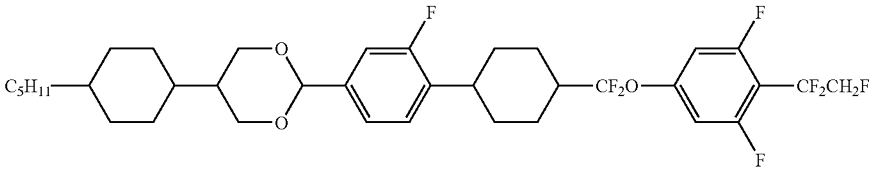
1-4-304
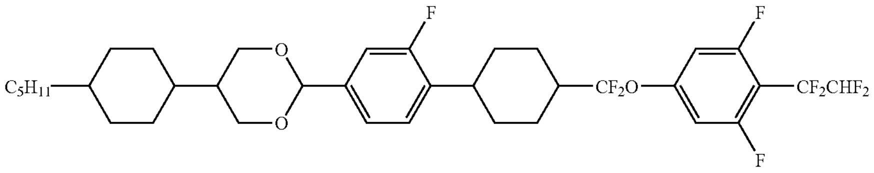
1-4-305
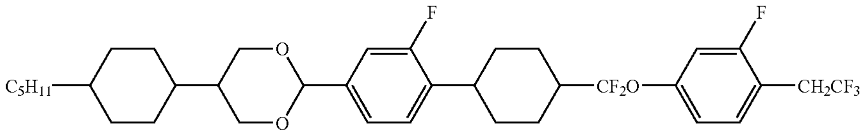
1-4-306
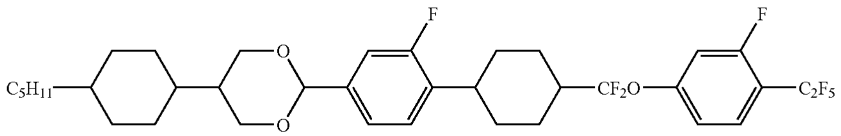
1-4-307
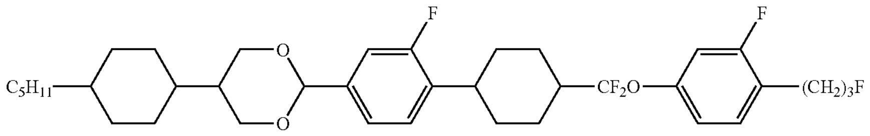
1-4-308
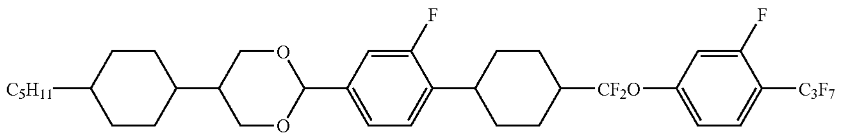

-continued
No.
1-4-309
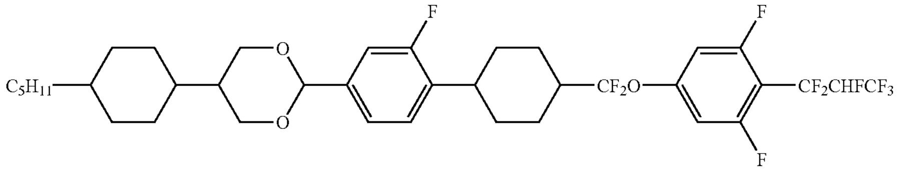
1-4-310
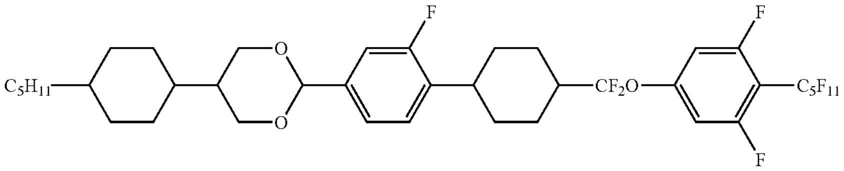
1-4-311
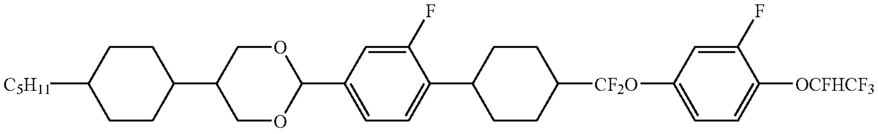
1-4-312
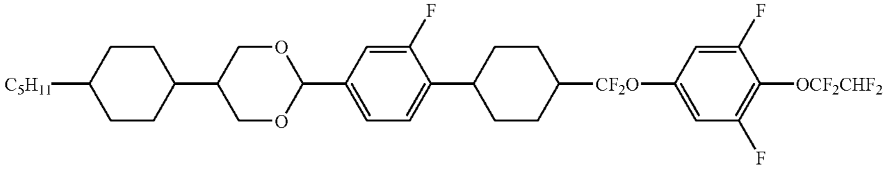
1-4-313
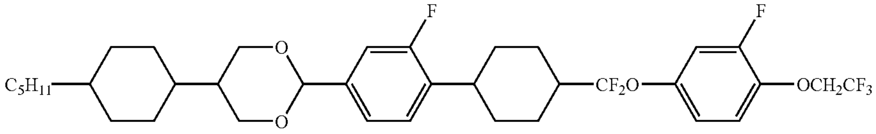
1-4-314
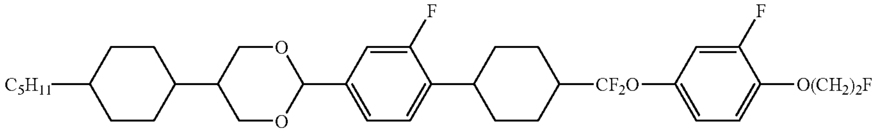
1-4-315
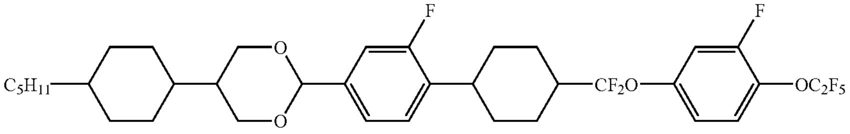
1-4-316
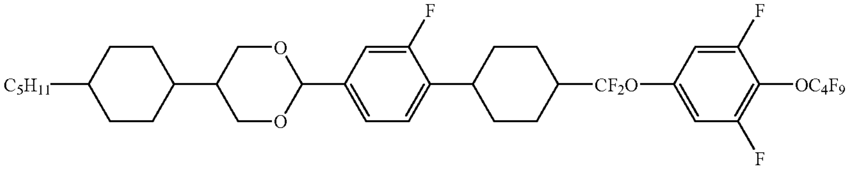
1-4-317
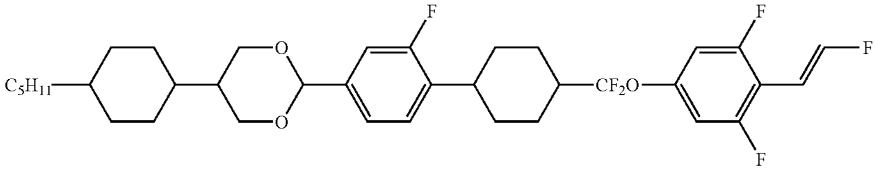

-continued
| No. | |
|---|---|
| 1-4-318 | 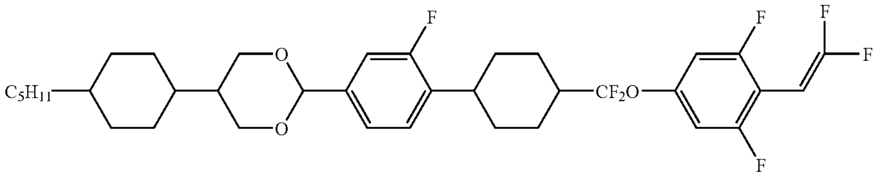 |
| 1-4-319 | 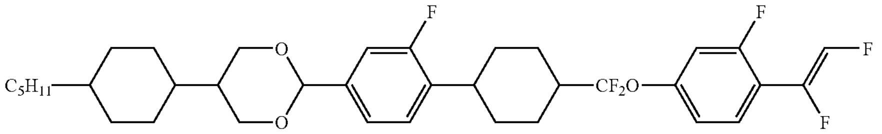 |
| 1-4-320 | 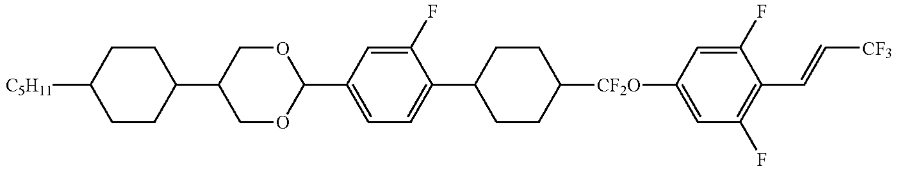 |
| 1-4-321 | 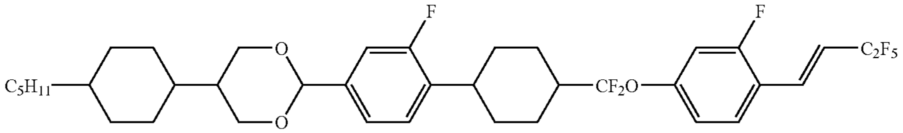 |
| 1-4-322 | 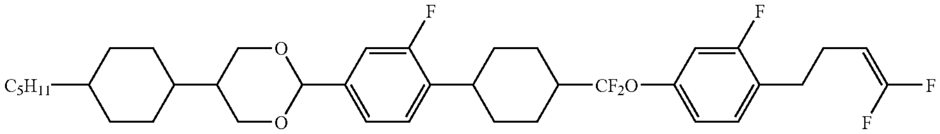 |
| 1-4-323 | 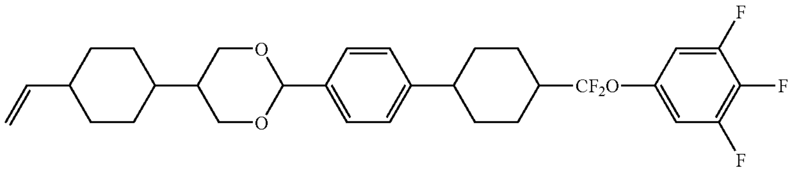 |
| 1-4-324 | 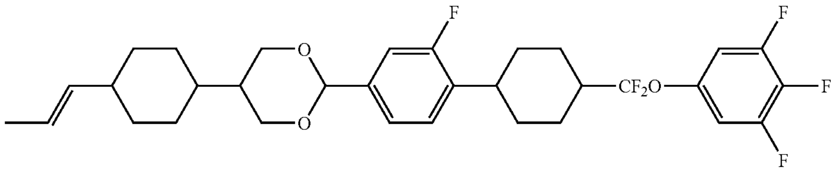 |
| 1-4-325 | 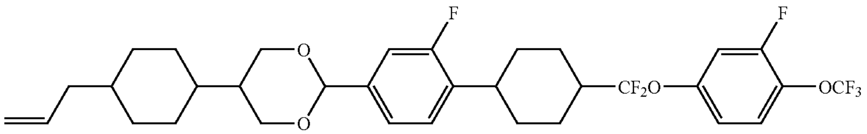 |
| 1-4-326 | 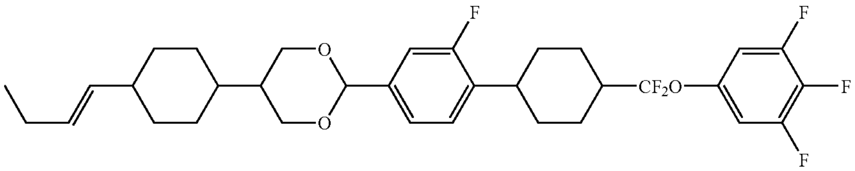 |

-continued
| No. | |
|---|---|
| 1-4-327 | 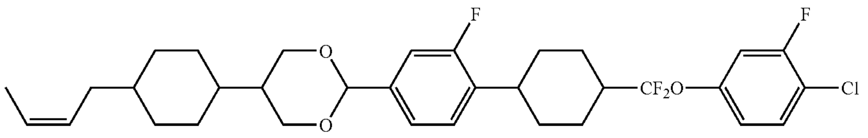 |
| 1-4-328 | 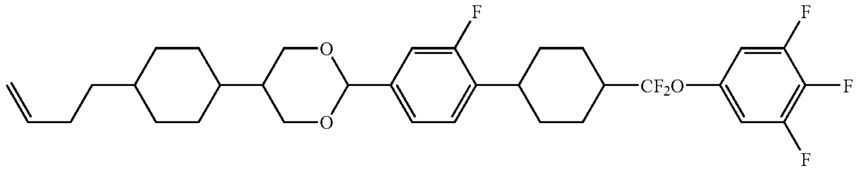 |
| 1-4-329 | 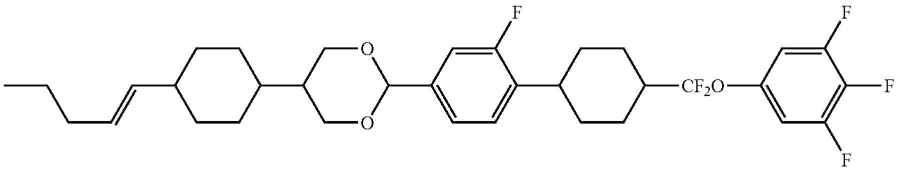 |
| 1-4-330 | 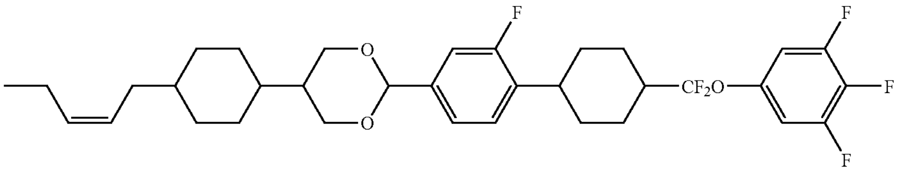 |
| 1-4-331 | 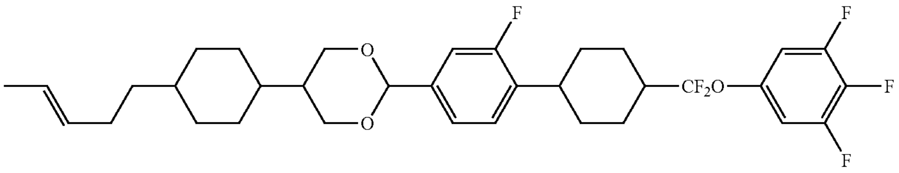 |
| 1-4-332 | 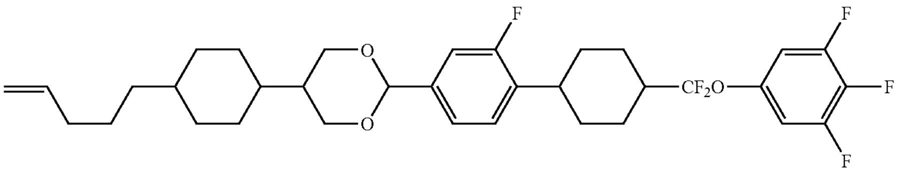 |
| 1-4-333 | 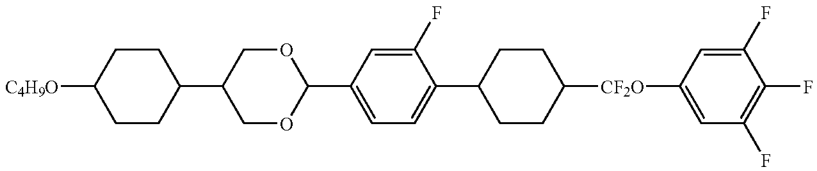 |
| 1-4-334 | 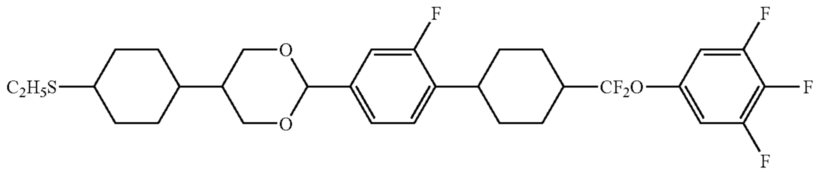 |
| 1-4-335 | 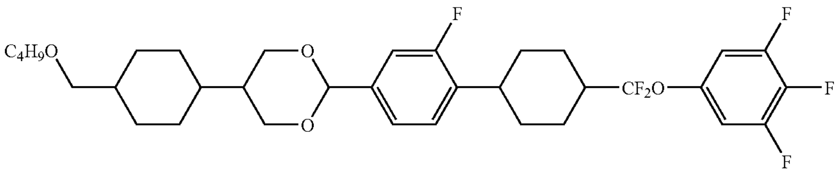 |

-continued
| No. | |
|---|---|
| 1-4-336 | 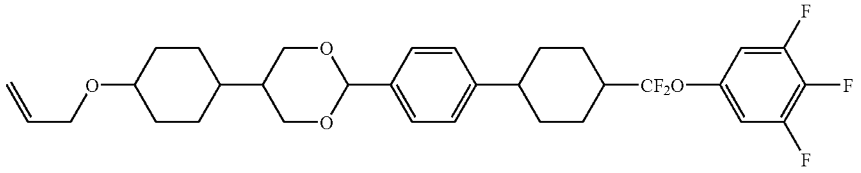 |
| 1-4-337 | 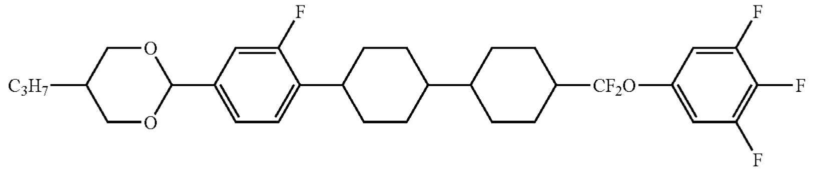 |
| 1-4-338 | 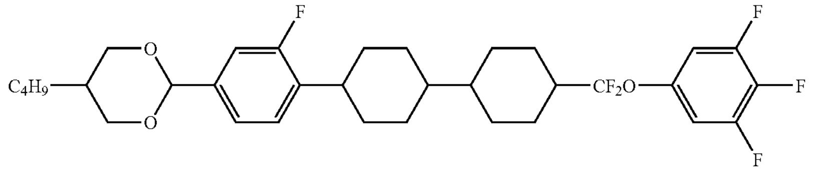 |
| 1-4-339 | 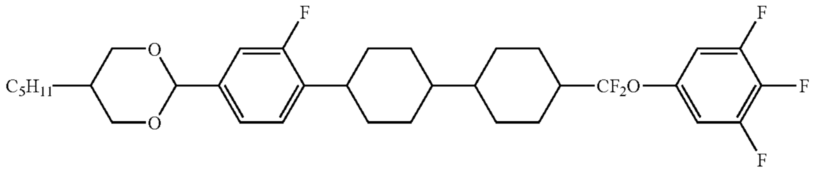 |
| 1-4-340 | 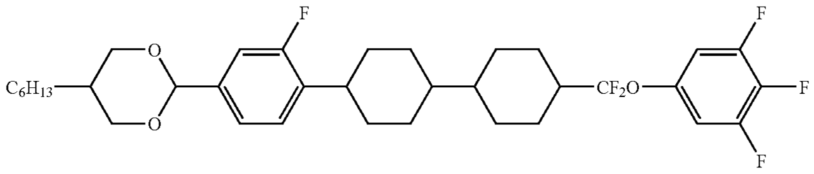 |
| 1-4-341 | 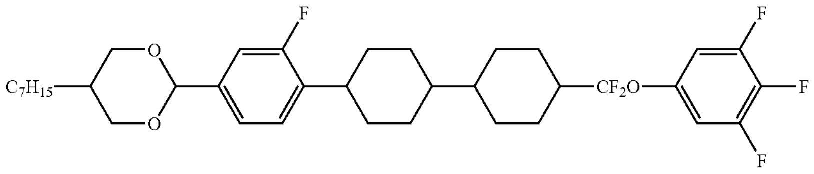 |
| 1-4-342 | 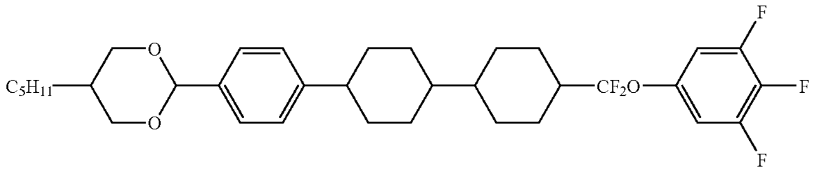 |
| 1-4-343 | 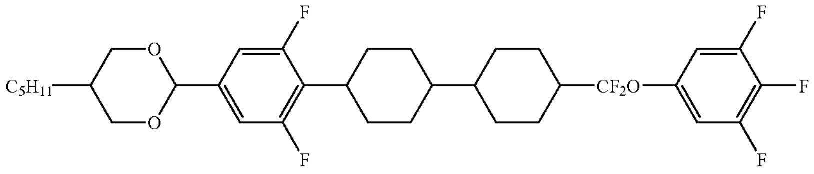 |

-continued
| No. | |
|---|---|
| 1-4-344 | 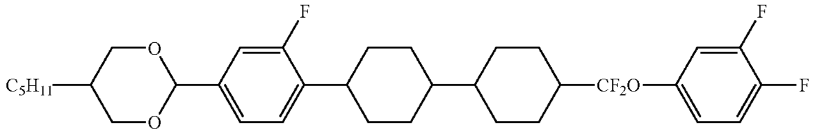 |
| 1-4-345 | 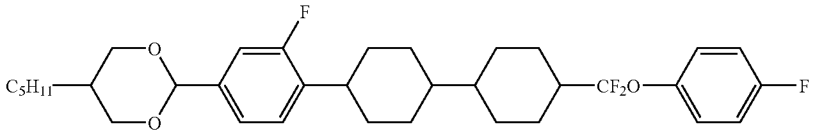 |
| 1-4-346 | 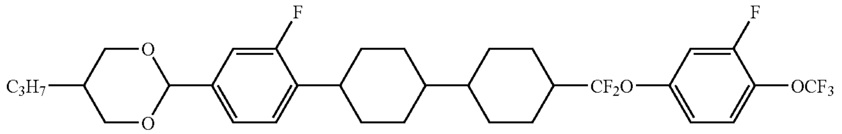 |
| 1-4-347 | 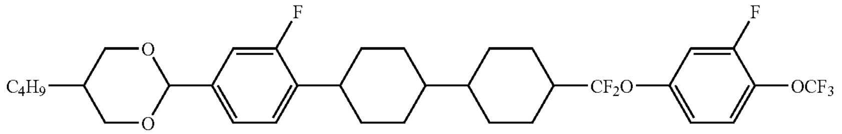 |
| 1-4-348 | 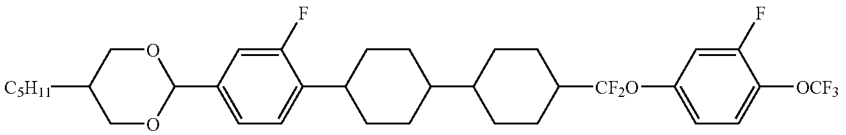 |
| 1-4-349 | 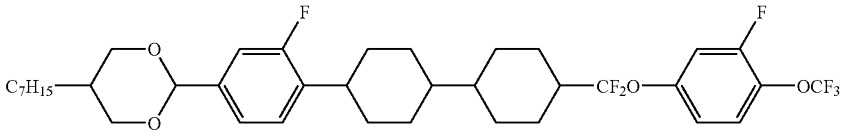 |
| 1-4-350 | 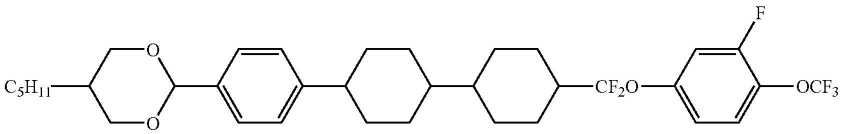 |
| 1-4-351 | 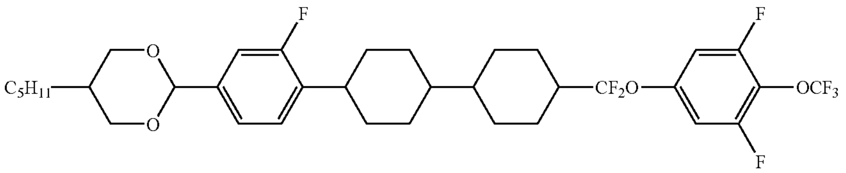 |
| 1-4-352 | 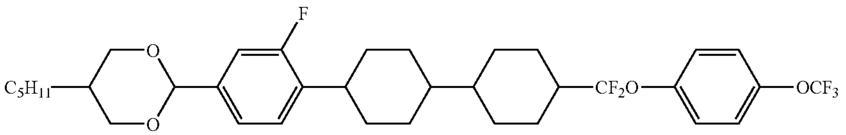 |
| 1-4-353 | 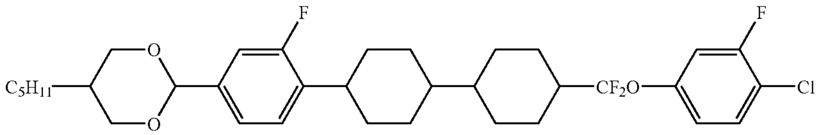 |

-continued
| No. | |
|---|---|
| 1-4-354 | 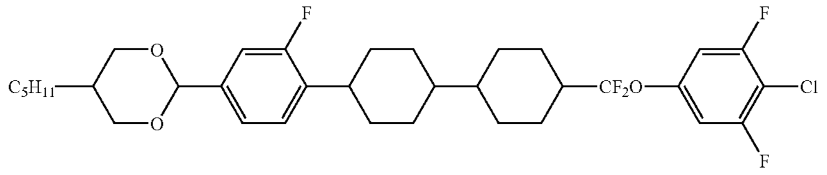 |
| 1-4-355 | 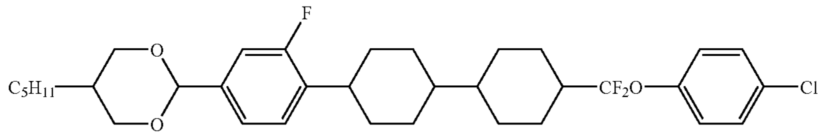 |
| 1-4-356 | 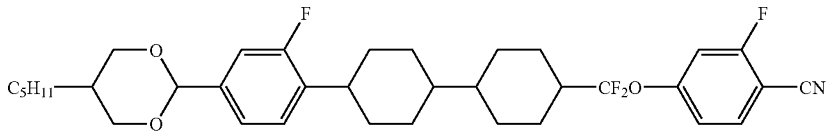 |
| 1-4-357 | 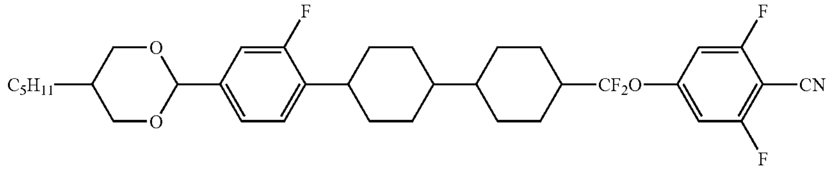 |
| 1-4-358 | 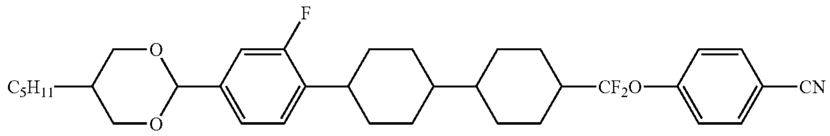 |
| 1-4-359 | 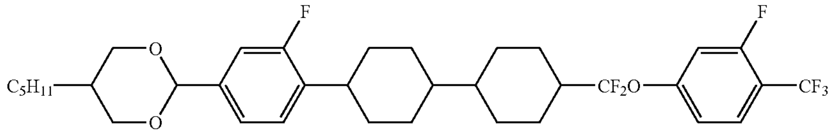 |
| 1-4-360 | 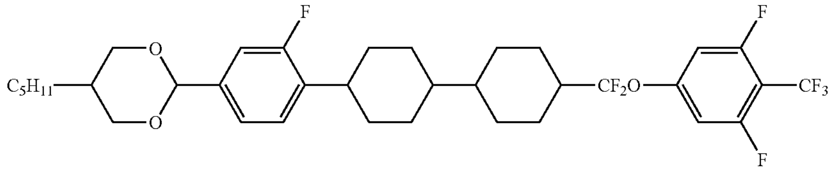 |
| 1-4-361 | 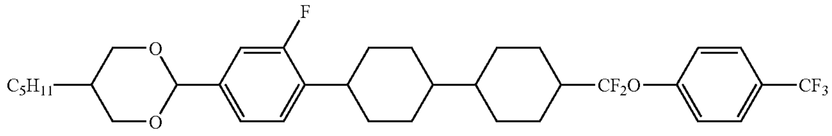 |
| 1-4-362 | 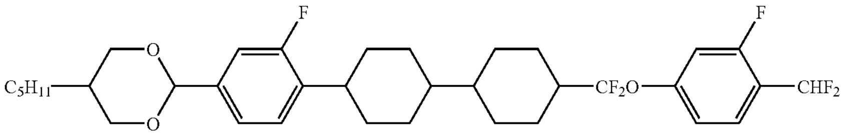 |

-continued
| No. | |
|---|---|
| 1-4-363 | 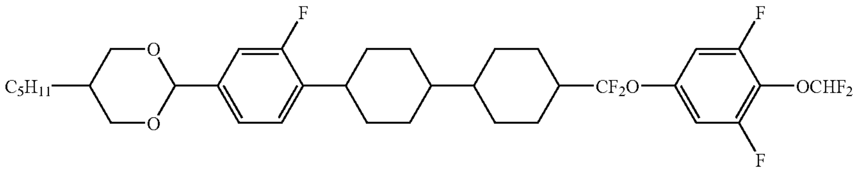 |
| 1-4-364 | 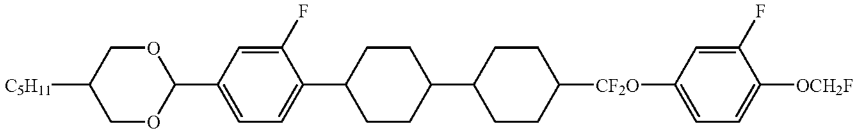 |
| 1-4-365 | 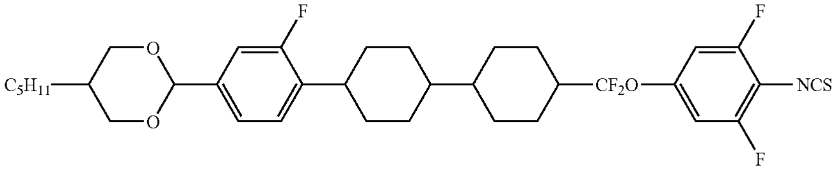 |
| 1-4-366 | 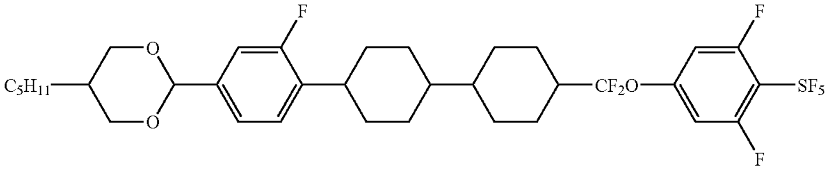 |
| 1-4-367 | 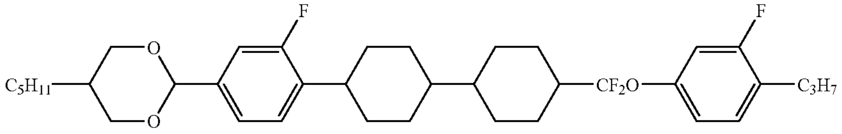 |
| 1-4-368 | 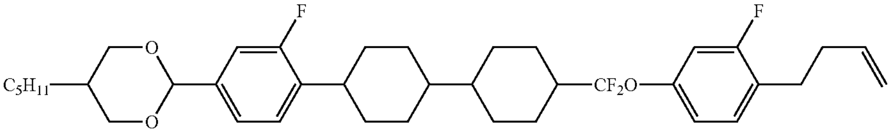 |
| 1-4-369 | 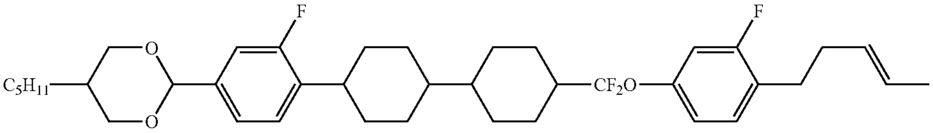 |
| 1-4-370 | 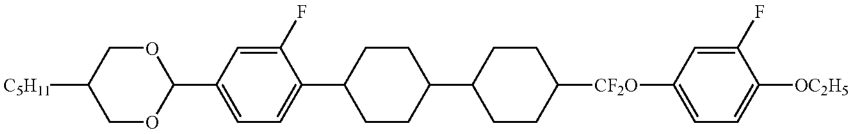 |
| 1-4-371 | 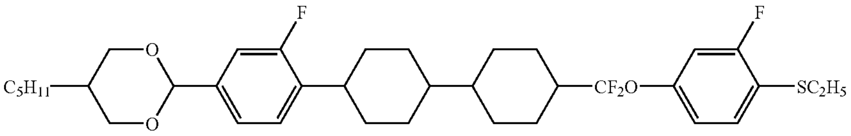 |

-continued
| No. | |
|---|---|
| 1-4-372 | 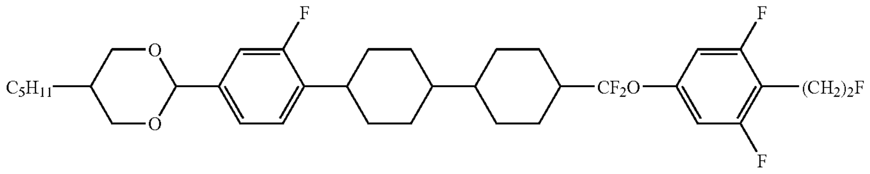 |
| 1-4-373 | 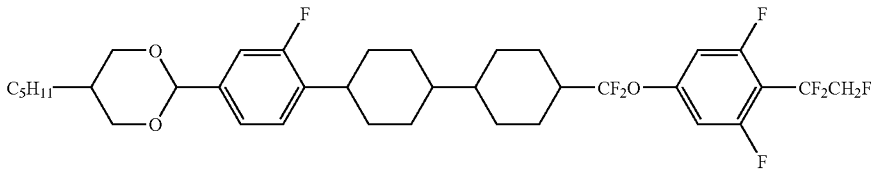 |
| 1-4-374 | 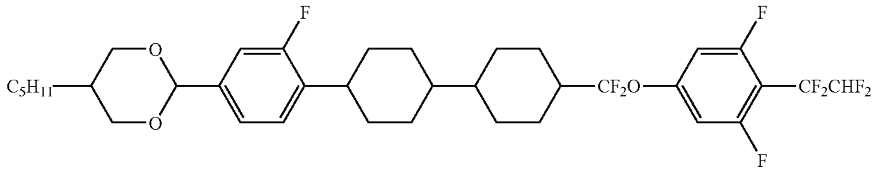 |
| 1-4-375 | 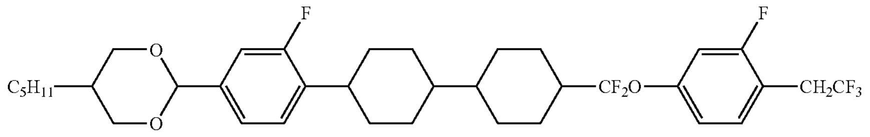 |
| 1-4-376 | 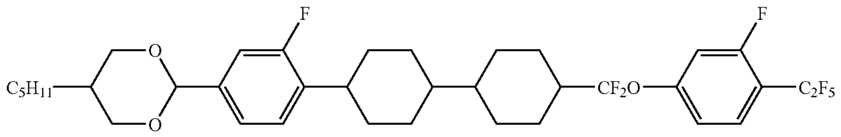 |
| 1-4-377 | 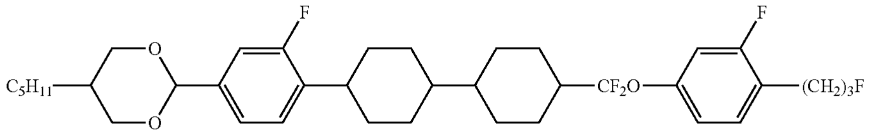 |
| 1-4-378 | 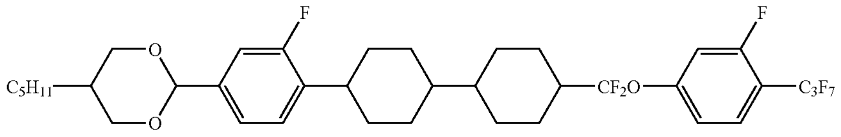 |
| 1-4-379 | 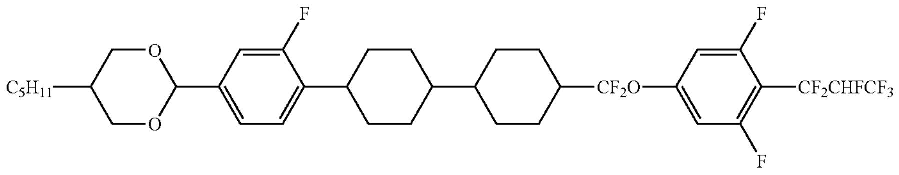 |
| 1-4-380 | 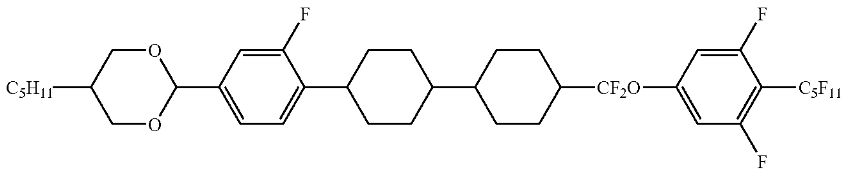 |

-continued
| No. | |
|---|---|
| 1-4-381 | 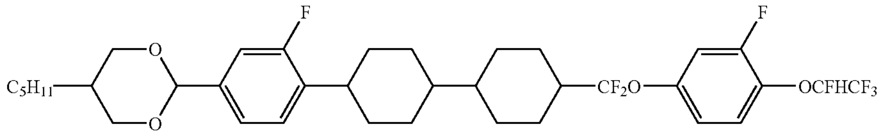 |
| 1-4-382 | 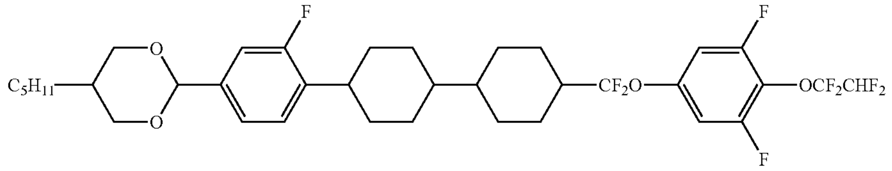 |
| 1-4-383 | 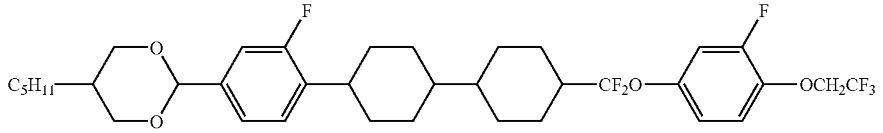 |
| 1-4-384 | 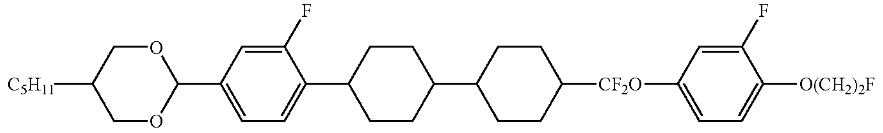 |
| 1-4-385 | 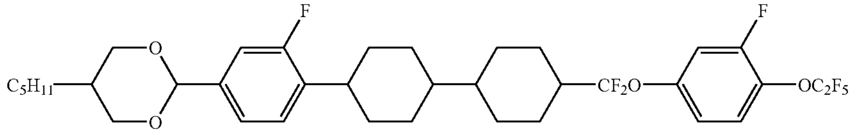 |
| 1-4-386 | 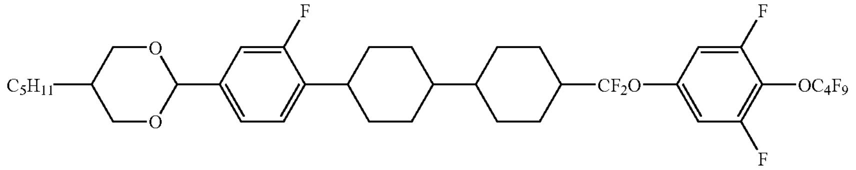 |
| 1-4-387 | 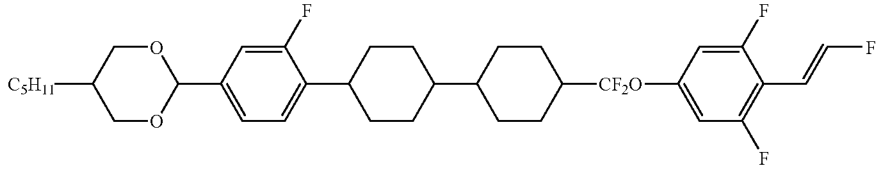 |
| 1-4-388 | 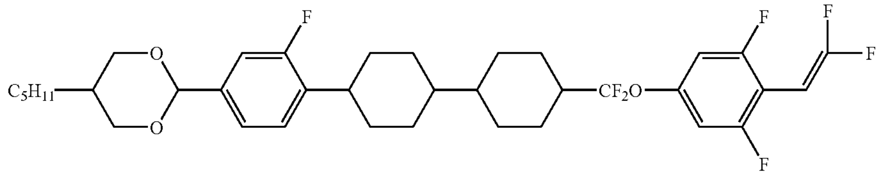 |
| 1-4-389 | 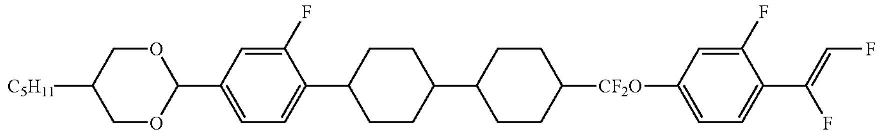 |

-continued
| No. | |
|---|---|
| 1-4-390 | 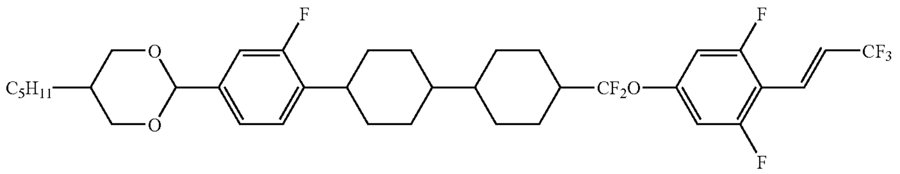 |
| 1-4-391 | 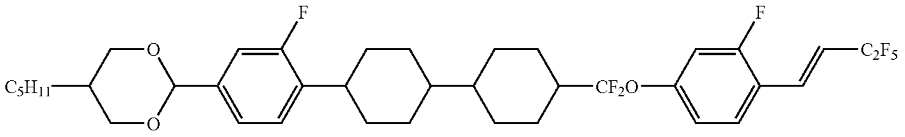 |
| 1-4-392 | 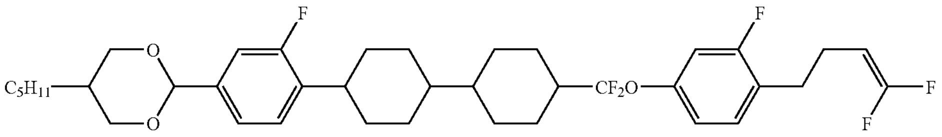 |
| 1-4-393 | 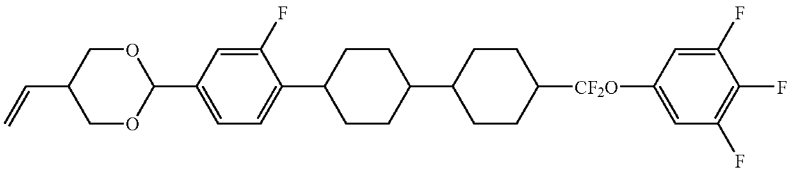 |
| 1-4-394 | 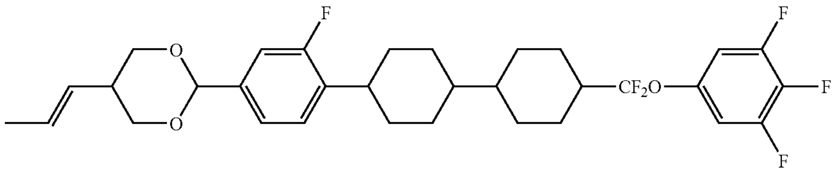 |
| 1-4-395 | 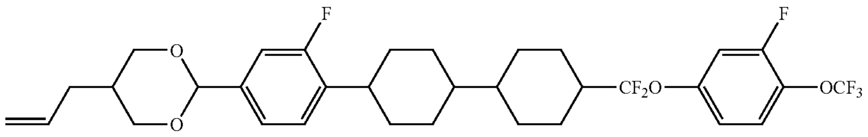 |
| 1-4-396 | 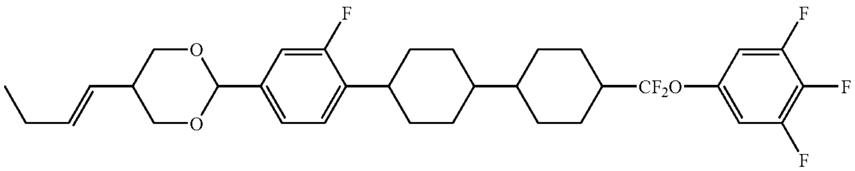 |
| 1-4-397 | 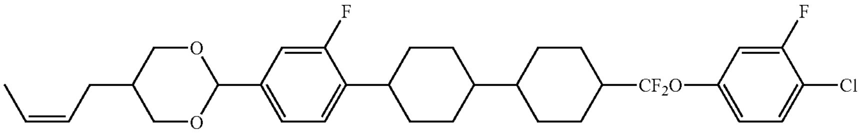 |
| 1-4-398 | 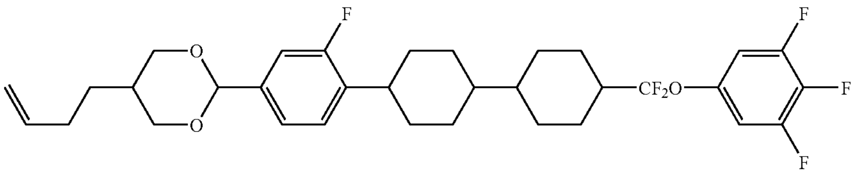 |

-continued
| No. | |
|---|---|
| 1-4-399 | 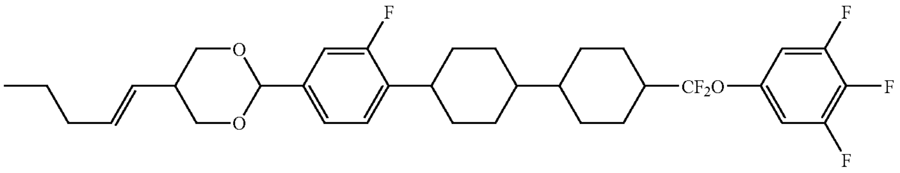 |
| 1-4-400 | 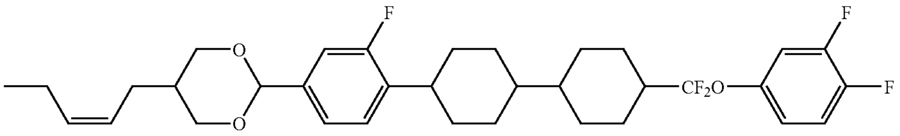 |
| 1-4-401 | 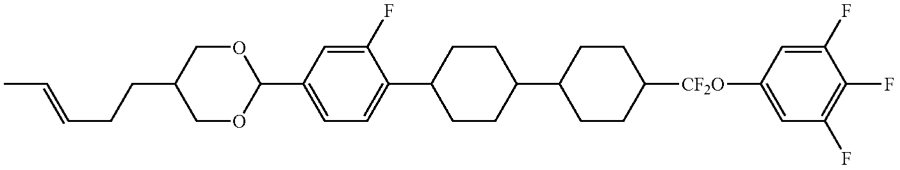 |
| 1-4-402 | 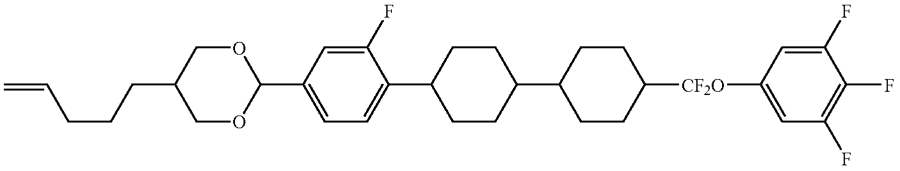 |
| 1-4-403 | 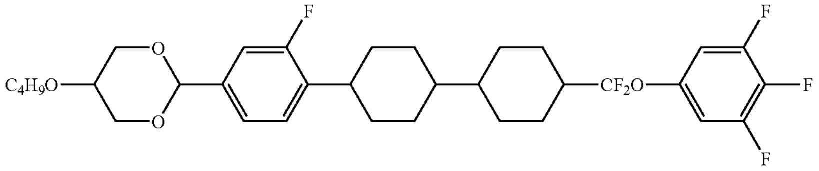 |
| 1-4-404 | 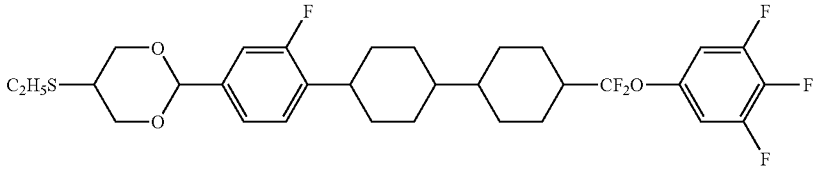 |
| 1-4-405 | 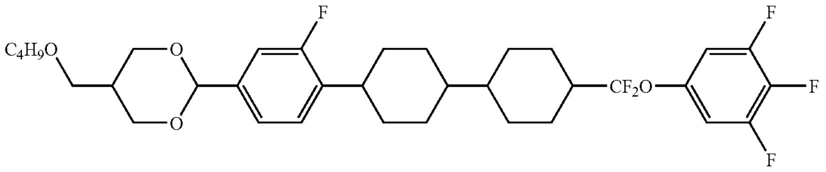 |
| 1-4-406 | 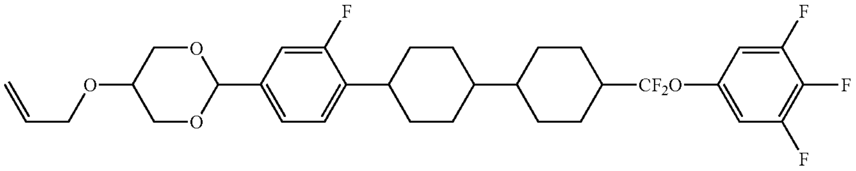 |
| 1-4-407 | 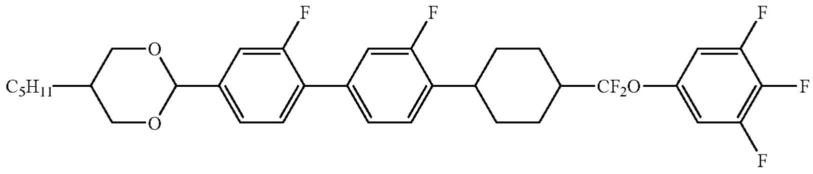 |

-continued
| No. | |
|---|---|
| 1-4-408 | 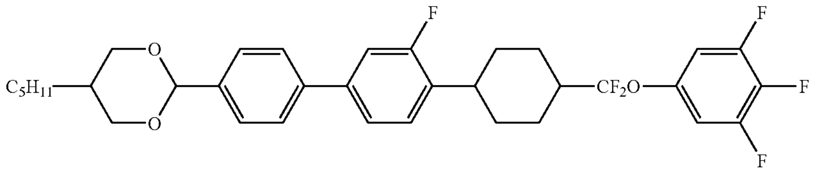 |
| 1-4-409 | 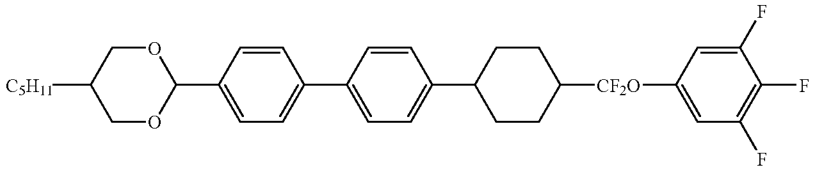 |
| 1-4-410 | 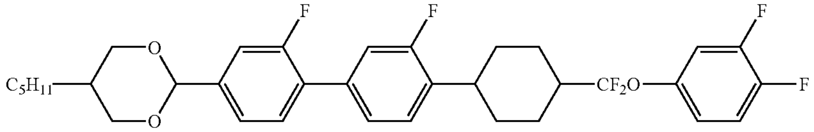 |
| 1-4-411 | 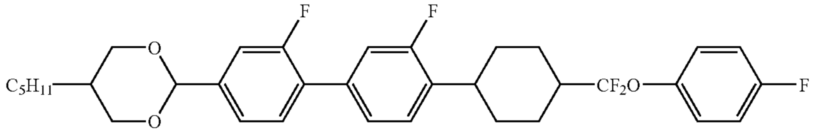 |
| 1-4-412 | 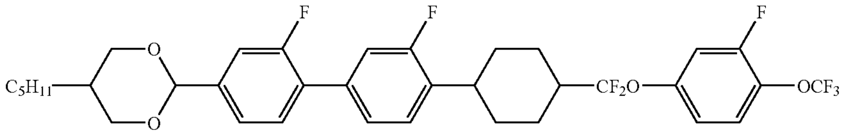 |
| 1-4-413 | 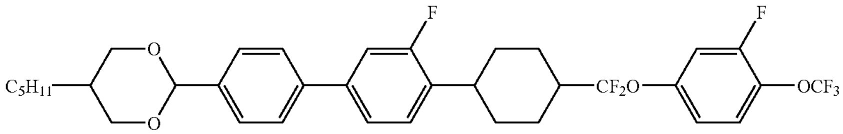 |
| 1-4-414 | 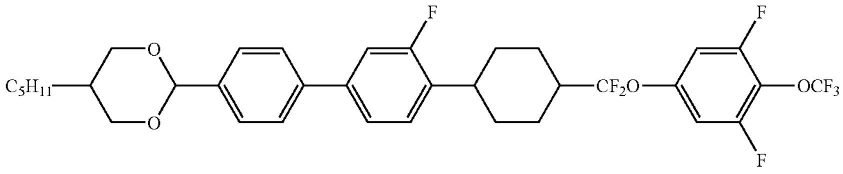 |
| 1-4-415 | 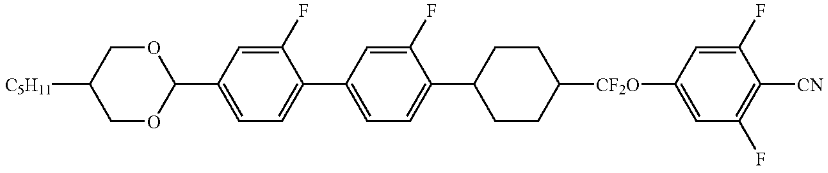 |
| 1-4-416 | 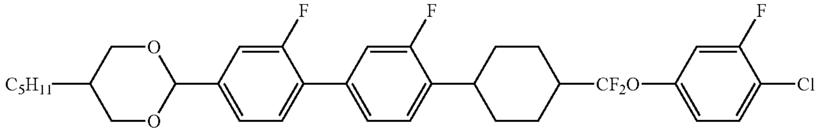 |

-continued
| No. | |
|---|---|
| 1-4-417 | 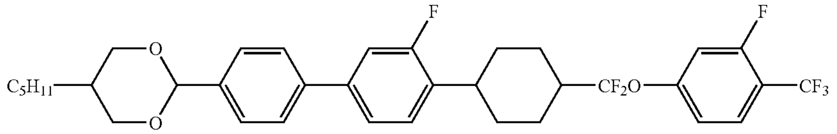 |
| 1-4-418 | 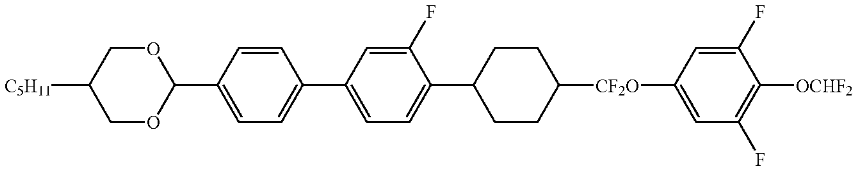 |
| 1-4-419 | 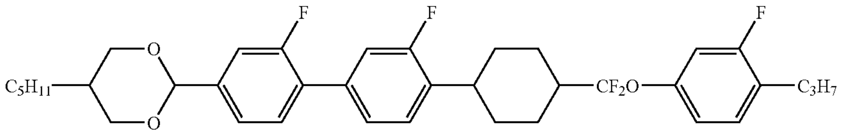 |
| 1-4-420 | 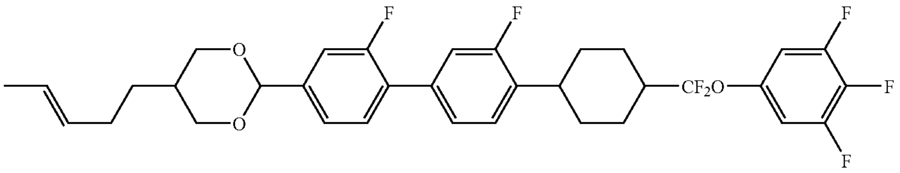 |
| 1-4-421 | 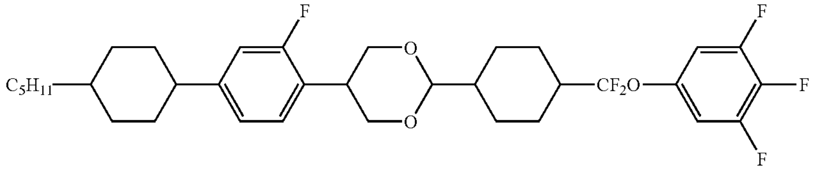 |
| 1-4-422 | 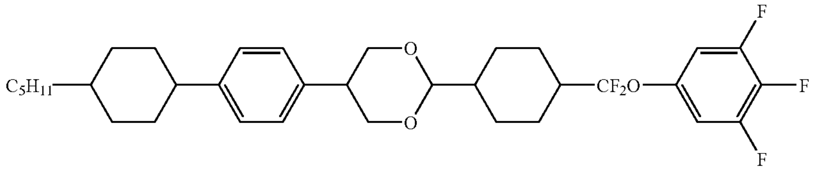 |
| 1-4-423 | 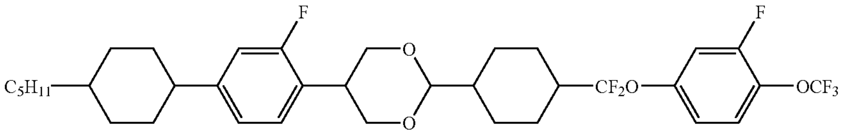 |
| 1-4-424 | 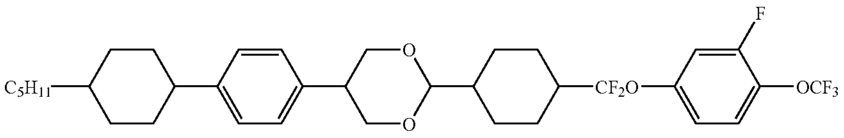 |
| 1-4-425 | 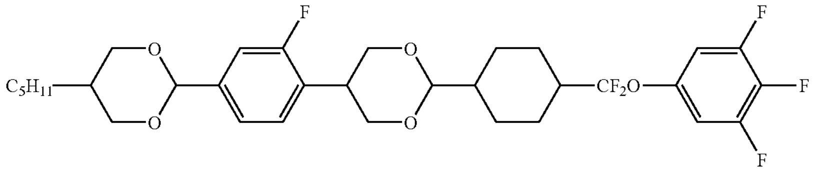 |

-continued
| No. | |
|---|---|
| 1-4-426 | 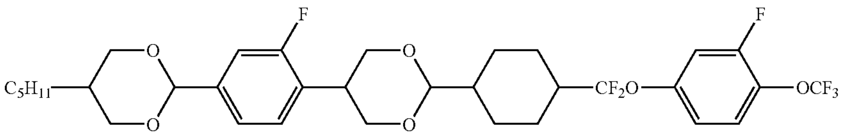 |
| 1-4-427 | 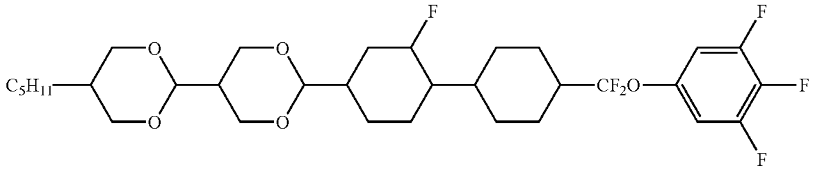 |
| 1-4-428 | 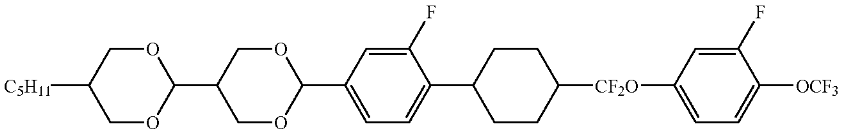 |
| 1-4-429 | 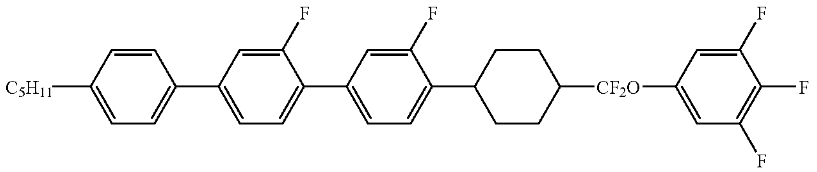 |
| 1-4-430 | 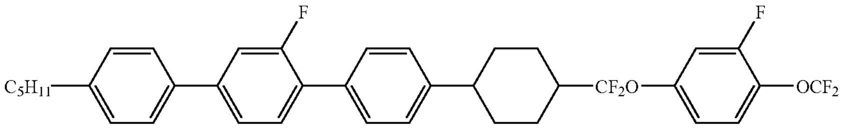 |
| 1-4-431 | 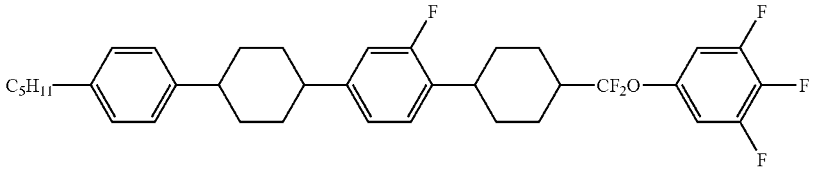 |
| 1-4-432 | 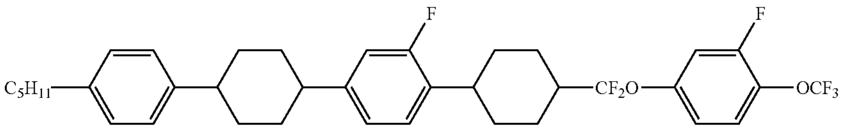 |
| 1-4-433 | 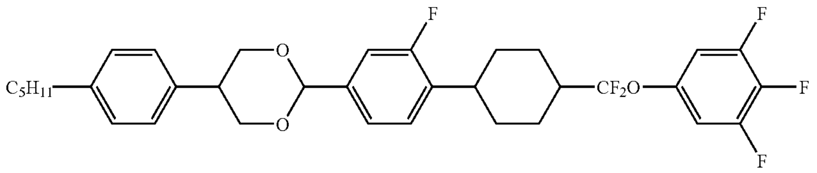 |
| 1-4-434 | 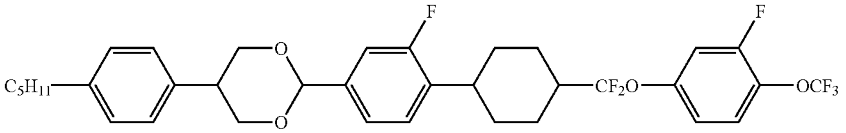 |

-continued
| No. | |
|---|---|
| 1-4-435 | 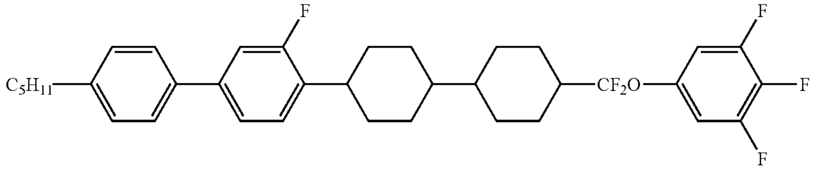 |
| 1-4-436 | 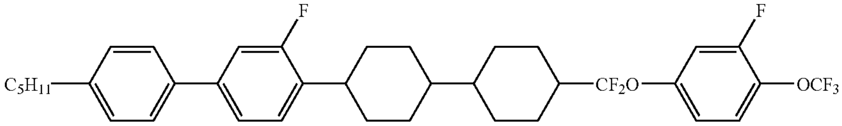 |
| 1-4-437 | 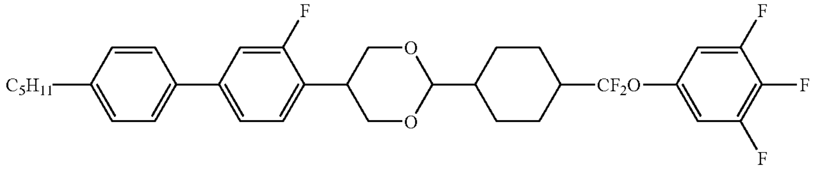 |
| 1-4-438 | 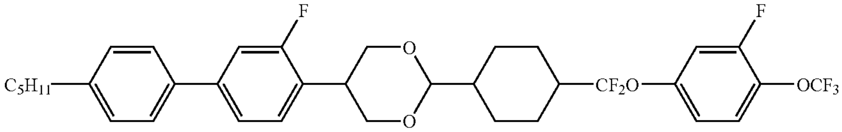 |
| 1-4-439 | 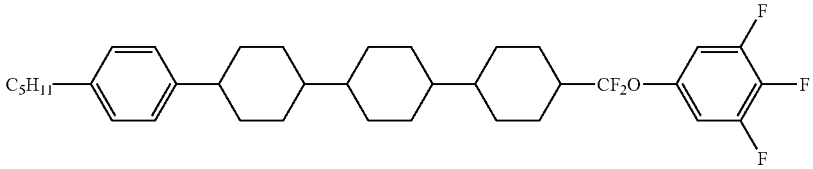 |
| 1-4-440 | 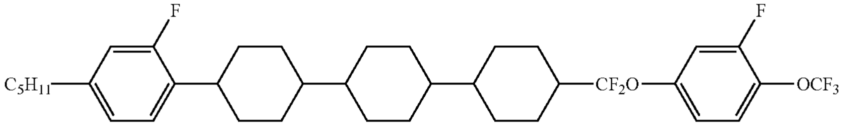 |
| 1-4-441 | 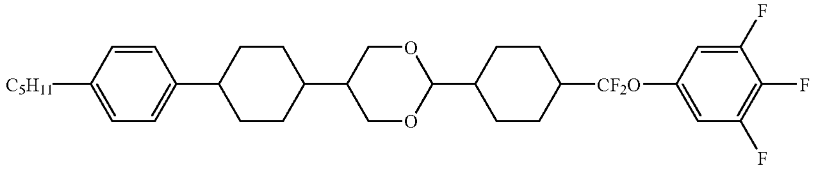 |
| 1-4-442 | 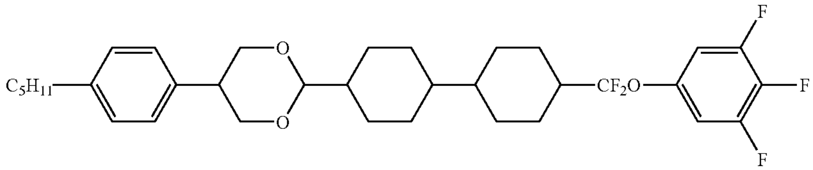 |
| 1-4-443 | 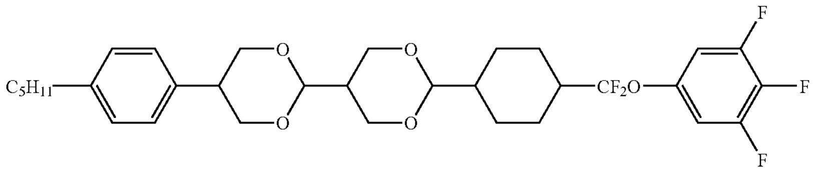 |

-continued
| No. | |
|---|---|
| 1-4-444 | 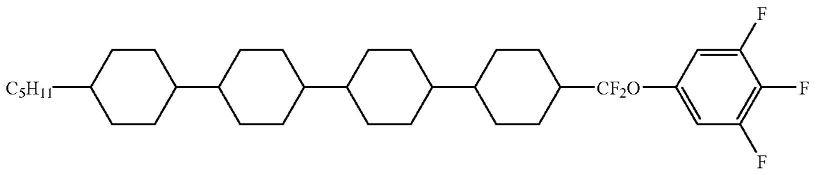 |
| 1-4-445 | 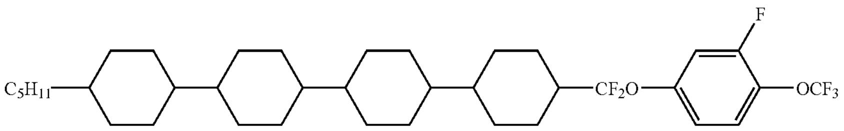 |
| 1-4-446 | 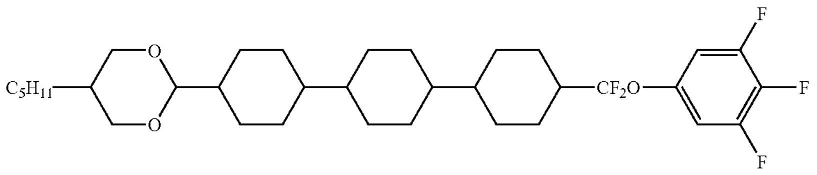 |
| 1-4-447 | 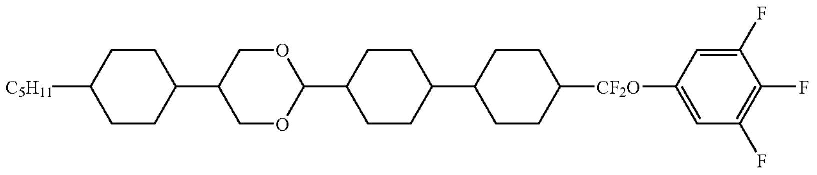 |
| 1-4-448 | 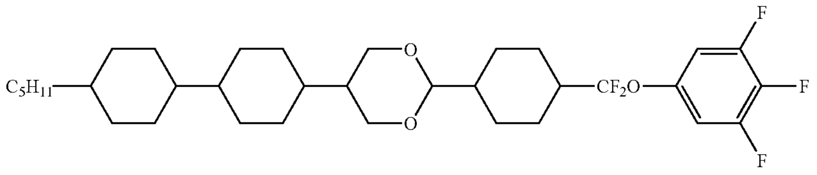 |
| 1-4-449 | 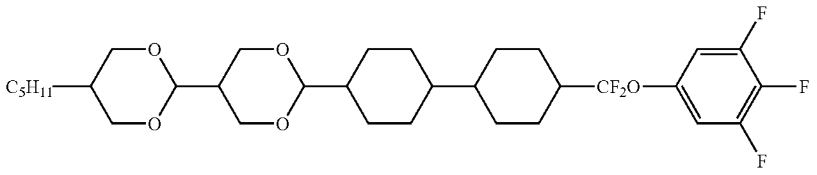 |
| 1-4-450 | 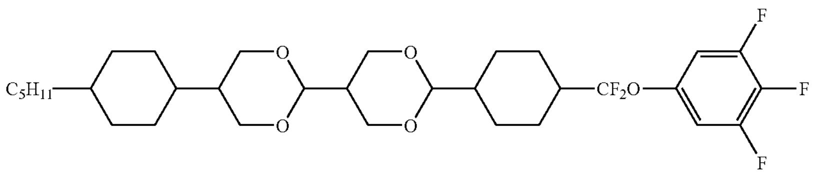 |
| 1-4-451 | 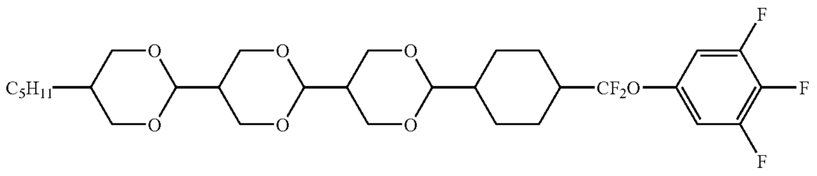 |
| 1-4-452 | 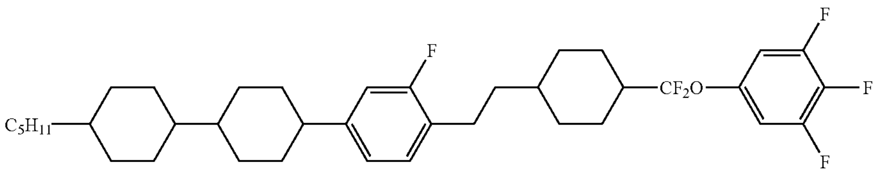 |

-continued
| No. | |
|---|---|
| 1-4-453 | 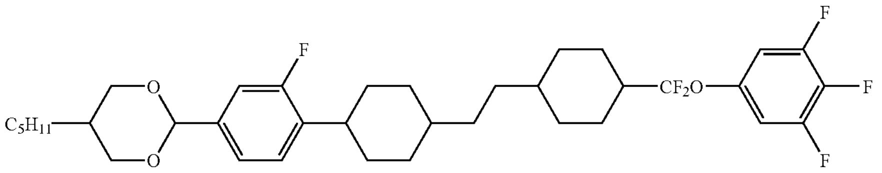 |
| 1-4-454 | 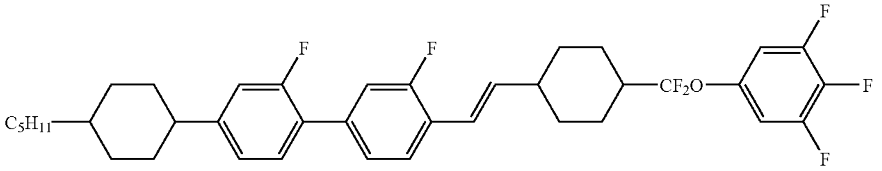 |
| 1-4-455 | 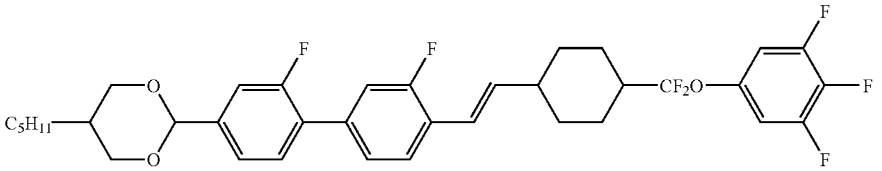 |
| 1-4-456 | 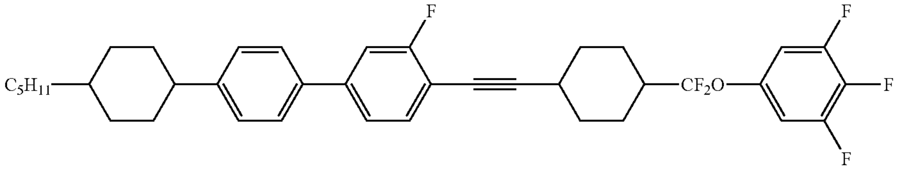 |
| 1-4-467 | 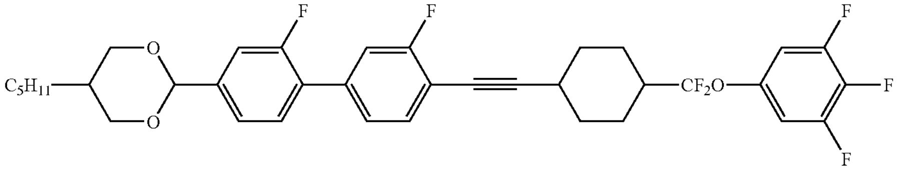 |
| 1-4-458 | 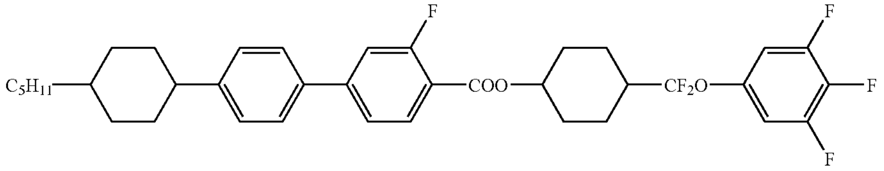 |
| 1-4-459 | 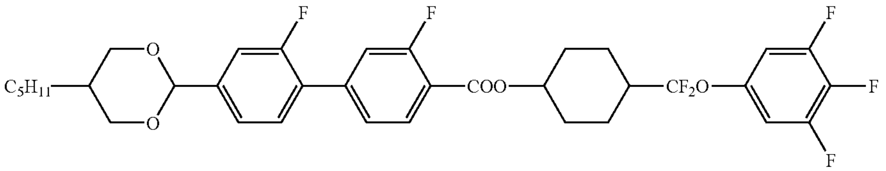 |
| 1-4-460 | 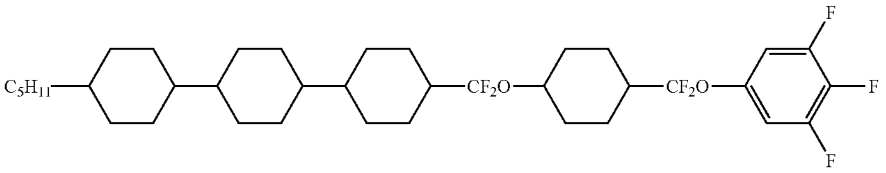 |

-continued
| No. | |
|---|---|
| 1-4-461 | 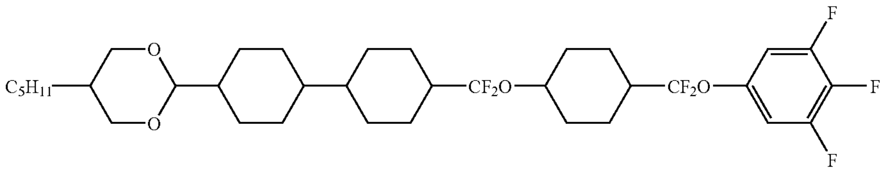 |
| 1-4-462 | 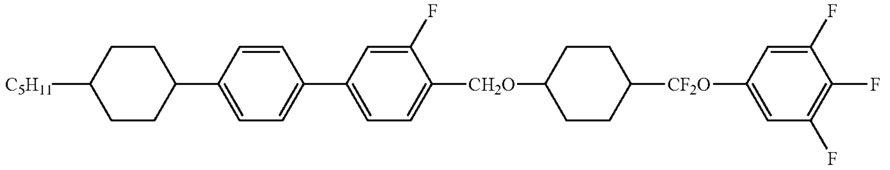 |
| 1-4-463 | 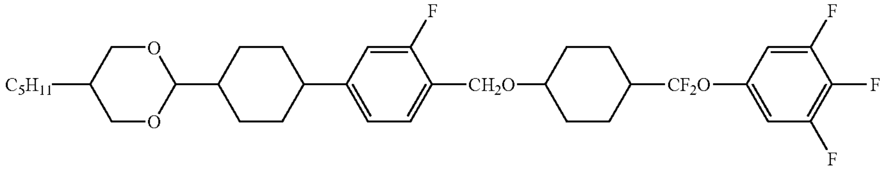 |
| 1-4-464 | 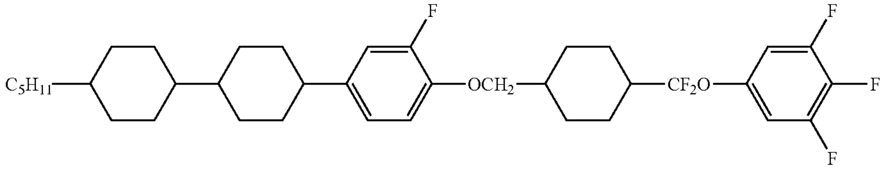 |
| 1-4-465 | 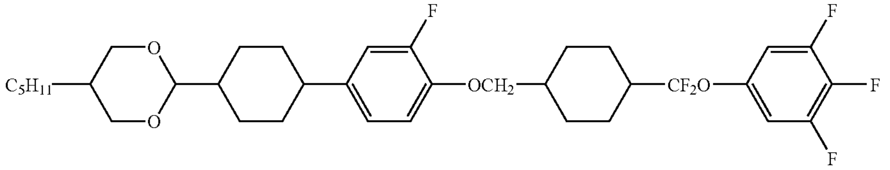 |
| 1-4-466 | 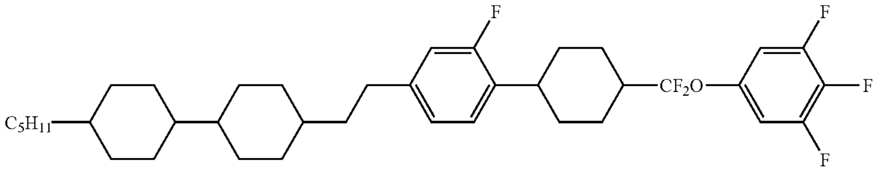 |
| 1-4-467 | 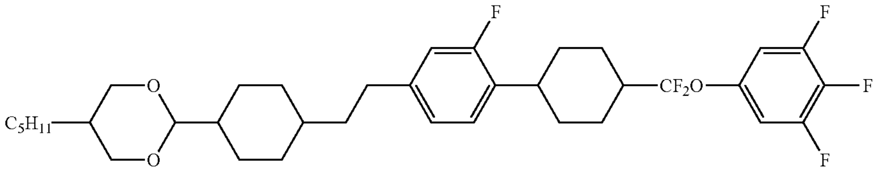 |
| 1-4-468 | 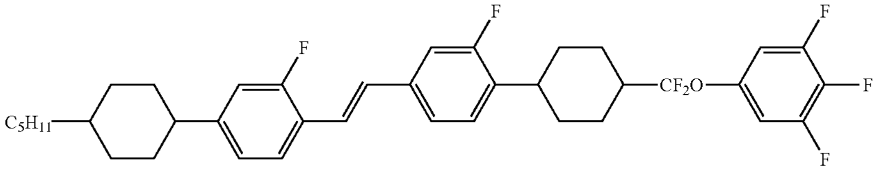 |

-continued
| No. | |
|---|---|
| 1-4-469 | 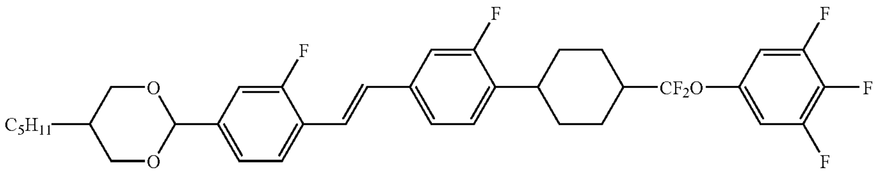 |
| 1-4-470 | 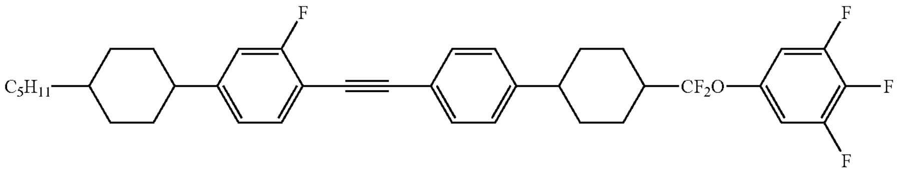 |
| 1-4-471 | 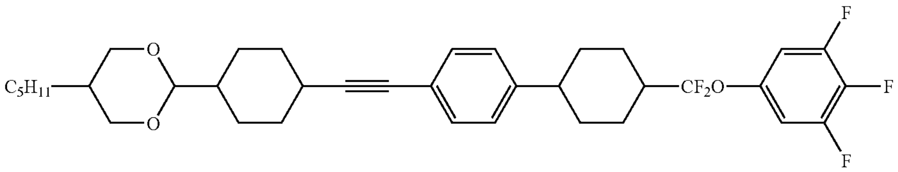 |
| 1-4-472 | 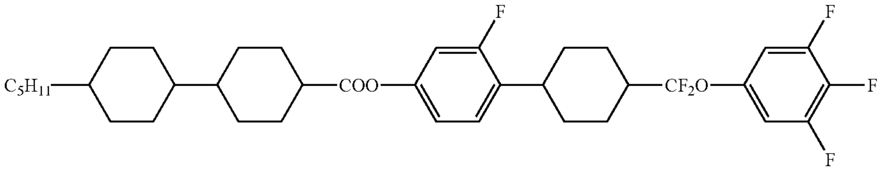 |
| 1-4-473 | 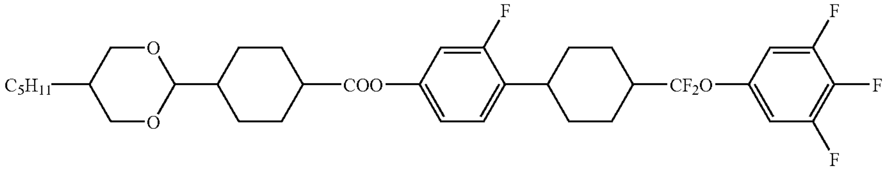 |
| 1-4-474 | 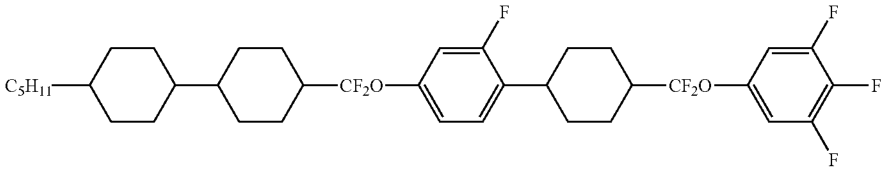 |
| 1-4-475 | 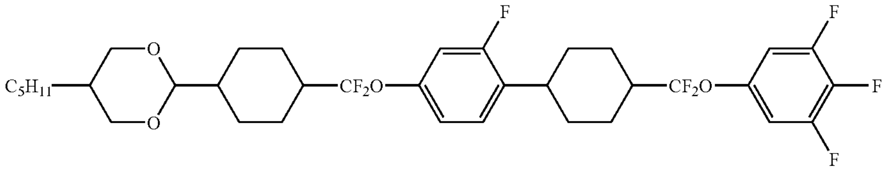 |
| 1-4-476 | 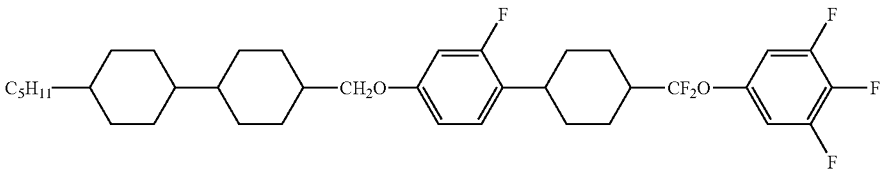 |

-continued
| No. | |
|---|---|
| 1-4-477 | 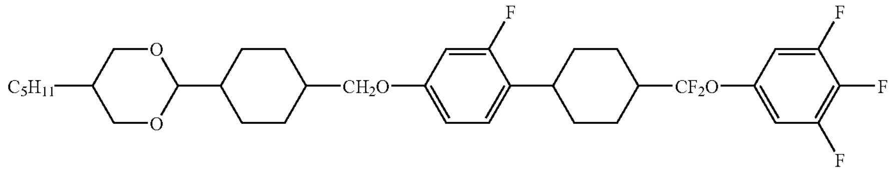 |
| 1-4-478 | 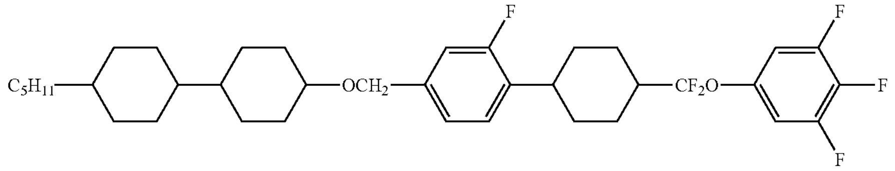 |
| 1-4-479 | 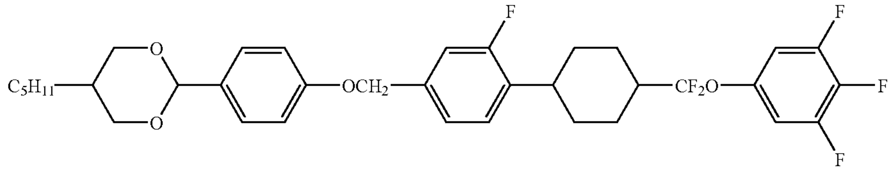 |
| 1-4-480 | 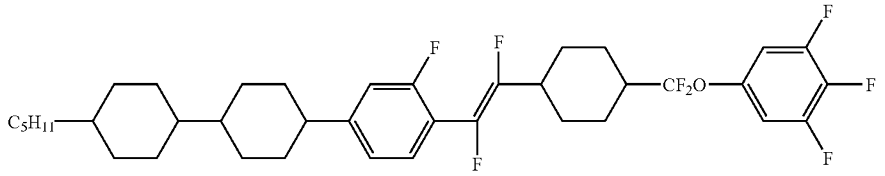 |
| 1-4-481 | 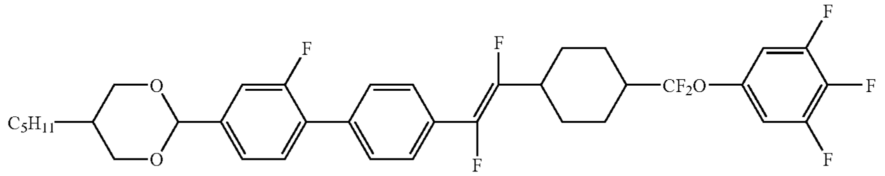 |
| 1-4-482 | 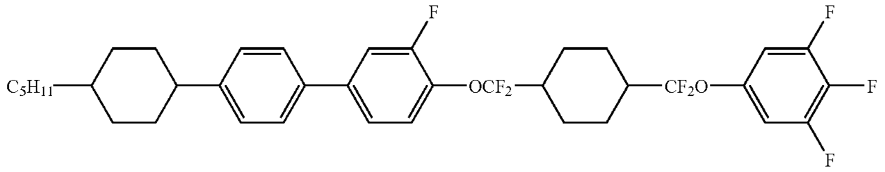 |
| 1-4-483 | 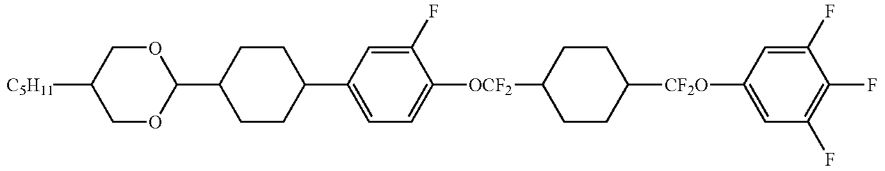 |
| 1-4-484 | 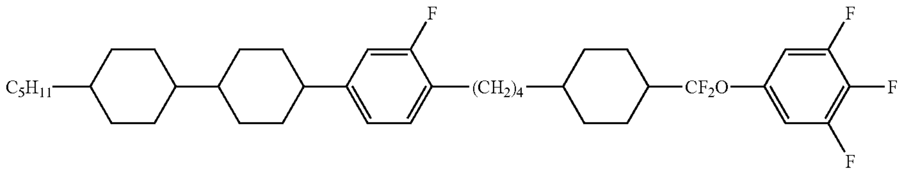 |

-continued
| No. | |
|---|---|
| 1-4-485 | 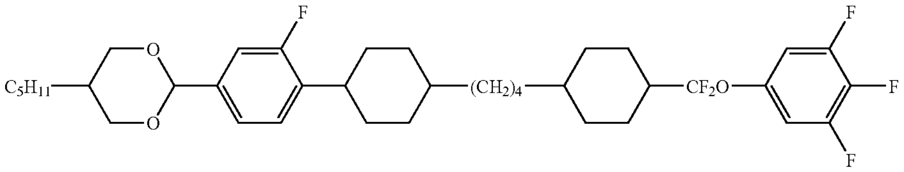 |
| 1-4-486 | 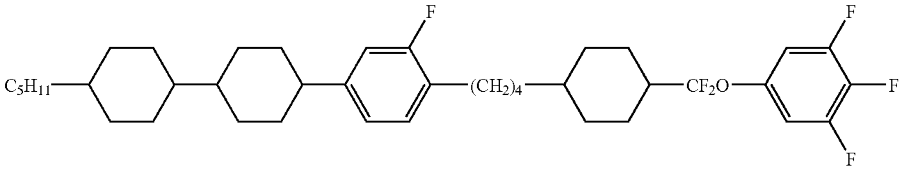 |
| 1-4-487 | 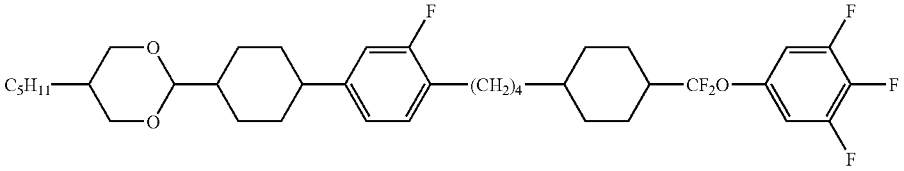 |
| 1-4-488 | 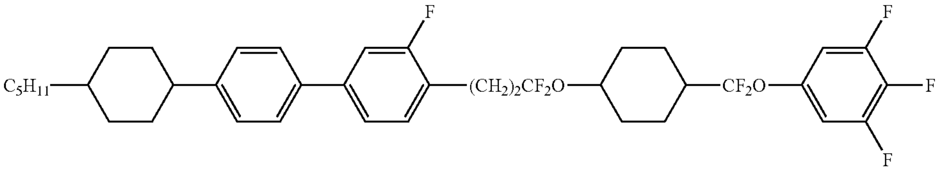 |
| 1-4-489 | 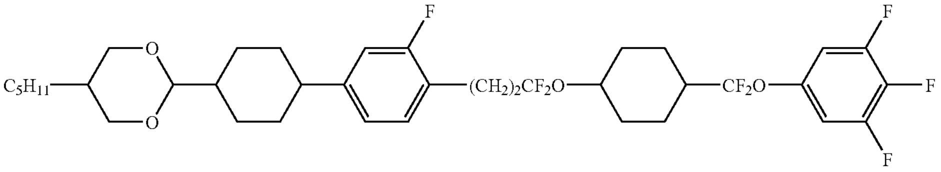 |
| 1-4-490 | 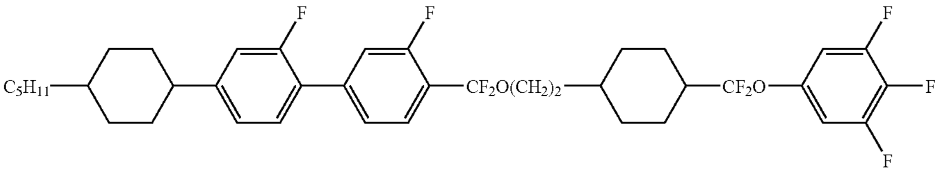 |
| 1-4-491 | 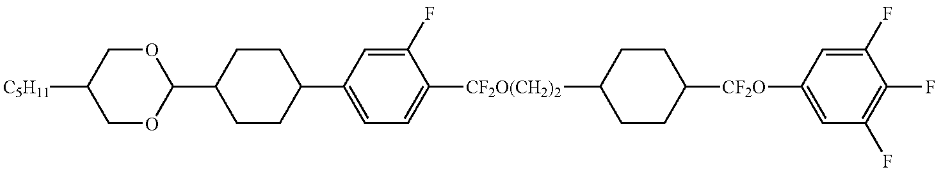 |
| 1-4-492 | 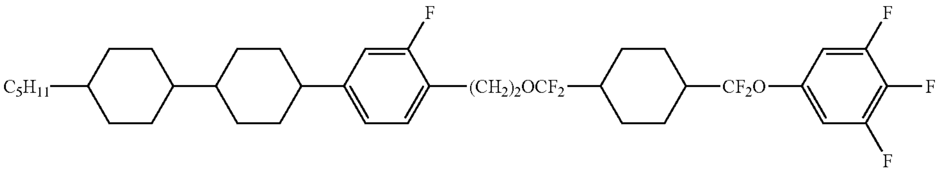 |

-continued
| No. | |
|---|---|
| 1-4-493 | 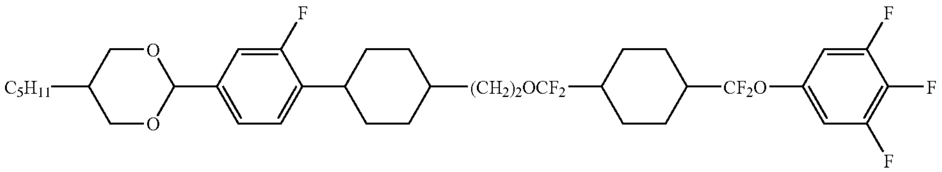 |
| 1-4-494 | 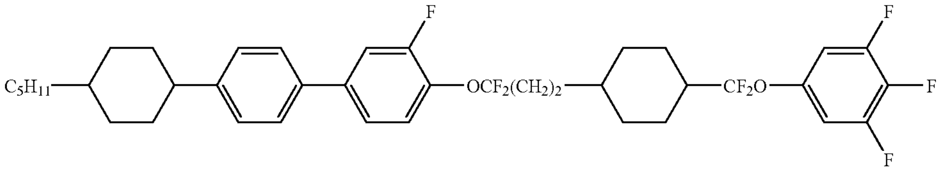 |
| 1-4-495 | 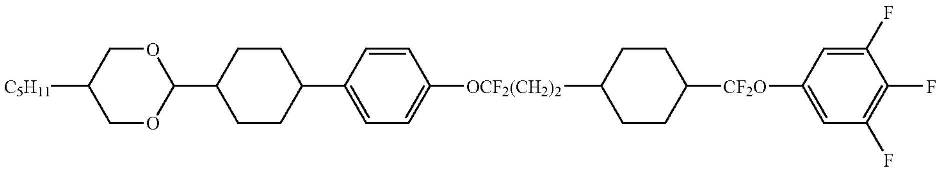 |
| 1-4-496 | 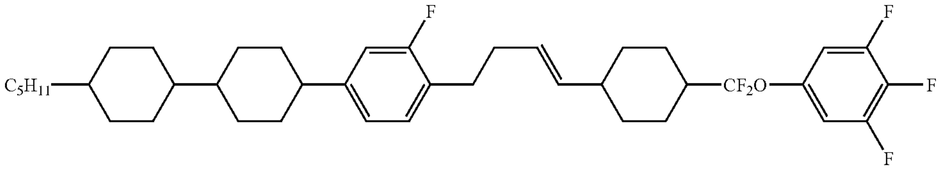 |
| 1-4-497 | 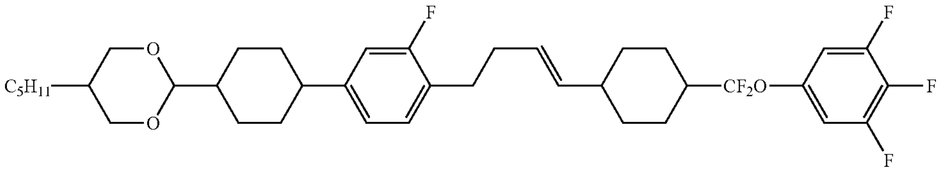 |
| 1-4-498 | 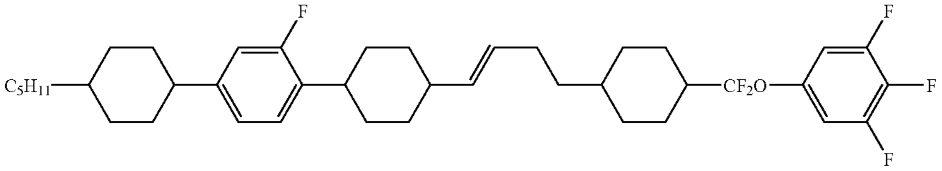 |
| 1-4-499 | 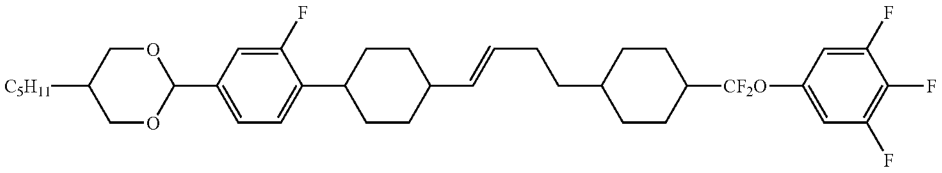 |

Comparative Example 1

As a Comparative Example, 4-[difluoro[(2,3',4',5'-tetrafluoro[1,1'-biphenyl]-4-yl)oxy]methyl]-4'-(5-propyltetrahydropyran-2-yl)-2',3,5,6'-tetrafluoro-1,1'-biphenyl (S-1-1), which is a five-ring liquid crystal compound having a tetrahydropyran ring described in WO 2005/019378 A1, was synthesized.

(S-1-1)

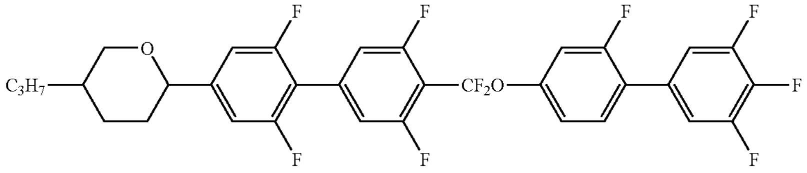

Chemical shift (δ; ppm) of $^1$H-NMR analysis was as follows and the compound obtained was identified as 4-[difluoro[(2,3',4',5'-tetrafluoro[1,1'-biphenyl]-4-yl)oxy]methyl]-4'-(5-propyltetrahydropyran-2-yl)-2',3,5,6'-tetrafluoro-1,1'-biphenyl.

Chemical shift (δ; ppm; $CDCl_3$); 7.38 (dd, J=8.65 Hz, J=8.40 Hz, 1H), 7.23-7.11 (m, 6H), 7.08-7.00 (m, 2H), 4.28 (dd, J=11.8 Hz, J=1.95 Hz, 1H), 4.10 (dq, J=11.2 Hz, J=2.00 Hz, 1H), 3.21 (t, J=11.2 Hz, 1H), 2.05-1.98 (m, 1H), 1.95-1.88 (m, 1H), 1.73-1.62 (m, 1H), 1.60-1.48 (m, 1H), 1.45-1.09 (m, 5H), 0.92 (t, J=6.80 Hz, 3H).

The phase transition temperature of the comparative compound (S-1-1) obtained was as follows.

Phase transition temperature: C 101 N 198 I.

The composition G consisting of 85% by weight of the mother liquid crystals A and 15% by weight of the comparative compound (S-1-1) was prepared. Physical properties of the composition G obtained were measured and the extrapolated values of the comparative compound (S-1-1) were calculated by extrapolating the measured values. The results were as follows.

Maximum temperature ($T_{NI}$)=118° C.; dielectric anisotropy ($\Delta\epsilon$)=52.3; optical anisotropy ($\Delta n$)=0.177.

The comparative compound (S-1-1) is compared with the compounds (1-4-59), (1-4-199), (1-4-66), (1-3-171), and (1-2-8). First, comparison of phase transition temperatures shows that the compounds (1-4-59), (1-4-199), (1-4-66), (1-3-171), and (1-2-8) have a wider temperature range of liquid crystal phases. In particular, the compound of the invention has a low minimum temperature and a high compatibility with other compounds.

Next, comparison of the maximum temperature (extrapolated values) of the comparative compound (S-1-1) and the compound of the invention shows that the compounds (1-4-59), (1-4-199), (1-4-66), (1-3-171), and (1-2-8) have higher maximum temperatures. Therefore, it is concluded that the compounds (1-4-59), (1-4-199), (1-4-66), (1-3-171), and (1-2-8) are usable in a wider temperature range and excellent.

Comparative Example 2

As a further Comparative Example, 4-[difluoro(3,4,5-trifluorophenoxy)methyl]-3,5-difluoro-4'-(4-propylcyclohexyl)-1,1'-biphenyl, which is a four-ring compound having a $CF_2O$ bonding group described in WO 1996/11897 A1, was synthesized.

(S-6)

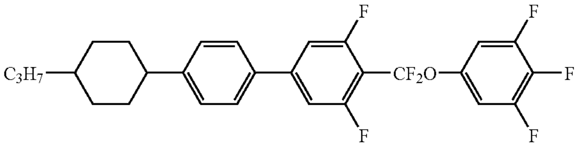

Chemical shift δ (ppm) of $^1$H-NMR analysis was as follows and the compound obtained was identified as 4-[difluoro(3,4,5-trifluorophenoxy)methyl]-3,5-difluoro-4'-(4-propylcyclohexyl)-1,1'-biphenyl.

Chemical shift δ (ppm; $CDCl_3$); 7.49 (d, J=8.23 Hz, 2H), 7.32 (d, J=8.23 Hz, 2H), 7.20 (d, J=10.6 Hz, 2H), 7.03-6.90 (m, 2H), 2.53 (tt, J=12.1 Hz, J=3.00 Hz, 1H), 1.97-1.86 (m, 4H), 1.51-1.40 (m, 2H), 1.40-1.18 (m, 4H), 1.13-1.01 (m, 2H), 0.91 (t, J=7.20 Hz, 3H).

The phase transition temperature of the comparative compound (S-6) obtained was as follows.

Phase transition temperature: C 82.1 N 141 I.

The composition H consisting of 85% by weight of the mother liquid crystals A and 15% by weight of the comparative compound (S-6) was prepared. Physical properties of the composition H obtained were measured and the values of physical properties on the comparative compound (S-6) were calculated by extrapolating the measured values. The results were as follows.

Maximum temperature ($T_{NI}$)=110° C.; dielectric anisotropy ($\Delta\epsilon$)=23.4; optical anisotropy ($\Delta n$)=0.157.

The comparative compound (S-6) was compared with the compounds (1-4-59), (1-4-199), (1-4-66), (1-3-171), and (1-2-8) of the invention shown in Example. First, comparison of phase transition temperatures shows that the compounds (1-4-59), (1-4-199), (1-4-66), (1-3-171), and (1-2-8) have a wider temperature range of liquid crystal phases.

Next, comparison of maximum temperatures (extrapolated values) of the comparative compound (S-6) and the compound of the invention shows that the compounds (1-4-59), (1-4-199), (1-4-66), (1-3-171), and (1-2-8) have a higher clearing point. Therefore, it is concluded that the compounds (1-4-59), (1-4-199), (1-4-66), (1-3-171), and (1-2-8) are usable in a wider temperature range and excellent.

Comparative Example 3

Furthermore, a phase transition temperature of 4-[difluoro(3,4,5-trifluorophenoxy)methyl]-3,5-difluoro-4'-(4-propylcyclohexyl)-1,1'-biphenyl (S-4), which is a five-ring compound including a tetrahydropyran ring and a dioxane ring described in WO 2006/12551 A1, is compared with.

(S-4)

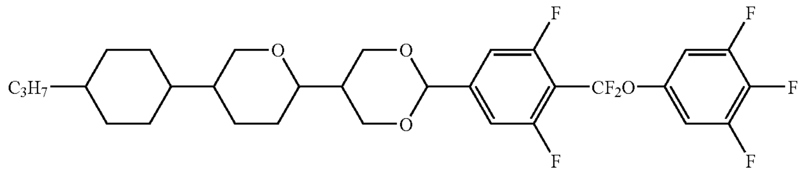

The phase transition temperature of the compound (S-4) described in WO2006/12551 A1 was as follows.

Phase transition temperature: C 95 N 251 I.

Comparison of the phase transition temperature of the comparative compound (S-4) and the compounds (1-4-59), (1-4-199), (1-4-66), (1-3-171), and (1-2-8) of the invention shown in Example shows that the compounds (1-4-59), (1-4-199), (1-4-66), (1-3-171), and (1-2-8) have a lower minimum temperature and a high maximum temperature. Therefore, it is concluded that the compounds (1-4-59), (1-4-199), (1-4-66), (1-3-171), and (1-2-8) are usable in a wider temperature range and excellent.

Example 12

Furthermore, representative compositions of the invention were summarized in [Composition Example 1] to [Composition Example 16]. First, compounds as components of a composition and their amounts (% by weight) were shown. The compounds were represented by means of symbols of left-terminal groups, bonding groups, rings, and right-terminal groups according to the definition in Table 1. The configuration of 1,4-cyclohexylene and 1,3-dioxane-2,5-diyl is trans. In case of no symbols of terminal groups are shown, the terminal groups means hydrogen. Numbers described after the names of the compounds represented by the symbols correspond to the compounds of the invention. Next, physical properties (measured values) were described.

TABLE 1

| Method of Description of Compounds using Symbols | |
|---|---|
| $R—(A_1)—Z_1— \ldots —A_n—(A_n)—R'$ | |
| 1) Left Terminal Groups R— | Symbols |
| $C_nH_{2n+1}$— | n— |
| $C_nH_{2n+1}O$— | nO— |
| $C_nH_{2n+1}OC_mH_{2m}$— | nOm— |
| $CH_2$═CH— | V— |
| $CH_2$═$CHC_nH_{2n}$— | Vn— |
| $C_nH_{2n+1}CH$═CH— | nV— |
| $C_nH_{2n+1}CH$═$CHC_mH_{2m}$— | nVm— |
| $CF_2$═CH— | VFF— |
| $CF_2$═$CHC_nH_{2n}$— | VFFn— |
| 2) Rings —An— | Symbols |
| 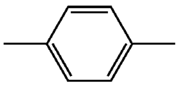 | B |
| 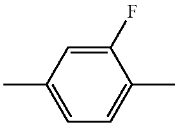 | B(F) |
| 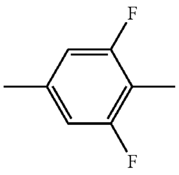 | B(F,F) |
| 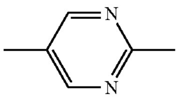 | Py |
| 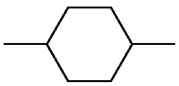 | H |

TABLE 1-continued

| Method of Description of Compounds using Symbols | |
|---|---|
| R—($A_1$)—$Z_1$— . . . —$A_n$—($A_n$)—R' | |
| 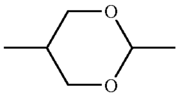 | G |
| 3) Bonding Groups —$Z_n$— | Symbols |
| —$C_2H_4$— | 2 |
| —$C_4H_8$— | 4 |
| —CH═CH— | V |
| —$CF_2$0— | X |
| —COO— | E |
| —C≡C— | T |
| 4) Right Terminal Groups —R' | Symbols |
| —$C_nH_{2n+1}$ | —n |
| —$OC_nH_{2n+1}$ | —On |
| —CH═$CH_2$ | —V |
| —CH═$CHC_nH_{2n+1}$ | —Vn |
| —$C_nH_{2n}CH$═$CH_2$ | —nV |
| —$C_nH_{2n}CH$═$CHC_mH_{2m+1}$ | —nVm |
| —CH═$CF_2$ | —VFF |
| —$COOCH_3$ | —EMe |
| —F | —F |
| —Cl | —CL |
| —CN | —C |
| —$OCF_2H$ | —OCF2H |
| —$OCF_3$ | —OCF3 |
| —$CF_3$ | —CF3 |
| 5) Examples of Descrption | |
| Example 1. 5-HHB(F)HXB(F,F)-F | |
| 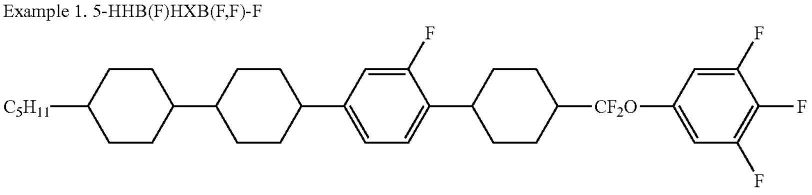 | |
| Example 2. 5-HBB(F)B-3 | |
| 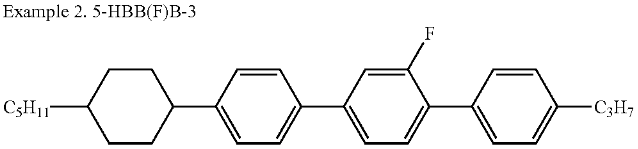 | |
| Example 3. 5-HH-V | |
| 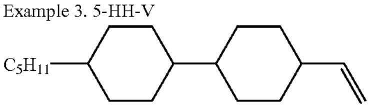 | |

Measurement of physical properties was carried out according to the following methods. Most methods are described in the Standard of Electric Industries Association of Japan, EIAJ·ED-2521 A or those with some modifications. No TFT was attached to a TN device used for measurement.

Maximum Temperature of a Nematic Phase (NI; ° C.): A sample was placed on a hot plate in a melting point measurement apparatus equipped with a polarizing microscope and was heated at the rate of 1° C. per minute. A temperature was measured when a part of the sample began to change from a nematic phase into an isotropic liquid. A maximum temperature of a nematic phase may be abbreviated to "a maximum temperature".

Minimum Temperature of a Nematic Phase ($T_c$; ° C.): A sample having a nematic phase was kept in a freezer at temperatures of 0° C., −10° C., −20° C., −30° C., and −40° C. for ten days, and liquid crystal phases was observed. For example, when the sample still remained in a nematic phase at −20° C. and changed to crystals (or a smectic phase) at −30° C., $T_c$ was expressed as ≦−20° C. A minimum temperature of a nematic phase may be abbreviated to "a minimum temperature".

Viscosity (η; measured at 20° C., mPa·s): Viscosity was measured by means of an E-type viscometer.

Rotational Viscosity (γ1; measured at 25° C.; mPa·s): Two methods were used depending on the kinds of samples.

1) Sample having a positive dielectric anisotropy: Rotational viscosity was measured according to the method disclosed in M. Imai, et al., Molecular Crystals and Liquid Crystals, vol. 259, p. 37 (1995). A sample was put in a TN device in which a twist angle was 0 degrees and a cell gap between two glass plates was 5 micrometers. The TN device was impressed with a voltage in the range of from 16 V to 19.5 V stepwise by 0.5 V. After a period of 0.2 second with no impress of voltage, voltage impress was repeated with only one rectangular wave (rectangular pulse of 0.2 second) and application of no voltage (2 seconds). A peak current and a peak time of a transient current generated by the voltage impress were measured. Rotational viscosity was obtained from the measured values and the calculating equation (8) in the literature by M. Imai, et al., p. 40. The dielectric anisotropy necessary for the calculation was obtained with the TN device used for measuring this rotational viscosity by means of the method described below.

2) Sample having a negative dielectric anisotropy: Rotational viscosity was measured according to the method described in M. Imai, et al., Molecular Crystals and Liquid Crystals, vol. 259, 37 (1995). A sample was put in a VA device in which a cell gap between two glass plates was 20 micrometers. The VA device was impressed with a voltage in the range of from 30 V to 50 V stepwise by 1 V. After a period of 0.2 second with no impress of voltage, voltage impress was repeated with only one rectangular wave (rectangular pulse of 0.2 second) and application of no voltage (2 seconds). A peak current and a peak time of a transient current generated by the voltage impress were measured. The value of the rotational viscosity was obtained from the measured values and the calculating equation (8) in the literature by M. Imai, et al., p. 40. The value of dielectric anisotropy necessary for the calculation was obtained by means of the method described below.

Optical Anisotropy (Δn; measured at 25° C.): Measurement was carried out with an Abbe refractometer equipped with a polarizing plate on an ocular using light of a wavelength of 589 nanometers. The surface of a main prism was rubbed in one direction, and then a sample was dropped on the main prism. Refractive index (n∥) was measured when the direction of polarized light was parallel to that of the rubbing. Refractive index (n⊥) was measured when the direction of polarized light was perpendicular to that of the rubbing. The value of the optical anisotropy was calculated from the equation: $\Delta n = n\| - n\perp$.

Dielectric Anisotropy (Δ∈; measured at 25° C.) was measured with two methods depending of samples.

1) Sample having a positive dielectric anisotropy: A sample was put in a TN device having a distance between two glass substrates (cell gap) of 9 μm and a twist angle of 80 degrees. A voltage of 20 V was impressed onto the device, and a dielectric constant (∈∥) in a major axis direction of liquid crystal molecules was measured. A voltage of 0.5 V was impressed onto the device, and a dielectric constant (∈⊥) in a minor axis direction of liquid crystal molecules was measured. The value of the dielectric anisotropy was calculated from the equation: $\Delta\in = \in\| - \in\perp$.

2) Sample having a negative dielectric anisotropy: A sample was put in a device treated to a homeotropic orientation and a voltage of 0.5 V was impressed, and a dielectric constant (∈∥) was measured. The sample was put in a device treated to a homogeneous orientation and a voltage of 0.5 V was impressed, and a dielectric constant (∈⊥) was measured. The value of the dielectric anisotropy was calculated from the equation: $\Delta\in = \in\| - \in\perp$.

Threshold Voltage (Vth; measured at 25° C.; V) was measured with two methods depending of samples.

1) Sample having a positive dielectric anisotropy: A sample was put in a TN device of a normally white mode, in which a cell gap between two glass plates was (0.5/Δn) micrometers, and a twist angle was 80 degrees. Δn (optical anisotropy) is a value measured according to the method described above. The TN device was impressed with rectangular waves having a frequency of 32 Hz. The voltage of the rectangular waves was increased, and the value of voltage was measured when transmittance of light through the device became 90%.

2) Sample having a negative dielectric anisotropy: A sample was put in a VA device of a normally black mode treated to a homeotropic orientation, in which a cell gap between two glass plates was 9 micrometers, and a twist angle was 80 degrees. The VA device was impressed with rectangular waves having a frequency of 32 Hz. The voltage of the rectangular waves was increased, and the value of voltage was measured when transmittance of light through the device became 10%.

Voltage Holding Ratio (VHR; measured at 25° C.; %): A TN device used for measurement has a polyimide-alignment film and the cell gap between two glass plates is 6 micrometers. A sample was put in the device, and then the device was sealed with an adhesive which was polymerizable by irradiating an ultraviolet light. The TN device was impressed and charged with pulse voltage (60 microseconds at 5 V). Decreasing voltage was measured for 16.7 milliseconds with a High Speed Voltmeter and the area A between a voltage curve and a horizontal axis in a unit cycle was obtained. The area B was an area without decreasing. The voltage holding ratio was a percentage of the area A to the area B.

Helical pitch (measured at 20° C.; micrometer): A Cano's wedge cell method was used for the measurement of a helical pitch. A sample was put to a Cano's wedge cell and a distance (a; micrometer) between disclination lines was measured on the cell. A helical pitch (P) was calculated from the equation: $P = 2 \times a \times \tan\theta$. The symbol of theta (θ) is an angle between two glass plates of the wedge cell.

The ratio of the amount (percentage) of components is a percentage by weight (% by weight) based on the total weight of the components.

Composition Example 1

| | | |
|---|---|---|
| 5-HHB(F)HXB(F,F)-F | (1-4-59) | 10% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 12% |
| 3-HB-O2 | (11-5) | 10% |
| 3-HH-4 | (11-1) | 3% |
| 3-HHB-F | (3-1) | 3% |
| 3-HHB-1 | (12-1) | 4% |
| 3-HHB-O1 | (12-1) | 4% |
| 3-HBEB-F | (3-37) | 4% |
| 3-HHEB-F | (3-10) | 6% |
| 5-HHEB-F | (3-10) | 6% |
| 3-H2BTB-2 | (12-16) | 4% |
| 3-H2BTB-3 | (12-16) | 4% |
| 3-H2BTB-4 | (12-16) | 4% |
| 3-HB(F)TB-2 | (12-17) | 5% |

NI = 98.4° C.;
Δn = 0.127;
Δϵ = 26.0;
Vth = 1.09 V.

Composition Example 2

| | | |
|---|---|---|
| 5-GHB(F)HXB(F,F)-F | (1-4-199) | 10% |
| 2-HB-C | (5-1) | 5% |
| 3-HB-C | (5-1) | 10% |
| 3-HB-O2 | (11-5) | 15% |
| 2-BTB-1 | (11-10) | 3% |
| 3-HHB-F | (3-1) | 4% |
| 3-HHB-1 | (12-1) | 8% |
| 3-HHB-O1 | (12-1) | 5% |
| 3-HHB-3 | (12-1) | 6% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

NI = 106.1° C.;
Δn = 0.100;
Δε = 9.0;
Vth = 1.87 V.

Composition Example 3

| | | |
|---|---|---|
| 5-HB(F)HXB(F)B(F,F)-F | (1-3-171) | 10% |
| 3-BEB(F)-C | (5-14) | 8% |
| 3-HB-C | (5-1) | 8% |
| V-HB-C | (5-1) | 8% |
| 1V-HB-C | (5-1) | 8% |
| 3-HB-O2 | (11-5) | 3% |
| 3-HH-2V | (11-1) | 11% |
| 3-HH-2V1 | (11-1) | 7% |
| V2-HHB-1 | (12-1) | 8% |
| 3-HHB-1 | (12-1) | 5% |
| 3-HHEB-F | (3-10) | 7% |
| 3-H2BTB-2 | (12-16) | 6% |
| 3-H2BTB-3 | (12-16) | 6% |
| 3-H2BTB-4 | (12-16) | 5% |

NI = 93.1° C.;
Δn = 0.128;
Δε = 12.2;
Vth = 1.02 V.

Composition Example 4

| | | |
|---|---|---|
| 5-GHB(F)HXB(F,F)-F | (1-4-199) | 6% |
| 5-HHB(F)HXB(F)-OCF3 | (1-4-66) | 6% |
| 5-BEB(F)-C | (5-14) | 5% |
| V-HB-C | (5-1) | 11% |
| 5-PyB-C | (5-9) | 6% |
| 4-BB-3 | (11-8) | 11% |
| 3-HH-2V | (11-1) | 10% |
| 5-HH-V | (11-1) | 11% |
| V-HHB-1 | (12-1) | 7% |
| V2-HHB-1 | (12-1) | 9% |
| 3-HHB-1 | (12-1) | 9% |
| 1V2-HBB-2 | (12-4) | 4% |
| 3-HHEBH-3 | (13-6) | 5% |

Composition Example 5

| | | |
|---|---|---|
| 5-HHB(F)HXB(F,F)-F | (1-4-59) | 4% |
| 5-HHHXB(F)B(F,F)-F | (1-3-3) | 4% |
| 1V2-BEB(F,F)-C | (5-15) | 6% |
| 3-HB-C | (5-1) | 18% |
| 2-BTB-1 | (11-10) | 10% |
| 5-HH-VFF | (11-1) | 22% |
| 3-HHB-1 | (12-1) | 4% |
| VFF-HHB-1 | (12-1) | 8% |
| VFF2-HHB-1 | (12-1) | 11% |
| 3-H2BTB-2 | (12-16) | 5% |
| 3-H2BTB-3 | (12-16) | 4% |
| 3-H2BTB-4 | (12-16) | 4% |

Composition Example 6

| | | |
|---|---|---|
| 5-GHB(F)HXB(F,F)-F | (1-4-199) | 3% |
| 5-GHXBB(F)B(F,F)-F | (1-2-8) | 3% |
| 5-HB(F)HXB(F)B(F,F)-F | (1-3-171) | 3% |
| 5-HB-CL | (2-2) | 19% |
| 3-HH-4 | (11-1) | 12% |
| 3-HH-5 | (11-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 6% |
| 4-HHB(F)-F | (3-2) | 6% |
| 7-HHB(F)-F | (3-2) | 6% |
| 5-HBB(F)-F | (3-23) | 4% |
| 1O1-HBBH-5 | (13-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

Composition Example 7

| | | |
|---|---|---|
| 5-HB(F)HXB(F)B(F,F)-F | (1-3-171) | 5% |
| 5-HHHXB(F)B(F,F)-F | (1-3-3) | 5% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 21% |
| 5-HBB(F,F)-F | (3-24) | 15% |
| 3-H2BB(F,F)-F | (3-27) | 5% |
| 5-HHBB(F,F)-F | (4-6) | 3% |
| 5-HHEBB-F | (4-13) | 3% |
| 3-HH2BB(F,F)-F | (4-15) | 2% |
| 1O1-HBBH-4 | (13-1) | 4% |
| 1O1-HBBH-5 | (13-1) | 4% |

Composition Example 8

| | | |
|---|---|---|
| 5-GHB(F)HXB(F)-OCF3 | (1-4-208) | 10% |
| 5-HB-F | (2-2) | 12% |
| 6-HB-F | (2-2) | 9% |
| 7-HB-F | (2-2) | 7% |

-continued

| | | |
|---|---|---|
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-4) | 5% |
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 5% |
| 5-HBB(F)-F | (3-23) | 5% |
| 5-HBBH-3 | (13-1) | 3% |
| 3-HB(F)BH-3 | (13-2) | 3% |

Composition Example 9

| | | |
|---|---|---|
| 5-GHB(F)HXB(F,F)-F | (1-4-199) | 8% |
| 5-HB-CL | (5-1) | 11% |
| 3-HH-4 | (11-1) | 8% |
| 3-HHB-1 | (12-1) | 5% |
| 3-HHB(F,F)-F | (3-3) | 8% |
| 3-HBB(F,F)-F | (3-24) | 20% |
| 5-HBB(F,F)-F | (3-24) | 7% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

Composition Example 10

| | | |
|---|---|---|
| 5-HHB(F)HXB(F,F)-F | (1-4-59) | 10% |
| 3-HB-CL | (2-2) | 6% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 15% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 7% |
| 2-H2BB(F)-F | (3-26) | 2% |
| 3-H2BB(F)-F | (3-26) | 3% |
| 3-HBEB(F,F)-F | (3-39) | 5% |

Composition Example 11

| | | |
|---|---|---|
| 5-GHB(F)HXB(F,F)-F | (1-4-199) | 15% |
| 5-HB-CL | (2-2) | 17% |
| 7-HB(F,F)-F | (2-4) | 3% |
| 3-HH-4 | (11-1) | 10% |
| 3-HH-5 | (11-1) | 5% |
| 3-HB-O2 | (11-5) | 4% |
| 3-HHB-1 | (12-1) | 5% |
| 3-HHB-O1 | (12-1) | 4% |
| 2-HHB(F)-F | (3-2) | 4% |
| 3-HHB(F)-F | (3-2) | 3% |

-continued

| | | |
|---|---|---|
| 5-HHB(F)-F | (3-2) | 3% |
| 3-HHB(F,F)-F | (3-3) | 6% |
| 3-H2HB(F,F)-F | (3-15) | 5% |
| 4-H2HB(F,F)-F | (3-15) | 5% |

NI = 79.3° C.;
Δn = 0.092;
Δε = 6.1;
Vth = 1.56 V.

Composition Example 12

| | | |
|---|---|---|
| 5-HHB(F)HXB(F,F)-F | (1-4-59) | 4% |
| 5-HHB(F)HXB(F)-OCF3 | (1-4-66) | 4% |
| 5-HB(F)HXB(F)B(F,F)-F | (1-3-171) | 4% |
| 5-HB-CL | (2-2) | 3% |
| 7-HB(F)-F | (2-3) | 7% |
| 3-HH-4 | (11-1) | 9% |
| 3-HH-EMe | (11-2) | 23% |
| 3-HHEB-F | (3-10) | 6% |
| 5-HHEB-F | (3-10) | 6% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 2% |
| 3-H2GB(F,F)-F | (3-106) | 3% |
| 5-GHB(F,F)-F | (3-109) | 3% |

Composition Example 13

| | | |
|---|---|---|
| 5-GHB(F)HXB(F,F)-F | (1-4-199) | 3% |
| 5-HGB(F)HXB(F,F)-F | (1-4-269) | 4% |
| 5-GHB(F)HXB(F)-OCF3 | (1-4-208) | 3% |
| 3-HH-4 | (11-1) | 8% |
| 3-HHB-1 | (12-1) | 6% |
| 3-HHB(F,F)-F | (3-3) | 10% |
| 3-H2HB(F,F)-F | (3-15) | 9% |
| 3-HBB(F,F)-F | (3-24) | 15% |
| 3-BB(F,F)XB(F,F)-F | (3-97) | 25% |
| 1O1-HBBH-5 | (13-1) | 7% |
| 2-HHBB(F,F)-F | (4-6) | 3% |
| 3-HHBB(F,F)-F | (4-6) | 3% |
| 3-HH2BB(F,F)-F | (4-15) | 4% |

NI = 97.6° C.;
Δn = 0.080;
Δε = 6.4;
Vth = 1.30 V.

Composition Example 14

| | | |
|---|---|---|
| 5-HHB(F)HXB(F,F)-F | (1-4-59) | 4% |
| 5-HHHXB(F)B(F,F)-F | (1-3-3) | 4% |
| 5-GHB(F)HXB(F)-OCF3 | (1-4-208) | 4% |
| 5-HB-CL | (2-2) | 13% |
| 3-HB-O2 | (11-5) | 10% |
| 3-PyB(F)-F | (2-15) | 10% |
| 5-PyB(F)-F | (2-15) | 10% |
| 3-HBB(F,F)-F | (3-24) | 7% |
| 3-PyBB-F | (3-80) | 6% |
| 4-PyBB-F | (3-80) | 6% |

-continued

| | | |
|---|---|---|
| 5-PyBB-F | (3-80) | 6% |
| 5-HBB(F)B-2 | (13-5) | 10% |
| 5-HBB(F)B-3 | (13-5) | 10% |

Composition Example 15

| | | |
|---|---|---|
| 5-HHB(F)HXB(F,F)-F | (1-4-59) | 10% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 12% |
| 3-HB-O2 | (11-5) | 10% |
| 3-HH-4 | (11-1) | 3% |
| 3-HHB-F | (3-1) | 3% |
| 3-HHB-1 | (12-1) | 4% |
| 3-HHB-O1 | (12-1) | 4% |
| 3-HBEB-F | (3-37) | 4% |
| 3-HHEB-F | (3-10) | 6% |
| 5-HHEB-F | (3-10) | 6% |
| 3-H2BTB-2 | (12-16) | 4% |
| 3-H2BTB-3 | (12-16) | 4% |
| 3-H2BTB-4 | (12-16) | 4% |
| 3-HB(F)TB-2 | (12-17) | 5% |

NI = 105.1° C.;
Δn = 0.133;
Δε = 24.6;
Vth = 1.22 V.

Composition Example 16

| | | |
|---|---|---|
| 5-GHB(F)HXB(F,F)-F | (1-4-199) | 10% |
| 2-BEB(F)-C | (5-14) | 5% |
| 3-BEB(F)-C | (5-14) | 4% |
| 4-BEB(F)-C | (5-14) | 12% |
| 1V2-BEB(F,F)-C | (5-15) | 12% |
| 3-HB-O2 | (11-5) | 10% |
| 3-HH-4 | (11-1) | 3% |
| 3-HHB-F | (3-1) | 3% |
| 3-HHB-1 | (12-1) | 4% |
| 3-HHB-O1 | (12-1) | 4% |
| 3-HBEB-F | (3-37) | 4% |
| 3-HHEB-F | (3-10) | 6% |
| 5-HHEB-F | (3-10) | 6% |
| 3-H2BTB-2 | (12-16) | 4% |

-continued

| | | |
|---|---|---|
| 3-H2BTB-3 | (12-16) | 4% |
| 3-H2BTB-4 | (12-16) | 4% |
| 3-HB(F)TB-2 | (12-17) | 5% |

NI = 98.8° C.;
Δn = 0.139;
Δε = 24.3;
Vth = 1.25 V.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A compound represented by formula (1):

(1)

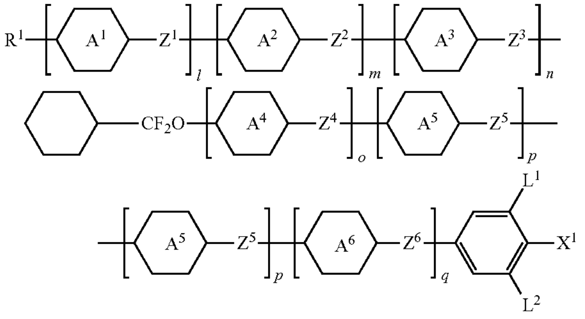

wherein $R^1$ is alkyl having 1 to 15 carbons, alkenyl having 2 to 15 carbons, alkoxy having 1 to 15 carbons, or alkenyloxy having 2 to 15 carbons; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by halogen; $Z^1$, $Z^2$, $Z^3$, $Z^4$, $Z^5$, and $Z^6$ are each independently a single bond, $—CH_2CH_2—$, $—CH{=}CH—$, $—C{\equiv}C—$, $—COO—$, $—CF_2O—$, $—CH_2O—$, or $—OCH_2—$; $L^1$ and $L^2$ are each independently hydrogen or fluorine; $X^1$ is fluorine, chlorine, $—C{\equiv}N$, $—CF_3$, $—CHF_2$, $—CH_2F$, $—OCF_3$, $—OCHF_2$ or $—OCH_2F$; and l, m, n, o, p, and q are each independently 0 or 1, and l+m+n+o+p+q is 3.

2. The compound according to claim 1, which is represented by any one of formulas (1-1) to (1-4):

(1-1)

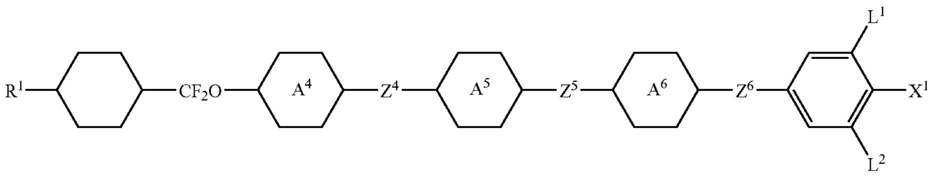

(1-2)

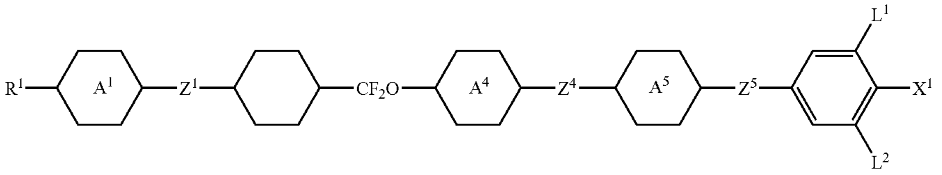

-continued (1-3)

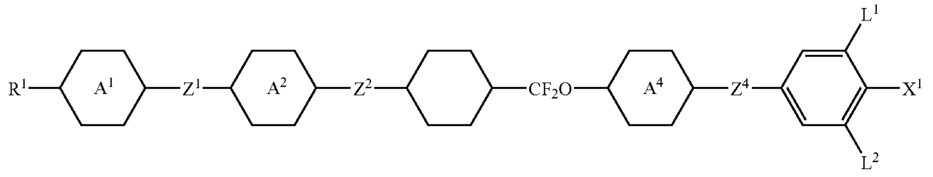

(1-4)

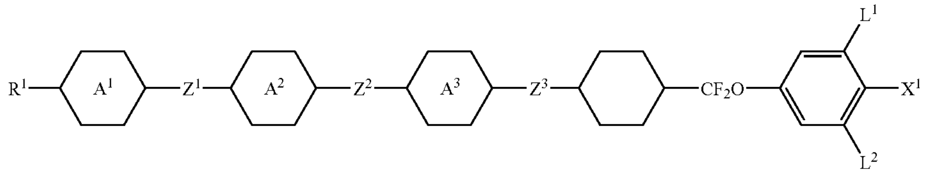

wherein $R^1$ is alkyl having 1 to 15 carbons, alkenyl having 2 to 15 carbons, alkoxy having 1 to 15 carbons, or alkenyloxy having 2 to 15 carbons; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by fluorine; $Z^1$, $Z^2$, $Z^3$, $Z^4$, $Z^5$, and $Z^6$ are each independently a single bond, $-CH_2CH_2-$, $-CH{=}CH-$, $-C{\equiv}C-$, $-COO-$, $-CF_2O-$, $-CH_2O-$, or $-OCH_2-$; $L^1$ and $L^2$ are each independently hydrogen or fluorine; $X^1$ is fluorine, chlorine, $-C{\equiv}N$, $-CF_3$, $-CHF_2$, $-CH_2F$, $-OCF_3$, $-OCHF_2$, or $-OCH_2F$.

3. The compound according to claim 1, which is represented by any one of formulas (1-5) to (1-8):

(1-5)

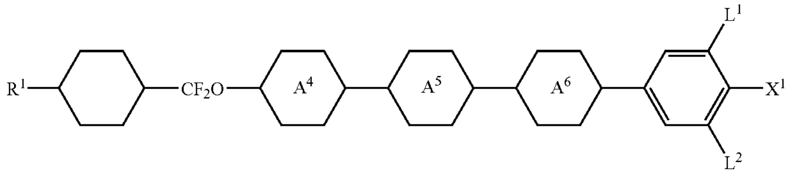

(1-6)

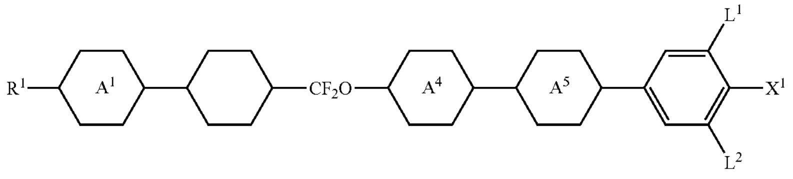

(1-7)

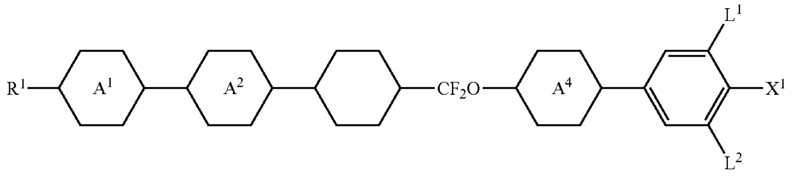

(1-8)

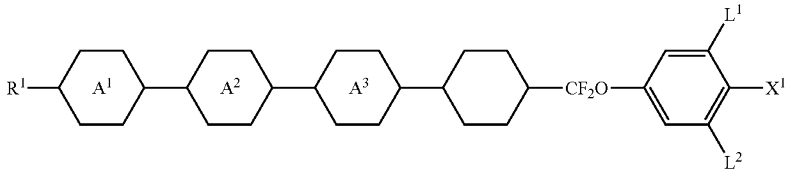

wherein $R^1$ is alkyl having 1 to 15 carbons or alkenyl having 2 to 15 carbons; ring $A^1$, ring $A^2$, ring $A^3$, ring $A^4$, ring $A^5$, and ring $A^6$ are each independently 1,4-cyclohexylene, 1,3-dioxane-2,5-diyl, 1,4-phenylene, or 1,4-phenylene in which arbitrary hydrogen is replaced by fluorine; $L^1$ and $L^2$ are each independently hydrogen or fluorine; and $X^1$ is fluorine, chlorine, $—C{\equiv}N$, $—CF_3$, $—CHF_2$, $—CH_2F$, $—OCF_3$, $—OCHF_2$, or $—OCH_2F$.

4. The compound according to claim 1, which is represented by any one of formulas (1-9) to (1-19):

(1-9)

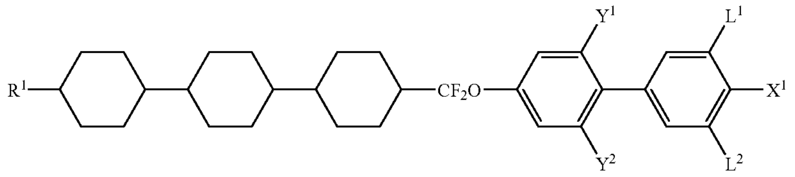

(1-10)

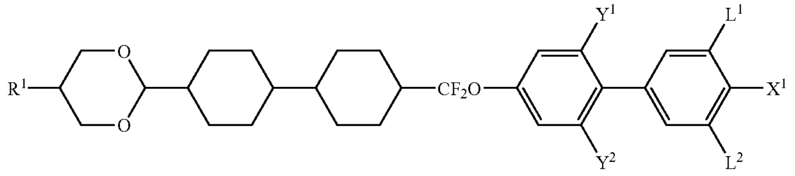

(1-11)

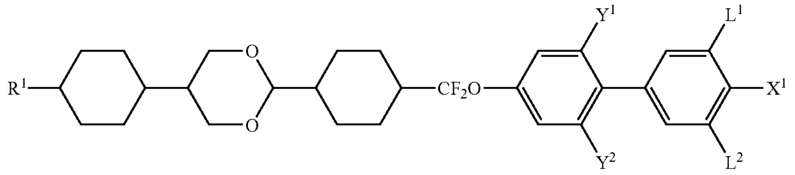

(1-12)

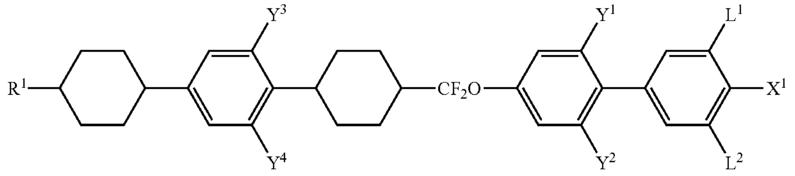

(1-13)

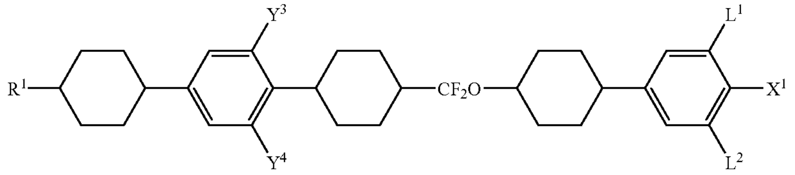

(1-14)

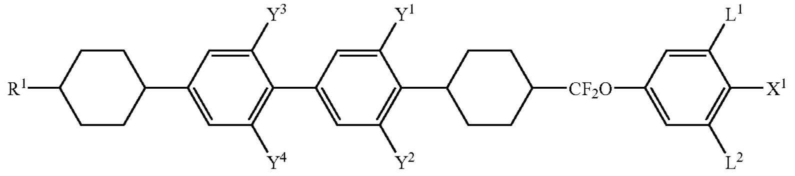

(1-15)

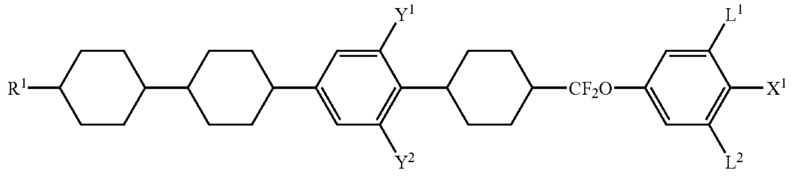

(1-16)

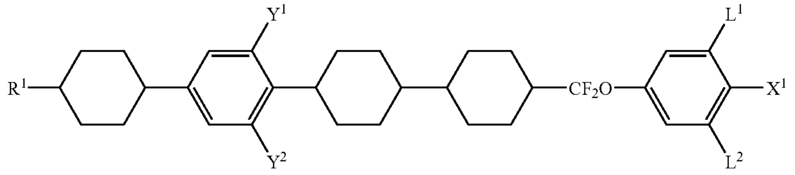

-continued
(1-18)
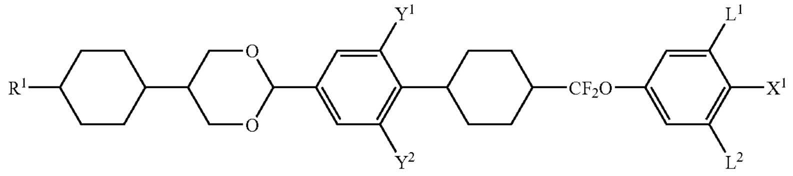
(1-19)
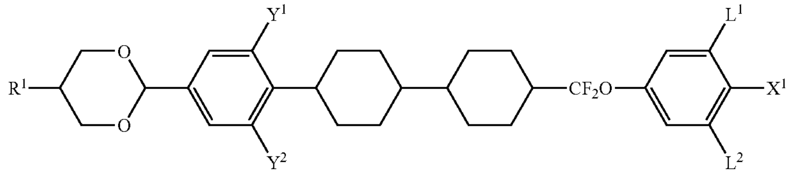
wherein $R^1$ is alkyl having 1 to 15 carbons; $L^1$, $L^2$, $Y^1$, $Y^2$, $Y^3$, and $Y^4$ are each independently hydrogen or fluorine; and $X^1$ is fluorine or —$OCF_3$.
5. The compound according to claim 1, which is represented by any one of formulas (1-20) to (1-41):
(1-20)
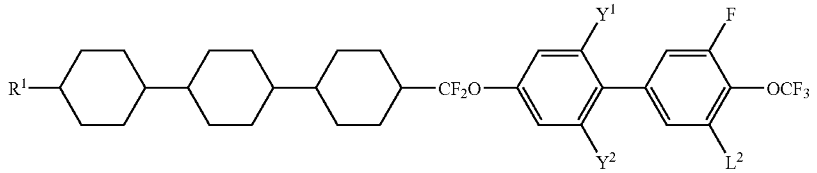
(1-21)
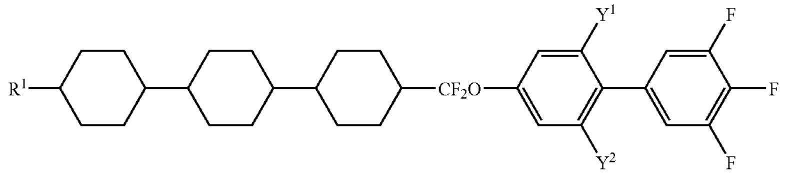
(1-22)
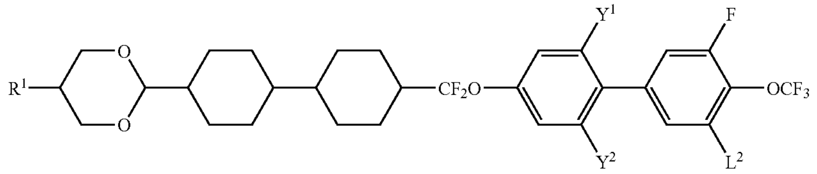
(1-23)
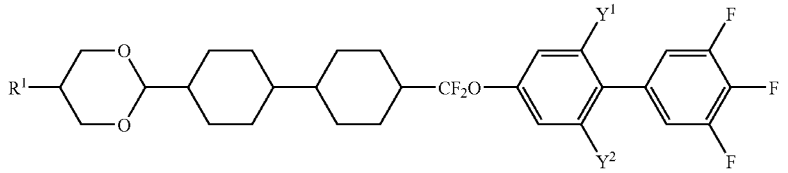
(1-24)
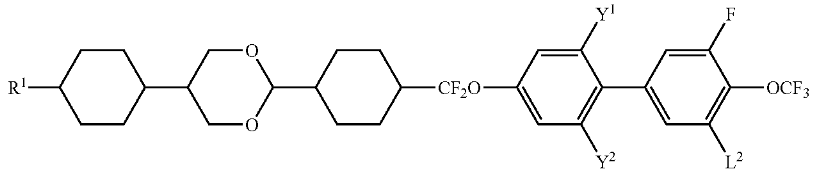

-continued
(1-25)
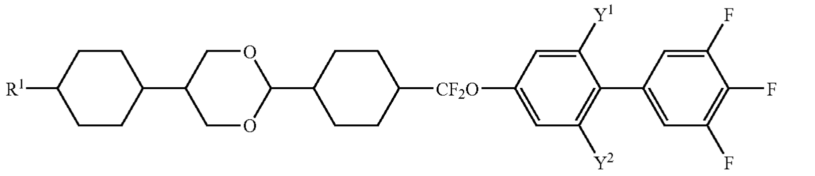
(1-26)
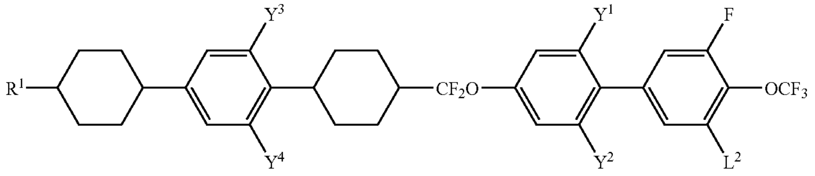
(1-27)
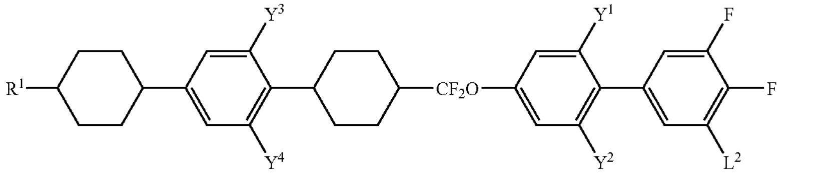
(1-28)
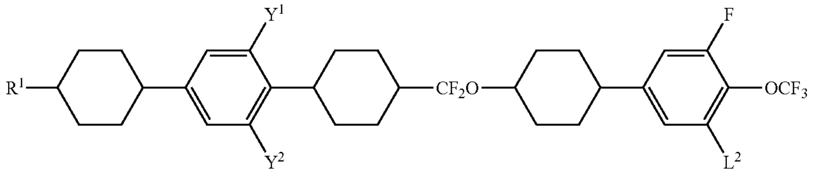
(1-29)
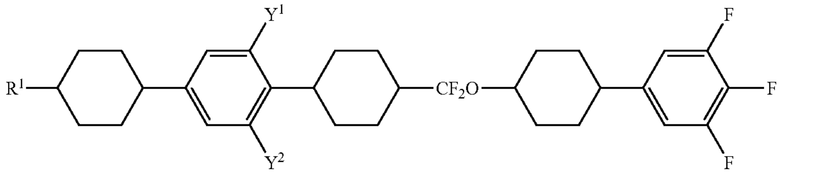
(1-30)
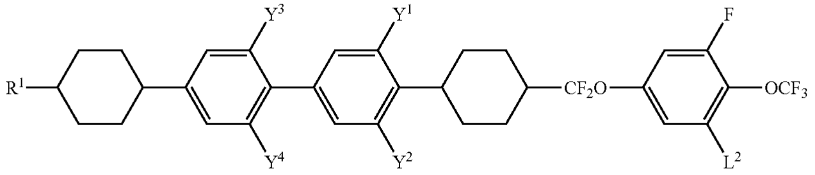
(1-31)
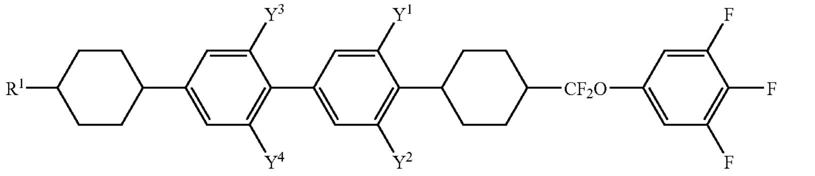
(1-32)
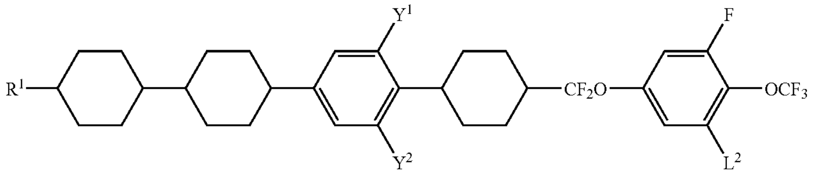

-continued
(1-33)
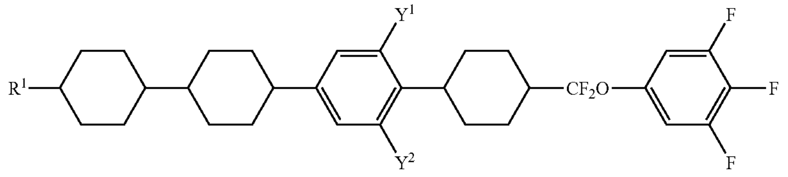
(1-34)
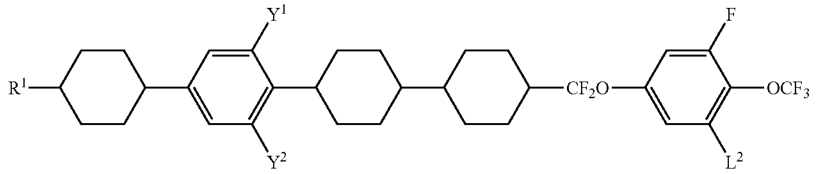
(1-35)
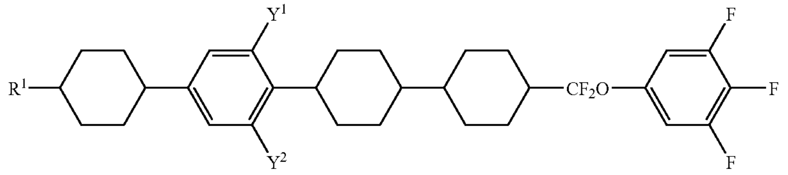
(1-36)
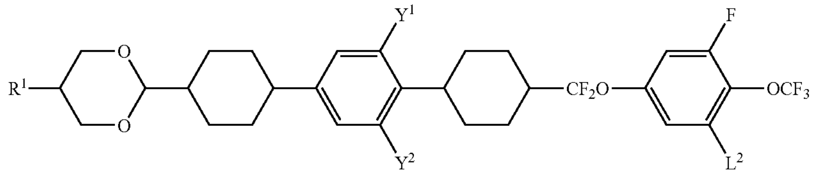
(1-37)
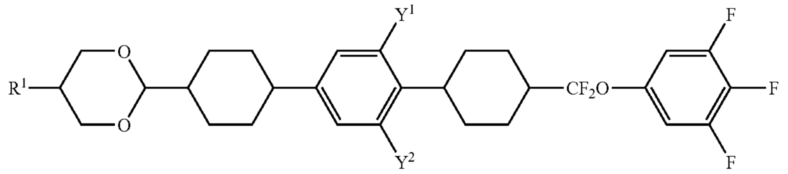
(1-38)
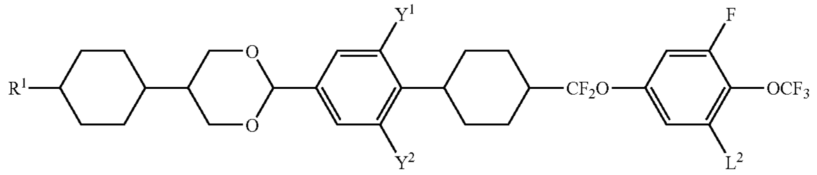
(1-39)
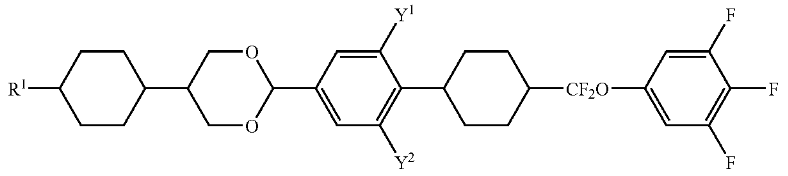
(1-40)
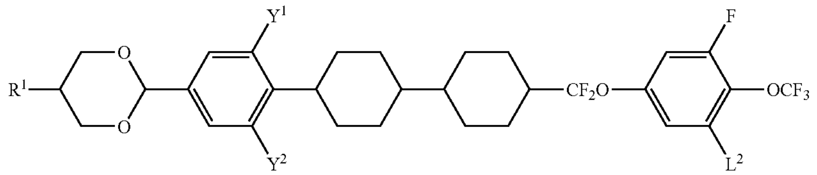

-continued (1-41)

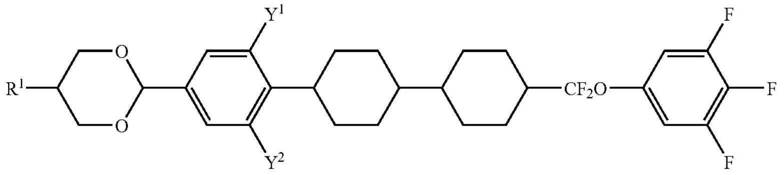

wherein $R^1$ is alkyl having 1 to 15 carbons; $L^2$, $Y^1$, $Y^2$, $Y^3$, and $Y^4$ are each independently hydrogen or fluorine.

6. A liquid crystal composition comprising a first component and a second component, wherein the first component is at least one compound according to claim 1.

7. The liquid crystal composition according to claim 6, comprising at least one compound selected from the group consisting of compounds represented by formulas (2), (3), and (4) as the second component:

(2)

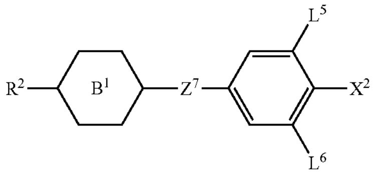

(3)

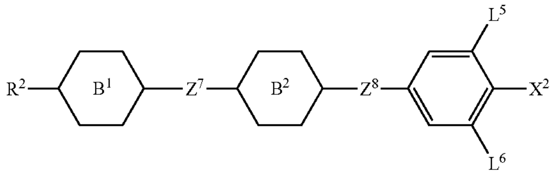

(4)

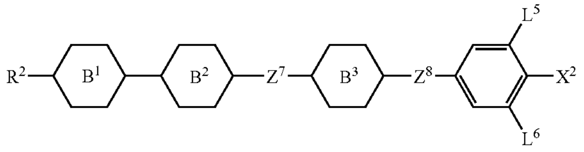

wherein $R^2$ is alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; $X^2$ is fluorine, chlorine, $—OCF_3$, $—OCHF_2$, $—CF_3$, $—CHF_2$, $—CH_2F$, $—OCF_2CHF_2$, or $—OCF_2CHFCF_3$; ring $B^1$, ring $B^2$ and ring $B^3$ are each independently 1,4-cyclohexylene, 1,3-dioxane-2,5-diyl, pyrimidine-2,5-diyl, tetrahydropyrane-2,5-diyl, 1,4-phenylene, or 1,4-phenylene in which arbitrary hydrogen is replaced by fluorine; $Z^7$ and $Z^8$ are each independently $—(CH_2)_2—$, $—(CH_2)_4—$, —COO—, $—CF_2O—$, $—OCF_2—$, —CH═CH—, —C≡C—, $—CH_2O—$, or a single bond; and $L^5$ and $L^6$ are each independently hydrogen or fluorine.

8. The liquid crystal composition according to claim 6, comprising at least one compound selected from the group of compounds represented by formula (5) as the second component:

(5)

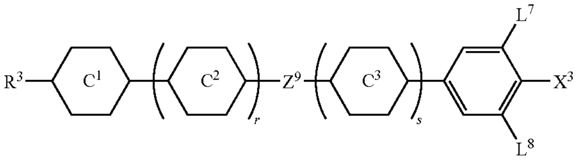

wherein $R^3$ is alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; $X^3$ is —C≡N or —C≡C—C≡N; ring $C^1$, ring $C^2$, and ring $C^3$ are each independently 1,4-cyclohexylene, 1,4-phenylene, 1,4-phenylene in which arbitrary hydrogen is replaced by fluorine, 1,3-dioxane-2,5-diyl, tetrahydropyrane-2,5-diyl, or pyrimidine-2,5-diyl; $Z^9$ is $—(CH_2)_2—$, —COO—, $—CF_2O—$, $—OCF_2—$, —C≡C—, $—CH_2O—$, or a single bond; $L^7$ and $L^8$ are each independently hydrogen or fluorine; and r and s are each independently 0 or 1.

9. The liquid crystal composition according to claim 6, comprising at least one compound selected from the group of compounds represented by formulas (6), (7), (8), (9), and (10) as the second component:

(6)

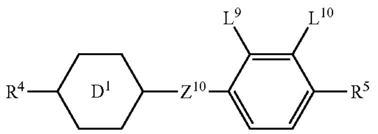

(7)

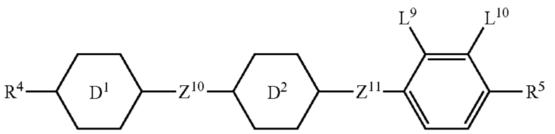

(8)

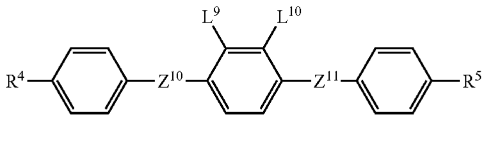

(9)

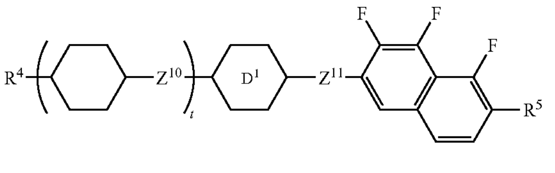

-continued (10)

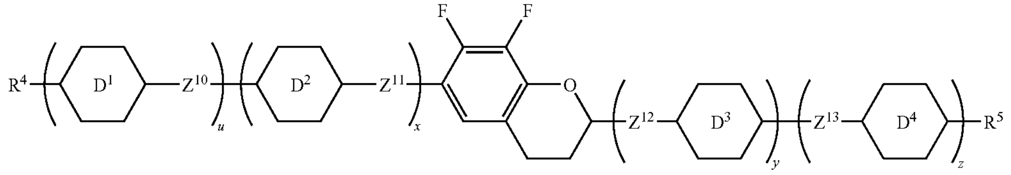

wherein $R^4$ and $R^5$ are each independently alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; ring $D^1$, ring $D^2$, ring $D^3$, and ring $D^4$ are each independently 1,4-cyclohexylene, 1,4-cyclohexenylene, 1,4-phenylene, 1,4-phenylene in which arbitrary hydrogen is replaced by fluorine, tetrahydropyrane-2,5-diyl, or decahydronaphthalene-2,6-diyl; $Z^{10}$, $Z^{11}$, $Z^{12}$, and $Z^{13}$ are each independently $—(CH_2)_2—$, —COO—, $—CH_2O—$, $—OCF_2—$, $—OCF_2(CH_2)_2—$, or a single bond; $L^9$ and $L^{10}$ are each independently fluorine or chlorine; and t, u, x, y, and z are each independently 0 or 1,and u+x+y+z is 1 or 2.

10. The liquid crystal composition according to claim 6, comprising at least one compound selected from the group of compounds represented by formulas (11), (12), and (13) as the second component:

(11)

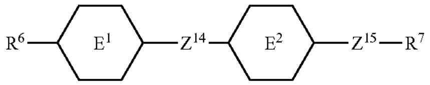

(12)

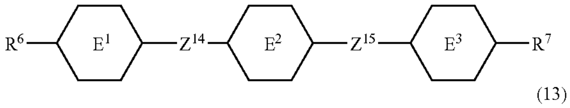

(13)

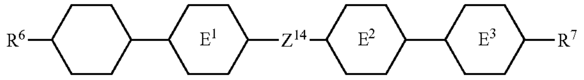

wherein, $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, or 2,5-difluoro-1,4-phenylene; and $Z^{14}$ and $Z^{15}$ are each independently —C≡C—, —COO—, $—(CH_2)_2—$, —CH═CH—, or a single bond.

11. The liquid crystal composition according to claim 7, further comprising at least one compound selected from the group of compounds represented by formula (5):

(5)

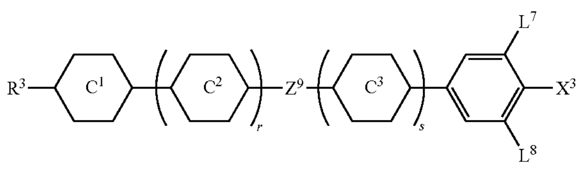

wherein $R^3$ is alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; $X^3$ is —C≡N or —C≡C—C≡N; ring $C^1$, ring $C^2$, and ring $C^3$ are each independently 1,4-cyclohexylene, 1,4-phenylene , 1,4-phenylene in which arbitrary hydrogen is replaced by fluorine, 1,3-dioxane-2,5-diyl, tetrahydropyrane-2,5-diyl, or pyrimidine-2,5-diyl; $Z^9$ is $—(CH_2)^2$, —COO—, $—CF_2O—$, $OCF_2$, —C≡C—, $—CH_2$ O—, or a single bond; $L^7$ and $L^8$ are each independently hydrogen or fluorine; and r and s are each independently 0 or 1.

12. The liquid crystal composition according to claim 7, further comprising at least one compound selected from the group of compounds represented by formulas (11), (12), and (13):

(11)

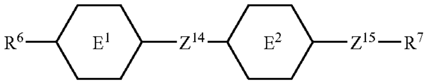

(12)

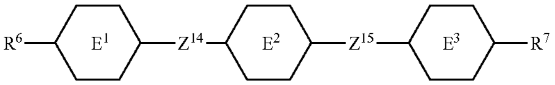

(13)

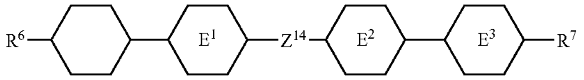

wherein, $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, or 2,5-difluoro-1,4-phenylene; and $Z^{14}$ and $Z^{15}$ are each independently —C≡C—, —COO—, $—(CH_2)_2—$, —CH═CH—, or a single bond.

13. The liquid crystal composition according to claim 8, further comprising at least one compound selected from the group of compounds represented by formulas (11), (12), and (13):

(11)

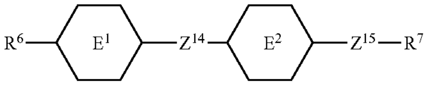

-continued (12)

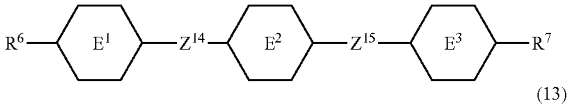

(13)

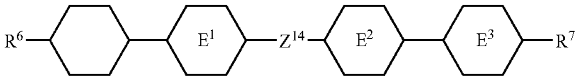

wherein, $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, or 2,5-difluoro-1,4-phenylene; and $Z^{14}$ and $Z^{15}$ are each independently —C≡C—, —COO—, $—(CH_2)_2—$, —CH═CH—, or a single bond.

14. The liquid crystal composition according to claim 9, further comprising at least one compound selected from the group of compounds represented by formulas (11), (12), and (13):

(11)

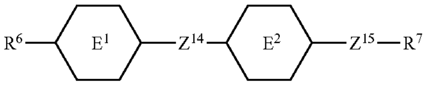

-continued (12)

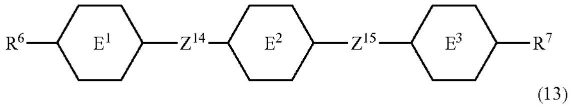

(13)

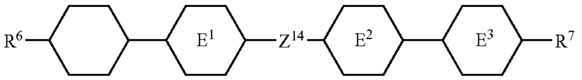

wherein, $R^6$ and $R^7$ are each independently alkyl having 1 to 10 carbons or alkenyl having 2 to 10 carbons, and in the alkyl and alkenyl, arbitrary hydrogen may be replaced by fluorine and arbitrary $—CH_2—$ may be replaced by —O—; ring $E^1$, ring $E^2$, and ring $E^3$ are each independently 1,4-cyclohexylene, pyrimidine-2,5-diyl, 1,4-phenylene, 2-fluoro-1,4-phenylene, or 2,5-difluoro-1,4-phenylene; and $Z^{14}$ and $Z^{15}$ are each independently —C≡C—, —COO—, $—(CH_2)_2—$, —CH═CH—, or a single bond.

15. The liquid crystal composition according to claim 6, further comprising at least one optically active compound.

16. The liquid crystal composition according to claim 6, further comprising at least one antioxidant and/or ultraviolet radiation absorbent.

17. A liquid crystal display device comprising the liquid crystal composition according to claim 6.

* * * * *